US011267865B2

(12) United States Patent
Kumar et al.

(10) Patent No.: US 11,267,865 B2
(45) Date of Patent: Mar. 8, 2022

(54) VARIANT ACTRIIB PROTEINS AND USES THEREOF

(71) Applicant: Acceleron Pharma Inc., Cambridge, MA (US)

(72) Inventors: Ravindra Kumar, Acton, MA (US); Asya Grinberg, Lexington, MA (US); Erik M. Vogan, Medford, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 265 days.

(21) Appl. No.: 16/340,048

(22) PCT Filed: Oct. 5, 2017

(86) PCT No.: PCT/US2017/055421
§ 371 (c)(1),
(2) Date: Apr. 5, 2019

(87) PCT Pub. No.: WO2018/067874
PCT Pub. Date: Apr. 12, 2018

(65) Prior Publication Data
US 2020/0055919 A1 Feb. 20, 2020

Related U.S. Application Data

(60) Provisional application No. 62/404,718, filed on Oct. 5, 2016.

(51) Int. Cl.
C07K 14/71 (2006.01)
A61P 21/00 (2006.01)
A61K 38/00 (2006.01)

(52) U.S. Cl.
CPC .............. *C07K 14/71* (2013.01); *A61P 21/00* (2018.01); *A61K 38/00* (2013.01); *C07K 2319/30* (2013.01)

(58) Field of Classification Search
CPC .... C07K 14/71; C07K 2319/30; A61K 38/00; A61P 21/00
See application file for complete search history.

(56) References Cited

U.S. PATENT DOCUMENTS

| 5,932,448 | A | 8/1999 | Tso et al. | |
| 7,893,213 | B2 * | 2/2011 | Mathews | C07K 14/71 530/387.1 |
| 8,343,933 | B2 | 1/2013 | Knopf et al. | |
| 2003/0078385 | A1 | 4/2003 | Arathoon et al. | |
| 2006/0068468 | A1 | 3/2006 | Knopf et al. | |
| 2010/0286374 | A1 | 11/2010 | Kannan et al. | |
| 2011/0092670 | A1 | 4/2011 | Knopf et al. | |
| 2012/0015877 | A1 | 1/2012 | Seehra et al. | |
| 2012/0302737 | A1 | 11/2012 | Christensen et al. | |
| 2013/0177559 | A1 | 7/2013 | Seehra et al. | |
| 2016/0289292 | A1 | 10/2016 | Kumar et al. | |
| 2016/0289298 | A1 | 10/2016 | Kumar et al. | |
| 2016/0297867 | A1 | 10/2016 | Kumar et al. | |
| 2016/0298093 | A1 | 10/2016 | Kumar et al. | |
| 2017/0306027 | A1 | 10/2017 | Knopf et al. | |
| 2018/0009872 | A1 | 1/2018 | Sherman et al. | |
| 2018/0148491 | A1 | 5/2018 | Han et al. | |
| 2018/0163187 | A1 | 6/2018 | Kumar et al. | |
| 2019/0100570 | A1 | 4/2019 | Kumar et al. | |
| 2019/0263876 | A1 | 8/2019 | Seehra et al. | |

FOREIGN PATENT DOCUMENTS

| WO | WO-1993/011162 | | 6/1993 |
| WO | WO-00/43781 | A2 | 7/2000 |
| WO | WO-2005/084699 | A1 | 9/2005 |
| WO | WO-2006/012627 | A2 | 2/2006 |
| WO | WO-2007/147901 | A1 | 12/2007 |
| WO | WO-2008/076437 | A2 | 6/2008 |
| WO | WO-2008/097541 | A2 | 8/2008 |
| WO | WO-2009/089004 | A1 | 7/2009 |
| WO | WO-2009/134428 | A2 | 11/2009 |
| WO | WO-2009/158015 | A2 | 12/2009 |
| WO | WO-2010/019261 | A1 | 2/2010 |
| WO | WO-2010/083034 | A1 | 7/2010 |
| WO | WO-2010/151426 | A1 | 12/2010 |
| WO | WO-2011/031901 | A1 | 3/2011 |
| WO | WO-2011/034605 | A2 | 3/2011 |
| WO | WO-2012/027065 | A2 | 3/2012 |
| WO | WO-2013/000234 | A1 | 1/2013 |
| WO | WO-2013/059347 | A1 | 4/2013 |
| WO | WO-2013/063536 | A1 | 5/2013 |
| WO | WO-2015/027082 | A1 | 2/2015 |

(Continued)

OTHER PUBLICATIONS

Database Accession No. BDB79662 "Human ActRIIB-Fc mature fusion protein SEQ ID No. 8." (Aug. 25, 2016).
Database Accession No. AYN43338 "Human activin type-IIB receptor (20-134)-IgGl Fc fusion protein." (Mar. 3, 2011).
Database Accession No. BDB17016 "Human actRIIB extracellular domain-IgGl Fc domain fusion protein, SEQ 31." (Jul. 28, 2016).
Laurent et al., "Muscle-bone interactions: From experimental models to the clinic? A critical update," Molecular and Cellular Endocrinology, vol. 432: 14-36 (2016).
Amthor, et al., "The Regulation and Action of Myostatin as a Negative Regulator of Muscle Development during Avian Embryogenesis," Developmental Biology, vol. 251: 241-257 (2002).
Ashmore, et al., "Comparative Aspects of Muscle Fiber Types in Fetuses of the Normal and "Double-Muscled" Cattle," Growth, vol. 38: 501-506 (1974).

(Continued)

*Primary Examiner* — Ruixiang Li
(74) *Attorney, Agent, or Firm* — White & Case LLP

(57) ABSTRACT

In certain aspects, the present invention provides compositions and methods for modulating (promoting or inhibiting) growth of red blood cells or a tissue, such as bone, cartilage, muscle, fat, and/or neuronal tissue. The present invention also provides methods of screening compounds that modulate activity of an ActRIIB protein and/or an ActRIIB ligand. The compositions and methods provided herein are useful in treating diseases associated with abnormal activity of an ActRIIB protein and/or an ActRIIB ligand.

21 Claims, 14 Drawing Sheets
(7 of 14 Drawing Sheet(s) Filed in Color)
Specification includes a Sequence Listing.

(56) References Cited

FOREIGN PATENT DOCUMENTS

| WO | WO-2015/143403 A1 | 9/2015 |
|---|---|---|
| WO | WO-2015/161220 A1 | 10/2015 |
| WO | WO-2015/192111 A1 | 12/2015 |
| WO | WO-2016/164089 A2 | 10/2016 |
| WO | WO-2016/164497 A1 | 10/2016 |
| WO | WO-2016/205370 A1 | 12/2016 |
| WO | WO-2017/037634 A1 | 3/2017 |
| WO | WO-2018/009624 A1 | 1/2018 |
| WO | WO-2018/067873 A2 | 4/2018 |
| WO | WO 2018/075747 | 4/2018 |
| WO | WO 2018/089706 | 5/2018 |
| WO | WO 2018/089715 | 5/2018 |

OTHER PUBLICATIONS

Attisano, et al., "Novel Activin Receptors: Distinct Genes and Alternative mRNA Splicing Generate a Repertoire of Serine/Threonine Kinase Receptors," Cell, vol. 68: 97-108 (1992).

Davis, et al., "SEEDbodies: fusion proteins based on strand-exchange engineered domain (SEED) CH3 heterodimers in an Fc analogue platform for asymmetric binders or immunofusions and bispecific antibodies," Protein Engineering, Design & Selection, vol. 23(4): 195-202 (2010).

Gamer, et al., "A Novel BMP Expressed in Developing Mouse Limb, Spinal Cord, and Tail Bud Is a Potent Mesoderm Inducer in Xenopus Embryos," Developmental Biology, vol. 208: 222-232 (1999).

Gonzalez-Cadavid, et al., "Organization of the human myostatin gene and expression in healthy men and HIV-infected men with muscle wasting," PNAS, 95:14938-14943 (1998).

Grobet et al., "A deletion in the bovine myostatin gene causes the double-muscled phenotype in cattle," Nat Genet, vol. 17(1): 71-74 (1997).

Groopman et al., "Chemotherapy-Induced Anemia in Adults: Incidence and Treatment," Journal of the National Cancer Institute, vol. 91(19): 1616-1634 (1999).

Gunasekaran, et al., "Enhancing Antibody Fc Heterodimer Formation through Electrostatic Steering Effects," The Journal of Biological Chemistry, vol. 285(25): 19637-19646 (2010).

Hildén, et al., "Expression of Type II Activin Receptor Genes During Differentiation of Human K562 Cells and cDNA Cloning of the Human Type IIb Activin Receptor," Blood, vol. 83(8): 2163-2170 (1994).

Jacobs, et al., "European Best Practice Guidelines 5 Target haemoglobin," Nephrology Dialysis Transplantation, vol. 15(Suppl. 4): 15-19 (2000).

Kambadur, et al., "Mutations in myostatin (GDF8) in Double-Muscled Belgian Blue and Piedmontese Cattle," Genome Research, vol. 7: 910-915 (1997).

Konrad, et al., "Alternative splicing of TGF-betas and their high-affinity receptors TβRI, TβRII and TβRIII (betaglycan) reveal new variants in human prostatic cells," BMC Genomics, vol. 8(318): 13 pages (2007).

Lee, et al., "Regulation of Myostatin Activity and Muscle Growth," PNAS, 98(16):9306-9311 (2001).

Levin, "Prevalent Left Ventricular Hypertrophy in the Predialysis Population: Identifying Opportunities for Intervention," American Journal of Kidney Diseases, vol. 27(3): 347-354 (1996).

McPherron, et al., "Regulation of Skeletal Muscle Mass in Mice by a Bew TGF-β Superfamily Member," Nature, 387:83-90 (1997).

McPherron, et al., "Double muscling in cattle due to mutations in the myostatin gene," Proceedings of the National Academy of Sciences, vol. 94: 12457-12461 (1997).

Merchant, et al., "An efficient route to human bispecific IgG," Nature Biotechnology, vol. 16: 677-681 (1998).

Oh, et al., "Activin type IIA and IIB receptors mediate Gdf11 signaling in axial vertebral patterning," Genes & Development, 16:2749-2754 (2002).

Qin et al., "A novel highly potent trivalent TGF-β receptor trap inhibits early-stage tumorigenesis and tumor cell invasion in murine Pten-deficient prostate glands," Oncotarget, vol. 7(52): 86087-86102 (2016).

Ridgway, et al., "'Knobs-into-holes' engineering of antibody CH3 domains for heavy chain heterodimerization," Protein Engineering, vol. 9(7): 617-621 (1996).

Roberts, et al., "Identification of Novel Isoforms of Activin Receptor-Like Kinase 7 (ALK7) Generated by Alternative Splicing and Expression of ALK7 and Its Ligand, Nodal, in Human Placenta," Biology of Reproduction, vol. 68: 1719-1726 (2003).

Schuelke, et al., "Myostatin Mutation Associated with Gross Muscle Hypertrophy in a Child," New England Journal of Medicine, 350(26):2682-2688 (2004).

Spiess, et al., "Alternative molecular formats and therapeutic applications for bispecific antibodies," Molecular Immunology, vol. 67: 95-106 (2015).

Swatland and Kieffer, "Fetal Development of the Double Muscled Condition in Cattle," Journal of Animal Science, vol. 38(4): 752-757 (1974).

Whittemore, et al., "Inhibition of myostatin in adult mice increases skeletal muscle mass and strength," Biochemical and Biophysical Research Communications, vol. 300: 965-971 (2003).

Wranik, et al., "LUZ-Y, a Novel Platform for the Mammalian Cell Production of Full-length IgG-bispecific Antibodies," The Journal of Biological Chemistry, vol. 287(52): 43331-43339 (2012).

Wu, et al., "Autoregulation of Neurogenesis by GDF11," Neuron, vol. 37: 197-207 (2003).

Yamashita, et al., Osteogenic protein-1 binds to activin type II receptors and induces certain activin-like effects, The Journal of Cell Biology: JCB, The Rockefeller University Press US, vol. 130(1): 217-226 (1995).

Yeo and Whitman, "Nodal Signals to Smads through Cripto-Dependent and Cripto-Independent Mechanisms," Molecular Cell, vol. 7: 949-957 (2001).

Issued U.S. Pat. No. 8,343,933 (U.S. Appl. No. 12/893,976), filed Sep. 29, 2010.

Issued U.S. Pat. No. 9,181,533 (U.S. Appl. No. 13/657,649), filed Oct. 22, 2012.

Issued U.S. Pat. No. 8,361,957 (U.S. Appl. No. 13/247,748), filed Sep. 28, 2011.

Issued U.S. Pat. No. 9,399,669 (U.S. Appl. No. 13/730,418), filed Dec. 28, 2012.

Issued U.S. Pat. No. 7,842,663 (U.S. Appl. No. 12/012,652), filed Feb. 4, 2008.

Issued U.S. Patent No. 10,259,861 (U.S. Appl. No. 15/201,031), filed Jul. 1, 2016.

Pending U.S. Appl. No. 16/287,531, filed Feb. 27, 2019.

Issued U.S. Pat. No. 7,709,605 (U.S. Appl. No. 11/190,202), filed Jul. 25, 2005.

Issued U.S. Pat. No. 8,703,927 (U.S. Appl. No. 13/542,269), filed Jul. 5, 2012.

Issued U.S. Pat. No. 9,439,945 (U.S. Appl. No. 14/201,192), filed May 7, 2014.

Issued U.S. Pat. No. 9,932,379 (U.S. Appl. No. 15/221,341), filed Jul. 27, 2016.

Pending U.S. Appl. No. 16/455,301, filed Jun. 27, 2019.

Issued U.S. Pat. No. 8,293,881 (U.S. Appl. No. 12/796,307), filed Jun. 8, 2010.

Issued U.S. Pat. No. 9,745,559 (U.S. Appl. No. 14/814,040), filed Jul. 30, 2015.

Issued U.S. Patent No. 10,358,633 (U.S. Appl. No. 15/664,172), filed Jul. 31, 2017.

Pending U.S. Appl. No. 16/434,841, filed Jun. 7, 2019.

Abandoned U.S. Appl. No. 12/459,204, filed Jun. 26, 2009.

Abandoned U.S. Appl. No. 13/218,264, filed Aug. 25, 2011.

Pending U.S. Appl. No. 15/652,722, filed Jul. 18, 2017.

Pending U.S. Appl. No. 16/570,695, filed Sep. 13, 2019.

Gray, P.C., et al., "Identification of a binding site on the type II activin receptor for activin and inhibin", Journal of Biological Chemistry, 275(5):3206-3212 (2000).

(56) References Cited

OTHER PUBLICATIONS

Sako, D., et al., "Characterization of the Ligand Binding Functionality of the Extracellular Domain of Activin Receptor Type IIB," The Journal of Biological Chemistry, 285(27):21037-21048 (2010).

* cited by examiner

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPPT
           GGPEVTYEPP PTAPT
```

FIGURE 2

```
IgG1    -------THTCPPCPAPELLGGPSVFLFPPKPKDTLMISRTPEVTCVVVDVSHEDPEVKF  53
IgG4    ---ESKYGPPCPSCPAPEFLGGPSVFLFPPKPKDTLMISRTPEVTCVVVDVSQEDPEVQF  57
IgG2    --------VECPPCPAPPVAG-PSVFLFPPKPKDTLMISRTPEVTCVVVDVSHEDPEVQF  51
IgG3    EPKSCDTPPPCPRCPAPELLGGPSVFLFPPKPKDTLMISRTPEVTCVVVDVSHEDPEVQF  60
                  **  ****  ,  *  ****************************** ;****;*

IgG1    NWYVDGVEVHNAKTKPREEQYNSTYRVVSVLTVLHQDWLNGKEYKCKVSNKALPAPIEKT  113
IgG4    NWYVDGVEVHNAKTKPREEQFNSTYRVVSVLTVLHQDWLNGKEYKCKVSNKGLPSSIEKT  117
IgG2    NWYVDGVEVHNAKTKPREEQFNSTFRVVSVLTVVHQDWLNGKEYKCKVSNKGLPAPIEKT  111
IgG3    KWYVDGVEVHNAKTKPREEQYNSTFRVVSVLTVLHQDWLNGKEYKCKVSNKALPAPIEKT  120
        ;****************** ;***;*******;****************.**;;****

IgG1    ISKAKGQPREPQVYTLPPSREEMTKNQVSLTCLVKGFYPSDIAVEWESNGQPENNYKTTP  173
IgG4    ISKAKGQPREPQVYTLPPSQEEMTKNQVSLTCLVKGFYPSDIAVEWESNGQPENNYKTTP  177
IgG2    ISKTKGQPREPQVYTLPPSREEMTKNQVSLTCLVKGFYPSDIAVEWESNGQPENNYKTTP  171
IgG3    ISKTKGQPREPQVYTLPPSREEMTKNQVSLTCLVKGFYPSDIAVEWESSGQPENNYNTTP  180
        ***;************** ;***********************,*******;***

IgG1    PVLDSDGSFFLYSKLTVDKSRWQQGNVFSCSVMHEALHNHYTQKSLSLSPGK  225
IgG4    PVLDSDGSFFLYSRLTVDKSRWQEGNVFSCSVMHEALHNHYTQKSLSLSLGK  229
IgG2    PMLDSDGSFFLYSKLTVDKSRWQQGNVFSCSVMHEALHNHYTQKSLSLSPGK  223
IgG3    PMLDSDGSFFLYSKLTVDKSRWQQGNIFSCSVMHEALHNRFTQKSLSLSPGK  232
        *;**********;*********;**;************;;*******  **
```

FIGURE 4

```
 20    GRGEAETRECR  IYYNANWELE  RTNQSGLERC  EGEQDKRLHC  YASWRNSSGT
 70    IELVKKGCWL   DDFNCYDRQE  CVATEENPQV  YFCCCEGNFC  NERFTHLPEA
120    GGPEVTYEPP   PTAPT       (SEQ ID NO: 1)
```

FIGURE 5

```
  1  MTAPWVALAL LWGSLCAGSG RGEAETRECI YYNANWELER TNQSGLERCE
 51  GEQDKRLHCY ASWRNSSGTI ELVKKGCWLD DFNCYDRQEC VATEENPQVY
101  FCCCEGNFCN ERFTHLPEAG GPEVTYEPPP TAPTLLTVLA YSLLPIGGLS
151  LIVLLAFWMY RHRKPPYGHV DIHEDPGPPP PSPLVGLKPL QLLEIKARGR
201  FGCVWKAQLM NDFVAVKIFP LQDKQSWQSE REIFSTPGMK HENLLQFIAA
251  EKRGSNLEVE LWLITAFHDK GSLTDYLKGN IITWNELCHV AETMSRGLSY
301  LHEDVPWCRG EGHKPSIAHR DFKSKNVLLK SDLTAVLADF GLAVRFEPGK
351  PPGDTHGQVG TRRYMAPEVL EGAINFQRDA FLRIDMYAMG LVLWELVSRC
401  KAADGPVDEY MLPFEEEIGQ HPSLEELQEV VVHKKMRPTI KDHWLKHPGL
451  AQLCVTIEEC WDHDAEARLS AGCVEERVSL IRRSVNGTTS DCLVSLVTSV
501  TNVDLPPKES SI         (SEQ ID NO: 2)
```

FIGURE 6

```
GGGCGTGGGGAGGCTGAGACACGGGAGTGCATCTACTACAACGCCAACTGGGAGCTGGAGCGCACCAACC
AGAGCGGCCTGGAGCGCTGCGAAGGCGAGCAGGACAAGCGGCTGCACTGCTACGCCTCCTGGCGCAACAG
CTCTGGCACCATCGAGCTCGTGAAGAAGGGCTGCTGGCTAGATGACTTCAACTGCTACGATAGGCAGGAG
TGTGTGGCCACTGAGGAGAACCCCCAGGTGTACTTCTGCTGCTGTGAAGGCAACTTCTGCAACGAGCGCT
TCACTCATTTGCCAGAGGCTGGGGGCCCGGAAGTCACGTACGAGCCACCCCCGACAGCCCCCACC
(SEQ ID NO: 3)
```

FIGURE 7

```
ATGACGGCGCCCTGGGTGGCCCTCGCCCTCCTCTGGGGATCGCTGTGGCCCGGCTCTGGGCGTGGGGAGG
CTGAGACACGGGAGTGCATCTACTACAACGCCAACTGGGAGCTGGAGCGCACCAACCAGAGCGGCCTGGA
GCGCTGCGAAGGCGAGCAGGACAAGCGGCTGCACTGCTACGCCTCCTGGCGCAACAGCTCTGGCACCATC
GAGCTCGTGAAGAAGGGCTGCTGGCTAGATGACTTCAACTGCTACGATAGGCAGGAGTGTGTGGCCACTG
AGGAGAACCCCCAGGTGTACTTCTGCTGCTGTGAAGGCAACTTCTGCAACGAGCGCTTCACTCATTTGCC
AGAGGCTGGGGGCCCGGAAGTCACGTACGAGCCACCCCCGACAGCCCCCACCCTGCTCACGGTGCTGGCC
TACTCACTGCTGCCCATCGGGGCCTTTCCCTCATCGTCCTGCTGGCCTTTTGGATGTACCGGCATCGCA
AGCCCCCCTACGGTCATGTGGACATCCATGAGGACCCTGGGCCTCCACCACCATCCCCTCTGGTGGGCCT
GAAGCCACTGCAGCTGCTGGAGATCAAGGCTCGGGGGCGCTTTGGCTGTGTCTGGAAGGCCCAGCTCATG
AATGACTTTGTAGCTGTCAAGATCTTCCCACTCCAGGACAAGCAGTCGTGGCAGAGTGAACGGGAGATCT
TCAGCACACCTGGCATGAAGCACGAGAACCTGCTACAGTTCATTGCTGCCGAGAAGCGAGGCTCCAACCT
CGAAGTAGAGCTGTGGCTCATCACGGCCTTCCATGACAAGGGCTCCCTCACGGATTACCTCAAGGGGAAC
ATCATCACATGGAACGAACTGTGTCATGTAGCAGAGACGATGTCACGAGGCCTCTCATACCTGCATGAGG
ATGTGCCCTGGTGCCGTGGCGAGGGCCACAAGCCGTCTATTGCCCACAGGGACTTTAAAAGTAAGAATGT
ATTGCTGAAGAGCGACCTCACAGCCGTGCTGGCTGACTTTGGCTTGGCTGTTCGATTTGAGCCAGGGAAA
CCTCCAGGGGACACCCACGGACAGGTAGGCACGAGACGGTACATGGCTCCTGAGGTGCTCGAGGGAGCCA
TCAACTTCCAGAGAGATGCCTTCCTGCGCATTGACATGTATGCCATGGGGTTGGTGCTGTGGGAGCTTGT
GTCTCGCTGCAAGGCTGCAGACGGACCCGTGGATGAGTACATGCTGCCCTTTGAGGAAGAGATTGGCCAG
CACCCTTCGTTGGAGGAGCTGCAGGAGGTGGTGGTGCACAAGAAGATGAGGCCCACCATTAAAGATCACT
GGTTGAAACACCCGGGCCTGGCCCAGCTTTGTGTGACCATCGAGGAGTGCTGGGACCATGATGCAGAGGC
TCGCTTGTCCGCGGGCTGTGTGGAGGAGCGGGTGTCCCTGATTCGGAGGTCGGTCAACGGCACTACCTCG
GACTGTCTCGTTTCCCTGGTGACCTCTGTCACCAATGTGGACCTGCCCCCTAAAGAGTCAAGCATCTAA
(SEQ ID NO: 4)
```

FIGURE 8

| Ligand Binding by Homodimeric ActRIIB-Fc Proteins at 37°C ||||||||||||
| ActRIIB protein | Activin A ||| GDF11 ||| BMP9 ||| BMP10 |||
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
|---|---|---|---|---|---|---|---|---|---|---|---|---|
| Wild-type | $2.3 \times 10^6$ | $1.1 \times 10^{-4}$ | 47 | $1.0 \times 10^7$ | $1.2 \times 10^{-4}$ | 12 | $3.0 \times 10^7$ | $1.1 \times 10^{-3}$ | 37 | $3.6 \times 10^7$ | $1.6 \times 10^{-4}$ | 4 |
| K55A | $3.0 \times 10^6$ | $1.4 \times 10^{-4}$ | 46 | $1.6 \times 10^7$ | $4.0 \times 10^{-4}$ | 26 | $4.9 \times 10^7$ | $7.0 \times 10^{-3}$ | 142 | $3.2 \times 10^7$ | $7.4 \times 10^{-4}$ | 23 |
| K55A / F82I | $5.7 \times 10^6$ | $2.7 \times 10^{-4}$ | 47 | $3.2 \times 10^7$ | $2.8 \times 10^{-3}$ | 90 | $1.6 \times 10^7$ | $2.1 \times 10^{-3}$ | 134 | $1.3 \times 10^8$ | $8.6 \times 10^{-4}$ | 7 |
| K55E | $2.5 \times 10^6$ | $1.6 \times 10^{-4}$ | 64 | $1.2 \times 10^7$ | $6.3 \times 10^{-4}$ | 52 | $1.1 \times 10^8$ | $3.0 \times 10^{-2}$ | 270 | $3.4 \times 10^7$ | $4.7 \times 10^{-4}$ | 14 |
| K74A | $3.2 \times 10^7$ | $1.1 \times 10^{-3}$ | 34 | $1.9 \times 10^7$ | $8.1 \times 10^{-3}$ | 430 | $1.7 \times 10^8$ | $6.2 \times 10^{-2}$ | 360 | $7.5 \times 10^7$ | $2.5 \times 10^{-3}$ | 33 |
| L79H | $1.9 \times 10^6$ | $5.6 \times 10^{-4}$ | 300 | $2.0 \times 10^7$ | $7.5 \times 10^{-4}$ | 37 | $2.4 \times 10^6$ | $1.8 \times 10^{-3}$ | 760 | $1.9 \times 10^7$ | $2.1 \times 10^{-3}$ | 120 |
| L79H / F82I | $1.2 \times 10^6$ | $6.7 \times 10^{-4}$ | 580 | $2.6 \times 10^7$ | $1.7 \times 10^{-3}$ | 64 | $1.3 \times 10^7$ | $2.8 \times 10^{-3}$ | 220 | $2.7 \times 10^7$ | $3.0 \times 10^{-3}$ | 110 |
| L79K | $4.0 \times 10^6$ | $5.1 \times 10^{-4}$ | 130 | $1.2 \times 10^7$ | $1.7 \times 10^{-3}$ | 140 | $1.6 \times 10^7$ | $1.7 \times 10^{-2}$ | 1100 | $4.7 \times 10^6$ | $8.5 \times 10^{-3}$ | 1800 |
| L79K / F82K | $1.4 \times 10^6$ | $8.6 \times 10^{-4}$ | 640 | $4.5 \times 10^7$ | $6.7 \times 10^{-3}$ | 1600 | No binding ||| $2.2 \times 10^7$ | $1.5 \times 10^{-3}$ | 68 |
| F82I | $1.9 \times 10^6$ | $1.5 \times 10^{-4}$ | 78 | $8.2 \times 10^6$ | $8.4 \times 10^{-5}$ | 10 | $9.2 \times 10^7$ | $2.5 \times 10^{-2}$ | 275 | $2.3 \times 10^7$ | $1.5 \times 10^{-4}$ | 8 |
| F82K | $1.8 \times 10^6$ | $1.7 \times 10^{-4}$ | 93 | $1.8 \times 10^7$ | $9.1 \times 10^{-4}$ | 57 | Transient binding[a] ||| $3.1 \times 10^7$ | $2.6 \times 10^{-4}$ | 8 |

[a] Indeterminate due to transient nature of interaction

FIGURE 9

| Ligand Binding by Homodimeric ActRIIB-Fc Proteins at 25°C ||||||||||||
|---|---|---|---|---|---|---|---|---|---|---|---|---|
| ActRIIB protein | Activin A ||| GDF11 ||| BMP9 ||| BMP10 |||
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Wild-type | $2.3 \times 10^6$ | $5.2 \times 10^{-4}$ | 230 | $9.1 \times 10^6$ | $9.8 \times 10^{-5}$ | 11 | $7.4 \times 10^6$ | $4.4 \times 10^{-4}$ | 59 | $3.3 \times 10^6$ | $5.0 \times 10^{-4}$ | 169 |
| N35E | $1.3 \times 10^6$ | $1.0 \times 10^{-3}$ | 800 | $6.7 \times 10^6$ | $1.9 \times 10^{-4}$ | 28 | No binding ||| $4.3 \times 10^6$ | $1.2 \times 10^{-3}$ | 280 |
| N35F | $1.6 \times 10^6$ | $4.7 \times 10^{-4}$ | 290 | $8.2 \times 10^6$ | $1.4 \times 10^{-4}$ | 17 | Reduced binding ||| $2.6 \times 10^6$ | $5.8 \times 10^{-4}$ | 220 |
| N35Q | $2.0 \times 10^6$ | $6.5 \times 10^{-4}$ | 325 | $7.7 \times 10^6$ | $1.6 \times 10^{-4}$ | 20 | Little binding ||| $2.7 \times 10^6$ | $7.1 \times 10^{-4}$ | 270 |
| L38D | $1.7 \times 10^6$ | $4.0 \times 10^{-4}$ | 230 | $5.8 \times 10^6$ | $1.8 \times 10^{-4}$ | 30 | $6.6 \times 10^6$ | $4.2 \times 10^{-4}$ | 63 | $3.3 \times 10^6$ | $4.9 \times 10^{-4}$ | 150 |
| L38Q | $1.8 \times 10^6$ | $3.5 \times 10^{-4}$ | 200 | $7.0 \times 10^6$ | $1.5 \times 10^{-4}$ | 21 | $7.4 \times 10^6$ | $2.5 \times 10^{-4}$ | 33 | $3.9 \times 10^6$ | $3.5 \times 10^{-4}$ | 89 |
| L38R | $1.9 \times 10^6$ | $4.5 \times 10^{-4}$ | 230 | $6.4 \times 10^6$ | $4.6 \times 10^{-5}$ | 7 | $1.1 \times 10^7$ | $5.5 \times 10^{-4}$ | 50 | $1.6 \times 10^6$ | $1.7 \times 10^{-4}$ | 110 |
| K74M | No binding ||| No binding ||| No binding ||| No binding |||
| K74T | No binding ||| No binding ||| No binding ||| No binding |||
| L79W | $1.3 \times 10^6$ | $3.2 \times 10^{-4}$ | 260 | $1.2 \times 10^7$ | $5.2 \times 10^{-4}$ | 44 | $9.2 \times 10^6$ | $1.1 \times 10^{-3}$ | 110 | $2.9 \times 10^6$ | $4.7 \times 10^{-4}$ | 160 |
| F82Y | $2.3 \times 10^6$ | $3.9 \times 10^{-4}$ | 170 | $7.1 \times 10^6$ | $1.3 \times 10^{-4}$ | 18 | $8.4 \times 10^6$ | $6.9 \times 10^{-4}$ | 82 | $3.7 \times 10^6$ | $5.2 \times 10^{-4}$ | 140 |
| Q98A | $3.4 \times 10^6$ | $5.3 \times 10^{-4}$ | 155 | $4.7 \times 10^6$ | $1.8 \times 10^{-4}$ | 37 | $1.2 \times 10^7$ | $5.3 \times 10^{-4}$ | 43 | $2.6 \times 10^6$ | $5.4 \times 10^{-4}$ | 210 |
| Q98I | $4.1 \times 10^6$ | $6.4 \times 10^{-4}$ | 157 | $3.9 \times 10^6$ | $1.9 \times 10^{-4}$ | 49 | $1.6 \times 10^7$ | $9.4 \times 10^{-4}$ | 59 | $2.6 \times 10^6$ | $5.6 \times 10^{-4}$ | 210 |
| Q98K | $3.3 \times 10^6$ | $4.8 \times 10^{-4}$ | 145 | $4.6 \times 10^6$ | $1.7 \times 10^{-4}$ | 37 | $1.1 \times 10^7$ | $7.4 \times 10^{-4}$ | 69 | $7.4 \times 10^6$ | $5.0 \times 10^{-4}$ | 68 |
| Q98L | $3.8 \times 10^6$ | $8.2 \times 10^{-4}$ | 220 | $4.0 \times 10^6$ | $1.7 \times 10^{-4}$ | 43 | $1.6 \times 10^7$ | $1.2 \times 10^{-3}$ | 71 | $1.1 \times 10^7$ | $7.2 \times 10^{-4}$ | 65 |
| Q98R | $3.4 \times 10^6$ | $1.0 \times 10^{-3}$ | 300 | $5.5 \times 10^6$ | $1.1 \times 10^{-4}$ | 20 | $9.7 \times 10^6$ | $7.2 \times 10^{-4}$ | 74 | $2.5 \times 10^6$ | $8.1 \times 10^{-4}$ | 320 |
| Q98V | $3.6 \times 10^6$ | $6.0 \times 10^{-4}$ | 160 | $5.0 \times 10^6$ | $1.6 \times 10^{-4}$ | 33 | $1.1 \times 10^7$ | $5.0 \times 10^{-4}$ | 47 | $1.0 \times 10^7$ | $5.0 \times 10^{-4}$ | 48 |

FIGURE 10

VARIANT ActRIIB PROTEINS AND USES THEREOF

CROSS-REFERENCE TO RELATED APPLICATIONS

This application is a national stage filing under 35 U.S.C. § 371 of International Application No. PCT/US2017/055421, filed on Oct. 5, 2017, which claims the benefit of priority from U.S. Provisional Application No. 62/404,718, filed Oct. 5, 2016. The specifications of the foregoing applications are incorporated herein by reference in their entirety.

SEQUENCE LISTING

The instant application contains a Sequence Listing which has been submitted via EFS-Web and is hereby incorporated by reference in its entirety. Said ASCII copy, created on Apr. 4, 2019, is named 1848179-0002-119-301_Seq.txt and is 498,191 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Changes in red blood cell levels, bone, cartilage and other tissues may be achieved by agonizing or antagonizing signaling that is mediated by an appropriate TGF-beta family member. Thus, there is a need for agents that function as potent regulators of TGF-beta signaling.

SUMMARY OF THE INVENTION

In certain aspects, the present disclosure provides variant ActRIIB polypeptides, particularly variant ActRIIB homomultimer proteins and variant ActRIIB heteromultimer proteins. As demonstrated by the examples, several variant ActRIIB polypeptides have been identified that display altered binding affinity for one or more ActRIIB-binding ligands. ActRIIB variants that decrease and increase ligand-binding activities were identified. Such variants may be particularly useful for increasing or decreasing ligand selectively compared to a corresponding unmodified ActRIIB polypeptide in a variety of applications. For example, the examples further demonstrate that some of the variant ActRIIB polypeptides have various in vivo effects including, for example, the ability to increase body mass (e.g., muscle mass) as well as increasing red blood cell and hemoglobin levels. Therefore, variant ActRIIB polypeptides should be useful in a variety of therapeutic applications including, for example, those described herein.

In certain aspects, the disclosure relate to variant ActRIIB polypeptides comprising an amino acid sequence that is at least 75%, 80%, 85%, 90%, 91%, 92%, 93%, 94%, 95%, 96%, 97%, 98%, 99%, or 100% identical to an amino acid sequence that begins at any one of amino acid 20-29 (e.g., 20, 21, 22, 23, 24, 25, 26, 27, 28, or 29) of SEQ ID NO: 2 and ends at any one of amino acid 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 2, and wherein the polypeptide comprises one or more amino acid substitutions at a position of SEQ ID NO: 2 selected from the group consisting of: K55, F82, L79, A24, K74, R64, P129, P130, E37, R40, D54, R56, W78, D80, and F82 as well as heteromultimer complexes comprising one or more such ActRIIB polypeptides. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to amino acids 29-109 of SEQ ID NO: 2. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to amino acids 20-134 of SEQ ID NO: 2. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 53. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 12. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 5. In some embodiments, the polypeptide comprises an amino acid substitution at the amino acid position corresponding to K55 of SEQ ID NO: 2. For example, in some embodiments, the substitution is K55A. In some embodiments, the substitution is K55E. In some embodiments, the polypeptide comprises an amino acid substitution at the amino acid position corresponding to L79 of SEQ ID NO: 2. For example, in some embodiments, the substitution is L79D. In some embodiments, the substitution is L79E. In some embodiments, the substitution is L79P. In some embodiments, the substitution is L79A. In some embodiments, the polypeptide comprises an amino acid substitution at the amino acid position corresponding to F82 of SEQ ID NO: 2. For example, in some embodiments, the substitution is F82I. In some embodiments, the substitution is F82K. In some embodiments, the substitution is F82A. In some embodiments, the polypeptide comprises an amino acid substitution at the amino acid position corresponding to A24 of SEQ ID NO: 2. For example, in some embodiments, the substitution is A24N. In some embodiments, the polypeptide comprises an amino acid substitution at the amino acid position corresponding to K74 of SEQ ID NO: 2. For example, in some embodiments, the substitution is K74A. In some embodiments, the substitution is K74A. In some embodiments, the substitution is K74F. In some embodiments, the substitution is K74A. In some embodiments, the substitution is K74I. In some embodiments, the substitution is K74A. In some embodiments, the substitution is K74Y. In some embodiments, the polypeptide comprises an amino acid substitution at the amino acid position corresponding to D80 of SEQ ID NO: 2. For example, in some embodiments, the substitution is D80A. In some embodiments, the substitution is D80F. In some embodiments, the substitution is D80K. In some embodiments, the substitution is D80G. In some embodiments, the substitution is D80M. In some embodiments, the substitution is D80I. In some embodiments, the substitution is D80N. In some embodiments, the substitution is D80R. In some embodiments, the polypeptide comprises an amino acid substitution at the amino acid position corresponding to R64 of SEQ ID NO: 2. For example, in some embodiments, the substitution is R64K. In some embodiments, the substitution is R64N. In some embodiments, the polypeptide comprises an amino acid substitution at the amino acid position corresponding to P129 of SEQ ID NO: 2. For example, in some embodiments, the substitution is P129S. In some embodiments, the polypeptide comprises an amino acid substitution at the amino acid position corresponding to P130 of SEQ ID NO: 2. For example, in some embodiments, the substitution is P130A. In some embodiments, the substitution is P130R. In some embodiments, the polypeptide comprises an amino acid substitution at the amino acid position corresponding to E37 of SEQ ID NO: 2. For example, in some embodiments, the substitution is E37A. In some embodiments, the polypeptide comprises an amino acid substitution at the amino acid position corresponding to R40 of SEQ ID NO: 2. For example, in some embodiments, the substitution is R40A. In some embodiments, the polypeptide comprises an amino acid substitution at the amino acid position corresponding to D54 of SEQ ID NO: 2. For example, in some embodiments, the substitution is D54A. In some embodiments, the polypeptide comprises an amino acid substitution at the amino acid position corresponding to R56 of SEQ ID NO: 2. For example, in some embodiments, the substitution is R56A. In some embodiments, the polypeptide comprises an amino acid substitution at the amino acid position corresponding to W78 of SEQ ID NO: 2. For example, in some embodiments, the substitution is W78A.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 31. In some embodiments, the variant ActRIIB polypeptide comprises an alanine at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 33. In some embodiments, the variant ActRIIB polypeptide comprises an alanine at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 34. In some embodiments, the variant ActRIIB polypeptide comprises a glutamic acid at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 36. In some embodiments, the variant ActRIIB polypeptide comprises a glutamic acid at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 37. In some embodiments, the variant ActRIIB polypeptide comprises an isoleucine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 39. In some embodiments, the variant ActRIIB polypeptide comprises an isoleucine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 40. In some embodiments, the variant ActRIIB polypeptide comprises a lysine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 42. In some embodiments, the variant ActRIIB polypeptide comprises a lysine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 43. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 45. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 46. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 48. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 49. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 50. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 51. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 52. In some embodiments, the variant ActRIIB polypeptide comprises a glutamic acid at the position corresponding to L79 of SEQ ID NO: 2.

In certain aspects, variant ActRIIB polypeptide of the disclosure form homodimers. In some embodiments, variant ActRIIB polypeptides may from heterodimers through covalent interactions. In some embodiments, variant ActRIIB polypeptides may from heterodimers through non-covalent interactions. In some embodiments, variant ActRIIB polypeptides may from heterodimers through both covalent and non-covalent interactions.

In certain aspects, a variant ActRIIB polypeptide, including homomultimers thereof (e.g., homodimers), binds to one or more TGF-beta superfamily ligands. In some embodiments, variant ActRIIB polypeptide, including homomultimers thereof, binds to one or more TGF-beta superfamily ligands with a $K_D$ of at least $1\times10^{-7}$ M. In some embodiments, the one or more TGF-beta superfamily ligands is selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, a variant ActRIIB polypeptide, including homomultimers thereof (e.g., homodimers), inhibits one or more TGF-beta super family ligands. In some embodiments, variant ActRIIB polypeptide, including homomultimers thereof, inhibits signaling of one or more TGF-beta super family ligands. In some embodiments, variant ActRIIB polypeptide, including homomultimers thereof, inhibits Smad signaling of one or more TGF-beta super family ligands. In some embodiments, variant ActRIIB polypeptide, including homomultimers thereof, inhibits signaling of one or more TGF-beta super family ligands in a cell-based assay. In some embodiments, variant ActRIIB polypeptide, including homomultimers thereof, inhibits one or more TGF-beta super family ligands selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, the disclosure relates to heteromultimers that comprise at least one variant ActRIIB polypeptide (e.g., one or more variant ActRIIB polypeptides described herein). For example, in some embodiments, a heteromultimer protein of the disclosure comprises a first ActRIIB polypeptide and a second ActRIIB polypeptide, wherein the first ActRIIB polypeptide comprises an amino acid sequence that is at least 75%, 80%, 85%, 90%, 91%, 92%, 93%, 94%, 95%, 96%, 97%, 98%, 99%, or 100% identical to an amino acid sequence that begins at any one of amino acid 20-29 (e.g., 20, 21, 22, 23, 24, 25, 26, 27, 28, or 29) of SEQ ID NO: 2 and ends at any one of amino acid 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 2 and comprises one or more amino acid substitutions at positions corresponding to SEQ ID NO: 2 amino acids selected from the group consisting of: A24, K74, R64, P129, P130, E37, R40, D54, R56, W78, D80, and F82, wherein the second ActRIIB polypeptide comprises an amino acid sequence that is at least 75%, 80%, 85%, 90%, 91%, 92%, 93%, 94%, 95%, 96%, 97%, 98%, 99%, or 100% identical to an amino acid sequence that begins at any one of amino acid 20-29 (e.g., 20, 21, 22, 23, 24, 25, 26, 27, 28, or 29) of SEQ ID NO: 2 and ends at any one of amino acid 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 2, and wherein the first ActRIIB polypeptide comprises a different amino acid sequence compared to the second ActRIIB polypeptide. In some embodiments, the first polypeptide comprises an amino acid sequence that is at least 75%, 80%, 85%, 90%, 91%, 92%, 93%, 94%, 95%, 96%, 97%, 98%, 99%, or 100% identical to amino acids 29-109 of SEQ ID NO: 2. In some embodiments, the second polypeptide comprises an amino acid sequence that is at least 75%, 80%, 85%, 90%, 91%, 92%, 93%, 94%, 95%, 96%, 97%, 98%, 99%, or 100% identical to amino acids 29-109 of SEQ ID NO: 2. In some embodiments, the first polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the second polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the first polypeptide comprises an amino acid sequence that is at least 75%, 80%, 85%, 90%, 91%, 92%, 93%, 94%, 95%, 96%, 97%, 98%, 99%, or 100% identical to amino acids 20-134 of SEQ ID NO: 2. In some embodiments, the second polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the first polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 53. In some embodiments, the second polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 53. In some embodiments, the first polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 5. In some embodiments, the second polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 5. In some embodiments, the first polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 12. In some embodiments, the second polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 12. In some embodiments, the first polypeptide comprises an amino acid substitution at the amino acid position corresponding to K55 of SEQ ID NO: 2. For example, in some embodiments, the substitution is K55A. In some embodiments, the substitution is K55E. In some embodiments, the first polypeptide comprises an amino acid substitution at the amino acid position corresponding to L79 of SEQ ID NO: 2. For example, in some embodiments, the substitution is L79D. In some embodiments, the substitution is L79E. In some embodiments, the substitution is L79P. In some embodiments, the substitution is L79A. In some embodiments, the first polypeptide comprises an amino acid substitution at the amino acid position corresponding to F82 of SEQ ID NO: 2. For example, in some embodiments, the substitution is F82I. In some embodiments, the substitution is F82K. In some embodiments, the substitution is F82A. In some embodiments, the first polypeptide comprises an amino acid substitution at the amino acid position corresponding to A24 of SEQ ID NO: 2. For example, in some embodiments, the substitution is A24N. In some embodiments, the polypeptide comprises an amino acid substitution at the amino acid position corresponding to K74 of SEQ ID NO: 2. For example, in some embodiments, the substitution is K74A. In some embodiments, the substitution is K74A. In some embodiments, the substitution is K74F. In some embodiments, the substitution is K74A. In some embodiments, the substitution is K74I. In some embodiments, the substitution is K74A. In some embodiments, the substitution is K74Y. In some embodiments, the first polypeptide comprises an amino acid substitution at the amino acid position corresponding to D80 of SEQ ID NO: 2. For example, in some embodiments, the substitution is D80A. In some embodiments, the substitution is D80F. In some embodiments, the substitution is D80K. In some embodiments, the substitution is D80G. In some embodiments, the substitution is D80M. In some embodiments, the substitution is D80I. In some embodiments, the substitution is D80N. In some embodiments, the substitution is D80R. In some embodiments, the first polypeptide comprises an amino acid substitution at the amino acid position corresponding to R64 of SEQ ID NO: 2. For example, in some embodiments, the substitution is R64K. In some embodiments, the substitution is R64N. In some embodiments, the first polypeptide comprises an amino acid substitution at the amino acid position corresponding to P129 of SEQ ID NO: 2. For example, in some embodiments, the substitution is P129S. In some embodiments, the first polypeptide comprises an amino acid substitution at the amino acid position corresponding to P130 of SEQ ID NO: 2. For example, in some embodiments, the substitution is P130A. In some embodiments, the substitution is P130R. In some embodiments, the first polypeptide comprises an amino acid substitution at the amino acid position corresponding to E37 of SEQ ID NO: 2. For example, in some embodiments, the substitution is E37A. In some embodiments, the first polypeptide comprises an amino acid substitution at the amino acid position corresponding to R40 of SEQ ID NO: 2. For example, in some embodiments, the substitution is R40A. In some embodiments, the first polypeptide comprises an amino acid substitution at the amino acid position corresponding to D54 of SEQ ID NO: 2. For example, in some embodiments, the substitution is D54A. In some embodiments, the first polypeptide comprises an amino acid substitution at the amino acid position corresponding to R56 of SEQ ID NO: 2. For example, in some embodiments, the substitution is R56A. In some embodiments, the first polypeptide comprises an amino acid substitution at the amino acid position corresponding to W78 of SEQ ID NO: 2. For example, in some embodiments, the substitution is W78A. In some embodiments, the second ActRIIB polypeptide comprises one or more amino acid substitutions at a position of SEQ ID NO: 2 selected from the group consisting of: A24, K74, R64, P129, P130, E37, R40, D54, R56, W78, D80, and F82. For example, in some embodiments, the second ActRIIB polypeptide comprises one or more amino acid substitution with respect to the amino acid sequence of SEQ ID NO: 2 selected from the group consisting of: A24N, K74A, R64K, R64N, K74A, L79A, L79D, L79E, L79P, P129S, P130A, P130R, E37A, R40A, D54A, K55A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modifications that promote heteromultimer formation. In some embodiments, the first ActRIIB polypeptide and/or the second ActRIIB polypeptide comprise one or more amino acid modifications that inhibit heteromultimer formation. In some embodiments, the first ActRIIB polypeptide and/or the second ActRIIB polypeptide comprise one or more amino acid modifications that promote heteromultimer formation and one or more amino acid modifications that inhibit heteromultimer formation. In some embodiments, heteromultimers of the disclosure are heterodimers.

In certain aspects, an ActRIIB polypeptide of the disclosure, including a variant ActRIIB polypeptide, is a fusion protein comprising an ActRIIB polypeptide domain and one or more heterologous domains. In some embodiments, an ActRIIB polypeptide is an ActRIIB-Fc fusion protein. In some embodiments, an ActRIIB-Fc fusion protein further comprises a linker domain positioned between the ActRIIB polypeptide domain and the one or more heterologous domains or Fc domain. In some embodiments, the linker domain is selected from: TGGG (SEQ ID NO: 265), TGGGG (SEQ ID NO: 263), SGGGG (SEQ ID NO: 264), GGGGS (SEQ ID NO: 267), GGG (SEQ ID NO: 261), GGGG (SEQ ID NO: 262), and SGGG (SEQ ID NO: 266).

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 13, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 13.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 14, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 14.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 15, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 15.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 16, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 16.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 17, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 17.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 18, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 19.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 19, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 18.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 20, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 21.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 21, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 20.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 22, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 22.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 22, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 25.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 25, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 24.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 26, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 27.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 27, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 26.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 28, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 29. In some embodiments, the first ActRIIB-Fc fusion protein Fc domain comprises a cysteine at amino acid position 132, glutamic acid at amino acid position 138, a tryptophan at amino acid position 144, and a aspartic acid at amino acid position 217. In some embodiments, the second ActRIIB-Fc fusion protein Fc domain comprises a cysteine at amino acid position 127, a serine at amino acid position 144, an alanine at position 146 an arginine at amino acid position 162, an arginine at amino acid position 179, and a valine at amino acid position 185.

In certain aspects, the disclosure relates to ActRIIB heteromultimer proteins comprising a first ActRIIB-Fc fusion protein and a second ActRIIB-Fc fusion protein wherein the second ActRIIB-Fc fusion protein, wherein the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 28, and the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 29. In some embodiments, the second ActRIIB-Fc fusion protein Fc domain comprises a cysteine at amino acid position 132, glutamic acid at amino acid position 138, a tryptophan at amino acid position 144, and a aspartic acid at amino acid position 217. In some embodiments, the first ActRIIB-Fc fusion protein Fc domain comprises a cysteine at amino acid position 127, a serine at amino acid position 144, an alanine at position 146 an arginine at amino acid position 162, an arginine at amino acid position 179, and a valine at amino acid position 185.

In certain aspects, the disclosure relates to ActRIIB heteromultimer proteins comprising a first ActRIIB-Fc fusion protein and a second ActRIIB-Fc fusion protein wherein the second ActRIIB-Fc fusion protein, wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 30, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23. In some embodiments, the first ActRIIB-Fc fusion protein Fc domain comprises a cysteine at amino acid position 132, a tryptophan at amino acid position 144, and a arginine at amino acid position 435. In some embodiments, the second ActRIIB-Fc fusion protein Fc domain comprises cysteine at amino acid position 127, a serine at amino acid position 144, an alanine at amino acid position 146, and a valine at amino acid position 185.

In certain aspects, the disclosure relates to ActRIIB heteromultimer proteins comprising a first ActRIIB-Fc fusion protein and a second ActRIIB-Fc fusion protein wherein the second ActRIIB-Fc fusion protein, wherein the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 30, and the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23. In some embodiments, the second ActRIIB-Fc fusion protein Fc domain comprises a cysteine at amino acid position 132, a tryptophan at amino acid position 144, and a arginine at amino acid position 435. In some embodiments, the first ActRIIB-Fc fusion protein Fc domain comprises cysteine at amino acid position 127, a serine at amino acid position 144, an alanine at amino acid position 146, and a valine at amino acid position 185.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 33, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, the first ActRIIB polypeptide comprises a alanine at the amino acid position corresponding to 55 of SEQ ID NO: 2. In some embodiments, the second ActRIIB polypeptide does not comprise a alanine at the amino acid position corresponding to 55 of SEQ ID NO: 2. In some embodiments, the second ActRIIB polypeptide comprises a lysine at the amino acid position corresponding to 55 of SEQ ID NO: 2. In some embodiments, the first ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 36, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, the first ActRIIB polypeptide comprises a glutamic acid at the amino acid position corresponding to 55 of SEQ ID NO: 2. In some embodiments, the second ActRIIB polypeptide does not comprise a glutamic acid at the amino acid position corresponding to 55 of SEQ ID NO: 2. In some embodiments, the second ActRIIB polypeptide comprises a lysine at the amino acid position corresponding to 55 of SEQ ID NO: 2. In some embodiments, the first ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 39, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, the first ActRIIB polypeptide comprises a isoleucine at the amino acid position corresponding to 82 of SEQ ID NO: 2. In some embodiments, the second ActRIIB polypeptide does not comprise a isoleucine acid at the amino acid position corresponding to 82 of SEQ ID NO: 2. In some embodiments, the second ActRIIB polypeptide comprises a phenylalanine at the amino acid position corresponding to 82 of SEQ ID NO: 2. In some embodiments, the first ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the second ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 42, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, first ActRIIB polypeptide comprises a lysine at the amino acid position corresponding to 82 of SEQ ID NO: 2. In some embodiments, the second ActRIIB polypeptide does not comprise a lysine acid at the amino acid position corresponding to 82 of SEQ ID NO: 2. In some embodiments, the second ActRIIB polypeptide comprises a phenylalanine at the amino acid position corresponding to 82 of SEQ ID NO: 2. In some embodiments, the first ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the second ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 45, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 48, wherein the first ActRIIB polypeptide does not comprise the amino acid sequence of the second ActRIIB polypeptide. In some embodiments, the first ActRIIB polypeptide comprises an acidic amino acid position corresponding to 79 of SEQ ID NO: 2. In some embodiments, the acidic amino acid is an aspartic acid. In some embodiments, the acidic amino acid is a glutamic acid. In some embodiments, the second ActRIIB polypeptide does not comprise an acidic acid (e.g., aspartic acid or glutamic acid) at the amino acid position corresponding to 79 of SEQ ID NO: 2. In some embodiments, the second ActRIIB polypeptide comprises a leucine at the amino acid position corresponding to 79 of SEQ ID NO: 2. In some embodiments, the first ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 50, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 52, wherein the first ActRIIB polypeptide does not comprise the amino acid sequence of the second ActRIIB polypeptide. In some embodiments, the first ActRIIB polypeptide comprises an acidic amino acid position corresponding to 79 of SEQ ID NO: 2. In some embodiments, the acidic amino acid is an aspartic acid. In some embodiments, the acidic amino acid is a glutamic acid. In some embodiments, the second ActRIIB polypeptide does not comprise an acidic acid (e.g., aspartic acid or glutamic acid) at the amino acid position corresponding to 79 of SEQ ID NO: 2. In some embodiments, the second ActRIIB polypeptide comprises a leucine at the amino acid position corresponding to 79 of SEQ ID NO: 2. In some embodiments, the first ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, P129S, P130A, P130R, E37A, R40A, D54A, R56A, K74F, K74I, K74Y, W78A, D80A, D80F, D80G, D80I, D80K, D80M, D80M, D80N, D80R, and F82A.

In certain embodiments, the disclosure provides for a heteromultimer protein comprising any of the ActRIIB polypeptides disclosed herein and a second polypeptide selected from the group consisting of: ALK1, ALK2, ALK3, ALK4, ALK5, ALK6, ALK7, ActRIIA, TGFBRII, BMPRII, and MISRII polypeptide, or functional fragments thereof. In some embodiments, the second polypeptide is an ALK1 polypeptide or a functional fragment thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 54, or functional fragments thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 54, 55, 56, 57, 60, and 61, or functional fragments thereof. In some embodiments, the second polypeptide is an ALK2 polypeptide or a functional fragment thereof. In some embodiments, the ALK2 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 64 or 65, or functional fragments thereof. In some embodiments, the ALK2 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID Nos: 64, 65, 66, 67, 70, and 71, or functional fragments thereof. In some embodiments, the second polypeptide is an ALK3 polypeptide or a functional fragment thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, or functional fragments thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, 75, 76, 77, 80, or 81, or functional fragments thereof. In some embodiments, the second polypeptide is an ALK4 polypeptide or a functional fragment thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84 or 85, or functional fragments thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84, 86, 85, 87, 88, 89, 92, and 93, or functional fragments thereof. In some embodiments, the second polypeptide is an ALK5 polypeptide or a functional fragment thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96 or 97, or functional fragments thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96, 98, 97, 99, 100, 101, 104, and 105, or functional fragments thereof. In some embodiments, the second polypeptide is an ALK6 polypeptide or a functional fragment thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108 or 110, or functional fragments thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108, 109, 110, 111, 112, 113, 116, and 117, or functional fragments thereof. In some embodiments, the second polypeptide is an ALK7 polypeptide or a functional fragment thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 121, or 122, or functional fragments thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 123, 124, 125, 121, 126, 122, 127, 128, 129, 130, 133, and 134, or functional fragments thereof. In some embodiments, the second polypeptide is an ActRIIA polypeptide or a functional fragment thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, or functional fragments thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, 138, 139, 140, 141, 144, and 145, or functional fragments thereof. In some embodiments, the second polypeptide is an TGFBRII polypeptide or a functional fragment thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 204, or functional fragments thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 161, 162, 160, 163, 164, 165, 166, 167, 172, 173, 174, and 175, or functional fragments thereof. In some embodiments, the second polypeptide is an BMPRII polypeptide or a functional fragment thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148 or 149, or functional fragments thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148, 150, 149, 151, 152, 153, 156, and 157, or functional fragments thereof. In some embodiments, the second polypeptide is an MISRII polypeptide or a functional fragment thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 181, or 182, or functional fragments thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 183, 181, 184, 182, and 185, or functional fragments thereof.

In certain aspects, heteromultimers of the disclosure bind to one or more TGF-beta superfamily ligands. In some embodiments, heteromultimers of the disclosure binds to one or more TGF-beta superfamily ligands with a $K_D$ of at least $1 \times 10^{-7}$ M. In some embodiments, the one or more TGF-beta superfamily ligands is selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, heteromultimers of the disclosure inhibits one or more TGF-beta super family ligands. In some embodiments, heteromultimers of the disclosure inhibits signaling of one or more TGF-beta super family ligands. In some embodiments, heteromultimers of the disclosure inhibits Smad signaling of one or more TGF-beta super family ligands. In some embodiments, heteromultimers of the disclosure inhibits signaling of one or more TGF-beta super family ligands in a cell-based assay. In some embodiments, heteromultimers of the disclosure inhibits one or more TGF-beta super family ligands selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, the disclosure relates to ActRIIB polypeptides, including variant ActRIIB polypeptides as well as homomultimer and heteromultimers comprising the same, that comprises one or more amino acid modifications selected from the group consisting of: a glycosylated amino acid, a PEGylated amino acid, a farnesylated amino acid, an acetylated amino acid, a biotinylated amino acid, and an amino acid conjugated to a lipid moiety. In some embodiments, ActRIIB polypeptides of the disclosure are glycosylated and has a glycosylation pattern obtainable from of the polypeptide in a CHO cell.

In certain embodiments, the disclosure provides for a heteromultimer protein comprising any of the ActRIIB polypeptides disclosed herein and a second polypeptide selected from the group consisting of: ALK1, ALK2, ALK3, ALK4, ALK5, ALK6, ALK7, ActRIIA, TGFBRII, BMPRII, and MISRII polypeptide, or functional fragments thereof. In some embodiments, the second polypeptide is an ALK1 polypeptide or a functional fragment thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 54, or functional fragments thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 54, 55, 56, 57, 58, 59, 60, 61, 62, and 63, or functional fragments thereof. In some embodiments, the second polypeptide is an ALK2 polypeptide or a functional fragment thereof. In some embodiments, the ALK2 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 64 or 65, or functional fragments thereof. In some embodiments, the ALK2 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID Nos: 64, 65, 66, 67, 68, 69, 70, 71, 72, and 73, or functional fragments thereof. In some embodiments, the second polypeptide is an ALK3 polypeptide or a functional fragment thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, or functional fragments thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, 75, 76, 77, 80, or 81, or functional fragments thereof. In some embodiments, the second polypeptide is an ALK4 polypeptide or a functional fragment thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84 or 85, or functional fragments thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84, 86, 85, 87, 88, 89, 90, 91, 92, 93, 94, and 95, or functional fragments thereof. In some embodiments, the second polypeptide is an ALK5 polypeptide or a functional fragment thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96 or 97, or functional fragments thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96, 98, 97, 99, 100, 101, 102, 103, 104, 105, 106, and 107, or functional fragments thereof. In some embodiments, the second polypeptide is an ALK6 polypeptide or a functional fragment thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108 or 110, or functional fragments thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108, 109, 110, 111, 112, 113, 114, 115, 116, 117, 118, and 119, or functional fragments thereof. In some embodiments, the second polypeptide is an ALK7 polypeptide or a functional fragment thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 121, or 122, or functional fragments thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 123, 124, 125, 121, 126, 122, 127, 128, 129, 130, 131, 132, 133, 134, 135, and 136, or functional fragments thereof. In some embodiments, the second polypeptide is an ActRIIA polypeptide or a functional fragment thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, or functional fragments thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, 138, 139, 140, 141, 142, 143, 144, 145, 146, and 147, or functional fragments thereof. In some embodiments, the second polypeptide is an TGFBRII polypeptide or a functional fragment thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 204, or functional fragments thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 161, 162, 160, 163, 164, 165, 166, 167, 168, 169, 170, 171, 172, 173, 174, 175, 176, 177, 178, and 179, or functional fragments thereof. In some embodiments, the second polypeptide is an BMPRII polypeptide or a functional fragment thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148 or 149, or functional fragments thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148, 150, 149, 151, 152, 153, 154, 155, 156, 157, 158, and 159, or functional fragments thereof. In some embodiments, the second polypeptide is an MISRII polypeptide or a functional fragment thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 181, or 182, or functional fragments thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 183, 181, 184, 182, 185, 186, 187, 188, 189, 190, 191, 192, and 193, or functional fragments thereof.

In certain aspects, the disclosure relates to pharmaceutical preparations comprising a ActRIIB polypeptide, including variant ActRIIB polypeptides as well as homomultimer and heteromultimers comprising the same, a pharmaceutically acceptable carrier. In some embodiments, pharmaceutical preparations comprising one or more ActRIIB heteromultimers comprises less than about 10%, 9%, 8%, 7%, 6%, 5%, 4%, 3%, 2%, or less than about 1% homomultimers.

In certain aspects, the disclosure relates to isolated and/or recombinant nucleic acids comprising a coding sequence for one or more of the ActRIIB polypeptide(s) as described herein. For example, in some embodiments, the disclosure relates to an isolated and/or recombinant nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47. In some embodiments, an isolated and/or recombinant polynucleotide sequence of the disclosure comprises a promoter sequence operably linked to a coding sequence described herein (e.g., a nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47). In some embodiments, the disclosure relates to vectors comprising an isolated and/or recombinant nucleic acid described herein (e.g., a nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47). In some embodiments, the disclosure relates to a cell comprising an isolated and/or recombinant polynucleotide sequence described herein (e.g., a nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47). In some embodiments, the cell is a CHO cell. In some embodiments, the cell is a COS cell.

In certain aspects, the disclosure relates to methods of making ActRIIB polypeptides, including variant ActRIIB polypeptides as well as homomultimer and heteromultimers comprising the same, as described herein. Such a method may include expressing any of the nucleic acids) disclosed herein in a suitable cell (e.g., a CHO cell or COS cell). Such a method may comprise: a) culturing a cell under conditions suitable for expression of the soluble ActRIIB polypeptide, wherein said cell comprise with an ActRIIB polypeptide expression construct. In some embodiments, the method further comprises recovering the expressed ActRIIB polypeptide. ActRIIB polypeptides may be recovered as crude, partially purified or highly purified fractions using any of the well-known techniques for obtaining protein from cell cultures.

In some embodiments, the disclosure relates to methods for increasing red blood cell levels or hemoglobin levels in a patient, comprising administering a patient in need thereof an ActRIIB polypeptide, including variant ActRIIB polypeptides as well as homomultimer and heteromultimers comprising the same, as described herein.

In some embodiments, the disclosure relates to methods for treating anemia or a disorder associated with anemia (e.g., those described herein) in a patient, comprising administering a patient in need thereof an ActRIIB polypeptide, including variant ActRIIB polypeptides as well as homomultimer and heteromultimers comprising the same, as described herein.

In some embodiments, the disclosure relates to methods for increasing muscle mass and/or muscle strength in a patient, comprising administering a patient in need thereof an ActRIIB polypeptide, including variant ActRIIB polypeptides as well as homomultimer and heteromultimers comprising the same, as described herein.

In some embodiments, the disclosure relate to methods for treating a muscle-related disorder in a patient, comprising administering a patient in need thereof an ActRIIB, including variant ActRIIB polypeptides as well as homomultimer and heteromultimers comprising the same, as described herein. In some embodiments, the disorder is associated with undesirably low muscle growth and/or muscle weakness. Such disorders include muscle atrophy, muscular dystrophy, amyotrophic lateral sclerosis (ALS), and a muscle wasting disorder (e.g., cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies).

In some embodiments, the disclosure relate to methods for decreasing the body fat content or reducing the rate of increase in body fat content, and for treating a disorder associated with undesirable body weight gain, such as obesity, non-insulin dependent diabetes mellitus (NIDDM), cardiovascular disease, cancer, hypertension, osteoarthritis, stroke, respiratory problems, and gall bladder disease, comprising administering a patient in need thereof an ActRIIB, including variant ActRIIB polypeptides as well as homomultimer and heteromultimers comprising the same, as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows an alignment of extracellular domains of human ActRIIA and human ActRIIB with the residues that are deduced herein to directly contact ligand (indicated by boxes) based on composite analysis of multiple ActRIIB and ActRIIA crystal structures.

FIG. 4 shows multiple sequence alignment of Fc domains from human IgG isotypes using Clustal 2.1. Hinge regions are indicated by dotted underline. Double underline indicates examples of positions engineered in IgG1 (SEQ ID NO: 13) Fc to promote asymmetric chain pairing and the corresponding positions with respect to other isotypes IgG4 (SEQ ID NO: 17), IgG2 (SEQ ID NO: 14), and IgG3 (SEQ ID NO: 15).

FIG. 5 shows the amino acid sequence of a human ActRIIB extracellular domain polypeptide (SEQ ID NO: 1) in which numbering is based on the native human ActRIIB precursor sequence (see SEQ ID NO: 2).

FIG. 6 shows the amino acid sequence of human ActRIIB precursor protein (SEQ ID NO: 2; NCBI Reference Sequence NP_001097.2). The signal peptide is underlined, the extracellular domain is in bold (also referred to as SEQ ID NO: 1), and the potential N-linked glycosylation sites are boxed.

FIG. 7 shows a nucleic acid sequence encoding a human ActRIIB(20-134) extracellular domain polypeptide.

FIG. 8 shows a nucleic acid sequence encoding human ActRIIB precursor protein. SEQ ID NO: 4 consists of nucleotides 25-1560 of NCBI Reference Sequence NM_001106.

FIG. 9 shows values for ligand binding kinetics of homodimeric Fc-fusion proteins comprising variant or unmodified ActRIIB domains, as determined by surface plasmon resonance at 37° C. Amino acid numbering is based on SEQ ID NO: 2.

FIG. 10 shows values for ligand binding kinetics of homodimeric Fc-fusion proteins comprising variant or unmodified ActRIIB domains, as determined by surface plasmon resonance at 25° C. Amino acid numbering is based on SEQ ID NO: 2.

DETAILED DESCRIPTION

1. Overview

Figure 1A:
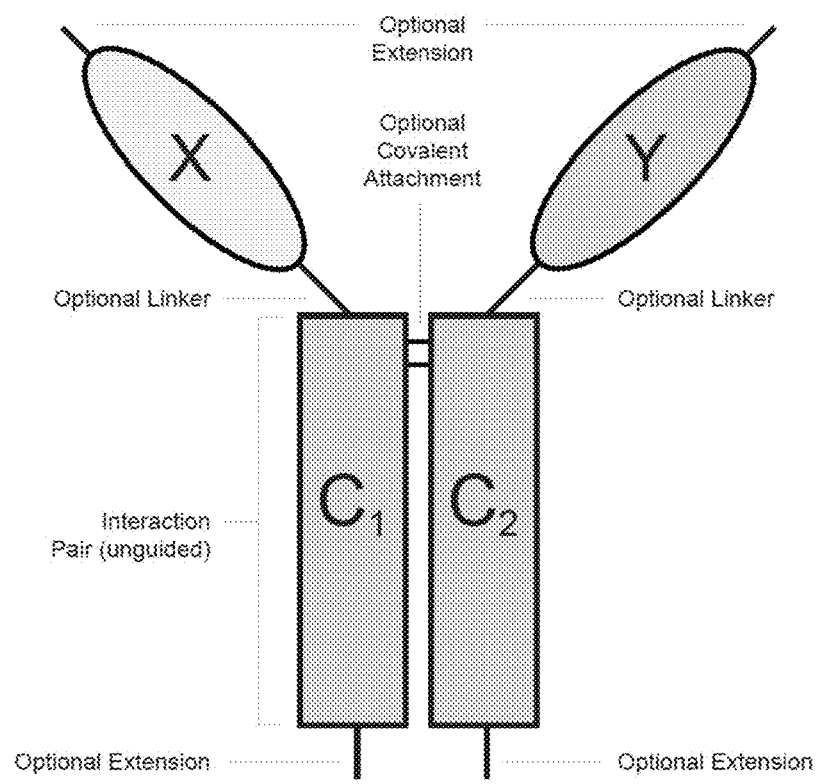
FIG. 1 shows schematic examples of heteromeric protein complexes comprising a first variant ActRIIB polypeptide (indicated as "X") and either a second variant ActRIIB polypeptide (indicated as "Y") or an unmodified ActRIIB polypeptide (indicated as "Y") In the illustrated embodiments, the first variant ActRIIB polypeptide is part of a fusion polypeptide that comprises a first member of an interaction pair ("$C_1$"), and either a second variant ActRIIB polypeptide or an unmodified ActRIIB polypeptide is part of a fusion polypeptide that comprises a second member of an interaction pair ("$C_2$"). Suitable interaction pairs include, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the first variant ActRIIB polypeptide, second variant ActRIIB polypeptide, or unmodified ActRIIB polypeptide and the corresponding member of the interaction pair. The first and second members of the interaction pair may be unguided, meaning that the members of the pair may associate with each other or self-associate without substantial preference, and they may have the same or different amino acid sequences. See FIG. 1A. Alternatively, the interaction pair may be a guided (asymmetric) pair, meaning that the members of the pair associate preferentially with each other rather than self-associate. See FIG. 1B.

In certain aspects, the present invention relates to ActRIIB polypeptides. As used herein, the term "ActRIIB" refers to a family of activin receptor type IIB (ActRIIB) proteins and ActRIIB-related proteins, derived from any species. Members of the ActRIIB family are generally all transmembrane proteins, composed of a ligand-binding extracellular domain with cysteine-rich region, a transmembrane domain, and a cytoplasmic domain with predicted serine/threonine kinase specificity. The amino acid sequence of human ActRIIB precursor protein is shown in FIG. 6 (SEQ ID NO: 2).

The term "ActRIIB polypeptide" is used to refer to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB having a sequence at least about 80% identical to the sequence of an ActRIIB polypeptide, and preferably at least 85%, 90%, 95%, 97%, 99% or greater identity.

In a specific embodiment, the invention relates to soluble ActRIIB polypeptides. As described herein, the term "soluble ActRIIB polypeptide" generally refers to polypeptides comprising an extracellular domain of an ActRIIB protein. The term "soluble ActRIIB polypeptide," as used herein, includes any naturally occurring extracellular domain of an ActRIIB protein as well as any variants thereof (including mutants, fragments and peptidomimetic forms) that retain a useful activity. For example, the extracellular domain of an ActRIIB protein binds to a ligand and is generally soluble. Examples of soluble ActRIIB polypeptides include an ActRIIB extracellular domain (SEQ ID NO: 1) shown in FIG. 5 as well as SEQ ID NO: 53. Other examples of soluble ActRIIB polypeptides comprise a signal sequence in addition to the extracellular domain of an ActRIIB protein (see Example 1). The signal sequence can be a native signal sequence of an ActRIIB, or a signal sequence from another protein, such as a tissue plasminogen activator (TPA) signal sequence or a honey bee melatin signal sequence.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are all transmembrane proteins, composed of a ligand-binding extracellular domain with cysteine-rich region, a transmembrane domain, and a cytoplasmic domain with predicted serine/threonine specificity. Type I receptors are essential for signaling, and type II receptors are required for binding ligands. Type I and type II activin receptors form a stable complex after ligand binding, resulting in phosphorylation of type I receptors by type II receptors.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). Applicants have found that soluble ActRIIA-Fc fusion proteins and ActRIIB-Fc fusion proteins have substantially different effects in vivo, with ActRIIA-Fc having primary effects on bone and ActRIIB-Fc having primary effects on skeletal muscle.

In certain embodiments, the present invention relates to antagonizing a ligand of ActRIIB receptors (also referred to as an ActRIIB ligand) with a subject ActRIIB polypeptide (e.g., a soluble ActRIIB polypeptide). Thus, compositions and methods of the present invention are useful for treating disorders associated with abnormal activity of one or more ligands of ActRIIB receptors. Exemplary ligands of ActRIIB receptors include some TGF-β family members, such as activin, Nodal, GDF8, GDF11, and BMP7.

Activins are dimeric polypeptide growth factors and belong to the TGF-beta superfamily. There are three activins (A, B, and AB) that are homo/heterodimers of two closely related β subunits ($\beta_A\beta_A$, $\beta_B\beta_B$, and $\beta_A\beta_B$). In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc SocEp Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It was suggested that activin A acts as a natural regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $\alpha_2$-macroglobulin, Cerberus, and endoglin.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as Smad proteins. Recent studies support the idea that ActRIIA and ActRIIB serve as type II receptors for Nodal (Sakuma et al., Genes Cells. 2002, 7:401-12). It is suggested that Nodal ligands interact with their co-factors (e.g., cripto) to activate activin type I and type II receptors, which phosphorylate Smad2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway Smads, Smad2 and Smad3. Further evidence has shown that the extracellular cripto protein is required for Nodal signaling, making it distinct from activin or TGF-beta signaling.

Growth and differentiation factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim. Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (1999) Dev. Biol., 208: 222-232).

Growth and differentiation factor-11 (GDF11), also known as BMP11, is a secreted protein (McPherron et al., 1999, Nat. Genet. 22: 260-264). GDF11 is expressed in the tail bud, limb bud, maxillary and mandibular arches, and dorsal root ganglia during mouse development (Nakashima et al., 1999, Mech. Dev. 80: 185-189). GDF11 plays a unique role in patterning both mesodermal and neural tissues (Gamer et al., 1999, Dev Biol., 208:222-32). GDF11 was shown to be a negative regulator of chondrogenesis and myogenesis in developing chick limb (Gamer et al., 2001, Dev Biol. 229:407-20). The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium (Wu et al., 2003, Neuron. 37:197-207). Hence, GDF11 may have in vitro and in vivo applications in the treatment of diseases such as muscle diseases and neurodegenerative diseases (e.g., amyotrophic lateral sclerosis).

Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and IIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different Smad pathways (Macias-Silva et al., 1998, J Biol Chem. 273:25628-36).

In certain aspects, the present invention relates to the use of certain ActRIIB polypeptides (e.g., soluble ActRIIB polypeptides) to antagonize the signaling of ActRIIB ligands generally, in any process associated with ActRIIB activity. Optionally, ActRIIB polypeptides of the invention may antagonize one or more ligands of ActRIIB receptors, such as activin, Nodal, GDF8, and GDF11, and may therefore be useful in the treatment of additional disorders.

Therefore, the present invention contemplates using ActRIIB polypeptides in treating or preventing diseases or conditions that are associated with abnormal activity of an ActRIIB or an ActRIIB ligand. ActRIIB or ActRIIB ligands are involved in the regulation of many critical biological processes. Due to their key functions in these processes, they may be desirable targets for therapeutic intervention. For example, ActRIIB polypeptides (e.g., soluble ActRIIB polypeptides) may be used to treat human or animal disorders or conditions. Example of such disorders or conditions include, but are not limited to, metabolic disorders such as type 2 diabetes, impaired glucose tolerance, metabolic syndrome (e.g., syndrome X), and insulin resistance induced by trauma (e.g., burns or nitrogen imbalance); adipose tissue disorders (e.g., obesity); muscle and neuromuscular disorders such as muscular dystrophy (including Duchenne muscular dystrophy); amyotrophic lateral sclerosis (ALS); muscle atrophy; organ atrophy; frailty; carpal tunnel syndrome; congestive obstructive pulmonary disease; and sarcopenia, cachexia and other muscle wasting syndromes. Other examples include osteoporosis, especially in the elderly and/or postmenopausal women; glucocorticoid-induced osteoporosis; osteopenia; osteoarthritis; and osteoporosis-related fractures. Yet further examples include low bone mass due to chronic glucocorticoid therapy, premature gonadal failure, androgen suppression, vitamin D deficiency, secondary hyperparathyroidism, nutritional deficiencies, and anorexia nervosa. These disorders and conditions are discussed below under "Exemplary Therapeutic Uses."

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including an unmodified (wild-type) sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is ±10%, Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

2. ActRIIB Polypeptides

In certain aspects, the invention relates to ActRIIB variant polypeptides (e.g., soluble ActRIIB polypeptides). Optionally, the fragments, functional variants, and modified forms have similar or the same biological activities of their corresponding wild-type ActRIIB polypeptides. For example, an ActRIIB variant of the invention may bind to and inhibit function of an ActRIIB ligand (e.g., activin A, activin AB, activin B, Nodal, GDF8, GDF11 or BMP7). Optionally, an ActRIIB polypeptide modulates growth of tissues such as bone, cartilage, muscle or fat. Examples of ActRIIB polypeptides include human ActRIIB precursor polypeptide (SEQ ID NO: 2), and soluble human ActRIIB polypeptides (e.g., SEQ ID NOs: 1, 5, 6 and 12).

The disclosure identifies functionally active portions and variants of ActRIIB. Applicants have ascertained that an Fc fusion protein having the sequence disclosed by Hilden et al. (Blood. 1994 Apr. 15; 83(8):2163-70), which has an alanine at the position corresponding to amino acid 64 of SEQ ID NO: 2 (A64), has a relatively low affinity for activin and GDF11. By contrast, the same Fc fusion protein with an arginine at position 64 (R64) has an affinity for activin and GDF-11 in the low nanomolar to high picomolar range. Therefore, a sequence with an R64 is used as the wild-type reference sequence for human ActRIIB in this disclosure.

Attisano et al. (Cell. 1992 Jan. 10; 68(1):97-108) showed that a deletion of the proline knot at the C-terminus of the extracellular domain of ActRIIB reduced the affinity of the receptor for activin. Data disclosed in WO2008097541 show that an ActRIIB-Fc fusion protein containing amino acids 20-119 of SEQ ID NO:2, "ActRIIB(20-119)-Fc" has reduced binding to GDF11 and activin relative to an ActRIIB(20-134)-Fc, which includes the proline knot region and the complete juxtamembrane domain. However, an ActRIIB(20-129)-Fc protein retains similar but somewhat reduced activity relative to the wild type, even though the proline knot region is disrupted. Thus, ActRIIB extracellular domains that stop at amino acid 134, 133, 132, 131, 130 and 129 are all expected to be active, but constructs stopping at 134 or 133 may be most active. Similarly, mutations at any of residues 129-134 are not expected to alter ligand binding affinity by large margins. In support of this, mutations of P129 and P130 do not substantially decrease ligand binding. Therefore, an ActRIIB-Fc fusion protein may end as early as amino acid 109 (the final cysteine), however, forms ending at or between 109 and 119 are expected to have reduced ligand binding. Amino acid 119 is poorly conserved and so is readily altered or truncated. Forms ending at 128 or later retain ligand binding activity. Forms ending at or between 119 and 127 will have an intermediate binding ability. Any of these forms may be desirable to use, depending on the clinical or experimental setting.

At the N-terminus of ActRIIB, it is expected that a protein beginning at amino acid 29 or before will retain ligand binding activity. Amino acid 29 represents the initial cysteine. An alanine-to-asparagine mutation at position 24 introduces an N-linked glycosylation sequence without substantially affecting ligand binding. This confirms that mutations in the region between the signal cleavage peptide and the cysteine cross-linked region, corresponding to amino acids 20-29, are well tolerated. In particular, constructs beginning at position 20, 21, 22, 23 and 24 will retain activity, and constructs beginning at positions 25, 26, 27, 28 and 29 are also expected to retain activity. Data are shown in WO2008097541 demonstrates that, surprisingly, a construct beginning at 22, 23, 24 or 25 will have the most activity.

Taken together, an active portion of ActRIIB comprises amino acids 29-109 of SEQ ID NO:2, and constructs may, for example, begin at a residue corresponding to amino acids 20-29 and end at a position corresponding to amino acids 109-134. Other examples include constructs that begin at a position from 20-29 or 21-29 and end at a position from 119-134, 119-133 or 129-134, 129-133. Other examples include constructs that begin at a position from 20-24 (or 21-24, or 22-25) and end at a position from 109-134 (or 109-133), 119-134 (or 119-133) or 129-134 (or 129-133). Variants within these ranges are also contemplated, particularly those having at least 80%, 85%, 90%, 95% or 99% identity to the corresponding portion of SEQ ID NO:4.

The disclosure includes the results of an analysis of composite ActRIIB structures, shown in FIG. 2, demonstrating that the ligand binding pocket is defined by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in Xenopus, indicating that basic amino acids at this position will be tolerated. Q53 is R in bovine ActRIIB and K in Xenopus ActRIIB, and therefore amino acids including R, K, Q, N and H will be tolerated at this position. Thus, a general formula for an active ActRIIB variant protein is one that comprises amino acids 29-109, but optionally beginning at a position ranging from 20-24 or 22-25 and ending at a position ranging from 129-134, and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may retain greater than 80%, 90%, 95% or 99% sequence identity to the sequence of amino acids 29-109 of SEQ ID NO: 2. Sites outside the binding pocket, at which variability may be particularly well tolerated, include the amino and carboxy termini of the extracellular domain (as noted above), and positions 42-46 and 65-73. An asparagine-to-alanine alteration at position 65 (N65A) actually improves ligand binding in the A64 background and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue such as H may be tolerated at position 64.

Figure 3:
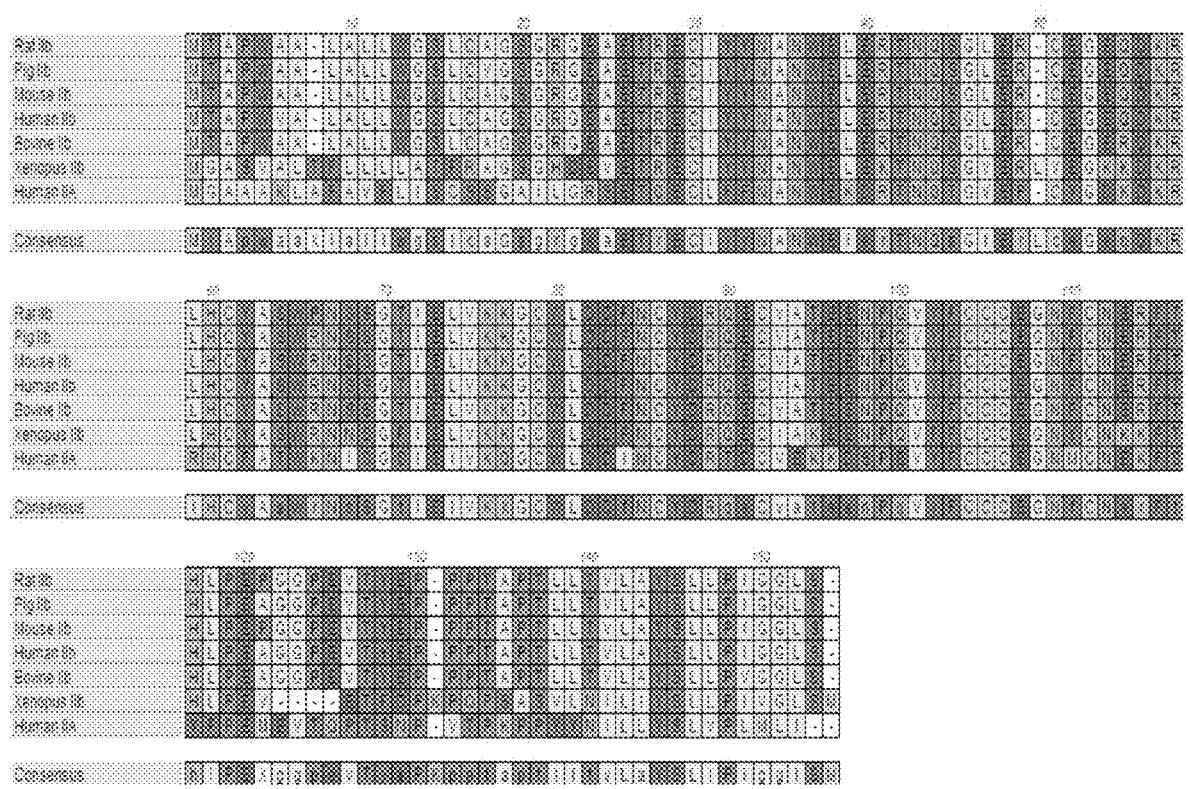
FIG. 3 shows a multiple sequence alignment of various vertebrate ActRIIB precursor proteins without their intracellular domains, human ActRIIA precursor protein without its intracellular domain, and a consensus ActRII precursor protein.

ActRIIB is well-conserved across nearly all vertebrates, with large stretches of the extracellular domain conserved completely. See FIG. 3. Many of the ligands that bind to ActRIIB are also highly conserverd. Accordingly, comparisons of ActRIIB sequences from various vertebrate organisms provide insights into residues that may be altered. Therefore, an active, human ActRIIB variant may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in Xenopus ActRIIB, and so this position may be altered, and optionally may be altered to another hydrophobic residue, such as V, I or F, or a non-polar residue such as A. E52 is a K in Xenopus, indicating that this site may be tolerant of a wide variety of changes, including polar residues, such as E, D, K, R, H, S, T, P, G, Y and probably A. T93 is a K in Xenopus, indicating that a wide structural variation is tolerated at this position, with polar residues favored, such as S, K, R, E, D, H, G, P, G and Y. F108 is a Y in Xenopus, and therefore Y or other hydrophobic group, such as I, V or L should be tolerated. E111 is K in Xenopus, indicating that charged residues will be tolerated at this position, including D, R, K and H, as well as Q and N. R112 is K in Xenopus, indicating that basic residues are tolerated at this position, including R and H. A at position 119 is relatively poorly conserved, and appears as P in rodents and V in Xenopus, thus essentially any amino acid should be tolerated at this position.

Data disclosed in WO2008097541 demonstrate that the addition of a further N-linked glycosylation site (N-X-S/T) does not affect the activity of an ActRIIB-Fc fusion protein, relative to the ActRIIB(R64)-Fc form. Other NX(T/S) sequences are found at 42-44 (NQS) and 65-67 (NSS), although the latter may not be efficiently glycosylated with the R at position 64. N-X-S/T sequences may be generally introduced at positions outside the ligand binding pocket defined in FIG. 2. Particularly suitable sites for the introduction of non-endogenous N-X-S/T sequences include amino acids 20-29, 20-24, 22-25, 109-134, 120-134 or 129-134. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T. Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are contemplated. Likewise, in an A24N variant, an S26T alteration may be used. Accordingly, an ActRIIB variant may include one or more additional, non-endogenous N-linked glycosylation consensus sequences.

Position L79 may be altered to confer altered activin-myostatin (GDF-11) binding properties. L79A or L79P reduces GDF-11 binding to a greater extent than activin binding. L79E or L79D retains GDF-11 binding. Remarkably, the L79E and L79D variants have greatly reduced activin binding. In vivo experiments indicate that these non-activin receptors retain significant ability to increase muscle mass but show decreased effects on other tissues. These data demonstrate the desirability and feasibility for obtaining polypeptides with reduced effects on activin.

The variations described may be combined in various ways. Additionally, the results of mutagenesis program described herein indicate that there are amino acid positions in ActRIIB that are often beneficial to conserve. These include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, in each of the variants disclosed herein, the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K).

In certain embodiments, isolated fragments of the ActRIIB polypeptides can be obtained by screening polypeptides recombinantly produced from the corresponding fragment of the nucleic acid encoding an ActRIIB polypeptide (e.g., SEQ ID NOs: 3 and 4). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of an ActRIIB protein or an ActRIIB ligand.

In certain embodiments, a functional variant of the ActRIIB polypeptides has an amino acid sequence that is at least 75% identical to an amino acid sequence selected from SEQ ID NOs: 1, 2, and 53. In certain cases, the functional variant has an amino acid sequence at least 80%, 85%, 90%, 95%, 97%, 98%, 99% or 100% identical to an amino acid sequence selected from SEQ ID NOs: 1, 2, and 53.

In certain embodiments, the present invention contemplates making functional variants by modifying the structure of an ActRIIB polypeptide for such purposes as enhancing therapeutic efficacy, or stability (e.g., ex vivo shelf life and resistance to proteolytic degradation in vivo). Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wild-type ActRIIB polypeptide, or to bind to one or more ligands, such as activin, GDF11, or GDF8, in a fashion similar to wild type.

In certain specific embodiments, the present invention contemplates making mutations in the extracellular domain (also referred to as ligand-binding domain) of an ActRIIB polypeptide such that the variant (or mutant) ActRIIB polypeptide has altered ligand-binding activities (e.g., binding affinity or binding selectivity). In certain cases, such variant ActRIIB polypeptides have altered (elevated or reduced) binding affinity for a specific ligand. In other cases, the variant ActRIIB polypeptides have altered binding selectivity for their ligands.

In certain embodiments, the present invention contemplates specific mutations of the ActRIIB polypeptides so as to alter the glycosylation of the polypeptide. Exemplary glycosylation sites in ActRIIB polypeptides are illustrated in FIG. 6 Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (0 the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of an ActRIIB polypeptide, including, optionally, truncation variants; pools of combinatorial mutants are especially useful for identifying functional variant sequences. The purpose of screening such combinatorial libraries may be to generate, for example, ActRIIB polypeptide variants which have altered properties, such as altered pharmacokinetics, or altered ligand binding. A variety of screening assays are provided below, and such assays may be used to evaluate variants. For example, an ActRIIB polypeptide variant may be screened for ability to bind to an ActRIIB polypeptide, to prevent binding of an ActRIIB ligand to an ActRIIB polypeptide.

The activity of an ActRIIB polypeptide or its variants may also be tested in a cell-based or in vivo assay. For example, the effect of an ActRIIB polypeptide variant on the expression of genes involved in bone production in an osteoblast or precursor may be assessed. This may, as needed, be performed in the presence of one or more recombinant ActRIIB ligand protein (e.g., BMP7), and cells may be transfected so as to produce an ActRIIB polypeptide and/or variants thereof, and optionally, an ActRIIB ligand. Likewise, an ActRIIB polypeptide may be administered to a mouse or other animal, and one or more bone properties, such as density or volume may be assessed. The healing rate for bone fractures may also be evaluated. Similarly, the activity of an ActRIIB polypeptide or its variants may be tested in muscle cells, adipocytes, and neuronal cells for any effect on growth of these cells, for example, by the assays as described below. Such assays are well known and routine in the art. A SMAD-responsive reporter gene may be used in such cell lines to monitor effects on downstream signaling.

Combinatorially-derived variants can be generated which have a selective potency relative to a naturally occurring ActRIIB polypeptide. Such variant proteins, when expressed from recombinant DNA constructs, can be used in gene therapy protocols. Likewise, mutagenesis can give rise to variants which have intracellular half-lives dramatically different than the corresponding a wild-type ActRIIB polypeptide. For example, the altered protein can be rendered either more stable or less stable to proteolytic degradation or other processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and, when part of an inducible expression system, can allow tighter control of recombinant ActRIIB polypeptide levels within the cell.

In certain embodiments, the ActRIIB polypeptides of the invention may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or mono-saccharide, and phosphates. Effects of such non-amino acid elements on the functionality of a ActRIIB polypeptide may be tested as described herein for other ActRIIB polypeptide variants. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing)

domains and functional domains (that confer an additional biological function, such as further stimulation of muscle growth).

Figure 1B:
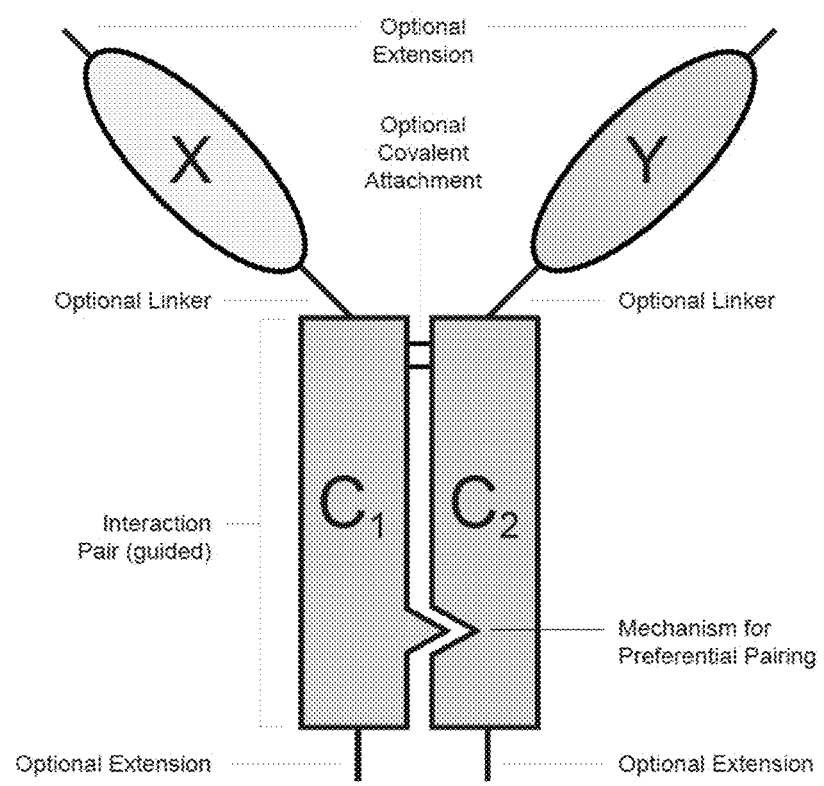

In certain aspects the polypeptides disclosed herein may form homomeric variant ActRIIB polypeptides, meaning that each fusion polypeptide chain in the protein complex comprises the same ActRIIB variant as any other such chain in the complex. In certain aspects, the polypeptides disclosed herein may form heteromultimers comprising at least one variant ActRIIB polypeptide associated, covalently or non-covalently, with at least one unmodified ActRIIB polypeptide or at least one variant ActRIIB polypeptide different from the first ActRIIB variant. In certain aspects, the polypeptides disclosed herein may form heteromultimers comprising at least one variant ActRIIB polypeptide associated, covalently or non-covalently, with at least one TGF-beta superfamily type I serine/threonine kinase receptor polypeptide (e.g., an ALK1, ALK2, ALK3, ALK4, ALK5, ALK6, and ALK7 polypeptide), including fragments and variants thereof. In certain aspects, the polypeptides disclosed herein may form heteromultimers comprising at least one variant ActRIIB polypeptide associated, covalently or non-covalently, with at least one TGF-beta superfamily type II serine/threonine kinase receptor polypeptide (e.g., ActRIIA, TGFBRII, BMPRII, and MISRII), including fragments and variants thereof. Preferably, heteromeric polypeptides disclosed herein form heterodimers, although higher order heteromultimers are also included such as, but not limited to, heterotrimers, heterotetramers, and further oligomeric structures. In some embodiments, variant ActRIIB polypeptides of the present disclosure comprise at least one multimerization domain. As disclosed herein, the term "multimerization domain" refers to an amino acid or sequence of amino acids that promote covalent or non-covalent interaction between at least a first polypeptide and at least a second polypeptide. Variant ActRIIB polypeptides disclosed herein may be joined covalently or non-covalently to a multimerization domain. Preferably, a multimerization domain promotes interaction between a first polypeptide (e.g., variant ActRIIB polypeptide) and a second polypeptide (e.g., an unmodified ActRIIB polypeptide or a variant ActRIIB polypeptide different from that present in the first polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIG. 1).

In certain embodiments, the disclosure relates to a heteromultimer comprising at least one ALK1-Fc fusion protein and at least one ActRIIB-Fc fusion protein. In some embodiments, an ALK1-Fc:ActRIIB-Fc heteromultimers binds to one or more TGF-beta superfamily ligands such as those described herein. In some embodiments, an ALK1-Fc:ActRIIB-Fc heteromultimers inhibit signaling of one or more TGF-beta superfamily ligands such as those described herein. In some embodiments, an ALK1-Fc:ActRIIB-Fc heteromultimers is a heterodimer.

In certain embodiments, the disclosure relates to a heteromultimer comprising at least one ALK2-Fc fusion protein and at least one ActRIIB-Fc fusion protein. In some embodiments, an ALK2-Fc:ActRIIB-Fc heteromultimers binds to one or more TGF-beta superfamily ligands such as those described herein. In some embodiments, an ALK2-Fc:ActRIIB-Fc heteromultimers inhibit signaling of one or more TGF-beta superfamily ligands such as those described herein. In some embodiments, an ALK2-Fc:ActRIIB-Fc heteromultimers is a heterodimer.

In certain embodiments, the disclosure relates to a heteromultimer comprising at least one ALK3-Fc fusion protein and at least one ActRIIB-Fc fusion protein. In some embodiments, an ALK3-Fc:ActRIIB-Fc heteromultimers binds to one or more TGF-beta superfamily ligands such as those described herein. In some embodiments, an ALK3-Fc:ActRIIB-Fc heteromultimers inhibit signaling of one or more TGF-beta superfamily ligands such as those described herein. In some embodiments, an ALK3-Fc:ActRIIB-Fc heteromultimers is a heterodimer.

In certain embodiments, the disclosure relates to a heteromultimer comprising at least one ALK4-Fc fusion protein and at least one ActRIIB-Fc fusion protein. In some embodiments, an ALK4-Fc:ActRIIB-Fc heteromultimers binds to one or more TGF-beta superfamily ligands such as those described herein. In some embodiments, an ALK4-Fc:ActRIIB-Fc heteromultimers inhibit signaling of one or more TGF-beta superfamily ligands such as those described herein. In some embodiments, an ALK4-Fc:ActRIIB-Fc heteromultimers is a heterodimer.

In certain embodiments, the disclosure relates to a heteromultimer comprising at least one ALK5-Fc fusion protein and at least one ActRIIB-Fc fusion protein. In some embodiments, an ALK5-Fc:ActRIIB-Fc heteromultimers binds to one or more TGF-beta superfamily ligands such as those described herein. In some embodiments, an ALK5-Fc:ActRIIB-Fc heteromultimers inhibit signaling of one or more TGF-beta superfamily ligands such as those described herein. In some embodiments, an ALK5-Fc:ActRIIB-Fc heteromultimers is a heterodimer.

In certain embodiments, the disclosure relates to a heteromultimer comprising at least one ALK6-Fc fusion protein and at least one ActRIIB-Fc fusion protein. In some embodiments, an ALK6-Fc:ActRIIB-Fc heteromultimers binds to one or more TGF-beta superfamily ligands such as those described herein. In some embodiments, an ALK6-Fc:ActRIIB-Fc heteromultimers inhibit signaling of one or more TGF-beta superfamily ligands such as those described herein. In some embodiments, an ALK6-Fc:ActRIIB-Fc heteromultimers is a heterodimer.

In certain embodiments, the disclosure relates to a heteromultimer comprising at least one ALK7-Fc fusion protein and at least one ActRIIB-Fc fusion protein. In some embodiments, an ALK7-Fc:ActRIIB-Fc heteromultimers binds to one or more TGF-beta superfamily ligands such as those described herein. In some embodiments, an ALK7-Fc:ActRIIB-Fc heteromultimers inhibit signaling of one or more TGF-beta superfamily ligands such as those described herein. In some embodiments, an ALK7-Fc:ActRIIB-Fc heteromultimers is a heterodimer.

In certain embodiments, the disclosure relates to a heteromultimer comprising at least one ActRIIB-Fc fusion protein and at least one ActRIIA-Fc fusion protein. In some embodiments, an ActRIIB-Fc:ActRIIA-Fc heteromultimers binds to one or more TGF-beta superfamily ligands such as those described herein. In some embodiments, an ActRIIB-Fc:ActRIIA-Fc heteromultimers inhibit signaling of one or more TGF-beta superfamily ligands such as those described herein. In some embodiments, an ActRIIB-Fc:ActRIIA-Fc heteromultimers is a heterodimer.

In certain embodiments, the disclosure relates to a heteromultimer comprising at least one ActRIIB-Fc fusion protein and at least one BMPRII-Fc fusion protein. In some embodiments, an ActRIIB-Fc:BMPRII-Fc heteromultimers binds to one or more TGF-beta superfamily ligands such as those described herein. In some embodiments, an ActRIIB-Fc:BMPRII-Fc heteromultimers inhibit signaling of one or more TGF-beta superfamily ligands such as those described herein. In some embodiments, an ActRIIB-Fc:BMPRII-Fc heteromultimers is a heterodimer.

In certain embodiments, the disclosure relates to a heteromultimer comprising at least one ActRIIB-Fc fusion protein and at least one TGFBRII-Fc fusion protein. In some embodiments, an ActRIIB-Fc:TGFBRII-Fc heteromultimers binds to one or more TGF-beta superfamily ligands such as those described herein. In some embodiments, an ActRIIB-Fc:TGFBRII-Fc heteromultimers inhibit signaling of one or more TGF-beta superfamily ligands such as those described herein. In some embodiments, an ActRIIB-Fc:TGFBRII-Fc heteromultimers is a heterodimer.

In certain embodiments, the disclosure relates to a heteromultimer comprising at least one ActRIIB-Fc fusion protein and at least one MISRII-Fc fusion protein. In some embodiments, an ActRIIB-Fc:MISRII-Fc heteromultimers binds to one or more TGF-beta superfamily ligands such as those described herein. In some embodiments, an ActRIIB-Fc:MISRII-Fc heteromultimers inhibit signaling of one or more TGF-beta superfamily ligands such as those described herein. In some embodiments, an ActRIIB-Fc:MISRII-Fc heteromultimers is a heterodimer.

In certain aspects, the disclosure relates to a heteromultimer that comprises an ALK1-Fc fusion protein. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids of 22-34 (e.g., amino acid residues 22, 23, 24, 25, 26, 27, 28, 29, 30, 31, 32, 33, and 34) SEQ ID NO: 54, ends at any one of amino acids 95-118 (e.g., amino acid residues 95, 96, 97, 98, 99, 100, 101, 102, 103, 104, 105, 106, 107, 108, 109, 110, 111, 112, 113, 114, 115, 116, 117, and 118) of SEQ ID NO: 54. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 22-118 of SEQ ID NO: 54. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-95 of SEQ ID NO: 54. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 54, 55, 56, 57, 58, 59, 60, 61, 62, and 63.

A representative ALK1-Fc fusion polypeptide (SEQ ID NO: 60) is as follows:

```
                                                    (SEQ ID NO: 60)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVCTLPPSR EEMTKNQVSL SCAVKGFYPS DIAVEWESNG QPENNYKTTP

301 PVLDSDGSFF LVSKLTVDKS RWQQGNVFSC SVMHEALHNH YTQKSLSLSP

351 GK
```

The leader sequence and linker sequence are underlined.
The mature ALK1-Fc fusion protein sequence (SEQ ID NO: 61) is as follows and may optionally be provided with the lysine removed from the C-terminus.

```
                                                    (SEQ ID NO: 61)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVC TLPPSREEMT KNQVSLSCAV

251 KGFYPSDIAV EWESNGQPEN NYKTTPPVLD SDGSFFLVSK LTVDKSRWQQ

301 GNVFSCSVMH EALHNHYTQK SLSLSPGK
```

In some embodiments, the ALK1-Fc fusion polypeptide (SEQ ID NO: 56) is as follows:

(SEQ ID NO: 56)
```
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR EEMTKNQVSL TCLVKGFYPS DIAVEWESNG QPENNYDTTP

301 PVLDSDGSFF LYSDLTVDKS RWQQGNVFSC SVMHEALHNH YTQKSLSLSP

351 G
```

The leader sequence and linker sequence are underlined. To guide heterodimer formation with certain Fc fusion polypeptides disclosed herein, two amino acid substitutions (replacing lysines with aspartic acids) can be introduced into the Fc domain of the ALK1-Fc fusion polypeptide as indicated by double underline above. The amino acid sequence of SEQ ID NO: 56 may optionally be provided with a lysine added at the C-terminus.

This ALK1-Fc fusion protein is encoded by the following nucleic acid (SEQ ID NO: 258):

(SEQ ID NO: 258)
```
   1 ATGGATGCAA TGAAGAGAGG GCTCTGCTGT GTGCTGCTGC TGTGTGGAGC

51 AGTCTTCGTT TCGCCCGGCG CCGACCCTGT GAAGCCGTCT CGGGGCCCGC

101 TGGTGACCTG CACGTGTGAG AGCCCACATT GCAAGGGGCC TACCTGCCGG

151 GGGGCCTGGT GCACAGTAGT GCTGGTGCGG GAGGAGGGGA GGCACCCCCA

201 GGAACATCGG GGCTGCGGGA ACTTGCACAG GGAGCTCTGC AGGGGCCGCC

251 CCACCGAGTT CGTCAACCAC TACTGCTGCG ACAGCCACCT CTGCAACCAC

301 AACGTGTCCC TGGTGCTGGA GGCCACCCAA CCTCCTTCGG AGCAGCCGGG

351 AACAGATGGC CAGCTGGCCA CCGGTGGTGG AACTCACACA TGCCCACCGT

401 GCCCAGCACC TGAACTCCTG GGGGGACCGT CAGTCTTCCT CTTCCCCCCA

451 AAACCCAAGG ACACCCTCAT GATCTCCCGG ACCCCTGAGG TCACATGCGT

501 GGTGGTGGAC GTGAGCCACG AAGACCCTGA GGTCAAGTTC AACTGGTACG

551 TGGACGGCGT GGAGGTGCAT AATGCCAAGA CAAAGCCGCG GGAGGAGCAG

601 TACAACAGCA CGTACCGTGT GGTCAGCGTC CTCACCGTCC TGCACCAGGA

651 CTGGCTGAAT GGCAAGGAGT ACAAGTGCAA GGTCTCCAAC AAAGCCCTCC

701 CAGCCCCCAT CGAGAAAACC ATCTCCAAAG CCAAAGGGCA GCCCCGAGAA

751 CCACAGGTGT ACACCCTGCC CCCATCCCGG GAGGAGATGA CCAAGAACCA

801 GGTCAGCCTG ACCTGCCTGG TCAAAGGCTT CTATCCCAGC GACATCGCCG

851 TGGAGTGGGA GAGCAATGGG CAGCCGGAGA ACAACTACGA CACCACGCCT

901 CCCGTGCTGG ACTCCGACGG CTCCTTCTTC CTCTATAGCG ACCTCACCGT

951 GGACAAGAGC AGGTGGCAGC AGGGGAACGT CTTCTCATGC TCCGTGATGC

1001 ATGAGGCTCT GCACAACCAC TACACGCAGA AGAGCCTCTC CCTGTCTCCG

1051 GGT
```

The mature ALK1-Fc fusion protein sequence (SEQ ID NO: 57) is as follows and may optionally be provided with a lysine added at the C-terminus.

```
                                                       (SEQ ID NO: 57)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVY TLPPSREEMT KNQVSLTCLV

251 KGFYPSDIAV EWESNGQPEN NYDTTPPVLD SDGSFFLYSD LTVDKSRWQQ

301 GNVFSCSVMH EALHNHYTQK SLSLSPG
```

In certain aspects, the present disclosure relates to protein complexes that comprise an ALK2 polypeptide. As used herein, the term "ALK2" refers to a family of activin receptor-like kinase-2 proteins from any species and variants derived from such ALK2 proteins by mutagenesis or other modification. Reference to ALK2 herein is understood to be a reference to any one of the currently identified forms. Members of the ALK2 family are generally transmembrane proteins, composed of a ligand-binding extracellular domain with a cysteine-rich region, a transmembrane domain, and a cytoplasmic domain with predicted serine/threonine kinase activity.

The term "ALK2 polypeptide" includes polypeptides comprising any naturally occurring polypeptide of an ALK2 family member as well as any variants thereof (including mutants, fragments, fusions, and peptidomimetic forms) that retain a useful activity.

A human ALK2 precursor protein sequence (NCBI Ref Seq NP_001096.1) is as follows:

A nucleic acid sequence encoding human ALK2 precursor protein is shown in SEQ ID NO: 217, corresponding to nucleotides 431-1957 of Genbank Reference Sequence NM_001105.4. A nucleic acid sequence encoding the extracellular ALK2 polypeptide is as in SEQ ID NO: 218.

In certain embodiments, the disclosure relates to heteromultimers that comprise at least one ALK2 polypeptide, which includes fragments, functional variants, and modified forms thereof. Preferably, ALK2 polypeptides for use in accordance with inventions of the disclosure (e.g., heteromultimers comprising an ALK2 polypeptide and uses thereof) are soluble (e.g., an extracellular domain of ALK2). In other preferred embodiments, ALK2 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK2 polypeptide that is at least 70%, 75%, 80%, 85%, 90%, 95%, 97%, 98%, 99%, or 100% identical to the amino acid sequence of SEQ

```
                                                       (SEQ ID NO: 64)
  1 MVDGVMILPV LIMIALPSPS MEDEKPKVNP KLYMCVCEGL SCGNEDHCEG

51 QQCFSSLSIN DGFHVYQKGC FQVYEQGKMT CKTPPSPGQA VECCQGDWCN

101 RNITAQLPTK GKSFPGTQNF HLEVGLIILS VVFAVCLLAC LLGVALRKFK

151 RRNQERLNPR DVEYGTIEGL ITTNVGDSTL ADLLDHSCTS GSGSGLPFLV

201 QRTVARQITL LECVGKGRYG EVWRGSWQGE NVAVKIFSSR DEKSWFRETE

251 LYNTVMLRHE NILGFIASDM TSRHSSTQLW LITHYHEMGS LYDYLQLTTL

301 DTVSCLRIVL SIASGLAHLH IEIFGTQGKP AIAHRDLKSK NILVKKNGQC

351 CIADLGLAVM HSQSTNQLDV GNNPRVGTKR YMAPEVLDET IQVDCFDSYK

401 RVDIWAFGLV LWEVARRMVS NGIVEDYKPP FYDVVPNDPS FEDMRKVVCV

451 DQQRPNIPNR WFSDPTLTSL AKLMKECWYQ NPSARLTALR IKKTLTKIDN

501 SLDKLKTDC
```

The signal peptide is indicated by a single underline and the extracellular domain is indicated in bold font.

A processed extracellular ALK2 polypeptide sequence is as follows:

```
                                                       (SEQ ID NO: 65)
MEDEKPKVNPKLYMCVCEGLSCGNEDHCEGQQCFSSLSINDGFHVYQKGC

FQVYEQGKMTCKTPPSPGQAVECCQGDWCNRNITAQLPTKGKSFPGTQNF

HLE
```

ID NO: 64 or 65. In some embodiments, heteromultimer complexes of the disclosure consist or consist essentially of at least one ALK2 polypeptide that is at least 70%, 75%, 80%, 85%, 90%, 95%, 97%, 98%, 99%, or 100% identical to the amino acid sequence of SEQ ID NO: 64 or 65.

In certain aspects, the disclosure relates to a heteromultimer that comprises an ALK2-Fc fusion protein. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-35 (e.g., amino acid residues 21, 22, 23, 24, 25, 26, 27, 28, 29, 30, 31, 32, 33, 34, and 35) SEQ ID NO: 64, and ends at any one of amino acids 99-123 (e.g., amino acid residues 99, 100, 101, 102, 103, 104, 105, 106, 107, 108, 109, 110, 111, 112, 113, 114, 115, 116, 117, 118, 119, 120, 121, 122, and 123) of SEQ ID NO: 64. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 35-99 of SEQ ID NO: 64. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-123 of SEQ ID NO: 64. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID Nos: 64, 65, 66, 67, 68, 69, 70, 71, 72, and 73.

In some embodiments, the ALK2-Fc fusion protein employs the TPA leader and is as follows (SEQ ID NO: 66):

```
                                                          (SEQ ID NO: 66)
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The signal sequence and linker sequence are underlined. To promote formation of the a heterodimer with certain other Fc fusions disclosed herein, two amino acid substitutions (replacing lysines with aspartic acids) can be introduced into the Fc domain of the fusion protein as indicated by double underline above. The amino acid sequence of SEQ ID NO: 66 may optionally be provided with a lysine added at the C-terminus.

This ALK2-Fc fusion protein is encoded by the following nucleic acid (SEQ ID NO: 244):

```
                                                         (SEQ ID NO: 244)
  1 ATGGATGCAA TGAAGAGAGG GCTCTGCTGT GTGCTGCTGC TGTGTGGAGC

51 AGTCTTCGTT TCGCCCGGCG CCATGGAAGA TGAGAAGCCC AAGGTCAACC

101 CCAAACTCTA CATGTGTGTG TGTGAAGGTC TCTCCTGCGG TAATGAGGAC

151 CACTGTGAAG GCCAGCAGTG CTTTTCCTCA CTGAGCATCA ACGATGGCTT

201 CCACGTCTAC CAGAAAGGCT GCTTCCAGGT TTATGAGCAG GGAAAGATGA

251 CCTGTAAGAC CCCGCCGTCC CCTGGCCAAG CTGTGGAGTG CTGCCAAGGG

301 GACTGGTGTA ACAGGAACAT CACGGCCCAG CTGCCCACTA AAGGAAAATC

351 CTTCCCTGGA ACACAGAATT TCCACTTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTACACCCTG CCCCCATCCC GGGAGGAGAT
```

```
 801  GACCAAGAAC CAGGTCAGCC TGACCTGCCT GGTCAAAGGC TTCTATCCCA

851  GCGACATCGC CGTGGAGTGG GAGAGCAATG GGCAGCCGGA GAACAACTAC

901  GACACCACGC CTCCCGTGCT GGACTCCGAC GGCTCCTTCT TCCTCTATAG

951  CGACCTCACC GTGGACAAGA GCAGGTGGCA GCAGGGGAAC GTCTTCTCAT

1001  GCTCCGTGAT GCATGAGGCT CTGCACAACC ACTACACGCA GAAGAGCCTC

1051  TCCCTGTCTC CGGGT
```

The mature ALK2-Fc fusion protein sequence (SEQ ID NO: 67) is as follows and may optionally be provided with a lysine added at the C-terminus.

```
                                               (SEQ ID NO: 67)
  1  MEDEKPKVNP KLYMCVCEGL SCGNEDHCEG QQCFSSLSIN DGFHVYQKGC

51  FQVYEQGKMT CKTPPSPGQA VECCQGDWCN RNITAQLPTK GKSFPGTQNF

101  HLETGGGTHT CPPCPAPELL GGPSVFLFPP KPKDTLMISR TPEVTCVVVD

151  VSHEDPEVKF NWYVDGVEVH NAKTKPREEQ YNSTYRVVSV LTVLHQDWLN

201  GKEYKCKVSN KALPAPIEKT ISKAKGQPRE PQVYTLPPSR EEMTKNQVSL

251  TCLVKGFYPS DIAVEWESNG QPENNYDTTP PVLDSDGSFF LYSDLTVDKS

301  RWQQGNVFSC SVMHEALHNH YTQKSLSLSP G
```

In another approach to promoting the formation of heteromultimer complexes using asymmetric Fc fusion proteins, the Fc domains are altered to introduce complementary hydrophobic interactions and an additional intermolecular disulfide bond.

In some embodiments, the ALK2-Fc fusion polypeptide (SEQ ID NO: 70) is as follows:

```
                                               (SEQ ID NO: 70)
  1  MDAMKRGLCC VLLLCGAVFV SPGAMEDEKP KVNPKLYMCV CEGLSCGNED

51  HCEGQQCFSS LSINDGFHVY QKGCFQVYEQ GKMTCKTPPS PGQAVECCQG

101  DWCNRNITAQ LPTKGKSFPG TQNFHLETGG GTHTCPPCPA PELLGGPSVF

151  LFPPKPKDTL MISRTPEVTC VVVDVSHEDP EVKFNWYVDG VEVHNAKTKP

201  REEQYNSTYR VVSVLTVLHQ DWLNGKEYKC KVSNKALPAP IEKTISKAKG

251  QPREPQVCTL PPSREEMTKN QVSLSCAVKG FYPSDIAVEW ESNGQPENNY

301  KTTPPVLDSD GSFFLVSKLT VDKSRWQQGN VFSCSVMHEA LHNHYTQKSL

351  SLSPGK
```

The leader sequence and linker sequence are underlined. To guide heterodimer formation with certain Fc fusion polypeptides disclosed herein, four amino acid substitutions can be introduced into the Fc domain of the ALK2 fusion polypeptide as indicated by double underline above. Furthermore, the C-terminal lysine residue of the Fc domain can be deleted. The amino acid sequence of SEQ ID NO: 70 may optionally be provided with the lysine removed from the C-terminus.

The mature ALK2-Fc fusion protein sequence (SEQ ID NO: 71) is as follows and may optionally be provided with the lysine removed from the C-terminus.

```
                                               (SEQ ID NO: 71)
  1  MEDEKPKVNP KLYMCVCEGL SCGNEDHCEG QQCFSSLSIN DGFHVYQKGC

51  FQVYEQGKMT CKTPPSPGQA VECCQGDWCN RNITAQLPTK GKSFPGTQNF

101  HLETGGGTHT CPPCPAPELL GGPSVFLFPP KPKDTLMISR TPEVTCVVVD

151  VSHEDPEVKF NWYVDGVEVH NAKTKPREEQ YNSTYRVVSV LTVLHQDWLN
```

```
201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

In certain aspects, the present disclosure relates to protein complexes that comprise an ALK2 polypeptide. As used herein, the term "ALK2" refers to a family of activin receptor-like kinase-2 proteins from any species and variants derived from such ALK2 proteins by mutagenesis or other modification. Reference to ALK2 herein is understood to be a reference to any one of the currently identified forms. Members of the ALK2 family are generally transmembrane proteins, composed of a ligand-binding extracellular domain with a cysteine-rich region, a transmembrane domain, and a cytoplasmic domain with predicted serine/threonine kinase activity.

The term "ALK2 polypeptide" includes polypeptides comprising any naturally occurring polypeptide of an ALK2 family member as well as any variants thereof (including mutants, fragments, fusions, and peptidomimetic forms) that retain a useful activity.

A representative human ALK2 precursor protein sequence (NCBI Ref Seq NP_001096.1) is as follows:

forms thereof. Preferably, ALK2 polypeptides for use in accordance with inventions of the disclosure (e.g., heteromultimers comprising an ALK2 polypeptide and uses thereof) are soluble (e.g., an extracellular domain of ALK2). In other preferred embodiments, ALK2 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK2 polypeptide that is at least 70%, 75%, 80%, 85%, 90%, 95%, 97%, 98%, 99%, or 100% identical to the amino acid sequence of SEQ ID NO: 64 or 65. In some embodiments, heteromultimer complexes of the disclosure consist or consist essentially of at least one ALK2 polypeptide that is at least 70%, 75%, 80%, 85%, 90%, 95%, 97%, 98%, 99%, or 100% identical to the amino acid sequence of SEQ ID NO: 64 or 65.

In certain aspects, the present disclosure relates to protein complexes that comprise an ALK3 polypeptide. As used

```
                                                    (SEQ ID NO: 64)
  1 MVDGVMILPV LIMIALPSPS MEDEKPKVNP KLYMCVCEGL SCGNEDHCEG

51 QQCFSSLSIN DGFHVYQKGC FQVYEQGKMT CKTPPSPGQA VECCQGDWCN

101 RNITAQLPTK GKSFPGTQNF HLEVGLIILS VVFAVCLLAC LLGVALRKFK

151 RRNQERLNPR DVEYGTIEGL ITTNVGDSTL ADLLDHSCTS GSGSGLPFLV

201 QRTVARQITL LECVGKGRYG EVWRGSWQGE NVAVKIFSSR DEKSWFRETE

251 LYNTVMLRHE NILGFIASDM TSRHSSTQLW LITHYHEMGS LYDYLQLTTL

301 DTVSCLRIVL SIASGLAHLH IEIFGTQGKP AIAHRDLKSK NILVKKNGQC

351 CIADLGLAVM HSQSTNQLDV GNNPRVGTKR YMAPEVLDET IQVDCFDSYK

401 RVDIWAFGLV LWEVARRMVS NGIVEDYKPP FYDVVPNDPS FEDMRKVVCV

451 DQQRPNIPNR WFSDPTLTSL AKLMKECWYQ NPSARLTALR IKKTLTKIDN

501 SLDKLKTDC
```

The signal peptide is indicated by a single underline and the extracellular domain is indicated in bold font.

A processed extracellular ALK2 polypeptide sequence is as follows:

```
                                              (SEQ ID NO: 65)
MEDEKPKVNPKLYMCVCEGLSCGNEDHCEGQQCFSSLSINDGFHVYQKG

CFQVYEQGKMTCKTPPSPGQAVECCQGDWCNRNITAQLPTKGKSFPGTQ

NFHLE
```

A nucleic acid sequence encoding human ALK2 precursor protein is shown in SEQ ID NO: 217, corresponding to nucleotides 431-1957 of Genbank Reference Sequence NM_001105.4. A nucleic acid sequence encoding the extracellular ALK2 polypeptide is as in SEQ ID NO: 218.

In certain embodiments, the disclosure relates to heteromultimers that comprise at least one ALK2 polypeptide, which includes fragments, functional variants, and modified herein, the term "ALK3" refers to a family of activin receptor-like kinase-3 proteins from any species and variants derived from such ALK3 proteins by mutagenesis or other modification. Reference to ALK3 herein is understood to be a reference to any one of the currently identified forms. Members of the ALK3 family are generally transmembrane proteins, composed of a ligand-binding extracellular domain with a cysteine-rich region, a transmembrane domain, and a cytoplasmic domain with predicted serine/threonine kinase activity.

The term "ALK3 polypeptide" includes polypeptides comprising any naturally occurring polypeptide of an ALK3 family member as well as any variants thereof (including mutants, fragments, fusions, and peptidomimetic forms) that retain a useful activity.

A human ALK3 precursor protein sequence (NCBI Ref Seq NP_004320.2) is as follows:

```
                                                              (SEQ ID NO: 74)
  1 MPQLYIYIRL LGAYLFIISR VQGQNLDSML HGTGMKSDSD QKKSENGVTL APEDTLPFLK

61 CYCSGHCPDD AINNTCITNG HCFAIIEEDD QGETTLASGC MKYEGSDFQC KDSPKAQLRR

121 TIECCRTNLC NQYLQPTLPP VVIGPFFDGS IRWLVLLISM AVCIIAMIIF SSCFCYKHYC

181 KSISSRRRYN RDLEQDEAFI PVGESLKDLI DQSQSSGSGS GLPLLVQRTI AKQIQMVRQV

241 GKGRYGEVWM GKWRGEKVAV KVFFTTEEAS WFRETEIYQT VLMRHENILG FIAADIKGTG

301 SWTQLYLITD YHENGSLYDF LKCATLDTRA LLKLAYSAAC GLCHLHTEIY GTQGKPAIAH

361 RDLKSKNILI KKNGSCCIAD LGLAVKFNSD TNEVDVPLNT RVGTKRYMAP EVLDESLNKN

421 HFQPYIMADI YSFGLIIWEM ARRCITGGIV EEYQLPYYNM VPSDPSYEDM REVVCVKRLR

481 PIVSNRWNSD ECLRAVLKLM SECWAHNPAS RLTALRIKKT LAKMVESQDV KI
```

The signal peptide is indicated by a single underline and the extracellular domain is indicated in bold font.

A processed extracellular ALK3 polypeptide sequence is as follows:

```
                                                              (SEQ ID NO: 75)
  1 QNLDSMLHGT GMKSDSDQKK SENGVTLAPE DTLPFLKCYC SGHCPDDAIN NTCITNGHCF

61 AIIEEDDQGE TTLASGCMKY EGSDFQCKDS PKAQLRRTIE CCRTNLCNQY LQPTLPPVVI

121 GPFFDGSIR
```

A nucleic acid sequence encoding human ALK3 precursor protein is shown in SEQ ID NO: 219, corresponding to nucleotides 549-2144 of Genbank Reference Sequence NM_004329.2. The signal sequence is underlined and the extracellular domain is indicated in bold font. A nucleic acid sequence encoding the extracelluar human ALK3 polypeptide is shown in SEQ ID NO: 220.

A general formula for an active (e.g., ligand binding) ALK3 polypeptide is one that comprises a polypeptide that begins at any amino acid position 25-31 (i.e., position 25, 26, 27, 28, 29, 30, or 31) of SEQ ID NO: 74 and ends at any amino acid position 140-152 of SEQ ID NO: 74 (i.e., 140, 141, 142, 143, 144, 145, 146, 147, 148, 149, 150, 151, or 152). See U.S. Pat. No. 8,338,377, the teachings of which are incorporated herein by reference in their entirety.

In certain embodiments, the disclosure relates to heteromultimers that comprise at least one ALK3 polypeptide, which includes fragments, functional variants, and modified forms thereof. Preferably, ALK3 polypeptides for use in accordance with inventions of the disclosure (e.g., heteromultimers comprising an ALK3 polypeptide and uses thereof) are soluble (e.g., an extracellular domain of ALK3). In other preferred embodiments, ALK3 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK3 polypeptide that comprises an amino acid beginning at any amino acid position 25-31 (i.e., position 25, 26, 27, 28, 29, 30, or 31) of SEQ ID NO: 74 and ending at any amino acid position 140-153 of SEQ ID NO: 74 (i.e., 140, 141, 142, 143, 144, 145, 146, 147, 148, 149, 150, 151, or 152) of SEQ ID NO: 74. In some embodiments, heteromultimer complexes of the disclosure comprise at least one ALK3 polypeptide that is at least 70%, 75%, 80%, 85%, 90%, 95%, 97%, 98%, 99%, or 100% identical to the amino acid sequence of SEQ ID NO: 74, 75, 76, 77, 80, or 81. In some embodiments, heteromultimer complexes of the disclosure consist or consist essentially of at least one ALK3 polypeptide that is at least 70%, 75%, 80%, 85%, 90%, 95%, 97%, 98%, or 99% identical to the amino acid sequence of SEQ ID NO: 74, 75, 76, 77, 80, or 81.

In certain aspects, the disclosure relates to a heteromultimer that comprises an ALK3-Fc fusion protein. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 24-61 (e.g., amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, and 61) SEQ ID NO: 74, and ends at any one of amino acids 130-152 (e.g., amino acid residues 130, 131, 132, 133, 134, 135, 136, 137, 138, 139, 140, 141, 142, 143, 144, 145, 146, 147, 148, 149, 150, 151, and 152) of SEQ ID NO: 74. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 61-130 of SEQ ID NO: 74. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-152 of SEQ ID NO: 74. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 74, 75, 76, 77, 78, 79, 80, 81, 82, and 83.

In some embodiments, the ALK3-Fc fusion protein employs the TPA leader and is as follows:

```
                                                        (SEQ ID NO: 76)
  1 MDAMKRGLCC VLLLCGAVFV SPGAQNLDSM LHGTGMKSDS DQKKSENGVT

51 LAPEDTLPFL KCYCSGHCPD DAINNTCITN GHCFAIIEED DQGETTLASG

101 CMKYEGSDFQ CKDSPKAQLR RTIECCRTNL CNQYLQPTLP PVVIGPFFDG

151 SIRTGGGTHT CPPCPAPELL GGPSVFLFPP KPKDTLMISR TPEVTCVVVD

201 VSHEDPEVKF NWYVDGVEVH NAKTKPREEQ YNSTYRVVSV LTVLHQDWLN

251 GKEYKCKVSN KALPAPIEKT ISKAKGQPRE PQVYTLPPSR EEMTKNQVSL

301 TCLVKGFYPS DIAVEWESNG QPENNYDTTP PVLDSDGSFF LYSDLTVDKS

351 RWQQGNVFSC SVMHEALHNH YTQKSLSLSP G
```

The leader and linker sequences are underlined. To promote formation of the ActRIIB-Fc:ALK3-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 76 may optionally be provided with a lysine added at the C-terminus.

This ALK3-Fc fusion protein is encoded by the following nucleic acid (SEQ ID NO: 245).

```
                                                        (SEQ ID NO: 245)
   1 ATGGATGCAA TGAAGAGAGG GCTCTGCTGT GTGCTGCTGC TGTGTGGAGC

51 AGTCTTCGTT TCGCCCGGCG CCCAGAATCT GGATAGTATG CTTCATGGCA

101 CTGGGATGAA ATCAGACTCC GACCAGAAAA AGTCAGAAAA TGGAGTAACC

151 TTAGCACCAG AGGATACCTT GCCTTTTTTA AAGTGCTATT GCTCAGGGCA

201 CTGTCCAGAT GATGCTATTA ATAACACATG CATAACTAAT GGACATTGCT

251 TTGCCATCAT AGAAGAAGAT GACCAGGGAG AAACCACATT AGCTTCAGGG

301 TGTATGAAAT ATGAAGGATC TGATTTTCAG TGCAAAGATT CTCCAAAAGC

351 CCAGCTACGC CGGACAATAG AATGTTGTCG GACCAATTTA TGTAACCAGT

401 ATTTGCAACC CACACTGCCC CCTGTTGTCA TAGGTCCGTT TTTTGATGGC

451 AGCATTCGAA CCGGTGGTGG AACTCACACA TGCCCACCGT GCCCAGCACC

501 TGAACTCCTG GGGGGACCGT CAGTCTTCCT CTTCCCCCCA AAACCCAAGG

551 ACACCCTCAT GATCTCCCGG ACCCCTGAGG TCACATGCGT GGTGGTGGAC

601 GTGAGCCACG AAGACCCTGA GGTCAAGTTC AACTGGTACG TGGACGGCGT

651 GGAGGTGCAT AATGCCAAGA CAAAGCCGCG GGAGGAGCAG TACAACAGCA

701 CGTACCGTGT GGTCAGCGTC CTCACCGTCC TGCACCAGGA CTGGCTGAAT

751 GGCAAGGAGT ACAAGTGCAA GGTCTCCAAC AAAGCCCTCC CAGCCCCCAT

801 CGAGAAAACC ATCTCCAAAG CCAAAGGGCA GCCCCGAGAA CCACAGGTGT

851 ACACCCTGCC CCCATCCCGG GAGGAGATGA CCAAGAACCA GGTCAGCCTG

901 ACCTGCCTGG TCAAAGGCTT CTATCCCAGC GACATCGCCG TGGAGTGGGA

951 GAGCAATGGG CAGCCGGAGA ACAACTACGA CACCACGCCT CCCGTGCTGG

1001 ACTCCGACGG CTCCTTCTTC CTCTATAGCG ACCTCACCGT GGACAAGAGC

1051 AGGTGGCAGC AGGGGAACGT CTTCTCATGC TCCGTGATGC ATGAGGCTCT

1101 GCACAACCAC TACACGCAGA AGAGCCTCTC CCTGTCTCCG GGT
```

The mature ALK3-Fc fusion protein sequence is as follows (SEQ ID NO: 77) and may optionally be provided with a lysine added at the C-terminus.

```
                                                          (SEQ ID NO: 77)
  1 GAQNLDSMLH GTGMKSDSDQ KKSENGVTLA PEDTLPFLKC YCSGHCPDDA

51 INNTCITNGH CFAIIEEDDQ GETTLASGCM KYEGSDFQCK DSPKAQLRRT

101 IECCRTNLCN QYLQPTLPPV VIGPFFDGSI RTGGGTHTCP PCPAPELLGG

151 PSVFLFPPKP KDTLMISRTP EVTCVVVDVS HEDPEVKFNW YVDGVEVHNA

201 KTKPREEQYN STYRVVSVLT VLHQDWLNGK EYKCKVSNKA LPAPIEKTIS

251 KAKGQPREPQ VYTLPPSREE MTKNQVSLTC LVKGFYPSDI AVEWESNGQP

301 ENNYDTTPPV LDSDGSFFLY SDLTVDKSRW QQGNVFSCSV MHEALHNHYT

351 QKSLSLSPG
```

The complementary form of ALK3-Fc fusion polypeptide (SEQ ID NO: 80) is as follows:

```
                                                          (SEQ ID NO: 80)
  1 MDAMKRGLCC VLLLCGAVFV SPGAQNLDSM LHGTGMKSDS DQKKSENGVT

51 LAPEDTLPFL KCYCSGHCPD DAINNTCITN GHCFAIIEED DQGETTLASG

101 CMKYEGSDFQ CKDSPKAQLR RTIECCRTNL CNQYLQPTLP PVVIGPFFDG

151 SIRTGGGTHT CPPCPAPELL GGPSVFLFPP KPKDTLMISR TPEVTCVVVD

201 VSHEDPEVKF NWYVDGVEVH NAKTKPREEQ YNSTYRVVSV LTVLHQDWLN

251 GKEYKCKVSN KALPAPIEKT ISKAKGQPRE PQVCTLPPSR EEMTKNQVSL

301 SCAVKGFYPS DIAVEWESNG QPENNYKTTP PVLDSDGSFF LVSKLTVDKS

351 RWQQGNVFSC SVMHEALHNH YTQKSLSLSP GK
```

The leader sequence and linker are underlined. To guide heterodimer formation with certain Fc fusion polypeptides disclosed herein, four amino acid substitutions can be introduced into the Fc domain of the ALK3 fusion polypeptide as indicated by double underline above. The amino acid sequence of SEQ ID NO: 80 may optionally be provided with the lysine removed from the C-terminus.

The mature ALK3-Fc fusion protein sequence (SEQ ID NO: 81) is as follows and may optionally be provided with the lysine (K) removed from the C-terminus.

```
                                                          (SEQ ID NO: 81)
  1 GAQNLDSMLH GTGMKSDSDQ KKSENGVTLA PEDTLPFLKC YCSGHCPDDA

51 INNTCITNGH CFAIIEEDDQ GETTLASGCM KYEGSDFQCK DSPKAQLRRT

101 IECCRTNLCN QYLQPTLPPV VIGPFFDGSI RTGGGTHTCP PCPAPELLGG

151 PSVFLFPPKP KDTLMISRTP EVTCVVVDVS HEDPEVKFNW YVDGVEVHNA

201 KTKPREEQYN STYRVVSVLT VLHQDWLNGK EYKCKVSNKA LPAPIEKTIS

251 KAKGQPREPQ VCTLPPSREE MTKNQVSLSC AVKGFYPSDI AVEWESNGQP

301 ENNYKTTPPV LDSDGSFFLV SKLTVDKSRW QQGNVFSCSV MHEALHNHYT

351 QKSLSLSPGK
```

In certain aspects, the present disclosure relates to protein complexes that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms.

Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity.

A human ALK4 precursor protein sequence (NCBI Ref Seq NP_004293) is as follows:

(SEQ ID NO: 84)
```
  1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK DNGTWTQLWL VSDYHEHGSL FDYLNRYTVT

301 IEGMIKLALS AASGLAHLHM EIVGTQGKPG IAHRDLKSKN ILVKKNGMCA IADLGLAVRH

361 DAVTDTIDIA PNQRVGTKRY MAPEVLDETI NMKHFDSFKC ADIYALGLVY WEIARRCNSG

421 GVHEEYQLPY YDLVPSDPSI EEMRKVVCDQ KLRPNIPNWW QSYEALRVMG KMMRECWYAN

481 GAARLTALRI KKTLSQLSVQ EDVKI
```

The signal peptide is indicated by a single underline and the extracellular domain is indicated in bold font.

A processed extracellular human ALK4 polypeptide sequence is as follows:

(SEQ ID NO: 86)
```
SGPRGVQALLCACTSCLQANYTCETDGACMVSIFNLDGMEHHVRTCIPK

VELVPAGKPFYCLSSEDLRNTHCCYTDYCNRIDLRVPSGHLKEPEHPSM

WGPVE
```

A nucleic acid sequence encoding an ALK4 precursor protein is shown in SEQ ID NO: 221), corresponding to nucleotides 78-1592 of Genbank Reference Sequence NM_004302.4. A nucleic acid sequence encoding the extracellular ALK4 polypeptide is shown in SEQ ID NO: 222.

An alternative isoform of human ALK4 precursor protein sequence, isoform C (NCBI Ref Seq NP_064733.3), is as follows:

(SEQ ID NO: 85)
```
  1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK ADCSFLTLPW EVVMVSAAPK LRSLRLQYKG

301 GRGRARFLFP LNNGTWTQLW LVSDYHEHGS LFDYLNRYTV TIEGMIKLAL SAASGLAHLH

361 MEIVGTQGKP GIAHRDLKSK NILVKKNGMC AIADLGLAVR HDAVTDTIDI APNQRVGTKR

421 YMAPEVLDET INMKHFDSFK CADIYALGLV YWEIARRCNS GGVHEEYQLP YYDLVPSDPS

481 IEEMRKVVCD QKLRPNIPNW WQSYEALRVM GKMMRECWYA NGAARLTALR IKKTLSQLSV

541 QEDVKI
```

The signal peptide is indicated by a single underline and the extracellular domain is indicated in bold font.

A processed extracellular ALK4 polypeptide sequence (isoform C) is as follows:

(SEQ ID NO: 87)
```
SGPRGVQALLCACTSCLQANYTCETDGACMVSIFNLDGMEHHVRTCIPK

VELVPAGKPFYCLSSEDLRNTHCCYTDYCNRIDLRVPSGHLKEPEHPSM

WGPVE
```

A nucleic acid sequence encoding an ALK4 precursor protein (isoform C) is shown in SEQ ID NO: 223, corresponding to nucleotides 78-1715 of Genbank Reference Sequence NM_020328.3. A nucleic acid sequence encoding the extracelluar ALK4 polypeptide (isoform C) is shown in SEQ ID NO: 224.

In certain embodiments, the disclosure relates to heteromultimers that comprise at least one ALK4 polypeptide, which includes fragments, functional variants, and modified forms thereof. Preferably, ALK4 polypeptides for use in accordance with inventions of the disclosure (e.g., heteromultimers comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK4 polypeptide that is at least 70%, 75%, 80%, 85%, 90%, 95%, 97%, 98%, 99%, or 100% identical to the amino acid sequence of SEQ ID NO: 84, 86, 85, 87, 88, 89, 92, or 93. In some embodiments, heteromultimers of the disclosure consist or consist essentially of at least one ALK4 polypeptide that is at least 70%, 75%, 80%, 85%, 90%, 95%, 97%, 98%, 99%, or 100% identical to the amino acid sequence of SEQ ID NO: 84, 86, 85, 87, 88, 89, 92, or 93.

In certain aspects, the disclosure relates to a heteromultimer that comprises an ALK4-Fc fusion protein. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-34 (e.g., amino acid residues 23, 24, 25, 26, 27, 28, 29, 30, 31, 32, 33, 34) SEQ ID NO: 84 or 85, and ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, and 126) of SEQ ID NO: 84 or 85. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NOs: 84 or 85.

In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-126 of SEQ ID Nos: 84 or 85. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 84, 86, 85, 87, 88, 89, 90, 91, 92, 93, 94, and 95.

In certain embodiments, the polypeptide comprises an ALK4-Fc fusion polypeptide (SEQ ID NO: 88) as follows:

```
                                                      (SEQ ID NO: 88)
  1 AMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The leader sequence and linker sequence are underlined. To guide heterodimer formation with certain Fc fusion polypeptides of the disclosure, two amino acid substitutions (replacing lysines with aspartic acids) can be introduced into the Fc domain of the ALK4-Fc fusion polypeptide as indicated by double underline above. The amino acid sequence of SEQ ID NO: 88 may optionally be provided with lysine added at the C-terminus.

This ALK4-Fc fusion protein is encoded by the following nucleic acid (SEQ ID NO: 243):

```
                                                     (SEQ ID NO: 243)
  1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG
```

```
 751 CAGCCCCGAG AACCACAGGT GTACACCCTG CCCCCATCCC GGGAGGAGAT

801 GACCAAGAAC CAGGTCAGCC TGACCTGCCT GGTCAAAGGC TTCTATCCCA

851 GCGACATCGC CGTGGAGTGG GAGAGCAATG GGCAGCCGGA GAACAACTAC

901 GACACCACGC CTCCCGTGCT GGACTCCGAC GGCTCCTTCT TCCTCTATAG

951 CGACCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGT
```

The mature ALK4-Fc fusion protein sequence (SEQ ID NO: 89) is as follows and may optionally be provided with lysine added at the C-terminus.

```
                                                    (SEQ ID NO: 89)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

In some embodiments, the ALK4-Fc fusion polypeptide (or any Fc fusion polypeptide disclosed herein) employs the tissue plasminogen activator (TPA) leader: MDAMKR-GLCCVLLLCGAVFVSP (SEQ ID NO: 246).

In some embodiments, the ALK4-Fc fusion polypeptide (SEQ ID NO: 92) is as follows and may optionally be provided with lysine removed from the C-terminus.

```
                                                    (SEQ ID NO: 92)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and the linker are underlined. To guide heterodimer formation with certain Fc fusion polypeptides disclosed herein, four amino acid substitutions can be introduced into the Fc domain of the ALK4 fusion polypeptide as indicated by double underline above. The amino acid sequence of SEQ ID NO: 92 may optionally be provided with lysine removed from the C-terminus.

The mature ALK4-Fc fusion protein sequence is as follows and may optionally be provided with lysine removed from the C-terminus.

```
                                                      (SEQ ID NO: 93)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

Purification of various ActRIIB-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In some embodiments, the ALK4-Fc fusion polypeptide (SEQ ID NO: 247) is as follows and may optionally be provided with lysine removed from the C-terminus.

```
                                                      (SEQ ID NO: 247)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVTTL PPSREEMTKN QVSLSCAVKG FYPSDIAVEW ESRGQPENNY

301 KTTPPVLDSR GSFFLVSKLT VDKSRWQQGN VFSCSVMHEA LHNHYTQKSL

351 SLSPGK
```

The leader sequence and the linker are underlined. To guide heterodimer formation with certain Fc fusion polypeptides disclosed herein, four amino acid substitutions (replacing a tyrosine with a cysteine, a threonine with a serine, a leucine with an alanine, and a tyrosine with a valine) can be introduced into the Fc domain of the ALK4 fusion polypeptide as indicated by double underline above. To facilitate purification of the ALK4-Fc:ActRIIB-Fc heterodimer, two amino acid substitutions (replacing an asparagine with an arginine and an aspartate with an arginine) can also be introduced into the Fc domain of the ALK4-Fc fusion polypeptide as indicated by double underline above. The amino acid sequence of SEQ ID NO: 247 may optionally be provided with lysine removed from the C-terminus.

This ALK4-Fc fusion polypeptide is encoded by the following nucleic acid (SEQ ID NO: 248):

```
                                                      (SEQ ID NO: 248)
  1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC
```

-continued

```
 351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTGCACCCTG CCCCCATCCC GGGAGGAGAT

801 GACCAAGAAC CAGGTCAGCC TGTCCTGCGC CGTCAAAGGC TTCTATCCCA

851 GCGACATCGC CGTGGAGTGG GAGAGCCGCG GGCAGCCGGA GAACAACTAC

901 AAGACCACGC CTCCCGTGCT GGACTCCCGC GGCTCCTTCT TCCTCGTGAG

951 CAAGCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGTAAA
```

The mature ALK4-Fc fusion polypeptide sequence is as follows (SEQ ID NO: 249) and may optionally be provided with lysine removed from the C-terminus.

```
                                                   (SEQ ID NO: 249)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESRG QPENNYKTTP PVLDSRGSFF LVSKLTVDKS

301 RWQQGNVFSC SVMHEALHNH YTQKSLSLSP GK
```

This ALK4-Fc fusion polypeptide is encoded by the following nucleic acid (SEQ ID NO: 250):

```
                                                   (SEQ ID NO: 250)
  1 TCCGGGCCCC GGGGGGTCCA GGCTCTGCTG TGTGCGTGCA CCAGCTGCCT

51 CCAGGCCAAC TACACGTGTG AGACAGATGG GGCCTGCATG GTTTCCATTT

101 TCAATCTGGA TGGGATGGAG CACCATGTGC GCACCTGCAT CCCCAAAGTG

151 GAGCTGGTCC CTGCCGGGAA GCCCTTCTAC TGCCTGAGCT CGGAGGACCT

201 GCGCAACACC CACTGCTGCT ACACTGACTA CTGCAACAGG ATCGACTTGA

251 GGGTGCCCAG TGGTCACCTC AAGGAGCCTG AGCACCCGTC CATGTGGGGC

301 CCGGTGGAGA CCGGTGGTGG AACTCACACA TGCCCACCGT GCCCAGCACC

351 TGAACTCCTG GGGGGACCGT CAGTCTTCCT CTTCCCCCCA AAACCCAAGG

401 ACACCCTCAT GATCTCCCGG ACCCCTGAGG TCACATGCGT GGTGGTGGAC

451 GTGAGCCACG AAGACCCTGA GGTCAAGTTC AACTGGTACG TGGACGGCGT

501 GGAGGTGCAT AATGCCAAGA CAAAGCCGCG GGAGGAGCAG TACAACAGCA

551 CGTACCGTGT GGTCAGCGTC CTCACCGTCC TGCACCAGGA CTGGCTGAAT
```

```
601 GGCAAGGAGT ACAAGTGCAA GGTCTCCAAC AAAGCCCTCC CAGCCCCCAT

651 CGAGAAAACC ATCTCCAAAG CCAAAGGGCA GCCCCGAGAA CCACAGGTGT

701 GCACCCTGCC CCCATCCCGG GAGGAGATGA CCAAGAACCA GGTCAGCCTG

751 TCCTGCGCCG TCAAAGGCTT CTATCCCAGC GACATCGCCG TGGAGTGGGA

801 GAGCCGCGGG CAGCCGGAGA ACAACTACAA GACCACGCCT CCCGTGCTGG

851 ACTCCCGCGG CTCCTTCTTC CTCGTGAGCA AGCTCACCGT GGACAAGAGC

901 AGGTGGCAGC AGGGGAACGT CTTCTCATGC TCCGTGATGC ATGAGGCTCT

951 GCACAACCAC TACACGCAGA AGAGCCTCTC CCTGTCTCCG GGTAAA
```

In certain embodiments, the ALK4-Fc fusion polypeptide is SEQ ID NO: 92 (shown above), which contains four amino acid substitutions to guide heterodimer formation certain Fc fusion polypeptides disclosed herein, and may optionally be provided with lysine removed from the C-terminus.

This ALK4-Fc fusion polypeptide is encoded by the following nucleic acid (SEQ ID NO: 251):

```
                                              (SEQ ID NO: 251)
   1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTGCACCCTG CCCCCATCCC GGGAGGAGAT

801 GACCAAGAAC CAGGTCAGCC TGTCCTGCGC CGTCAAAGGC TTCTATCCCA

851 GCGACATCGC CGTGGAGTGG GAGAGCAATG GGCAGCCGGA GAACAACTAC

901 AAGACCACGC CTCCCGTGCT GGACTCCGAC GGCTCCTTCT TCCTCGTGAG

951 CAAGCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGTAAA
```

The mature ALK4-Fc fusion polypeptide sequence is SEQ ID NO: 93 (shown above) and may optionally be provided with lysine removed from the C-terminus.

This ALK4-Fc fusion polypeptide is encoded by the following nucleic acid (SEQ ID NO: 252):

(SEQ ID NO: 252)
```
  1 TCCGGGCCCC GGGGGGTCCA GGCTCTGCTG TGTGCGTGCA CCAGCTGCCT

51 CCAGGCCAAC TACACGTGTG AGACAGATGG GGCCTGCATG GTTTCCATTT

101 TCAATCTGGA TGGGATGGAG CACCATGTGC GCACCTGCAT CCCCAAAGTG

151 GAGCTGGTCC CTGCCGGGAA GCCCTTCTAC TGCCTGAGCT CGGAGGACCT

201 GCGCAACACC CACTGCTGCT ACACTGACTA CTGCAACAGG ATCGACTTGA

251 GGGTGCCAG TGGTCACCTC AAGGAGCCTG AGCACCCGTC CATGTGGGGC

301 CCGGTGGAGA CCGGTGGTGG AACTCACACA TGCCCACCGT GCCCAGCACC

351 TGAACTCCTG GGGGGACCGT CAGTCTTCCT CTTCCCCCCA AAACCCAAGG

401 ACACCCTCAT GATCTCCCGG ACCCCTGAGG TCACATGCGT GGTGGTGGAC

451 GTGAGCCACG AAGACCCTGA GGTCAAGTTC AACTGGTACG TGGACGGCGT

501 GGAGGTGCAT AATGCCAAGA CAAAGCCGCG GGAGGAGCAG TACAACAGCA

551 CGTACCGTGT GGTCAGCGTC CTCACCGTCC TGCACCAGGA CTGGCTGAAT

601 GGCAAGGAGT ACAAGTGCAA GGTCTCCAAC AAAGCCCTCC CAGCCCCCAT

651 CGAGAAAACC ATCTCCAAAG CCAAAGGGCA GCCCCGAGAA CCACAGGTGT

701 GCACCCTGCC CCCATCCCGG GAGGAGATGA CCAAGAACCA GGTCAGCCTG

751 TCCTGCGCCG TCAAAGGCTT CTATCCCAGC GACATCGCCG TGGAGTGGGA

801 GAGCAATGGG CAGCCGGAGA ACAACTACAA GACCACGCCT CCCGTGCTGG

851 ACTCCGACGG CTCCTTCTTC CTCGTGAGCA AGCTCACCGT GGACAAGAGC

901 AGGTGGCAGC AGGGGAACGT CTTCTCATGC TCCGTGATGC ATGAGGCTCT

951 GCACAACCAC TACACGCAGA AGAGCCTCTC CCTGTCTCCG GGTAAA
```

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography and epitope-based affinity chromatography (e.g., with an antibody or functionally equivalent ligand directed against an epitope on ALK4 or ActRIIB), and multimodal chromatography (e.g., with resin containing both electrostatic and hydrophobic ligands). The purification could be completed with viral filtration and buffer exchange.

In certain aspects, the present disclosure relates to protein complexes that comprise an ALK5 polypeptide. As used herein, the term "ALK5" refers to a family of activin receptor-like kinase-5 proteins from any species and variants derived from such ALK4 proteins by mutagenesis or other modification. Reference to ALK5 herein is understood to be a reference to any one of the currently identified forms. Members of the ALK5 family are generally transmembrane proteins, composed of a ligand-binding extracellular domain with a cysteine-rich region, a transmembrane domain, and a cytoplasmic domain with predicted serine/threonine kinase activity.

The term "ALK5 polypeptide" includes polypeptides comprising any naturally occurring polypeptide of an ALK5 family member as well as any variants thereof (including mutants, fragments, fusions, and peptidomimetic forms) that retain a useful activity.

A human ALK5 precursor protein sequence (NCBI Ref Seq NP_004603.1) is as follows:

(SEQ ID NO: 96)
```
  1 MEAAVAAPRP RLLLLVLAAA AAAAALLPG ATALQCFCHL CTKDNFTCVT DGLCFVSVTE

61 TTDKVIHNSM CIAEIDLIPR DRPFVCAPSS KTGSVTTTYC CNQDHCNKIE LPTTVKSSPG

121 LGPVELAAVI AGPVCFVCIS LMLMVYICHN RTVIHHRVPN EEDPSLDRPF ISEGTTLKDL

181 IYDMTTSGSG SGLPLLVQRT IARTIVLQES IGKGRFGEVW RGKWRGEEVA VKIFSSREER

241 SWFREAEIYQ TVMLRHENIL GFIAADNKDN GTWTQLWLVS DYHEGSLFD YLNRYTVTVE

301 GMIKLALSTA SGLAHLHMEI VGTQGKPAIA HRDLKSKNIL VKKNGTCCIA DLGLAVRHDS

361 ATDTIDIAPN HRVGTKRYMA PEVLDDSINM KHFESFKRAD IYAMGLVFWE IARRCSIGGI

421 HEDYQLPYYD LVPSDPSVEE MRKVVCEQKL RPNIPNRWQS CEALRVMAKI MRECWYANGA

481 ARLTALRIKK TLSQLSQQEG IKM
```

The signal peptide is indicated by a single underline and the extracellular domain is indicated in bold font.

A processed extracellular ALK5 polypeptide sequence is as follows:

(SEQ ID NO: 98)
AALLPGATALQCFCHLCTKDNFTCVTDGLCFVSVTETTDKVIHNSMCIAE

IDLIPRDRPFVCAPSSKTGSVTTTYCCNQDHCNKIELPTTVKSSPGLGPV

EL

A nucleic acid sequence encoding the ALK5 precursor protein is shown in SEQ ID NO: 225, corresponding to nucleotides 77-1585 of Genbank Reference Sequence NM_004612.2. A nucleic acid sequence encoding an extracellular human ALK5 polypeptide is shown in SEQ ID NO: 226.

An alternative isoform of the human ALK5 precursor protein sequence, isoform 2 (NCBI Ref Seq XP_005252207.1), is as follows:

(SEQ ID NO: 97)
```
  1 MEAAVAAPRP RLLLLVLAAA AAAAAALLPG ATALQCFCHL CTKDNFTCVT DGLCFVSVTE

61 TTDKVIHNSM CIAEIDLIPR DRPFVCAPSS KTGSVTTTYC CNQDHCNKIE LPTTGPFSVK

121 SSPGLGPVEL AAVIAGPVCF VCISLMLMVY ICHNRTVIHH RVPNEEDPSL DRPFISEGTT

181 LKDLIYDMTT SGSGSGLPLL VQRTIARTIV LQESIGKGRF GEVWRGKWRG EEVAVKIFSS

241 REERSWFREA EIYQTVMLRH ENILGFIAAD NKDNGTWTQL WLVSDYHEHG SLFDYLNRYT

301 VTVEGMIKLA LSTASGLAHL HMEIVGTQGK PAIAHRDLKS KNILVKKNGT CCIADLGLAV

361 RHDSATDTID IAPNHRVGTK RYMAPEVLDD SINMKHFESF KRADIYAMGL VFWEIARRCS

421 IGGIHEDYQL PYYDLVPSDP SVEEMRKVVC EQKLRPNIPN RWQSCEALRV MAKIMRECWY

481 ANGAARLTAL RIKKTLSQLS QQEGIKM
```

The signal peptide is indicated by a single underline and the extracellular domain is indicated in bold font.

A processed extracellular ALK5 polypeptide sequence (isoform 2) is as follows:

(SEQ ID NO: 99)
AALLPGATALQCFCHLCTKDNFTCVTDGLCFVSVTETTDKVIHNSMCIAE

IDLIPRDRPFVCAPSSKTGSVTTTYCCNQDHCNKIELPTTGPFSVKSSPG

LGPVEL

A nucleic acid sequence encoding human ALK5 precursor protein (isoform 2) is shown in SEQ ID NO: 227, corresponding to nucleotides 77-1597 of Genbank Reference Sequence XM_005252150.1. A nucleic acid sequence encoding a processed extracellular ALK5 polypeptide is shown in SEQ ID NO: 228.

In certain embodiments, the disclosure relates to heteromultimers that comprise at least one ALK5 polypeptide, which includes fragments, functional variants, and modified forms thereof. Preferably, ALK5 polypeptides for use in accordance with inventions of the disclosure (e.g., heteromultimers comprising an ALK5 polypeptide and uses thereof) are soluble (e.g., an extracellular domain of ALK5). In other preferred embodiments, ALK5 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK5 polypeptide that is at least 70%, 75%, 80%, 85%, 90%, 95%, 97%, 98%, 99%, or 100% identical to the amino acid sequence of SEQ ID NO: 96, 98, 97, or 99. In some embodiments, heteromultimer complexes of the disclosure consist or consist essentially of at least one ALK5 polypeptide that is at least 70%, 75%, 80%, 85%, 90%, 95%, 97%, 98%, 99%, or 100% identical to the amino acid sequence of SEQ ID NO: 96, 98, 97, or 99.

In certain aspects, the disclosure relates to a heteromultimer that comprises an ALK5-Fc fusion protein. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 25-36 (e.g., amino acid residues 25, 26, 27, 28, 29, 30, 31, 32, 33, 34, 35, and 36) SEQ ID NO: 96 or 97, and ends at any one of amino acids 106-126 (e.g., amino acid residues 106, 107, 108, 109, 110, 111, 112, 113, 114, 115, 116, 117, 118, 119, 120, 121, 122, 123, 124, 125, and 126) of SEQ ID NO: 96 or 97. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 36-106 of SEQ ID NOs: 96 or 97. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 25-126 of SEQ ID NOs: 96 or 97. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 96, 98, 97, 99, 100, 101, 102, 103, 104, 105, 106, and 107.

The complementary ALK5-Fc fusion protein employs the TPA leader and is as follows (SEQ ID NO: 100):

```
                                                      (SEQ ID NO: 100)
  1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVYTLPPS REEMTKNQVS LTCLVKGFYP SDIAVEWESN GQPENNYDTT

301 PPVLDSDGSF FLYSDLTVDK SRWQQGNVFS CSVMHEALHN HYTQKSLSLS

351 PG
```

The signal sequence and linker sequence are underlined. To promote formation of the ActRIIB-Fc:ALK5-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 100 may optionally be provided with a lysine added at the C-terminus.

This ALK5-Fc fusion protein is encoded by the following nucleic acid (SEQ ID NO: 253):

```
                                                      (SEQ ID NO: 253)
   1 ATGGATGCAA TGAAGAGAGG GCTCTGCTGT GTGCTGCTGC TGTGTGGAGC

51 AGTCTTCGTT TCGCCCGGCG CCGCGCTGCT CCCGGGGGCG ACGGCGTTAC

101 AGTGTTTCTG CCACCTCTGT ACAAAAGACA ATTTTACTTG TGTGACAGAT

151 GGGCTCTGCT TTGTCTCTGT CACAGAGACC ACAGACAAAG TTATACACAA

201 CAGCATGTGT ATAGCTGAAA TTGACTTAAT TCCTCGAGAT AGGCCGTTTG

251 TATGTGCACC CTCTTCAAAA ACTGGGTCTG TGACTACAAC ATATTGCTGC

301 AATCAGGACC ATTGCAATAA AATAGAACTT CCAACTACTG TAAAGTCATC

351 ACCTGGCCTT GGTCCTGTGG AAACCGGTGG TGGAACTCAC ACATGCCCAC

401 CGTGCCCAGC ACCTGAACTC CTGGGGGGAC CGTCAGTCTT CCTCTTCCCC

451 CCAAAACCCA AGGACACCCT CATGATCTCC CGGACCCCTG AGGTCACATG

501 CGTGGTGGTG GACGTGAGCC ACGAAGACCC TGAGGTCAAG TTCAACTGGT

551 ACGTGGACGG CGTGGAGGTG CATAATGCCA AGACAAAGCC GCGGGAGGAG

601 CAGTACAACA GCACGTACCG TGTGGTCAGC GTCCTCACCG TCCTGCACCA

651 GGACTGGCTG AATGGCAAGG AGTACAAGTG CAAGGTCTCC AACAAAGCCC

701 TCCCAGCCCC CATCGAGAAA ACCATCTCCA AAGCCAAAGG GCAGCCCCGA

751 GAACCACAGG TGTACACCCT GCCCCCATCC CGGGAGGAGA TGACCAAGAA

801 CCAGGTCAGC CTGACCTGCC TGGTCAAAGG CTTCTATCCC AGCGACATCG

851 CCGTGGAGTG GGAGAGCAAT GGGCAGCCGG AGAACAACTA CGACACCACG

901 CCTCCCGTGC TGGACTCCGA CGGCTCCTTC TTCCTCTATA GCGACCTCAC

951 CGTGGACAAG AGCAGGTGGC AGCAGGGGAA CGTCTTCTCA TGCTCCGTGA

1001 TGCATGAGGC TCTGCACAAC CACTACACGC AGAAGAGCCT CTCCCTGTCT

1051 CCGGGT
```

The mature ALK5-Fc fusion protein sequence (SEQ ID NO: 101) is as follows and may optionally be provided with a lysine added at the C-terminus.

```
                                                         (SEQ ID NO: 101)
   1 ALLPGATALQ CFCHLCTKDN FTCVTDGLCF VSVTETTDKV IHNSMCIAEI

51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV YTLPPSREEM TKNQVSLTCL

251 VKGFYPSDIA VEWESNGQPE NNYDTTPPVL DSDGSFFLYS DLTVDKSRWQ

301 QGNVFSCSVM HEALHNHYTQ KSLSLSPG
```

In another approach to promoting the formation of heteromultimer complexes using asymmetric Fc fusion proteins, the Fc domains are altered to introduce complementary hydrophobic interactions and an additional intermolecular disulfide bond.

In some embodiments, the ALK5-Fc fusion polypeptide (SEQ ID NO: 104) is as follows:

```
                                                         (SEQ ID NO: 104)
   1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVCTLPPS REEMTKNQVS LSCAVKGFYP SDIAVEWESN GQPENNYKTT

301 PPVLDSDGSF FLVSKLTVDK SRWQQGNVFS CSVMHEALHN HYTQKSLSLS

351 PGK
```

The leader sequence and linker sequence are underlined. To guide heterodimer formation with certain Fc fusion polypeptides disclosed herein, four amino acid substitutions can be introduced into the Fc domain of the ALK5 fusion polypeptide as indicated by double underline above. Furthermore, the C-terminal lysine residue of the Fc domain can be deleted. The amino acid sequence of SEQ ID NO: 104 may optionally be provided with the lysine removed from the C-terminus.

The mature ALK5-Fc fusion protein sequence (SEQ ID NO: 105) is as follows and may optionally be provided with the lysine removed from the C-terminus.

In certain aspects, the present disclosure relates to protein complexes that comprise an ALK6 polypeptide. As used herein, the term "ALK6" refers to a family of activin receptor-like kinase-6 proteins from any species and variants derived from such ALK6 proteins by mutagenesis or other modification. Reference to ALK6 herein is understood to be a reference to any one of the currently identified forms.

Members of the ALK6 family are generally transmembrane proteins, composed of a ligand-binding extracellular domain with a cysteine-rich region, a transmembrane domain, and a cytoplasmic domain with predicted serine/threonine kinase activity.

The term "ALK6 polypeptide" includes polypeptides comprising any naturally occurring polypeptide of an ALK6 family member as well as any variants thereof (including mutants, fragments, fusions, and peptidomimetic forms) that retain a useful activity.

A human ALK6 precursor protein sequence (NCBI Ref Seq NP_001194.1) is as follows:

```
                                                         (SEQ ID NO: 105)
   1 ALLPGATALQ CFCHLCTKDN FTCVTDGLCF VSVTETTDKV IHNSMCIAEI

51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV CTLPPSREEM TKNQVSLSCA

251 VKGFYPSDIA VEWESNGQPE NNYKTTPPVL DSDGSFFLVS KLTVDKSRWQ

301 QGNVFSCSVM HEALHNHYTQ KSLSLSPGK
```

(SEQ ID NO: 108)
```
  1 MLLRSAGKLN VGTKKEDGES TAPTPRPKVL RCKCHHHCPE DSVNNICSTD GYCFTMIEED

61 DSGLPVVTSG CLGLEGSDFQ CRDTPIPHQR RSIECCTERN ECNKDLHPTL PPLKNRDFVD

121 GPIHHRALLI SVTVCSLLLV LIILFCYFRY KRQETRPRYS IGLEQDETYI PPGESLRDLI

181 EQSQSSGSGS GLPLLVQRTI AKQIQMVKQI GKGRYGEVWM GKWRGEKVAV KVFFTTEEAS

241 WFRETEIYQT VLMRHENILG FIAADIKGTG SWTQLYLITD YHENGSLYDY LKSTTLDAKS

301 MLKLAYSSVS GLCHLHTEIF STQGKPAIAH RDLKSKNILV KKNGTCCIAD LGLAVKFISD

361 TNEVDIPPNT RVGTKRYMPP EVLDESLNRN HFQSYIMADM YSFGLILWEV ARRCVSGGIV

421 EEYQLPYHDL VPSDPSYEDM REIVCIKKLR PSFPNRWSSD ECLRQMGKLM TECWAHNPAS

481 RLTALRVKKT LAKMSESQDI KL
```

The signal peptide is indicated by a single underline and the extracellular domain is indicated in bold font.

The processed extracellular ALK6 polypeptide sequence is as follows:

(SEQ ID NO: 109)
```
KKEDGESTAPTPRPKVLRCKCHHHCPEDSVNNICSTDGYCFTMIEEDDS

GLPVVTSGCLGLEGSDFQCRDTPIPHQRRSIECCTERNECNKDLHPTLP

PLKNRDFVDGPIHHR
```

A nucleic acid sequence encoding the ALK6 precursor protein is shown in SEQ ID NO: 229, corresponding to nucleotides 275-1780 of Genbank Reference Sequence NM_001203.2. A nucleic acid sequence encoding processed extracellular ALK6 polypeptide is shown in SEQ ID NO: 230.

An alternative isoform of human ALK6 precursor protein sequence, isoform 2 (NCBI Ref Seq NP_001243722.1) is as follows:

(SEQ ID NO: 110)
```
  1 MGWLEELNWQ LHIFLLILLS MHTRANFLDN MLLRSAGKLN VGTKKEDGES TAPTPRPKVL

61 RCKCHHHCPE DSVNNICSTD GYCFTMIEED DSGLPVVTSG CLGLEGSDFQ CRDTPIPHQR

121 RSIECCTERN ECNKDLHPTL PPLKNRDFVD GPIHHRALLI SVTVCSLLLV LIILFCYFRY

181 KRQETRPRYS IGLEQDETYI PPGESLRDLI EQSQSSGSGS GLPLLVQRTI AKQIQMVKQI

241 GKGRYGEVWM GKWRGEKVAV KVFFTTEEAS WFRETEIYQT VLMRHENILG FIAADIKGTG

301 SWTQLYLITD YHENGSLYDY LKSTTLDAKS MLKLAYSSVS GLCHLHTEIF STQGKPAIAH

361 RDLKSKNILV KKNGTCCIAD LGLAVKFISD TNEVDIPPNT RVGTKRYMPP EVLDESLNRN

421 HFQSYIMADM YSFGLILWEV ARRCVSGGIV EEYQLPYHDL VPSDPSYEDM REIVCIKKLR

481 PSFPNRWSSD ECLRQMGKLM TECWAHNPAS RLTALRVKKT LAKMSESQDI KL
```

The signal peptide is indicated by a single underline and the extracellular domain is indicated in bold font.

A processed extracellular ALK6 polypeptide sequence (isoform 2) is as follows:

(SEQ ID NO: 111)
```
NFLDNMLLRSAGKLNVGTKKEDGESTAPTPRPKVLRCKCHHHCPEDSVN

NICSTDGYCFTMIEEDDSGLPVVTSGCLGLEGSDFQCRDTPIPHQRRSI

ECCTERNECNKDLHPTLPPLKNRDFVDGPIHHR
```

A nucleic acid sequence encoding human ALK6 precursor protein (isoform 2) is shown in SEQ ID NO: 231, corresponding to nucleotides 22-1617 of Genbank Reference Sequence NM_001256793.1. A nucleic acid sequence encoding a processed extracellular ALK6 polypeptide is shown in SEQ ID NO: 232.

In certain embodiments, the disclosure relates to heteromultimers that comprise at least one ALK6 polypeptide, which includes fragments, functional variants, and modified forms thereof. Preferably, ALK6 polypeptides for use in accordance with inventions of the disclosure (e.g., heteromultimers comprising an ALK6 polypeptide and uses thereof) are soluble (e.g., an extracellular domain of ALK6). In other preferred embodiments, ALK6 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK6 polypeptide that is at least 70%, 75%, 80%, 85%, 90%, 95%, 97%, 98%, 99%, or 100% identical to the amino acid sequence of SEQ ID NO: 108, 109, 110, or 111. In some embodiments, heteromultimers of the disclosure consist or consist essentially of at least one ALK6 polypeptide that is at least 70%, 75%, 80%, 85%, 90%, 95%, 97%, 98%, 99%, or 100% identical to the amino acid sequence of SEQ ID NO: 108, 109, 110, or 111.

In certain aspects, the disclosure relates to a heteromultimer that comprises an ALK6-Fc fusion protein. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 14-32 (e.g., amino acid residues 14, 15, 16, 17, 18, 19, 20, 21, 22, 23, 24, 25, 26, 27, 28, 29, 30, 31, and 32) SEQ ID NO: 108, and ends at any one of amino acids 102-126 (e.g., amino acid residues 102, 103, 104, 105, 106, 107, 108, 109, 110, 111, 112, 113, 114, 115, 116, 117, 118, 119, 120, 121, 122, 123, 124, 125, and 126) of SEQ ID NO: 108. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 32-102 of SEQ ID NO: 108. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 14-126 of SEQ ID NO: 108. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 108, 109, 110, 111, 112, 113, 114, 115, 116, 117, 118, and 119.

In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 26-62 (e.g., amino acid residues 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, and 62) SEQ ID NO: 110, and ends at any one of amino acids 132-156 (e.g., amino acid residues 132, 133, 134, 135, 136, 137, 138, 139, 140, 141, 142, 143, 144, 145, 146, 147, 148, 149, 150, 151, 152, 153, 154, 155, and 156) of SEQ ID NO: 110. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 62-132 of SEQ ID NO: 110. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 26-156 of SEQ ID NO: 110.

The complementary ALK6-Fc fusion protein employs the TPA leader and is as follows (SEQ ID NO: 112):

```
                                                         (SEQ ID NO: 112)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPSREEMTKN QVSLTCLVKG FYPSDIAVEW

301 ESNGQPENNY DTTPPVLDSD GSFFLYSDLT VDKSRWQQGN VFSCSVMHEA

351 LHNHYTQKSL SLSPG
```

The signal sequence and linker sequence are underlined. To promote formation of the ActRIIB-Fc:ALK6-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 112 may optionally be provided with a lysine added at the C-terminus.

This ALK6-Fc fusion protein is encoded by the following nucleic acid (SEQ ID NO: 254):

```
                                                         (SEQ ID NO: 254)
  1 ATGGATGCAA TGAAGAGAGG GCTCTGCTGT GTGCTGCTGC TGTGTGGAGC

51 AGTCTTCGTT TCGCCCGGCG CCAAGAAAGA GGATGGTGAG AGTACAGCCC

101 CCACCCCCCG TCCAAAGGTC TTGCGTTGTA AATGCCACCA CCATTGTCCA

151 GAAGACTCAG TCAACAATAT TTGCAGCACA GACGGATATT GTTTCACGAT

201 GATAGAAGAG GATGACTCTG GGTTGCCTGT GGTCACTTCT GGTTGCCTAG

251 GACTAGAAGG CTCAGATTTT CAGTGTCGGG ACACTCCCAT TCCTCATCAA

301 AGAAGATCAA TTGAATGCTG CACAGAAAGG AACGAATGTA ATAAAGACCT

351 ACACCCTACA CTGCCTCCAT TGAAAAACAG AGATTTTGTT GATGGACCTA
```

```
401 TACACCACAG GACCGGTGGT GGAACTCACA CATGCCCACC GTGCCCAGCA

451 CCTGAACTCC TGGGGGGACC GTCAGTCTTC CTCTTCCCCC CAAAACCCAA

501 GGACACCCTC ATGATCTCCC GGACCCCTGA GGTCACATGC GTGGTGGTGG

551 ACGTGAGCCA CGAAGACCCT GAGGTCAAGT TCAACTGGTA CGTGGACGGC

601 GTGGAGGTGC ATAATGCCAA GACAAAGCCG CGGGAGGAGC AGTACAACAG

651 CACGTACCGT GTGGTCAGCG TCCTCACCGT CCTGCACCAG GACTGGCTGA

701 ATGGCAAGGA GTACAAGTGC AAGGTCTCCA ACAAAGCCCT CCCAGCCCCC

751 ATCGAGAAAA CCATCTCCAA AGCCAAAGGG CAGCCCCGAG AACCACAGGT

801 GTACACCCTG CCCCCATCCC GGGAGGAGAT GACCAAGAAC CAGGTCAGCC

851 TGACCTGCCT GGTCAAAGGC TTCTATCCCA GCGACATCGC CGTGGAGTGG

901 GAGAGCAATG GGCAGCCGGA GAACAACTAC GACACCACGC CTCCCGTGCT

951 GGACTCCGAC GGCTCCTTCT TCCTCTATAG CGACCTCACC GTGGACAAGA

1001 GCAGGTGGCA GCAGGGGAAC GTCTTCTCAT GCTCCGTGAT GCATGAGGCT

1051 CTGCACAACC ACTACACGCA GAAGAGCCTC TCCCTGTCTC CGGGT
```

The mature ALK6-Fc fusion protein sequence (SEQ ID NO: 113) is as follows and may optionally be provided with a lysine added at the C-terminus.

```
                                                    (SEQ ID NO: 113)
  1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL

101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR

251 EEMTKNQVSL TCLVKGFYPS DIAVEWESNG QPENNYDTTP PVLDSDGSFF

301 LYSDLTVDKS RWQQGNVFSC SVMHEALHNH YTQKSLSLSP G
```

In another approach to promoting the formation of heteromultimer complexes using asymmetric Fc fusion proteins, the Fc domains can be altered to introduce complementary hydrophobic interactions and an additional intermolecular disulfide bond.

The complementary form of ALK6-Fc fusion polypeptide (SEQ ID NO: 116) is as follows:

```
                                                    (SEQ ID NO: 116)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVCTL PPSREEMTKN QVSLSCAVKG FYPSDIAVEW

301 ESNGQPENNY KTTPPVLDSD GSFFLVSKLT VDKSRWQQGN VFSCSVMHEA

351 LHNHYTQKSL SLSPGK
```

The leader sequence and linker sequence are underlined. To guide heterodimer formation with certain Fc fusion polypeptides disclosed herein, four amino acid substitutions can be introduced into the Fc domain of the ALK6 fusion polypeptide as indicated by double underline above. Furthermore, the C-terminal lysine residue of the Fc domain can be deleted. The amino acid sequence of SEQ ID NO: 116 may optionally be provided with the lysine removed from the C-terminus.

The mature ALK6-Fc fusion protein sequence (SEQ ID NO: 117) can be as follows and may optionally be provided with the lysine removed from the C-terminus.

```
                                                    (SEQ ID NO: 117)
  1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL

101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVCTLPPSR

251 EEMTKNQVSL SCAVKGFYPS DIAVEWESNG QPENNYKTTP PVLDSDGSFF

301 LVSKLTVDKS RWQQGNVFSC SVMHEALHNH YTQKSLSLSP GK
```

In certain aspects, the present disclosure relates to protein complexes that comprise an ALK7 polypeptide. As used herein, the term "ALK7" refers to a family of activin receptor-like kinase-7 proteins from any species and variants derived from such ALK7 proteins by mutagenesis or other modification. Reference to ALK7 herein is understood to be a reference to any one of the currently identified forms. Members of the ALK7 family are generally transmembrane proteins, composed of a ligand-binding extracellular domain with a cysteine-rich region, a transmembrane domain, and a cytoplasmic domain with predicted serine/threonine kinase activity.

The term "ALK7 polypeptide" includes polypeptides comprising any naturally occurring polypeptide of an ALK7 family member as well as any variants thereof (including mutants, fragments, fusions, and peptidomimetic forms) that retain a useful activity.

Four naturally occurring isoforms of human ALK7 have been described. The sequence of human ALK7 isoform 1 precursor protein (NCBI Ref Seq NP_660302.2) is as follows:

```
                                                    (SEQ ID NO: 120)
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TASPNAPKLG PMELAIIITV

121 PVCLLSIAAM LTVWACQGRQ CSYRKKKRPN VEEPLSECNL VNAGKTLKDL IYDVTASGSG

181 SGLPLLVQRT IARTIVLQEI VGKGRFGEVW HGRWCGEDVA VKIFSSRDER SWFREAEIYQ

241 TVMLRHENIL GFIAADNKDN GTWTQLWLVS EYHEQGSLYD YLNRNIVTVA GMIKLALSIA

301 SGLAHLHMEI VGTQGKPAIA HRDIKSKNIL VKKCETCAIA DLGLAVKHDS ILNTIDIPQN

361 PKVGTKRYMA PEMLDDTMNV NIFESFKRAD IYSVGLVYWE IARRCSVGGI VEEYQLPYYD

421 MVPSDPSIEE MRKVVCDQKF RPSIPNQWQS CEALRVMGRI MRECWYANGA ARLTALRIKK

481 TISQLCVKED CKA
```

The signal peptide is indicated by a single underline and the extracellular domain is indicated in bold font.

A processed extracellular ALK7 isoform 1 polypeptide sequence is as follows:

(SEQ ID NO: 123)
ELSPGLKCVCLLCDSSNFTCQTEGACWASVMLTNGKEQVIKSCVSLPEL
NAQVFCHSSNNVTKTECCFTDFCNNITLHLPTASPNAPKLGPME

A nucleic acid sequence encoding human ALK7 isoform 1 precursor protein is shown below in SEQ ID NO: 233, corresponding to nucleotides 244-1722 of Genbank Reference Sequence NM_145259.2. A nucleic acid sequence encoding the processed extracellular ALK7 polypeptide (isoform 1) is show in in SEQ ID NO: 234.

An amino acid sequence of an alternative isoform of human ALK7, isoform 2 (NCBI Ref Seq NP_001104501.1), is shown in its processed form as follows (SEQ ID NO: 124), where the extracellular domain is indicated in bold font.

(SEQ ID NO: 124)
```
  1 MLTNGKEQVI KSCVSLPELN AQVFCHSSNN VTKTECCFTD FCNNITLHLP TASPNAPKLG

61 PMELAIIITV PVCLLSIAAM LTVWACQGRQ CSYRKKKRPN VEEPLSECNL VNAGKTLKDL

121 IYDVTASGSG SGLPLLVQRT IARTIVLQEI VGKGRFGEVW HGRWCGEDVA VKIFSSRDER

181 SWFREAEIYQ TVMLRHENIL GFIAADNKDN GTWTQLWLVS EYHEQGSLYD YLNRNIVTVA

241 GMIKLALSIA SGLAHLHMEI VGTQGKPAIA HRDIKSKNIL VKKCETCAIA DLGLAVKHDS

301 ILNTIDIPQN PKVGTKRYMA PEMLDDTMNV NIFESFKRAD IYSVGLVYWE IARRCSVGGI

361 VEEYQLPYYD MVPSDPSIEE MRKVVCDQKF RPSIPNQWQS CEALRVMGRI MRECWYANGA

421 ARLTALRIKK TISQLCVKED CKA
```

An amino acid sequence of the extracellular ALK7 polypeptide (isoform 2) is as follows:

(SEQ ID NO: 125)
MLTNGKEQVIKSCVSLPELNAQVFCHSSNNVTKTECCFTDFCNNITLHLP
TASPNAPKLGPME.

A nucleic acid sequence encoding the processed ALK7 polypeptide (isoform 2) is shown below in SEQ ID NO: 235, corresponding to nucleotides 279-1607 of NCBI Reference Sequence NM_001111031.1.

A nucleic acid sequence encoding an extracellular ALK7 polypeptide (isoform 2) is shown in SEQ ID NO: 236.

An amino acid sequence of an alternative human ALK7 precursor protein, isoform 3 (NCBI Ref Seq NP_001104502.1), is shown as follows (SEQ ID NO: 121), where the signal peptide is indicated by a single underline.

(SEQ ID NO: 121)
```
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TGLPLLVQRT IARTIVLQEI

121 VGKGRFGEVW HGRWCGEDVA VKIFSSRDER SWFREAEIYQ TVMLRHENIL GFIAADNKDN

181 GTWTQLWLVS EYHEQGSLYD YLNRNIVTVA GMIKLALSIA SGLAHLHMEI VGTQGKPAIA

241 HRDIKSKNIL VKKCETCAIA DLGLAVKHDS ILNTIDIPQN PKVGTKRYMA PEMLDDTMNV

301 NIFESFKRAD IYSVGLVYWE IARRCSVGGI VEEYQLPYYD MVPSDPSIEE MRKVVCDQKF

361 RPSIPNQWQS CEALRVMGRI MRECWYANGA ARLTALRIKK TISQLCVKED CKA
```

The amino acid sequence of a processed ALK7 polypeptide (isoform 3) is as follows (SEQ ID NO: 126). This isoform lacks a transmembrane domain and is therefore proposed to be soluble in its entirety (Roberts et al., 2003, Biol Reprod 68:1719-1726). N-terminal variants of SEQ ID NO: 126 are predicted as described below.

```
                                                          (SEQ ID NO: 126)
  1 ELSPGLKCVC LLCDSSNFTC QTEGACWASV MLTNGKEQVI KSCVSLPELN AQVFCHSSNN

61 VTKTECCFTD FCNNITLHLP TGLPLLVQRT IARTIVLQEI VGKGRFGEVW HGRWCGEDVA

121 VKIFSSRDER SWFREAEIYQ TVMLRHENIL GFIAADNKDN GTWTQLWLVS EYHEQGSLYD

181 YLNRNIVTVA GMIKLALSIA SGLAHLHMEI VGTQGKPAIA HRDIKSKNIL VKKCETCAIA

241 DLGLAVKHDS ILNTIDIPQN PKVGTKRYMA PEMLDDTMNV NIFESFKRAD IYSVGLVYWE

301 IARRCSVGGI VEEYQLPYYD MVPSDPSIEE MRKVVCDQKF RPSIPNQWQS CEALRVMGRI

361 MRECWYANGA ARLTALRIKK TISQLCVKED CKA
```

A nucleic acid sequence encoding an unprocessed ALK7 polypeptide precursor protein (isoform 3) is shown in SEQ ID NO: 237, corresponding to nucleotides 244-1482 of NCBI Reference Sequence NM_001111032.1. A nucleic acid sequence encoding a processed ALK7 polypeptide (isoform 3) is shown in SEQ ID NO: 238.

An amino acid sequence of an alternative human ALK7 precursor protein, isoform 4 (NCBI Ref Seq NP_001104503.1), is shown as follows (SEQ ID NO: 122), where the signal peptide is indicated by a single underline.

```
                                                          (SEQ ID NO: 122)
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TDNGTWTQLW LVSEYHEQGS

121 LYDYLNRNIV TVAGMIKLAL SIASGLAHLH MEIVGTQGKP AIAHRDIKSK NILVKKCETC

181 AIADLGLAVK HDSILNTIDI PQNPKVGTKR YMAPEMLDDT MNVNIFESFK RADIYSVGLV

241 YWEIARRCSV GGIVEEYQLP YYDMVPSDPS IEEMRKVVCD QKFRPSIPNQ WQSCEALRVM

301 GRIMRECWYA NGAARLTALR IKKTISQLCV KEDCKA
```

An amino acid sequence of a processed ALK7 polypeptide (isoform 4) is as follows (SEQ ID NO: 127). Like ALK7 isoform 3, isoform 4 lacks a transmembrane domain and is therefore proposed to be soluble in its entirety (Roberts et al., 2003, Biol Reprod 68:1719-1726). N-terminal variants of SEQ ID NO: 127 are predicted as described below.

```
                                                          (SEQ ID NO: 127)
  1 ELSPGLKCVC LLCDSSNFTC QTEGACWASV MLTNGKEQVI KSCVSLPELN AQVFCHSSNN

61 VTKTECCFTD FCNNITLHLP TDNGTWTQLW LVSEYHEQGS LYDYLNRNIV TVAGMIKLAL

121 SIASGLAHLH MEIVGTQGKP AIAHRDIKSK NILVKKCETC AIADLGLAVK HDSILNTIDI

181 PQNPKVGTKR YMAPEMLDDT MNVNIFESFK RADIYSVGLV YWEIARRCSV GGIVEEYQLP

240 YYDMVPSDPS IEEMRKVVCD QKFRPSIPNQ WQSCEALRVM GRIMRECWYA NGAARLTALR

301 IKKTISQLCV KEDCKA
```

A nucleic acid sequence encoding the unprocessed ALK7 polypeptide precursor protein (isoform 4) is shown in SEQ ID NO: 239, corresponding to nucleotides 244-1244 of NCBI Reference Sequence NM_001111033.1. A nucleic acid sequence encoding the processed ALK7 polypeptide (isoform 4) is shown in SEQ ID NO: 240.

Based on the signal sequence of full-length ALK7 (isoform 1) in the rat (see NCBI Reference Sequence NP_620790.1) and on the high degree of sequence identity between human and rat ALK7, it is predicted that a processed form of human ALK7 isoform 1 is as follows (SEQ ID NO: 128).

In certain aspects, the disclosure relates to a heteromultimer that comprises an ALK7-Fc fusion protein. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-28 (e.g., amino acid residues 21, 22, 23, 24, 25, 26, 27, and 28) SEQ ID NO: 120, 121, or 122, and ends at any one of amino acids 92-113 (e.g., amino acid residues 92, 93, 94, 95, 96, 97, 98, 99, 100, 101, 102, 103, 104, 105, 106, 107, 108, 109, 110, 111, 112, and 113) of SEQ

```
                                           (SEQ ID NO: 128)
  1 LKCVCLLCDS SNFTCQTEGA CWASVMLTNG KEQVIKSCVS LPELNAQVFC HSSNNVTKTE

61 CCFTDFCNNI TLHLPTASPN APKLGPME
```

Active variants of processed ALK7 isoform 1 are predicted in which SEQ ID NO: 123 is truncated by 1, 2, 3, 4, 5, 6, or 7 amino acids at the N-terminus and SEQ ID NO: 128 is truncated by 1 or 2 amino acids at the N-terminus. Consistent with SEQ ID NO: 128, it is further expected that leucine is the N-terminal amino acid in the processed forms of human ALK7 isoform 3 (SEQ ID NO: 126) and human ALK7 isoform 4 (SEQ ID NO: 127).

In certain embodiments, the disclosure relates to heteromultimers that comprise at least one ALK7 polypeptide, which includes fragments, functional variants, and modified forms thereof. Preferably, ALK7 polypeptides for use in accordance with inventions of the disclosure (e.g., heteromultimers comprising an ALK7 polypeptide and uses thereof) are soluble (e.g., an extracellular domain of ALK7). In other preferred embodiments, ALK7 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK7 polypeptide that is at least 70%, 75%, 80%, 85%, 90%, 95%, 97%, 98%, 99%, or 100% identical to the amino acid sequence of SEQ ID NO: 120, 123, 129, 130, 124, 125, 121, 126, 122, 127, 128, 133, or 134. In some embodiments, heteromultimers of the disclosure consist or consist essentially of at least one ALK7 polypeptide that is at least 70%, 75%, 80%, 85%, 90%, 95%, 97%, 98%, 99%, or 100% identical to the amino acid sequence of SEQ ID NO: 120, 123, 129, 130, 124, 125, 121, 126, 122, 127, 128, 133, or 134.

ID NO: 120, 121, or 122. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 28-92 of SEQ ID NOs: 120, 121, or 122. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-113 of SEQ ID NOs: 120, 121, or 122. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 120, 123, 124, 125, 121, 126, 122, 127, 128, 129, 130, 131, 132, 133, 134, 135, and 136.

In some embodiments, the ALK7-Fc fusion protein employs the TPA leader and is as follows (SEQ ID NO: 129):

```
                                                   (SEQ ID NO: 129)
  1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR

251 EEMTKNQVSL TCLVKGFYPS DIAVEWESNG QPENNYDTTP PVLDSDGSFF

301 LYSDLTVDKS RWQQGNVFSC SVMHEALHNH YTQKSLSLSP G
```

The signal sequence and linker sequence are underlined. To promote formation of the ActRIIB-Fc:ALK7-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 129 may optionally be provided with a lysine added at the C-terminus.

This ALK7-Fc fusion protein is encoded by the following nucleic acid (SEQ ID NO: 255):

```
                                                    (SEQ ID NO: 255)
   1 ATGGATGCAA TGAAGAGAGG GCTCTGCTGT GTGCTGCTGC TGTGTGGAGC

51 AGTCTTCGTT TCGCCCGGCG CCGGACTGAA GTGTGTATGT CTTTTGTGTG

101 ATTCTTCAAA CTTTACCTGC CAAACAGAAG GAGCATGTTG GCATCAGTC

151 ATGCTAACCA ATGGAAAAGA GCAGGTGATC AAATCCTGTG TCTCCCTTCC

201 AGAACTGAAT GCTCAAGTCT TCTGTCATAG TTCCAACAAT GTTACCAAAA

251 CCGAATGCTG CTTCACAGAT TTTTGCAACA ACATAACACT GCACCTTCCA

301 ACAGCATCAC CAAATGCCCC AAAACTTGGA CCCATGGAGA CCGGTGGTGG

351 AACTCACACA TGCCCACCGT GCCCAGCACC TGAACTCCTG GGGGGACCGT

401 CAGTCTTCCT CTTCCCCCCA AAACCCAAGG ACACCCTCAT GATCTCCCGG

451 ACCCCTGAGG TCACATGCGT GGTGGTGGAC GTGAGCCACG AAGACCCTGA

501 GGTCAAGTTC AACTGGTACG TGGACGGCGT GGAGGTGCAT AATGCCAAGA

551 CAAAGCCGCG GGAGGAGCAG TACAACAGCA CGTACCGTGT GGTCAGCGTC

601 CTCACCGTCC TGCACCAGGA CTGGCTGAAT GGCAAGGAGT ACAAGTGCAA

651 GGTCTCCAAC AAAGCCCTCC CAGCCCCCAT CGAGAAAACC ATCTCCAAAG

701 CCAAAGGGCA GCCCCGAGAA CCACAGGTGT ACACCCTGCC CCCATCCCGG

751 GAGGAGATGA CCAAGAACCA GGTCAGCCTG ACCTGCCTGG TCAAAGGCTT

801 CTATCCCAGC GACATCGCCG TGGAGTGGGA GAGCAATGGG CAGCCGGAGA

851 ACAACTACGA CACCACGCCT CCCGTGCTGG ACTCCGACGG CTCCTTCTTC

901 CTCTATAGCG ACCTCACCGT GGACAAGAGC AGGTGGCAGC AGGGGAACGT

951 CTTCTCATGC TCCGTGATGC ATGAGGCTCT GCACAACCAC TACACGCAGA

1001 AGAGCCTCTC CCTGTCTCCG GGT
```

The mature ALK7-Fc fusion protein sequence (SEQ ID NO: 130) is expected to be as follows and may optionally be provided with a lysine added at the C-terminus.

```
                                                    (SEQ ID NO: 130)
   1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVY TLPPSREEMT KNQVSLTCLV KGFYPSDIAV

251 EWESNGQPEN NYDTTPPVLD SDGSFFLYSD LTVDKSRWQQ GNVFSCSVMH

301 EALHNHYTQK SLSLSPG
```

The complementary form of ALK7-Fc fusion polypeptide (SEQ ID NO: 133) is as follows:

```
                                                    (SEQ ID NO: 133)
   1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVCTLPPSR
```

```
251 EEMTKNQVSL SCAVKGFYPS DIAVEWESNG QPENNYKTTP PVLDSDGSFF

301 LVSKLTVDKS RWQQGNVFSC SVMHEALHNH YTQKSLSLSP GK
```

The leader sequence and linker sequence are underlined. To guide heterodimer formation with certain Fc fusion polypeptides disclosed herein, four amino acid substitutions can be introduced into the Fc domain of the ALK7 fusion polypeptide as indicated by double underline above. Furthermore, the C-terminal lysine residue of the Fc domain can be deleted. The amino acid sequence of SEQ ID NO: 133 may optionally be provided with the lysine removed from the C-terminus.

The mature ALK7-Fc fusion protein sequence (SEQ ID NO: 134) is expected to be as follows and may optionally be provided with the lysine removed from the C-terminus.

```
                                                (SEQ ID NO: 134)
  1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVC TLPPSREEMT KNQVSLSCAV KGFYPSDIAV

251 EWESNGQPEN NYKTTPPVLD SDGSFFLVSK LTVDKSRWQQ GNVFSCSVMH

301 EALHNHYTQK SLSLSPGK
```

In certain embodiments, the present disclosure relates to a protein complex comprising an ActRIIA polypeptide. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety.

The human ActRIIA precursor protein sequence is as follows:

```
                                                (SEQ ID NO: 137)
  1 MGAAAKLAFA VFLISCSSGA ILGRSETQEC LFFNANWEKD RTNQTGVEPC

51 YGDKDKRRHC FATWKNISGS IEIVKQGCWL DDINCYDRTD CVEKKDSPEV

101 YFCCCEGNMC NEKFSYFPEM EVTQPTSNPV TPKPPYYNIL LYSLVPLMLI

151 AGIVICAFWV YRHHKMAYPP VLVPTQDPGP PPPSPLLGLK PLQLLEVKAR

201 GRFGCVWKAQ LLNEYVAVKI FPIQDKQSWQ NEYEVYSLPG MKHENILQFI

251 GAEKRGTSVD VDLWLITAFH EKGSLSDFLK ANVVSWNELC HIAETMARGL

301 AYLHEDIPGL KDGHKPAISH RDIKSKNVLL KNNLTACIAD FGLALKFEAG

351 KSAGDTHGQV GTRRYMAPEV LEGAINFQRD AFLRIDMYAM GLVLWELASR
```

```
401 CTAADGPVDE YMLPFEEEIG QHPSLEDMQE VVVHKKKRPV LRDYWQKHAG

451 MAMLCETIEE CWDHDAEARL SAGCVGERIT QMQRLTNIIT TEDIVTVVTM

501 VTNVDFPPKE SSL
```

The signal peptide is indicated by a single underline; the extracellular domain is indicated in bold font; and the potential, endogenous N-linked glycosylation sites are indicated by a double underline.

The processed extracellular human ActRIIA polypeptide sequence is as follows:

(SEQ ID NO: 138)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP

The C-terminal "tail" of the extracellular domain is indicated by a single underline. The sequence with the "tail" deleted (a Δ15 sequence) is as follows:

(SEQ ID NO: 139)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

A nucleic acid sequence encoding the human ActRIIA precursor protein is shown in SEQ ID NO: 241, corresponding to nucleotides 159-1700 of Genbank Reference Sequence NM_001616.4. A nucleic acid sequence encoding a processed extracellular ActRIIA polypeptide is as shown in SEQ ID NO: 242.

A general formula for an active (e.g., ligand binding) ActRIIA polypeptide is one that comprises a polypeptide that starts at amino acid 30 and ends at amino acid 110 of SEQ ID NO: 137. Accordingly, ActRIIA polypeptides of the present disclosure may comprise a polypeptide that is at least 80%, 85%, 90%, 95%, 96%, 97%, 98%, 99%, or 100% identical to amino acids 30-110 of SEQ ID NO: 137. Optionally, ActRIIA polypeptides of the present disclosure comprise a polypeptide that is at least 80%, 85%, 90%, 95%, 96%, 97%, 98%, 99%, or 100% identical to amino acids amino acids 12-82 of SEQ ID NO: 137 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115), respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO: 137.

In certain embodiments, the disclosure relates to heteromultimers that comprise at least one ActRIIA polypeptide, which includes fragments, functional variants, and modified forms thereof. Preferably, ActRIIA polypeptides for use in accordance with inventions of the disclosure (e.g., heteromultimers comprising an ActRIIA polypeptide and uses thereof) are soluble (e.g., an extracellular domain of ActRIIA). In other preferred embodiments, ActRIIA polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ActRIIA polypeptide that is at least 70%, 75%, 80%, 85%, 90%, 95%, 97%, 98%, 99%, or 100% identical to the amino acid sequence of any one of SEQ ID NOs: 137, 138, 139, 140, 141, 144, or 145. In some embodiments, heteromultimers of the disclosure comprise at least one ActRIIA polypeptide that is at least 70%, 75%, 80%, 85%, 90%, 95%, 97%, 98%, 99%, or 100% identical to the amino acid sequence of any one of SEQ ID NOs: 137, 138, 139, 140, 141, 144, or 145.

In certain aspects, the disclosure relates to a heteromultimer that comprises an ActRIIA-Fc fusion protein. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-30 (e.g., amino acid residues 21, 22, 23, 24, 25, 26, 27, 28, 29, or 30) SEQ ID NO: 137, and ends at any one of amino acids 110-135 (e.g., 110, 111, 112, 113, 114, 115, 116, 117, 118, 119, 120, 121, 122, 123, 124, 125, 126, 127, 128, 129, 130, 131, 132, 133, 134 or 135) of SEQ ID NO: 137. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 137. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-135 of SEQ ID NO: 137. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 137, 138, 139, 140, 141, 142, 143, 144, 145, 146, and 147.

The ActRIIA-Fc polypeptide sequence (SEQ ID NO: 140) is shown below:

```
                                                    (SEQ ID NO: 140)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY
```

```
201 VDGVEVHNAK TKPREEQYNS TYRVVSVLTV LHQDWLNGKE YKCKVSNKAL

251 PAPIEKTISK AKGQPREPQV YTLPPSRKEM TKNQVSLTCL VKGFYPSDIA
                                 ‾

301 VEWESNGQPE NNYKTTPPVL KSDGSFFLYS KLTVDKSRWQ QGNVFSCSVM
                         ‾

351 HEALHNHYTQ KSLSLSPGK
```

The leader sequence and linker sequence are underlined. To promote formation of the ActRIIA-Fc:ActRIIB-Fc heterodimer rather than either of the possible homodimeric complexes, two amino acid substitutions (replacing acidic amino acids with lysine) can be introduced into the Fc domain of the ActRIIA fusion protein as indicated by double underline above. The amino acid sequence of SEQ ID NO: 140 may optionally be provided with the lysine removed from the C-terminus.

This ActRIIA-Fc fusion protein is encoded by the following nucleic acid sequence (SEQ ID NO: 256):

```
                                                (SEQ ID NO: 256)
   1 ATGGATGCAA TGAAGAGAGG GCTCTGCTGT GTGCTGCTGC TGTGTGGAGC

51 AGTCTTCGTT TCGCCCGGCG CCGCTATACT TGGTAGATCA GAAACTCAGG

101 AGTGTCTTTT CTTTAATGCT AATTGGGAAA AGACAGAAC CAATCAAACT

151 GGTGTTGAAC CGTGTTATGG TGACAAAGAT AAACGGCGGC ATTGTTTTGC

201 TACCTGGAAG AATATTTCTG GTTCCATTGA ATAGTGAAA CAAGGTTGTT

251 GGCTGGATGA TATCAACTGC TATGACAGGA CTGATTGTGT AGAAAAAAAA

301 GACAGCCCTG AAGTATATTT CTGTTGCTGT GAGGGCAATA TGTGTAATGA

351 AAAGTTTTCT TATTTTCCGG AGATGGAAGT CACACAGCCC ACTTCAAATC

401 CAGTTACACC TAAGCCACCC ACCGGTGGTG GAACTCACAC ATGCCCACCG

451 TGCCCAGCAC CTGAACTCCT GGGGGGACCG TCAGTCTTCC TCTTCCCCCC

501 AAAACCCAAG GACACCCTCA TGATCTCCCG GACCCCTGAG GTCACATGCG

551 TGGTGGTGGA CGTGAGCCAC GAAGACCCTG AGGTCAAGTT CAACTGGTAC

601 GTGGACGGCG TGGAGGTGCA TAATGCCAAG ACAAAGCCGC GGGAGGAGCA

651 GTACAACAGC ACGTACCGTG TGGTCAGCGT CCTCACCGTC CTGCACCAGG

701 ACTGGCTGAA TGGCAAGGAG TACAAGTGCA AGGTCTCCAA CAAAGCCCTC

751 CCAGCCCCCA TCGAGAAAAC CATCTCCAAA GCCAAAGGGC AGCCCCGAGA

801 ACCACAGGTG TACACCCTGC CCCCATCCCG GAAGGAGATG ACCAAGAACC

851 AGGTCAGCCT GACCTGCCTG GTCAAAGGCT TCTATCCCAG CGACATCGCC

901 GTGGAGTGGG AGAGCAATGG GCAGCCGGAG AACAACTACA AGACCACGCC

951 TCCCGTGCTG AAGTCCGACG GCTCCTTCTT CCTCTATAGC AAGCTCACCG

1001 TGGACAAGAG CAGGTGGCAG CAGGGGAACG TCTTCTCATG CTCCGTGATG

1051 CATGAGGCTC TGCACAACCA CTACACGCAG AAGAGCCTCT CCCTGTCTCC

1101 GGGTAAA
```

The mature ActRIIA-Fc fusion polypeptide (SEQ ID NO: 141) is as follows and may optionally be provided with the lysine removed from the C-terminus.

```
                                              (SEQ ID NO: 141)
   1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM

101 EVTQPTSNPV TPKPPTGGGT HTCPPCPAPE LLGGPSVFLF PPKPKDTLMI

151 SRTPEVTCVV VDVSHEDPEV KFNWYVDGVE VHNAKTKPRE EQYNSTYRVV
```

```
201 SVLTVLHQDW LNGKEYKCKV SNKALPAPIE KTISKAKGQP REPQVYTLPP

251 SRKEMTKNQV SLTCLVKGFY PSDIAVEWES NGQPENNYKT TPPVLKSDGS

301 FFLYSKLTVD KSRWQQGNVF SCSVMHEALH NHYTQKSLSL SPGK
```

The ActRIIA-Fc polypeptide sequence (SEQ ID NO: 144) is shown below:

```
                                                    (SEQ ID NO: 144)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY

201 VDGVEVHNAK TKPREEQYNS TYRVVSVLTV LHQDWLNGKE YKCKVSNKAL

251 PAPIEKTISK AKGQPREPQV YTLPPCREEM TKNQVSLWCL VKGFYPSDIA

301 VEWESNGQPE NNYKTTPPVL DSDGSFFLYS KLTVDKSRWQ QGNVFSCSVM

351 HEALHNHYTQ KSLSLSPGK
```

The leader sequence and linker sequence are underlined. To promote formation of the ActRIIA-Fc:ALK4-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 144 may optionally be provided with the lysine removed from the C-terminus.

The mature ActRIIA-Fc fusion polypeptide (SEQ ID NO: 145) is as follows and may optionally be provided with the lysine removed from the C-terminus.

```
                                                    (SEQ ID NO: 145)
  1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM

101 EVTQPTSNPV TPKPPTGGGT HTCPPCPAPE LLGGPSVFLF PPKPKDTLMI

151 SRTPEVTCVV VDVSHEDPEV KFNWYVDGVE VHNAKTKPRE EQYNSTYRVV

201 SVLTVLHQDW LNGKEYKCKV SNKALPAPIE KTISKAKGQP REPQVYTLPP

251 CREEMTKNQV SLWCLVKGFY PSDIAVEWES NGQPENNYKT TPPVLDSDGS

301 FFLYSKLTVD KSRWQQGNVF SCSVMHEALH NHYTQKSLSL SPGK
```

In certain aspects, the present disclosure relates to protein complexes that comprise a BMPRII polypeptide. As used herein, the term "BMPRII" refers to a family of bone morphogenetic protein receptor type II (BMPRII) proteins from any species and variants derived from such BMPRII proteins by mutagenesis or other modification. Reference to BMPRII herein is understood to be a reference to any one of the currently identified forms. Members of the BMPRII family are generally transmembrane proteins, composed of a ligand-binding extracellular domain with a cysteine-rich region, a transmembrane domain, and a cytoplasmic domain with predicted serine/threonine kinase activity.

The term "BMPRII polypeptide" includes polypeptides comprising any naturally occurring polypeptide of a BMPRII family member as well as any variants thereof (including mutants, fragments, fusions, and peptidomimetic forms) that retain a useful activity.

A human BMPRII precursor protein sequence (NCBI Ref Seq NP_001195.2) is as follows:

```
                                                    (SEQ ID NO: 148)
  1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET

151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP
```

```
251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERN LSHNRRVPKI GPYPDYSSSS

551 YIEDSIHHTD SIVKNISSEH SMSSTPLTIG EKNRNSINYE RQQAQARIPS

601 PETSVTSLST NTTTTNTTGL TPSTGMTTIS EMPYPDETNL HTTNVAQSIG

651 PTPVCLQLTE EDLETNKLDP KEVDKNLKES SDENLMEHSL KQFSGPDPLS

701 STSSSLLYPL IKLAVEATGQ QDFTQTANGQ ACLIPDVLPT QIYPLPKQQN

751 LPKRPTSLPL NTKNSTKEPR LKFGSKHKSN LKQVETGVAK MNTINAAEPH

801 VVTVTMNGVA GRNHSVNSHA ATTQYANGTV LSGQTTNIVT HRAQEMLQNQ

851 FIGEDTRLNI NSSPDEHEPL LRREQQAGHD EGVLDRLVDR RERPLEGGRT

901 NSNNNNSNPC SEQDVLAQGV PSTAADPGPS KPRRAQRPNS LDLSATNVLD

951 GSSIQIGEST QDGKSGSGEK IKKRVKTPYS LKRWRPSTWV ISTESLDCEV

1001 NNNGSNRAVH SKSSTAVYLA EGGTATTMVS KDIGMNCL
```

The signal peptide is indicated by a single underline and an extracellular domain is indicated in bold font.

A processed extracellular BMPRII polypeptide sequence is as follows:

```
                                         (SEQ ID NO: 150)
SQNQERLCAFKDPYQQDLGIGESRISHENGTILCSKGSTCYGLWEKSKGD

INLVKQGCWSHIGDPQECHYEECVVTTTPPSIQNGTYRFCCCSTDLCNVN

FTENFPPPDTTPLSPPHSFNRDET
```

A nucleic acid sequence encoding BMPRII precursor protein is shown in SEQ ID NO: 205, as follows nucleotides 1149-4262 of Genbank Reference Sequence NM_001204.6. A nucleic acid sequence encoding an extracellular BMPRII polypeptide is shown in SEQ ID NO: 206.

An alternative isoform of BMPRII, isoform 2 (GenBank: AAA86519.1) is as follows:

```
                                         (SEQ ID NO: 149)
   1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET

151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP

251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERR
```

The signal peptide is indicated by a single underline and the extracellular domain is indicated in bold font.

A processed extracellular BMPRII polypeptide sequence (isoform 2) is as follows:

```
                                         (SEQ ID NO: 151)
SQNQERLCAFKDPYQQDLGIGESRISHENGTILCSKGSTCYGLWEKSKGD

INLVKQGCWSHIGDPQECHYEECVVTTTPPSIQNGTYRFCCCSTDLCNVN

FTENFPPPDTTPLSPPHSFNRDET
```

A nucleic acid sequence encoding human BMPRII precursor protein (isoform 2) is shown in SEQ ID NO: 207, corresponding to nucleotides 163-1752 of Genbank Reference Sequence U25110.1. The signal sequence is underlined. A nucleic acid sequence encoding an extracellular BMPRII polypeptide (isoform 2) is shown in SEQ ID NO: 208.

In certain embodiments, the disclosure relates to heteromultimers that comprise at least one BMPRII polypeptide, which includes fragments, functional variants, and modified forms thereof. Preferably, BMPRII polypeptides for use in accordance with inventions of the disclosure (e.g., heteromultimers comprising a BMPRII polypeptide and uses thereof) are soluble (e.g., an extracellular domain of BMPRII). In other preferred embodiments, BMPRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one BMPRII polypeptide that is at least 70%, 75%, 80%, 85%, 90%, 95%, 97%, 98%, 99%, or 100% identical to the amino acid sequence of SEQ ID NO: 148, 150, 149, 151, 152, 153, 156, or 157. In some embodiments, heteromultimer complexes of the disclosure consist or consist essentially of at least one BMPRII polypeptide that is at least 70%, 75%, 80%, 85%, 90%, 95%, 97%, 98%, 99%, or 100% identical to the amino acid sequence of SEQ ID NO: 148, 150, 149, 151, 152, 153, 156, or 157.

In certain aspects, the disclosure relates to a heteromultimer that comprises an BMPRII-Fc fusion protein. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 27-34 (e.g., amino acid residues 27, 28, 29, 30, 31, 32, 33, and 34) SEQ ID NO: 148 or 149, and ends at any one of amino acids 123-150 (e.g., amino acid residues 123, 124, 125, 126, 127, 128, 129, 130, 131, 132, 133, 134, 135, 136, 137, 138, 139, 140, 141, 142, 143, 144, 145, 146, 147, 148, 149, and 150) of SEQ ID NO: 148 or 149. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-123 of SEQ ID NO: 148 or 149. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 27-150 of SEQ ID NO: 148 or 149. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 148, 150, 149, 151, 152, 153, 154, 155, 156, 157, 158, and 159.

The BMPRII-Fc polypeptide sequence (SEQ ID NO: 152) is shown below:

```
                                                       (SEQ ID NO: 152)
  1 MDAMKRGLCC VLLLCGAVFV SPGASQNQER LCAFKDPYQQ DLGIGESRIS

51 HENGTILCSK GSTCYGLWEK SKGDINLVKQ GCWSHIGDPQ ECHYEECVVT

101 TTPPSIQNGT YRFCCCSTDL CNVNFTENFP PPDTTPLSPP HSFNRDETGG

151 GTHTCPPCPA PELLGGPSVF LFPPKPKDTL MISRTPEVTC VVVDVSHEDP

201 EVKFNWYVDG VEVHNAKTKP REEQYNSTYR VVSVLTVLHQ DWLNGKEYKC

251 KVSNKALPAP IEKTISKAKG QPREPQVYTL PPSRKEMTKN QVSLTCLVKG

301 FYPSDIAVEW ESNGQPENNY KTTPPVLKSD GSFFLYSKLT VDKSRWQQGN

351 VFSCSVMHEA LHNHYTQKSL SLSPGK
```

The leader sequence and linker sequence are underlined. To promote formation of the BMPRII-Fc:ActRIIB-Fc heterodimer rather than either of the possible homodimeric complexes, two amino acid substitutions (replacing acidic amino acids with lysine) can be introduced into the Fc domain of the BMPRII-Fc fusion protein as indicated by double underline above. The amino acid sequence of SEQ ID NO: 152 may optionally be provided with the lysine removed from the C-terminus.

This BMPRII-Fc fusion protein is encoded by the following nucleic acid sequence (SEQ ID NO: 257):

```
                                                       (SEQ ID NO: 257)
  1 ATGGATGCAA TGAAGAGAGG GCTCTGCTGT GTGCTGCTGC TGTGTGGAGC

51 AGTCTTCGTT TCGCCCGGCG CCTCGCAGAA TCAAGAACGC CTATGTGCGT

101 TTAAAGATCC GTATCAGCAA GACCTTGGGA TAGGTGAGAG TAGAATCTCT

151 CATGAAAATG GGACAATATT ATGCTCGAAA GGTAGCACCT GCTATGGCCT

201 TTGGGAGAAA TCAAAGGGG ACATAAATCT TGTAAAACAA GGATGTTGGT

251 CTCACATTGG AGATCCCCAA GAGTGTCACT ATGAAGAATG TGTAGTAACT

301 ACCACTCCTC CCTCAATTCA GAATGGAACA TACCGTTTCT GCTGTTGTAG

351 CACAGATTTA TGTAATGTCA ACTTTACTGA GAATTTTCCA CCTCCTGACA

401 CAACACCACT CAGTCCACCT CATTCATTTA ACCGAGATGA GACCGGTGGT
```

```
-continued
 451 GGAACTCACA CATGCCCACC GTGCCCAGCA CCTGAACTCC TGGGGGGACC

501 GTCAGTCTTC CTCTTCCCCC CAAAACCCAA GGACACCCTC ATGATCTCCC

551 GGACCCCTGA GGTCACATGC GTGGTGGTGG ACGTGAGCCA CGAAGACCCT

601 GAGGTCAAGT TCAACTGGTA CGTGGACGGC GTGGAGGTGC ATAATGCCAA

651 GACAAAGCCG CGGGAGGAGC AGTACAACAG CACGTACCGT GTGGTCAGCG

701 TCCTCACCGT CCTGCACCAG GACTGGCTGA ATGGCAAGGA GTACAAGTGC

751 AAGGTCTCCA ACAAAGCCCT CCCAGCCCCC ATCGAGAAAA CCATCTCCAA

801 AGCCAAAGGG CAGCCCCGAG AACCACAGGT GTACACCCTG CCCCCATCCC

851 GGAAGGAGAT GACCAAGAAC CAGGTCAGCC TGACCTGCCT GGTCAAAGGC

901 TTCTATCCCA GCGACATCGC CGTGGAGTGG GAGAGCAATG GGCAGCCGGA

951 GAACAACTAC AAGACCACGC CTCCCGTGCT GAAGTCCGAC GGCTCCTTCT

1001 TCCTCTATAG CAAGCTCACC GTGGACAAGA GCAGGTGGCA GCAGGGGAAC

1051 GTCTTCTCAT GCTCCGTGAT GCATGAGGCT CTGCACAACC ACTACACGCA

1101 GAAGAGCCTC TCCCTGTCTC CGGGTAAA
```

The mature BMPRII-Fc fusion polypeptide (SEQ ID NO: 153) is as follows and may optionally be provided with the lysine removed from the C-terminus.

```
                                              (SEQ ID NO: 153)
  1 SQNQERLCAF KDPYQQDLGI GESRISHENG TILCSKGSTC YGLWEKSKGD

51 INLVKQGCWS HIGDPQECHY EECVVTTTPP SIQNGTYRFC CCSTDLCNVN

101 FTENFPPPDT TPLSPPHSFN RDETGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR KEMTKNQVSL TCLVKGFYPS DIAVEWESNG QPENNYKTTP

301 PVLKSDGSFF LYSKLTVDKS RWQQGNVFSC SVMHEALHNH YTQKSLSLSP

351 GK
```

The BMPRII-Fc polypeptide sequence (SEQ ID NO: 156) is shown below:

```
                                              (SEQ ID NO: 156)
  1 MDAMKRGLCC VLLLCGAVFV SPGASQNQER LCAFKDPYQQ DLGIGESRIS

51 HENGTILCSK GSTCYGLWEK SKGDINLVKQ GCWSHIGDPQ ECHYEECVVT

101 TTPPSIQNGT YRFCCCSTDL CNVNFTENFP PDTTPLSPP HSFNRDETGG

151 GTHTCPPCPA PELLGGPSVF LFPPKPKDTL MISRTPEVTC VVVDVSHEDP

201 EVKFNWYVDG VEVHNAKTKP REEQYNSTYR VVSVLTVLHQ DWLNGKEYKC

251 KVSNKALPAP IEKTISKAKG QPREPQVYTL PPCREEMTKN QVSLWCLVKG

301 FYPSDIAVEW ESNGQPENNY KTTPPVLDSD GSFFLYSKLT VDKSRWQQGN

351 VFSCSVMHEA LHNHYTQKSL SLSPGK
```

The leader sequence and linker sequence are underlined. To promote formation of the BMPRII-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 156 may optionally be provided with the lysine removed from the C-terminus.

The mature BMPRII-Fc fusion polypeptide (SEQ ID NO: 157) is as follows and may optionally be provided with the lysine (K) removed from the C-terminus.

```
                                                     (SEQ ID NO: 157)
  1  SQNQERLCAF  KDPYQQDLGI  GESRISHENG  TILCSKGSTC  YGLWEKSKGD

51  INLVKQGCWS  HIGDPQECHY  EECVVTTTPP  SIQNGTYRFC  CCSTDLCNVN

101  FTENFPPPDT  TPLSPPHSFN  RDETGGGTHT  CPPCPAPELL  GGPSVFLFPP

151  KPKDTLMISR  TPEVTCVVVD  VSHEDPEVKF  NWYVDGVEVH  NAKTKPREEQ

201  YNSTYRVVSV  LTVLHQDWLN  GKEYKCKVSN  KALPAPIEKT  ISKAKGQPRE

251  PQVYTLPPCR  EEMTKNQVSL  WCLVKGFYPS  DIAVEWESNG  QPENNYKTTP

301  PVLDSDGSFF  LYSKLTVDKS  RWQQGNVFSC  SVMHEALHNH  YTQKSLSLSP

351  GK
```

In certain aspects, the present disclosure relates to protein complexes that comprise a TGFBRII polypeptide. As used herein, the term "TGFBRII" refers to a family of transforming growth factor-beta receptor II (TGFBRII) proteins from any species and variants derived from such proteins by mutagenesis or other modification. Reference to TGFBRII herein is understood to be a reference to any one of the currently identified forms. Members of the TGFBRII family are generally transmembrane proteins, composed of a ligand-binding extracellular domain with a cysteine-rich region, a transmembrane domain, and a cytoplasmic domain with predicted serine/threonine kinase activity.

The term "TGFBRII polypeptide" includes polypeptides comprising any naturally occurring polypeptide of a TGFBRII family member as well as any variants thereof (including mutants, fragments, fusions, and peptidomimetic forms) that retain a useful activity.

A human TGFBRII precursor protein sequence (NCBI Ref Seq NP_003233.4) is as follows:

```
                                                     (SEQ ID NO: 194)
  1  MGRGLLRGLW  PLHIVLWTRI  ASTIPPHVQK  SVNNDMIVTD  NNGAVKFPQL

51  CKFCDVRFST  CDNQKSCMSN  CSITSICEKP  QEVCVAVWRK  NDENITLETV

101  CHDPKLPYHD  FILEDAASPK  CIMKEKKKPG  ETFFMCSCSS  DECNDNIIFS

151  EEYNTSNPDL  LLVIFQVTGI  SLLPPLGVAI  SVIIIFYCYR  VNRQQKLSST

201  WETGKTRKLM  EFSEHCAIIL  EDDRSDISST  CANNINHNTE  LLPIELDTLV

251  GKGRFAEVYK  AKLKQNTSEQ  FETVAVKIFP  YEEYASWKTE  KDIFSDINLK

301  HENILQFLTA  EERKTELGKQ  YWLITAFHAK  GNLQEYLTRH  VISWEDLRKL

351  GSSLARGIAH  LHSDHTPCGR  PKMPIVHRDL  KSSNILVKND  LTCCLCDFGL

401  SLRLDPTLSV  DDLANSGQVG  TARYMAPEVL  ESRMNLENVE  SFKQTDVYSM

451  ALVLWEMTSR  CNAVGEVKDY  EPPFGSKVRE  HPCVESMKDN  VLRDRGRPEI

501  PSFWLNHQGI  QMVCETLTEC  WDHDPEARLT  AQCVAERFSE  LEHLDRLSGR

551  SCSEEKIPED  GSLNTTK
```

The signal peptide is indicated by a single underline and the extracellular domain is indicated in bold font.

A processed extracellular TGFBRII polypeptide sequence is as follows:

```
                                                     (SEQ ID NO: 195)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDLLLVIFQ
```

A nucleic acid sequence encoding TGFBRII precursor protein is shown in SEQ ID NO:196, corresponding to nucleotides 383-2083 of Genbank Reference Sequence NM_003242.5. A nucleic acid sequence encoding a processed extracellular TGFBRII polypeptide is shown in SEQ ID NO: 197.

An alternative isoform of TGFBRII, isoform A (NP_001020018.1), is as follows:

```
                                                       (SEQ ID NO: 198)
  1 MGRGLLRGLW PLHIVLWTRI ASTIPPHVQK SDVEMEAQKD EIICPSCNRT

51 AHPLRHINND MIVTDNNGAV KFPQLCKFCD VRFSTCDNQK SCMSNCSITS

101 ICEKPQEVCV AVWRKNDENI TLETVCHDPK LPYHDFILED AASPKCIMKE

151 KKKPGETFFM CSCSSDECND NIIFSEEYNT SNPDLLLVIF QVTGISLLPP

201 LGVAISVIII FYCYRVNRQQ KLSSTWETGK TRKLMEFSEH CAIILEDDRS

251 DISSTCANNI NHNTELLPIE LDTLVGKGRF AEVYKAKLKQ NTSEQFETVA

301 VKIFPYEEYA SWKTEKDIFS DINLKHENIL QFLTAEERKT ELGKQYWLIT

351 AFHAKGNLQE YLTRHVISWE DLRKLGSSLA RGIAHLHSDH TPCGRPKMPI

401 VHRDLKSSNI LVKNDLTCCL CDFGLSLRLD PTLSVDDLAN SGQVGTARYM

451 APEVLESRMN LENVESFKQT DVYSMALVLW EMTSRCNAVG EVKDYEPPFG

501 SKVREHPCVE SMKDNVLRDR GRPEIPSFWL NHQGIQMVCE TLTECWDHDP

551 EARLTAQCVA ERFSELEHLD RLSGRSCSEE KIPEDGSLNT TK
```

The signal peptide is indicated by a single underline and the extracellular domain is indicated in bold font.

A processed extracellular TGFBRII polypeptide sequence (isoform A) is as follows:

```
                                                       (SEQ ID NO: 199)
TIPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENITL

ETVCHDPKLPYHDFILEDAASPKCIMKEKKKPGETFFMCSCSSDECNDNI

IFSEEYNTSNPDLLLVIFQ
```

A nucleic acid sequence encoding the TGFBRII precursor protein (isoform A) is shown in SEQ ID NO: 202, corresponding to nucleotides 383-2158 of Genbank Reference Sequence NM_001024847.2. A nucleic acid sequence encoding the processed extracellular TGFBRII polypeptide (isoform A) is shown in SEQ ID NO: 203.

Either of the foregoing TGFβRII isoforms (SEQ ID NOs: 194, 195, 198, and 199) could incorporate an insertion of 36 amino acids (SEQ ID NO: 204) between the pair of glutamate residues (positions 151 and 152 of SEQ ID NO: 194; positions 129 and 130 of SEQ ID NO: 195; positions 176 and 177 of SEQ ID NO: 198; or positions 154 and 155 of SEQ ID NO: 199) located near the C-terminus of the TGFβRII ECD, as occurs naturally in the TGFβRII isoform C (Konrad et al., BMC Genomics 8:318, 2007).

```
                                                       (SEQ ID NO: 204)
GRCKIRHIGS NNRLQRSTCQ NTGWESAHVM KTPGFR
```

In certain embodiments, the disclosure relates to heteromultimers that comprise at least one TGFBRII polypeptide, which includes fragments, functional variants, and modified forms thereof. Preferably, TGFBRII polypeptides for use in accordance with inventions of the disclosure (e.g., heteromultimers comprising a TGFBRII polypeptide and uses thereof) are soluble (e.g., an extracellular domain of TGFBRII). In other preferred embodiments, TGFBRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one TGFBRII polypeptide that is at least 70%, 75%, 80%, 85%, 90%, 95%, 97%, 98%, 99%, or 100% identical to the amino acid sequence of SEQ ID NOs: 194, 195, 198, or 199, with or without insertion of SEQ ID NO: 204 as described above. In some embodiments, heteromultimer complexes of the disclosure consist or consist essentially of at least one TGFBRII polypeptide that is at least 70%, 75%, 80%, 85%, 90%, 95%, 97%, 98%, 99%, or 100% identical to the amino acid sequence of SEQ ID NOs: 194, 195, 198, or 199, with or without insertion of SEQ ID NO: 204.

In certain aspects, the disclosure relates to a heteromultimer that comprises an TGFBII-Fc fusion protein. In some embodiments, the TGFBII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-44 (e.g., 23, 24, 25, 26, 27, 28, 29, 30, 31, 32, 33, 34, 35, 36, 37, 38, 39, 40, 41, 42, 43 or 44) of SEQ ID NO: 160, and ends at any one of amino acids 168-191 (e.g., 168, 169, 170, 171, 172, 173, 174, 175, 176, 177, 178, 179, 180, 181, 182, 183, 184, 185, 186, 187, 188, 189, 190 or 191) of SEQ ID NO: 160. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 44-168 of SEQ ID NO: 160. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-191 of SEQ ID NO: 160. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 161, 162, 160, 163, 164, 165, 166, 167, 168, 169, 170, 171, 172, 173, 174, 175, 176, 177, 178, and 179. In some embodiments, the TGFBII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-51 (e.g., 23, 24, 25, 26, 27, 28, 29, 30, 31, 32, 33, 34, 35, 36, 37, 38, 39, 40, 41, 42, 43, 44, 45, 46, 47, 48, 49, 50, and 51) of SEQ ID NO: 161, and ends at any one of amino acids 143-166 (e.g., 143, 144, 145, 146, 147, 148, 149, 150, 151, 152, 153, 154, 155, 156, 157, 158, 159, 160, 161, 162, 163, 164, 165, and 166) of SEQ ID NO: 161. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 51-143 of SEQ ID NO: 161. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-166 of SEQ ID NO: 161.

A human TGFBRII precursor protein sequence (NCBI Ref Seq NP_003233.4) is as follows:

```
                                                          (SEQ ID NO: 161)
  1 MGRGLLRGLW PLHIVLWTRI ASTIPPHVQK SVNNDMIVTD NNGAVKFPQL

51 CKFCDVRFST CDNQKSCMSN CSITSICEKP QEVCVAVWRK NDENITLETV

101 CHDPKLPYHD FILEDAASPK CIMKEKKKPG ETFFMCSCSS DECNDNIIFS

151 EEYNTSNPDL LLVIFQVTGI SLLPPLGVAI SVIIIFYCYR VNRQQKLSST

201 WETGKTRKLM EFSEHCAIIL EDDRSDISST CANNINHNTE LLPIELDTLV

251 GKGRFAEVYK AKLKQNTSEQ FETVAVKIFP YEEYASWKTE KDIFSDINLK

301 HENILQFLTA EERKTELGKQ YWLITAFHAK GNLQEYLTRH VISWEDLRKL

351 GSSLARGIAH LHSDHTPCGR PKMPIVHRDL KSSNILVKND LTCCLCDFGL

401 SLRLDPTLSV DDLANSGQVG TARYMAPEVL ESRMNLENVE SFKQTDVYSM

451 ALVLWEMTSR CNAVGEVKDY EPPFGSKVRE HPCVESMKDN VLRDRGRPEI

501 PSFWLNHQGI QMVCETLTEC WDHDPEARLT AQCVAERFSE LEHLDRLSGR

551 SCSEEKIPED GSLNTTK
```

The signal peptide is indicated by a single underline and the extracellular domain is indicated in bold font.

A processed extracellular TGFBRII polypeptide sequence is as follows:

```
                                                          (SEQ ID NO: 162)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDLLLVIFQ
```

An alternative isoform of TGFBRII, isoform A (NP_001020018.1), is as follows:

```
                                                          (SEQ ID NO: 160)
  1 MGRGLLRGLWPLHIVLWTRIASTIPPHVQK SDVEMEAQKD EIICPSCNRT

51 AHPLRHINND MIVTDNNGAV KFPQLCKFCD VRFSTCDNQK SCMSNCSITS

101 ICEKPQEVCV AVWRKNDENI TLETVCHDPK LPYHDFILED AASPKCIMKE

151 KKKPGETFFM CSCSSDECND NIIFSEEYNT SNPDLLLVIF QVTGISLLPP

201 LGVAISVIII FYCYRVNRQQ KLSSTWETGK TRKLMEFSEH CAIILEDDRS

251 DISSTCANNI NHNTELLPIE LDTLVGKGRF AEVYKAKLKQ NTSEQFETVA

301 VKIFPYEEYA SWKTEKDIFS DINLKHENIL QFLTAEERKT ELGKQYWLIT

351 AFHAKGNLQE YLTRHVISWE DLRKLGSSLA RGIAHLHSDH TPCGRPKMPI

401 VHRDLKSSNI LVKNDLTCCL CDFGLSLRLD PTLSVDDLAN SGQVGTARYM

451 APEVLESRMN LENVESFKQT DVYSMALVLW EMTSRCNAVG EVKDYEPPFG

501 SKVREHPCVE SMKDNVLRDR GRPEIPSFWL NHQGIQMVCE TLTECWDHDP

551 EARLTAQCVA ERFSELEHLD RLSGRSCSEE KIPEDGSLNT TK
```

The signal peptide is indicated by a single underline and the extracellular domain is indicated in bold font.

A processed extracellular TGFBRII polypeptide sequence (isoform A) is as follows:

(SEQ ID NO: 163)
TIPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENITL

ETVCHDPKLPYHDFILEDAASPKCIMKEKKKPGETFFMCSCSSDECNDNI

IFSEEYNTSNPDLLLVIFQ

The TGFβRII$_{SHORT}$-Fc polypeptide sequence (SEQ ID NO: 164) is shown below:

(SEQ ID NO: 164)
```
  1 MDAMKRGLCC VLLLCGAVFV SPGATIPPHV QKSVNNDMIV TDNNGAVKFP
 51 QLCKFCDVRF STCDNQKSCM SNCSITSICE KPQEVCVAVW RKNDENITLE
101 TVCHDPKLPY HDFILEDAAS PKCIMKEKKK PGETFFMCSC SSDECNDNII
151 FSEEYNTSNP DTGGGTHTCP PCPAPELLGG PSVFLFPPKP KDTLMISRTP
201 EVTCVVVDVS HEDPEVKFNW YVDGVEVHNA KTKPREEQYN STYRVVSVLT
251 VLHQDWLNGK EYKCKVSNKA LPAPIEKTIS KAKGQPREPQ VYTLPPSRKE
301 MTKNQVSLTC LVKGFYPSDI AVEWESNGQP ENNYKTTPPV LKSDGSFFLY
351 SKLTVDKSRW QQGNVFSCSV MHEALHNHYT QKSLSLSPGK
```

The leader sequence and linker sequence are underlined. To promote formation of the TGFβRII$_{SHORT}$-Fc:ActRIIB-Fc heterodimer rather than either of the possible homodimeric complexes, two amino acid substitutions (replacing acidic amino acids with lysine) can be introduced into the Fc domain of the TGFβRII$_{SHORT}$-Fc fusion protein as indicated by double underline above. The amino acid sequence of SEQ ID NO: 164 may optionally be provided with the lysine removed from the C-terminus.

This TGFβRII$_{SHORT}$-Fc fusion protein is encoded by the following nucleic acid sequence (SEQ ID NO: 259):

(SEQ ID NO: 259)
```
  1 ATGGATGCAA TGAAGAGAGG GCTCTGCTGT GTGCTGCTGC TGTGTGGAGC
 51 AGTCTTCGTT TCGCCCGGCG CCACGATCCC ACCGCACGTT CAGAAGTCGG
101 TTAATAACGA CATGATAGTC ACTGACAACA ACGGTGCAGT CAAGTTTCCA
151 CAACTGTGTA AATTTTGTGA TGTGAGATTT TCCACCTGTG ACAACCAGAA
201 ATCCTGCATG AGCAACTGCA GCATCACCTC CATCTGTGAG AAGCCACAGG
251 AAGTCTGTGT GGCTGTATGG AGAAAGAATG ACGAGAACAT AACACTAGAG
301 ACAGTTTGCC ATGACCCCAA GCTCCCCTAC CATGACTTTA TTCTGGAAGA
351 TGCTGCTTCT CCAAAGTGCA TTATGAAGGA AAAAAAAAAG CCTGGTGAGA
401 CTTTCTTCAT GTGTTCCTGT AGCTCTGATG AGTGCAATGA CAACATCATC
451 TTCTCAGAAG AATATAACAC CAGCAATCCT GACACCGGTG GTGGAACTCA
501 CACATGCCCA CCGTGCCCAG CACCTGAACT CCTGGGGGGA CCGTCAGTCT
551 TCCTCTTCCC CCCAAAACCC AAGGACACCC TCATGATCTC CCGGACCCCT
601 GAGGTCACAT GCGTGGTGGT GGACGTGAGC CACGAAGACC CTGAGGTCAA
651 GTTCAACTGG TACGTGGACG GCGTGGAGGT GCATAATGCC AAGACAAAGC
701 CGCGGGAGGA GCAGTACAAC AGCACGTACC GTGTGGTCAG CGTCCTCACC
751 GTCCTGCACC AGGACTGGCT GAATGGCAAG GAGTACAAGT GCAAGGTCTC
801 CAACAAAGCC CTCCCAGCCC CCATCGAGAA AACCATCTCC AAAGCCAAAG
```

-continued

```
 851  GGCAGCCCCG AGAACCACAG GTGTACACCC TGCCCCCATC CCGGAAGGAG

901  ATGACCAAGA ACCAGGTCAG CCTGACCTGC CTGGTCAAAG GCTTCTATCC

951  CAGCGACATC GCCGTGGAGT GGGAGAGCAA TGGGCAGCCG GAGAACAACT

1001  ACAAGACCAC GCCTCCCGTG CTGAAGTCCG ACGGCTCCTT CTTCCTCTAT

1051  AGCAAGCTCA CCGTGGACAA GAGCAGGTGG CAGCAGGGGA ACGTCTTCTC

1101  ATGCTCCGTG ATGCATGAGG CTCTGCACAA CCACTACACG CAGAAGAGCC

1151  TCTCCCTGTC TCCGGGTAAA
```

The mature TGFβRII$_{SHORT}$-Fc fusion polypeptide (SEQ ID NO: 165) is as follows and may optionally be provided with the lysine removed from the C-terminus.

```
                                                 (SEQ ID NO: 165)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPSRKEMTKN QVSLTCLVKG FYPSDIAVEW

301 ESNGQPENNY KTTPPVLKSD GSFFLYSKLT VDKSRWQQGN VFSCSVMHEA

351 LHNHYTQKSL SLSPGK
```

The TGFβRII$_{LONG}$-Fc polypeptide sequence (SEQ ID NO: 166) is shown below:

```
                                                 (SEQ ID NO: 166)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PSRKEMTKNQ VSLTCLVKGF YPSDIAVEWE

351 SNGQPENNYK TTPPVLKSDG SFFLYSKLTV DKSRWQQGNV FSCSVMHEAL

401 HNHYTQKSLS LSPGK
```

The leader sequence and linker sequence are underlined. To promote formation of the TGFβRII$_{LONG}$-Fc:ActRIIB-Fc heterodimer rather than either of the possible homodimeric complexes, two amino acid substitutions (replacing acidic amino acids with lysine) can be introduced into the Fc domain of the TGFβRII$_{LONG}$-Fc fusion protein as indicated by double underline above. The amino acid sequence of SEQ ID NO: 166 may optionally be provided with the lysine removed from the C-terminus.

This TGFβRII$_{LONG}$-Fc fusion protein is encoded by the following nucleic acid sequence (SEQ ID NO: 260):

```
                                                 (SEQ ID NO: 260)
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT
```

```
 151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA ACTCACACAT GCCCACCGTG CCCAGCACCT

601 GAACTCCTGG GGGGACCGTC AGTCTTCCTC TTCCCCCCAA AACCCAAGGA

651 CACCCTCATG ATCTCCCGGA CCCCTGAGGT CACATGCGTG GTGGTGGACG

701 TGAGCCACGA AGACCCTGAG GTCAAGTTCA ACTGGTACGT GGACGGCGTG

751 GAGGTGCATA ATGCCAAGAC AAAGCCGCGG GAGGAGCAGT ACAACAGCAC

801 GTACCGTGTG GTCAGCGTCC TCACCGTCCT GCACCAGGAC TGGCTGAATG

851 GCAAGGAGTA CAAGTGCAAG GTCTCCAACA AAGCCCTCCC AGCCCCCATC

901 GAGAAAACCA TCTCCAAAGC CAAAGGGCAG CCCCGAGAAC CACAGGTGTA

951 CACCCTGCCC CCATCCCGGA AGGAGATGAC CAAGAACCAG GTCAGCCTGA

1001 CCTGCCTGGT CAAAGGCTTC TATCCCAGCG ACATCGCCGT GGAGTGGGAG

1051 AGCAATGGGC AGCCGGAGAA CAACTACAAG ACCACGCCTC CCGTGCTGAA

1101 GTCCGACGGC TCCTTCTTCC TCTATAGCAA GCTCACCGTG GACAAGAGCA

1151 GGTGGCAGCA GGGGAACGTC TTCTCATGCT CCGTGATGCA TGAGGCTCTG

1201 CACAACCACT ACACGCAGAA GAGCCTCTCC CTGTCTCCGG GTAAA
```

The mature TGFβRII$_{LONG}$-Fc fusion polypeptide (SEQ ID NO: 167) is as follows and may optionally be provided with the lysine removed from the C-terminus.

```
                                             (SEQ ID NO: 167)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT

201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPSRK

301 EMTKNQVSLT CLVKGFYPSD IAVEWESNGQ PENNYKTTPP VLKSDGSFFL

351 YSKLTVDKSR WQQGNVFSCS VMHEALHNHY TQKSLSLSPG K
```

In a second approach to promote the formation of heteromultimer complexes using asymmetric Fc fusion proteins, the Fc domains are altered to introduce complementary hydrophobic interactions and an additional intermolecular disulfide bond.

The TGFβRII$_{SHORT}$-Fc polypeptide sequence (SEQ ID NO: 172) is shown below:

```
                                                 (SEQ ID NO: 172)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPCREE

301 MTKNQVSLWC LVKGFYPSDI AVEWESNGQP ENNYKTTPPV LDSDGSFFLY

351 SKLTVDKSRW QQGNVFSCSV MHEALHNHYT QKSLSLSPGK
```

The leader sequence and linker sequence are underlined. To promote formation of the TGFβRII$_{SHORT}$-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 172 may optionally be provided with the lysine removed from the C-terminus.

The mature TGFβRII$_{SHORT}$-Fc fusion polypeptide (SEQ ID NO: 173) is as follows and may optionally be provided with the lysine removed from the C-terminus.

```
                                                 (SEQ ID NO: 173)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPCREEMTKN QVSLWCLVKG FYPSDIAVEW

301 ESNGQPENNY KTTPPVLDSD GSFFLYSKLT VDKSRWQQGN VFSCSVMHEA

351 LHNHYTQKSL SLSPGK
```

To guide heterodimer formation with the certain Fc fusion polypeptides disclosed herein, four amino acid substitutions can be introduced into the Fc domain of the ALK1 fusion polypeptide.

In some embodiments, the TGFβRII$_{LONG}$-Fc polypeptide sequence (SEQ ID NO: 174) is below:

```
                                                 (SEQ ID NO: 174)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PCREEMTKNQ VSLWCLVKGF YPSDIAVEWE

351 SNGQPENNYK TTPPVLDSDG SFFLYSKLTV DKSRWQQGNV FSCSVMHEAL

401 HNHYTQKSLS LSPGK
```

The leader sequence and linker sequence are underlined. To promote formation of the TGFβRII$_{LONG}$-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 174 may optionally be provided with the lysine removed from the C-terminus.

The mature TGFβRII$_{LONG}$-Fc fusion polypeptide (SEQ ID NO: 175) is as follows and may optionally be provided with the lysine removed from the C-terminus.

```
                                                    (SEQ ID NO: 175)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT

201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPCRE

301 EMTKNQVSLW CLVKGFYPSD IAVEWESNGQ PENNYKTTPP VLDSDGSFFL

351 YSKLTVDKSR WQQGNVFSCS VMHEALHNHY TQKSLSLSPG K
```

In certain aspects, the present disclosure relates to protein complexes that comprise an MISRII polypeptide. As used herein, the term "MISRII" refers to a family of Müllerian inhibiting substance receptor type II (MISRII) proteins from any species and variants derived from such MISRII proteins by mutagenesis or other modification. Reference to MISRII herein is understood to be a reference to any one of the currently identified forms. Members of the MISRII family are generally transmembrane proteins, composed of a ligand-binding extracellular domain with a cysteine-rich region, a transmembrane domain, and a cytoplasmic domain with predicted serine/threonine kinase activity.

The term "MISRII polypeptide" includes polypeptides comprising any naturally occurring polypeptide of an MIS-RII family member as well as any variants thereof (including mutants, fragments, fusions, and peptidomimetic forms) that retain a useful activity.

A human MISRII precursor protein sequence (NCBI Ref Seq NP_065434.1) is as follows:

```
                                                    (SEQ ID NO: 180)
  1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME AGTQRYMAPE LLDKTLDLQD

401 WGMALRRADI YSLALLLWEI LSRCPDLRPD SSPPPFQLAY EAELGNTPTS

451 DELWALAVQE RRRPYIPSTW RCFATDPDGL RELLEDCWDA DPEARLTAEC

501 VQQRLAALAH PQESHPFPES CPRGCPPLCP EDCTSIPAPT ILPCRPQRSA

551 CHFSVQQGPC SRNPQPACTL SPV
```

The signal peptide is indicated by a single underline and an extracellular domain is indicated in bold font.

A processed extracellular MISRII polypeptide sequence is as follows:

(SEQ ID NO: 183)
PPNRRTCVFFEAPGVRGSTKTLGELLDTGTELPRAIRCLYSRCCFGIWNL
TQDRAQVEMQGCRDSDEPGCESLHCDPSPRAHPSPGSTLFTCSCGTDFCN
ANYSHLPPPGSPGTPGSQGPQAAPGESIWMAL

A nucleic acid sequence encoding the MISRII precursor protein is shown in SEQ ID NO: 209, corresponding to nucleotides 81-1799 of Genbank Reference Sequence NM_020547.2. A nucleic acid sequence encoding the extracellular human MISRII polypeptide is shown in SEQ ID NO: 210.

An alternative isoform of the human MISRII precursor protein sequence, isoform 2 (NCBI Ref Seq NP_001158162.1), is as follows:

(SEQ ID NO: 181)
```
  1 MLGSLGLWAL LPTAVEAPPN RRTCVFFEAP GVRGSTKTLG ELLDTGTELP
 51 RAIRCLYSRC CFGIWNLTQD RAQVEMQGCR DSDEPGCESL HCDPSPRAHP
101 SPGSTLFTCS CGTDFCNANY SHLPPPGSPG TPGSQGPQAA PGESIWMALV
151 LLGLFLLLLL LLGSIILALL QRKNYRVRGE PVPEPRPDSG RDWSVELQEL
201 PELCFSQVIR EGGHAVVWAG QLQGKLVAIK AFPPRSVAQF QAERALYELP
251 GLQHDHIVRF ITASRGGPGR LLSGPLLVLE LHPKGSLCHY LTQYTSDWGS
301 SLRMALSLAQ GLAFLHEERW QNGQYKPGIA HRDLSSQNVL IREDGSCAIG
351 DLGLALVLPG LTQPPAWTPT QPQGPAAIME AGTQRYMAPE LLDKTLDLQD
401 WGMALRRADI YSLALLLWEI LSRCPDLRPA VHHPSNWPMR QNWAIPLPLM
451 SYGPWQCRRG GVPTSHPPGA ALPQTLMG
```

The signal peptide is indicated by a single underline and the extracellular domain is indicated in bold font.

A processed extracellular MISRII polypeptide sequence (isoform 2) is as follows:

(SEQ ID NO: 184)
PPNRRTCVFFEAPGVRGSTKTLGELLDTGTELPRAIRCLYSRCCFGIWNL
TQDRAQVEMQGCRDSDEPGCESLHCDPSPRAHPSPGSTLFTCSCGTDFCN
ANYSHLPPPGSPGTPGSQGPQAAPGESIWMAL

A nucleic acid sequence encoding the MISRII precursor protein (isoform 2) is shown in SEQ ID NO: 211, corresponding to nucleotides 81-1514 of Genbank Reference Sequence NM_001164690.1. A nucleic acid sequence encoding processed soluble (extracellular) human MISRII polypeptide (isoform 2) is shown in SEQ ID NO: 212.

An alternative isoform of the human MISRII precursor protein sequence, isoform 3 (NCBI Ref Seq NP_001158163.1), is as follows:

(SEQ ID NO: 182)
```
  1 MLGSLGLWAL LPTAVEAPPN RRTCVFFEAP GVRGSTKTLG ELLDTGTELP
 51 RAIRCLYSRC CFGIWNLTQD RAQVEMQGCR DSDEPGCESL HCDPSPRAHP
101 SPGSTLFTCS CGTDFCNANY SHLPPPGSPG TPGSQGPQAA PGESIWMALV
151 LLGLFLLLLL LLGSIILALL QRKNYRVRGE PVPEPRPDSG RDWSVELQEL
201 PELCFSQVIR EGGHAVVWAG QLQGKLVAIK AFPPRSVAQF QAERALYELP
251 GLQHDHIVRF ITASRGGPGR LLSGPLLVLE LHPKGSLCHY LTQYTSDWGS
301 SLRMALSLAQ GLAFLHEERW QNGQYKPGIA HRDLSSQNVL IREDGSCAIG
351 DLGLALVLPG LTQPPAWTPT QPQGPAAIME DPDGLRELLE DCWDADPEAR
```

```
-continued
401 LTAECVQQRL AALAHPQESH PFPESCPRGC PPLCPEDCTS IPAPTILPCR

451 PQRSACHFSV QQGPCSRNPQ PACTLSPV
```

The signal peptide is indicated by a single underline and the extracellular domain is indicated in bold font.

A processed extracellular MISRII polypeptide sequence (isoform 3) is as follows:

(SEQ ID NO: 185)
PPNRRTCVFFEAPGVRGSTKTLGELLDTGTELPRAIRCLYSRCCFGIWNL

TQDRAQVEMQGCRDSDEPGCESLHCDPSPRAHPSPGSTLFTCSCGTDFCN

ANYSHLPPPGSPGTPGSQGPQAAPGESIWMAL

A nucleic acid sequence encoding human MISRII precursor protein (isoform 3) is shown in SEQ ID NO: 213, corresponding to nucleotides 81-1514 of Genbank Reference Sequence NM_001164691.1. A nucleic acid sequence encoding a processed soluble (extracellular) human MISRII polypeptide (isoform 3) is shown in SEQ ID NO: 214.

In certain embodiments, the disclosure relates to heteromultimers that comprise at least one MISRII polypeptide, which includes fragments, functional variants, and modified forms thereof. Preferably, MISRII polypeptides for use in accordance with inventions of the disclosure (e.g., heteromultimers comprising a MISRII polypeptide and uses thereof) are soluble (e.g., an extracellular domain of MISRII). In other preferred embodiments, MISRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one MISRII polypeptide that is at least 70%, 75%, 80%, 85%, 90%, 95%, 97%, 98%, 99%, or 100% identical to the amino acid sequence of SEQ ID NOs: 180, 183, 181, 184, 182, or 185. In some embodiments, heteromultimers of the disclosure consist or consist essentially of at least one MISRII polypeptide that is at least 70%, 75%, 80%, 85%, 90%, 95%, 97%, 98%, 99%, or 100% identical to the amino acid sequence of SEQ ID NOs: 180, 183, 181, 184, 182, or 185.

In certain aspects, the disclosure relates to a heteromultimer that comprises an MISRII-Fc fusion protein. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 17-24 (e.g., amino acid residues 17, 18, 19, 20, 21, 22, 23, and 24) SEQ ID NO: 180, 181, or 182, and ends at any one of amino acids 116-149 (e.g., amino acid residues 116, 117, 118, 119, 120, 121, 122 123, 124, 125, 126, 127, 128, 129, 130, 131, 132, 133, 134, 135, 136, 137, 138, 139, 140, 141, 142, 143, 144, 145, 146, 147, 148, and 149) of SEQ ID NO: 180, 181, or 182. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-116 of SEQ ID NO: 180, 181, or 182. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 17-149 of SEQ ID NO: 180, 181, or 182. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 180, 183, 181, 184, 182, 185, 186, 187, 188, 189, 190, 191, 192, and 193.

In some embodiments, the present disclosure contemplates making functional variants by modifying the structure of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta superfamily ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty.

In some embodiments, the present disclosure contemplates making functional variants by modifying the structure of the TGF-beta superfamily type I receptor polypeptide and/or TGF-beta superfamily type II receptor polypeptide for such purposes as enhancing therapeutic efficacy or stability (e.g., increased shelf-life and/or increased resistance to proteolytic degradation).

In certain embodiments, the present disclosure contemplates specific mutations of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) receptor of the disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, TGF-beta superfamily type I and II receptor complexes of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) disclosed herein, as well as truncation mutants. Pools of combinatorial mutants are especially useful for identifying functionally active (e.g., ligand binding) TGF-beta superfamily type I and/or TGF-beta superfamily type II receptor sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, TGF-beta superfamily type I and II receptor complex variants may be screened for ability to bind to a TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), to prevent binding of a TGF-beta superfamily ligand to a TGF-beta superfamily receptor, and/or to interfere with signaling caused by an TGF-beta superfamily ligand.

The activity of a TGF-beta superfamily heteromultimer of the disclosure also may be tested, for example in a cell-based or in vivo assay. For example, the effect of a heteromultimer complex on the expression of genes or the activity of proteins involved in muscle production in a muscle cell may be assessed. This may, as needed, be performed in the presence of one or more recombinant TGF-beta superfamily ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), and cells may be transfected so as to produce a TGF-beta superfamily type I and II receptor complex, and optionally, a TGF-beta superfamily ligand. Likewise, a heteromultimer complex of the disclosure may be administered to a mouse or other animal, and one or more measurements, such as muscle formation and strength may be assessed using art-recognized methods. Similarly, the activity of a heteromultimer, or variants thereof, may be tested in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference TGF-beta superfamily heteromultimer. Such variants, when expressed from recombinant DNA constructs, can be used in gene therapy protocols. Likewise, mutagenesis can give rise to variants which have intracellular half-lives dramatically different than the corresponding unmodified TGF-beta superfamily heteromultimer. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter one or more activities of the TGF-beta superfamily heteromultimer complex including, for example, immunogenicity, half-life, and solubility.

Many methods known in the art can be used to generate heteromultimers of the disclosure. For example, non-naturally occurring disulfide bonds may be constructed by replacing on a first polypeptide (e.g., a variant ActRIIB polypeptide) a naturally occurring amino acid with a free thiol-containing residue, such as cysteine, such that the free thiol interacts with another free thiol-containing residue on a second polypeptide (e.g., an unmodified ActRIIB polypeptide or a variant ActRIIB polypeptide different from that present in the first polypeptide) such that a disulfide bond is formed between the first and second polypeptides. Additional examples of interactions to promote heteromultimer formation include, but are not limited to, ionic interactions such as described in Kjaergaard et al., WO2007147901;

electrostatic steering effects such as described in Kannan et al., U.S. Pat. No. 8,592,562; coiled-coil interactions such as described in Christensen et al., U.S. 20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of a variant ActRIIB polypeptide and the amino acid sequence of a first member of an interaction pair; and the second polypeptide comprises the amino acid sequence of an unmodified ActRIIB polypeptide, or a variant ActRIIB polypeptide different from that present in the first polypeptide, and the amino acid sequence of a second member of an interaction pair. The interaction pair may be any two polypeptide sequences that interact to form a complex, particularly a heterodimeric complex although operative embodiments may also employ an interaction pair that can form a homodimeric complex. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIG. 1B). Alternatively, the interaction pair may be unguided, meaning that the members of the pair may associate with each other or self-associate without substantial preference and thus may have the same or different amino acid sequences (see, e.g., FIG. 1A). Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion proteins comprising a variant ActRIIB polypeptide or an unmodified ActRIIB polypeptide fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimers of the disclosure. Optionally, the IgG1 Fc domain of SEQ ID NO: 13 has one or more mutations at residues such as Asp-265, Lys-322, and Asn-434 (numbered in accordance with the corresponding full-length IgG1). In certain cases, the variant Fc domain having one or more of these mutations (e.g., Asp-265 mutation) has reduced ability of binding to the Fcγ receptor relative to a wildtype Fc domain. In other cases, the variant Fc domain having one or more of these mutations (e.g., Asn-434 mutation) has increased ability of binding to the MHC class I-related Fc-receptor (FcRN) relative to a wild-type Fc domain.

An example of a native amino acid sequence that may be used for the Fc portion of human IgG1 (G1Fc) is shown below (SEQ ID NO: 13). Dotted underline indicates the hinge region, and solid underline indicates positions with naturally occurring variants. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 13. Naturally occurring variants in G1Fc would include E134D and M136L according to the numbering system used in SEQ ID NO: 13 (see Uniprot P01857).

```
                                                        (SEQ ID NO: 13)
  1    THTCPPCPAP ELLGGPSVFL FPPKPKDTLM ISRTPEVTCV VVDVSHEDPE

51    VKFNWYVDGV EVHNAKTKPR EEQYNSTYRV VSVLTVLHQD WLNGKEYKCK

101    VSNKALPAPI EKTISKAKGQ PREPQVYTLP PSREEMTKNQ VSLTCLVKGF

151    YPSDIAVEWE SNGQPENNYK TTPPVLDSDG SFFLYSKLTV DKSRWQQGNV

201    FSCSVMHEAL HNHYTQKSLS LSPGK
```

An example of a native amino acid sequence that may be used for the Fc portion of human IgG2 (G2Fc) is shown below (SEQ ID NO: 14). Dotted underline indicates the hinge region and double underline indicates positions where there are data base conflicts in the sequence (according to UniProt P01859). In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 14.

```
                                                        (SEQ ID NO: 14)
  1    VECPPCPAPP VAGPSVFLFP PKPKDTLMIS RTPEVTCVVV DVSHEDPEVQ

51    FNWYVDGVEV HNAKTKPREE QFNSTFRVVS VLTVVHQDWL NGKEYKCKVS
```

```
101  NKGLPAPIEK TISKTKGQPR EPQVYTLPPS REEMTKNQVS LTCLVKGFYP

151  SDIAVEWESN GQPENNYKTT PPMLDSDGSF FLYSKLTVDK SRWQQGNVFS

201  CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 15) contains a short hinge region consisting of a single 15-residue segment, whereas the second G3Fc sequence (SEQ ID NO: 16) contains a full-length hinge region. In each case, dotted underline indicates the hinge region, and solid underline indicates positions with naturally occurring variants according to UniProt P01859. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NOs: 15 and 16.

```
                                                  (SEQ ID NO: 15)
  1  EPKSCDTPPP CPRCPAPELL GGPSVFLFPP KPKDTLMISR TPEVTCVVVD

51  VSHEDPEVQF KWYVDGVEVH NAKTKPREEQ YNSTFRVVSV LTVLHQDWLN

101  GKEYKCKVSN KALPAPIEKT ISKTKGQPRE PQVYTLPPSR EEMTKNQVSL

151  TCLVKGFYPS DIAVEWESSG QPENNYNTTP PMLDSDGSFF LYSKLTVDKS

201  RWQQGNIFSC SVMHEALHNR FTQKSLSLSP GK
                                                  (SEQ ID NO: 16)
  1  ELKTPLGDTT HTCPRCPEPK SCDTPPPCPR CPEPKSCDTP PPCPRCPEPK

51  SCDTPPPCPR CPAPELLGGP SVFLFPPKPK DTLMISRTPE VTCVVVDVSH

101  EDPEVQFKWY VDGVEVHNAK TKPREEQYNS TFRVVSVLTV LHQDWLNGKE

151  YKCKVSNKAL PAPIEKTISK TKGQPREPQV YTLPPSREEM TKNQVSLTCL

201  VKGFYPSDIA VEWESSGQPE NNYNTTPPML DSDGSFFLYS KLTVDKSRWQ

251  QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 15, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 17). Dotted underline indicates the hinge region. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 17.

```
                                                          (SEQ ID NO: 17)
  1   ESKYGPPCPS CPAPEFLGGP SVFLFPPKPK DTLMISRTPE VTCVVVDVSQ

51   EDPEVQFNWY VDGVEVHNAK TKPREEQFNS TYRVVSVLTV LHQDWLNGKE

101   YKCKVSNKGL PSSIEKTISK AKGQPREPQV YTLPPSQEEM TKNQVSLTCL

151   VKGFYPSDIA VEWESNGQPE NNYKTTPPVL DSDGSFFLYS RLTVDKSRWQ

201   EGNVFSCSVM HEALHNHYTQ KSLSLSLGK
```

A variety of engineered mutations in the Fc domain are presented herein with respect to the G1Fc sequence (SEQ ID NO: 13), and analogous mutations in G2Fc, G3Fc, and G4Fc can be derived from their alignment with G1Fc in FIG. 4. Due to unequal hinge lengths, analogous Fc positions based on isotype alignment (FIG. 4) possess different amino acid numbers in SEQ ID NOs: 13, 14, 15, and 17. It can also be appreciated that a given amino acid position in an immunoglobulin sequence consisting of hinge, $C_H2$, and $C_H3$ regions (e.g., SEQ ID NOs: 13, 14, 15, 16, or 17) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 13), the human IgG1 heavy chain constant domain (Uniprot P01857), and the human IgG1 heavy chain is as follows.

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
| --- | --- | --- |
| Y127 | Y232 | Y349 |
| S132 | S237 | S354 |
| E134 | E239 | E356 |
| K138 | K243 | K360 |
| T144 | T249 | T366 |
| L146 | L251 | L368 |
| N162 | N267 | N384 |
| K170 | K275 | K392 |
| D177 | D282 | D399 |
| D179 | D284 | D401 |
| Y185 | Y290 | Y407 |
| K187 | K292 | K409 |
| H213 | H318 | H435 |
| K217 | K322 | K439 |

*Kabat et al. (eds) 1991; pp. 688-696 in *Sequences of Proteins of Immunological Interest*, 5th ed., Vol. 1, NIH, Bethesda, MD.

A problem that arises in large-scale production of asymmetric immunoglobulin-based proteins from a single cell line is known as the "chain association issue". As confronted prominently in the production of bispecific antibodies, the chain-association issue concerns the challenge of efficiently producing a desired multichain protein from among the multiple combinations that inherently result when different heavy chains and/or light chains are produced in a single cell line [see, for example, Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [see, for example, Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing. See, for example, Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605. As described herein, these methods may be used to generate heterodimers comprising a variant ActRIIB polypeptide and another, optionally different, variant ActRIIB polypeptide or an unmodified ActRIIB polypeptide.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance heteromultimer formation of the heteromultimers disclosed herein.

Examples of Pair-Wise Charged Residue Mutations to Enhance Heterodimer Formation

| Position in first chain | Mutation in first chain | Interacting position in second chain | Corresponding mutation in second chain |
| --- | --- | --- | --- |
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to a first variant ActRIIB polypeptide, a second variant ActRIIB polypeptide, or an unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence complementary to the first Fc sequence to favor generation of the desired multichain construct (e.g., a variant ActRIIB-Fc heteromultimer). In this example based on electrostatic steering, SEQ ID NO: 200 [human G1Fc(E134K/D177K)] and SEQ ID NO: 201 [human G1Fc(K170D/K187D)] are examples of complementary Fc sequences in which the engineered amino acid substitutions are double underlined, and a first variant ActRIIB polypeptide, second variant ActRIIB polypeptide, or unmodified ActRIIB polypeptide of the construct can be fused to either SEQ ID NO: 18 or SEQ ID NO: 19, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 18 and 19).

```
                                                              (SEQ ID NO: 18)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSRKEMTKNQ VSLTCLVKGF

151 YPSDIAVEWE SNGQPENNYK TTPPVLKSDG SFFLYSKLTV DKSRWQQGNV

201 FSCSVMHEAL HNHYTQKSLS LSPGK
```

```
                                                              (SEQ ID NO: 19)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYD TTPPVLDSDG SFFLYSDLTV DKSRWQQGNV

201 FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to a first variant ActRIIB polypeptide, a second variant ActRIIB polypeptide, or an unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence complementary to the first Fc sequence to favor generation of the desired multichain construct. In this example based on knobs-into-holes pairing, SEQ ID NO: 20 [human G1Fc(T144Y)] and SEQ ID NO: 21 [human G1Fc(Y185T)] are examples of complementary Fc sequences in which the engineered amino acid substitutions are double underlined, and a first variant ActRIIB polypeptide, second variant ActRIIB polypeptide, or unmodified ActRIIB polypeptide of the construct can be fused to either SEQ ID NO: 20 or SEQ ID NO: 21, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 20 and 21).

```
                                                   (SEQ ID NO: 20)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLYCLVKGF

151 YPSDIAVEWE SNGQPENNYK TTPPVLDSDG SFFLYSKLTV DKSRWQQGNV

201 FSCSVMHEAL HNHYTQKSLS LSPGK
```

```
                                                   (SEQ ID NO: 21)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLTSKLTV DKSRWQQGNV

201 FSCSVMHEAL HNHYTQKSLS LSPGK
```

An example of Fc complementarity based on knobs-into-holes pairing combined with an engineered disulfide bond is disclosed in SEQ ID NO: 22 [hG1Fc(S132C/T144W)] and SEQ ID NO: 23 [hG1Fc(Y127C/T144S/L146A/Y185V)]. The engineered amino acid substitutions in these sequences are double underlined, and a first variant ActRIIB polypeptide, second variant ActRIIB polypeptide, or unmodified ActRIIB polypeptide of the construct can be fused to either SEQ ID NO: 22 or SEQ ID NO: 23, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 22 and 23).

```
                                                   (SEQ ID NO: 22)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNHYTQKSLS LSPGK
```

```
                                                   (SEQ ID NO: 23)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

151 YPSDIAVEWE SNGQPENNYK TTPPVLDSDG SFFLVSKLTV DKSRWQQGNV

201 FSCSVMHEAL HNHYTQKSLS LSPGK
```

In part, the disclosure provides desired pairing of asymmetric Fc-containing polypeptide chains using Fc sequences engineered to generate interdigitating β-strand segments of human IgG and IgA $C_H3$ domains. Such methods include the use of strand-exchange engineered domain (SEED) $C_H3$ heterodimers allowing the formation of SEEDbody fusion proteins [see, for example, Davis et al (2010) Protein Eng Design Sel 23:195-202]. One of a pair of Fc sequences with SEEDbody complementarity can be arbitrarily fused to a first variant ActRIIB polypeptide, second variant ActRIIB polypeptide, or unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence complementary to the first Fc sequence to favor generation of the desired multichain construct. In this example based on SEEDbody (Sb) pairing, SEQ ID NO: 24 [hG1Fc(Sb$_{AG}$)] and SEQ ID NO: 25 [hG1Fc(Sb$_{GA}$)] are examples of complementary IgG Fc sequences in which the engineered amino acid substitutions from IgA Fc are double underlined, and a first variant ActRIIB polypeptide, second variant ActRIIB polypeptide, or unmodified ActRIIB polypeptide of the construct can be fused to either SEQ ID NO: 24 or SEQ ID NO: 25, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 4) will generate an Fc monomer which may be used in the complementary IgG-IgA pair below (SEQ ID NOs: 24 and 25).

$C_H3$ domains. Attachment of a leucine zipper is sufficient to cause preferential assembly of heterodimeric antibody heavy chains. See, e.g., Wranik et al (2012) J Biol Chem 287:43331-43339. As disclosed herein, one of a pair of Fc sequences attached to a leucine zipper-forming strand can be arbitrarily fused to a first variant ActRIIB polypeptide, second variant ActRIIB polypeptide, or unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence attached to a complementary leucine zipper-forming strand to favor generation of the desired multichain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 26 [hG1Fc-Ap1 (acidic)] and SEQ ID NO: 27 [hG1Fc-Bp1 (basic)] are examples of complementary IgG Fc sequences in which the engineered complimentary leucine zipper sequences are underlined, and a first variant ActRIIB polypeptide, second variant ActRIIB polypeptide, or wild-type ActRIIB polypeptide of the construct can be fused to either SEQ ID NO: 26 or SEQ ID NO: 27, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc,

```
                                                              (SEQ ID NO: 24)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PFRPEVHLLP PSREEMTKNQ VSLTCLARGF

151 YPKDIAVEWE SNGQPENNYK TTPSRQEPSQ GTTTFAVTSK LTVDKSRWQQ

201 GNVFSCSVMH EALHNHYTQK TISLSPGK
                                                              (SEQ ID NO: 25)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PPSEELALNE LVTLTCLVKG

151 FYPSDIAVEW ESNGQELPRE KYLTWAPVLD SDGSFFLYSI LRVAAEDWKK

201 GDTFSCSVMH EALHNHYTQK SLDRSPGK
```

In part, the disclosure provides desired pairing of asymmetric Fc-containing polypeptide chains with a cleavable leucine zipper domain attached at the C-terminus of the Fc or hG4Fc (see FIG. 4) will generate an Fc monomer which may be used in the complementary leucine zipper-forming pair below (SEQ ID NOs: 26 and 27).

```
                                                              (SEQ ID NO: 26)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGKGGSAQ LEKELQALEK ENAQLEWELQ

251 ALEKELAQGA T
```

```
                                                          (SEQ ID NO: 27)
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVYTLP  PSREEMTKNQ  VSLTCLVKGF

151  YPSDIAVEWE  SNGQPENNYK  TTPPVLDSDG  SFFLYSKLTV  DKSRWQQGNV

201  FSCSVMHEAL  HNHYTQKSLS  LSPGKGGSAQ  LKKKLQALKK  KNAQLKWKLQ

251  ALKKKLAQGA  T
```

In part, the disclosure provides desired pairing of asymmetric Fc-containing polypeptide chains by methods described above in combination with additional mutations in the Fc domain which facilitate purification of the desired heteromeric species. An example uses complementarity of Fc domains based on knobs-into-holes pairing combined with an engineered disulfide bond, as disclosed in SEQ ID NOs: 22 and 23, plus additional substitution of two negatively charged amino acids (aspartic acid or glutamic acid) in one Fc-containing polypeptide chain and two positively charged amino acids (e.g., arginine) in the complementary Fc-containing polypeptide chain (SEQ ID NOs: 28-29). These four amino acid substitutions facilitate selective purification of the desired heteromeric fusion protein from a heterogeneous polypeptide mixture based on differences in isoelectric point or net molecular charge. The engineered amino acid substitutions in these sequences are double underlined below, and a first variant ActRIIB polypeptide, second variant ActRIIB polypeptide, or unmodified ActRIIB polypeptide of the construct can be fused to either SEQ ID NO: 28 or SEQ ID NO: 29, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 28-29).

Another example involves complementarity of Fc domains based on knobs-into-holes pairing combined with an engineered disulfide bond, as disclosed in SEQ ID NOs: 22-23, plus a histidine-to-arginine substitution at position 213 in one Fc-containing polypeptide chain (SEQ ID NO: 30). This substitution (denoted H435R in the numbering system of Kabat et al.) facilitates separation of desired heteromer from undesirable homodimer based on differences in affinity for protein A. The engineered amino acid substitution is indicated by double underline, and a first variant ActRIIB polypeptide, second variant ActRIIB polypeptide, or unmodified ActRIIB polypeptide of the construct can be fused to either SEQ ID NO: 30 or SEQ ID NO: 23, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair of SEQ ID NO: 30 (below) and SEQ ID NO: 23.

```
                                                          (SEQ ID NO: 28)
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVYTLP  PCREEMTENQ  VSLWCLVKGF

151  YPSDIAVEWE  SNGQPENNYK  TTPPVLDSDG  SFFLYSKLTV  DKSRWQQGNV

201  FSCSVMHEAL  HNHYTQDSLS  LSPGK
```

```
                                                          (SEQ ID NO: 29)
  1  THTCPPCPAP  ELLGGPSVFL  FPPKPKDTLM  ISRTPEVTCV  VVDVSHEDPE

51  VKFNWYVDGV  EVHNAKTKPR  EEQYNSTYRV  VSVLTVLHQD  WLNGKEYKCK

101  VSNKALPAPI  EKTISKAKGQ  PREPQVCTLP  PSREEMTKNQ  VSLSCAVKGF

151  YPSDIAVEWE  SRGQPENNYK  TTPPVLDSRG  SFFLVSKLTV  DKSRWQQGNV

201  FSCSVMHEAL  HNHYTQKSLS  LSPGK
```

(SEQ ID NO: 30)
```
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNRYTQKSLS LSPGK
```

A variety of engineered mutations in the Fc domain are presented above with respect to the G1Fc sequence (SEQ ID NO: 13). Analogous mutations in G2Fc, G3Fc, and G4Fc can be derived from their alignment with G1Fc in FIG. 4. Due to unequal hinge lengths, analogous Fc positions based on isotype alignment (FIG. 4) possess different amino acid numbers in SEQ ID NOs: 13, 14, 15, 16, and 17 as summarized in the following table.

Correspondence between $C_H3$ Positions for Human Fc Isotypes*

| IgG1 SEQ ID NO: 13 Numbering begins at THT . . . | IgG4 SEQ ID NO: 17 Numbering begins at ESK . . . | IgG2 SEQ ID NO: 14 Numbering begins at VEC . . . | IgG3 SEQ ID NO: 15 Numbering begins at EPK . . . |
|---|---|---|---|
| Y127 | Y131 | Y125 | Y134 |
| S132 | S136 | S130 | S139 |
| E134 | E138 | E132 | E141 |
| K138 | K142 | K136 | K145 |
| T144 | T148 | T142 | T151 |
| L146 | L150 | L144 | L153 |
| N162 | N166 | N160 | S169 |
| K170 | K174 | K168 | N177 |
| D177 | D181 | D175 | D184 |
| D179 | D183 | D177 | D186 |
| Y185 | Y189 | Y183 | Y192 |
| K187 | R191 | K185 | K194 |
| H213 | H217 | H211 | R220 |
| K217 | K221 | K215 | K224 |

*Numbering based on multiple sequence alignment shown in FIG. 4

It is understood that different elements of the fusion proteins (e.g., immunoglobulin Fc fusion proteins) may be arranged in any manner that is consistent with desired functionality. For example, an ActRIIB polypeptide domain may be placed C-terminal to a heterologous domain, or alternatively, a heterologous domain may be placed C-terminal to an ActRIIB polypeptide domain. The ActRIIB polypeptide domain and the heterologous domain need not be adjacent in a fusion protein, and additional domains or amino acid sequences may be included C- or N-terminal to either domain or between the domains.

For example, a ActRIIB polypeptide may comprise an amino acid sequence as set forth in the formula A-B-C. The B portion corresponds to an ActRIIB polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 261), GGGG (SEQ ID NO: 262), TGGGG (SEQ ID NO: 263), SGGGG (SEQ ID NO: 264), TGGG (SEQ ID NO: 265), or SGGG (SEQ ID NO: 266) singlets, or repeats. In certain embodiments, an ActRIIB fusion protein comprises an amino acid sequence as set forth in the formula A-B-C, wherein A is a leader (signal) sequence, B consists of an ActRIIB polypeptide domain, and C is a polypeptide portion that enhances one or more of in vivo stability, in vivo half-life, uptake/administration, tissue localization or distribution, formation of protein complexes, and/or purification. In certain embodiments, an ActRIIB fusion protein comprises an amino acid sequence as set forth in the formula A-B-C, wherein A is a TPA leader sequence, B consists of an ActRIIB polypeptide domain, and C is an immunoglobulin Fc domain.

In certain embodiments, the variant ActRIIB polypeptides of the present invention contain one or more modifications that are capable of stabilizing the variant ActRIIB polypeptides. For example, such modifications enhance the in vitro half life of the variant ActRIIB polypeptides, enhance circulatory half life of the variant ActRIIB polypeptides or reducing proteolytic degradation of the variant ActRIIB polypeptides. Such stabilizing modifications include, but are not limited to, fusion proteins (including, for example, fusion proteins comprising a variant ActRIIB polypeptide and a stabilizer domain), modifications of a glycosylation site (including, for example, addition of a glycosylation site to a variant ActRIIB polypeptide), and modifications of carbohydrate moiety (including, for example, removal of carbohydrate moieties from a variant ActRIIB polypeptide). In the case of fusion proteins, a variant ActRIIB polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the variant ActRIIB polypeptides, which are isolated from, or otherwise substantially free of, other proteins.

In certain embodiments, ActRIIB polypeptides (unmodified or modified) of the invention can be produced by a variety of art-known techniques. For example, such ActRIIB polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the ActRIIB polypeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified ActRIIB polypeptides may be produced by digestion of naturally occurring or recombinantly produced full-length ActRIIB polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such ActRIIB polypeptides may be produced from naturally occurring or recombinantly produced full-length ActRIIB polypeptides such as standard techniques known in the art, such as by chemical cleavage (e.g., cyanogen bromide, hydroxylamine).

3. Nucleic Acids Encoding ActRIIB Polypeptides

In certain aspects, the invention provides isolated and/or recombinant nucleic acids encoding any of the ActRIIB polypeptides (e.g., soluble ActRIIB polypeptides), including any of the variants disclosed herein. For example, SEQ ID NO: 4 encodes a naturally occurring ActRIIB precursor polypeptide, while SEQ ID NO: 3 encodes a soluble ActRIIB polypeptide. The subject nucleic acids may be single-stranded or double stranded. Such nucleic acids may be DNA or RNA molecules. These nucleic acids are may be used, for example, in methods for making ActRIIB polypeptides or as direct therapeutic agents (e.g., in a gene therapy approach).

In certain aspects, the subject nucleic acids encoding ActRIIB polypeptides are further understood to include nucleic acids that are variants of SEQ ID NO: 3. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 4.

In certain embodiments, the invention provides isolated or recombinant nucleic acid sequences that are at least 80%, 85%, 90%, 95%, 97%, 98%, 99% or 100% identical to SEQ ID NO: 3. One of ordinary skill in the art will appreciate that nucleic acid sequences complementary to SEQ ID NO: 3, and variants of SEQ ID NO: 3 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 3, complement sequence of SEQ ID NO: 3, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NO: 3 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIB polypeptide and operably linked to at least one regulatory sequence. Regulatory sequences are art-recognized and are selected to direct expression of the variant ActRIIB polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a variant ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant variant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

In a preferred embodiment, a vector will be designed for production of the subject variant ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject variant ActRIIB polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 4) for one or more of the subject variant ActRIIB polypeptides. The host cell may be any prokaryotic or eukaryotic cell. For example, a variant ActRIIB polypeptide of the invention may be expressed in bacterial cells such as E. coli, insect cells (e.g., using a baculovirus expression system), yeast, or mammalian cells. Other suitable host cells are known to those skilled in the art.

Accordingly, the present invention further pertains to methods of producing the subject variant ActRIIB polypeptides. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the ActRIIB polypeptides. In a preferred embodiment, the variant ActRIIB polypeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant variant ActRIIB polypeptide, can allow purification of the expressed fusion protein by affinity chromatography using a $Ni^{2+}$ metal resin. The purification leader sequence can then be subsequently removed by treatment with enterokinase to provide the purified variant ActRIIB polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Screening Assays

In certain aspects, the present invention relates to the use of the subject variant ActRIIB polypeptides (e.g., soluble ActRIIB polypeptides) to identify compounds (agents) which are agonist or antagonists of the variant ActRIIB polypeptides. Compounds identified through this screening can be tested in tissues such as bone, cartilage, muscle, fat, and/or neurons, to assess their ability to modulate tissue growth in vitro. Optionally, these compounds can further be tested in animal models to assess their ability to modulate tissue growth in vivo.

There are numerous approaches to screening for therapeutic agents for modulating tissue growth by targeting the variant ActRIIB polypeptides. In certain embodiments, high-throughput screening of compounds can be carried out to identify agents that perturb ActRIIB-mediated effects on growth of bone, cartilage, muscle, fat, and/or neurons. In certain embodiments, the assay is carried out to screen and identify compounds that specifically inhibit or reduce binding of an ActRIIB polypeptide to its binding partner, such as an ActRIIB ligand (e.g., activin, Nodal, GDF8, GDF11 or BMP7). Alternatively, the assay can be used to identify compounds that enhance binding of an ActRIIB polypeptide to its binding protein such as an ActRIIB ligand. In a further embodiment, the compounds can be identified by their ability to interact with an ActRIIB polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIB polypeptide and its binding protein (e.g., an ActRIIB ligand).

Merely to illustrate, in an exemplary screening assay of the present invention, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added a composition containing an ActRIIB ligand. Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIB polypeptide and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIB polypeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRIIB polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRIIB polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ActRIIB polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with a variant ActRIIB polypeptide of the invention. The interaction between the compound and the variant ActRIIB polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a variant ActRIIB polypeptide. This may include a solid phase or fluid phase binding event. Alternatively, the gene encoding a variant ActRIIB polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for stimulating muscle growth and increasing muscle mass, for example, by antagonizing functions of an ActRIIB polypeptide and/or an ActRIIB ligand. Therefore, any compound identified can be tested in whole cells or tissues, in vitro or in vivo, to confirm their ability to modulate muscle growth. Various methods known in the art can be utilized for this purpose. For example, methods of the invention are performed such that the signal transduction through an ActRIIB protein activated by binding to an ActRIIB ligand (e.g., GDF8) has been reduced or inhibited. It will be recognized that the growth of muscle tissue in the organism would result in an increased muscle mass in the organism as compared to the muscle mass of a corresponding organism (or population of organisms) in which the signal transduction through an ActRIIB protein had not been so effected.

For example, the effect of the variant ActRIIB polypeptides or test compounds on muscle cell growth/proliferation can be determined by measuring gene expression of Pax-3 and Myf-5 which are associated with proliferation of myogenic cells, and gene expression of MyoD which is associated with muscle differentiation (e.g., Amthor et al., Dev Biol. 2002, 251:241-57). It is known that GDF8 downregulates gene expression of Pax-3 and Myf-5, and prevents gene expression of MyoD. The variant ActRIIB polypeptides or test compounds are expected to antagonize this activity of GDF8. Another example of cell-based assays includes measuring the proliferation of myoblasts such as C(2)C(12) myoblasts in the presence of the ActRIIB polypeptides or test compounds (e.g., Thomas et al., J Biol Chem. 2000, 275:40235-43).

The present invention also contemplates in vivo assays to measure muscle mass and strength. For example, Whittemore et al. (Biochem Biophys Res Commun. 2003, 300: 965-71) discloses a method of measuring increased skeletal muscle mass and increased grip strength in mice. Optionally, this method can be used to determine therapeutic effects of test compounds (e.g., variant ActRIIB polypeptides) on muscle diseases or conditions, for example those diseases for which muscle mass is limiting.

In certain aspects, the present invention provides methods and agents for modulating (stimulating or inhibiting) bone formation and increasing bone mass. Therefore, any compound identified can be tested in whole cells or tissues, in vitro or in vivo, to confirm their ability to modulate bone or cartilage growth. Various methods known in the art can be utilized for this purpose.

For example, the effect of the variant ActRIIB polypeptides or test compounds on bone or cartilage growth can be determined by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9). Another example of cell-based assays includes analyzing the osteogenic activity of the subject ActRIIB polypeptides and test compounds in mesenchymal progenitor and osteoblastic cells. To illustrate, recombinant adenoviruses expressing an ActRIIB polypeptide were constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

The present invention also contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, the present invention makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

In certain aspects, the present invention provides methods and agents for controlling weight gain and obesity. At the cellular level, adipocyte proliferation and differentiation is critical in the development of obesity, which leads to the generation of additional fat cells (adipocytes). Therefore, any compound identified can be tested in whole cells or tissues, in vitro or in vivo, to confirm their ability to modulate adipogenesis by measuring adipocyte proliferation or differentiation. Various methods known in the art can be utilized for this purpose. For example, the effect of a variant ActRIIB polypeptide (e.g., a soluble ActRIIB polypeptide) or test compounds on adipogenesis can be determined by measuring differentiation of 3T3-L1 preadipocytes to mature adipocytes in cell based assays, such as, by observing the accumulation of triacylglycerol in Oil Red O staining vesicles and by the appearance of certain adipocyte markers such as FABP (aP2/422) and PPARγ2. See, for example, Reusch et al., 2000, Mol Cell Biol. 20:1008-20; Deng et al., 2000, Endocrinology. 141:2370-6; Bell et al., 2000, Obes Res. 8:249-54. Another example of cell-based assays includes analyzing the role of variant ActRIIB polypeptides and test compounds in proliferation of adipocytes or adipocyte precursor cells (e.g., 3T3-L1 cells), such as, by monitoring bromodeoxyuridine (BrdU)-positive cells. See, for example, Pico et al., 1998, Mol Cell Biochem. 189:1-7; Masuno et al., 2003, Toxicol Sci. 75:314-20.

It is understood that the screening assays of the present invention apply to not only the subject ActRIIB polypeptides and variants of the ActRIIB polypeptides, but also any test compounds including agonists and antagonist of the ActRIIB polypeptides. Further, these screening assays are useful for drug target verification and quality control purposes.

6. Exemplary Therapeutic Uses

In certain embodiments, compositions of the present invention (e.g., variant ActRIIB proteins in either homomeric or heteromeric forms) can be used for treating or preventing a disease or condition that is associated with abnormal activity of ActRIIB and/or an ActRIIB ligand (e.g., GDF8 or GDF11). These diseases, disorders or conditions are generally referred to herein as "ActRIIB-associated conditions." In certain embodiments, the present invention provides methods of treating or preventing an individual in need thereof through administering to the individual a therapeutically effective amount of a variant ActRIIB protein as described above. These methods are particularly aimed at therapeutic and prophylactic treatments of animals, and more particularly, humans. The terms "subject," an "individual," or a "patient" are interchangeable throughout the specification and generally refer to mammals. Mammals include, but are not limited to, domesticated animals (e.g., cows, sheep, cats, dogs, and horses), primates (e.g., humans and non-human primates such as monkeys), rabbits, and rodents (e.g., mice and rats).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established.

Endogenous complexes between ActRIIB and ActRIIB ligands play essential roles in tissue growth as well as early developmental processes such as the correct formation of various structures or in one or more post-developmental capacities including sexual development, pituitary hormone production, and creation of bone and cartilage. Thus, ActRIIB-associated conditions include abnormal tissue growth and developmental defects. In addition, ActRIIB-associated conditions include, but are not limited to, disorders of cell growth and differentiation such as inflammation, allergy, autoimmune diseases, infectious diseases, and tumors.

Exemplary ActRIIB-associated conditions include neuromuscular disorders (e.g., muscular dystrophy and muscle atrophy), congestive obstructive pulmonary disease (and muscle wasting associated with COPD), muscle wasting syndrome, sarcopenia, cachexia, adipose tissue disorders (e.g., obesity), type 2 diabetes, and bone degenerative disease (e.g., osteoporosis). Other exemplary ActRIIB-associated conditions include anemia, musculodegenerative and neuromuscular disorders, tissue repair (e.g., wound healing), neurodegenerative diseases (e.g., amyotrophic lateral sclerosis), immunologic disorders (e.g., disorders related to abnormal proliferation or function of lymphocytes), and obesity or disorders related to abnormal proliferation of adipocytes.

In certain embodiments, compositions of the invention (e.g., variant ActRIIB proteins) are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject variant ActRIIB proteins include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic dystrophy (MMD) (also known as Steinert's disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, studies demonstrate that blocking or eliminating function of GDF8 in vivo can effectively treat at least certain symptoms in DMD and BMD patients. Thus, the subject variant ActRIIB proteins may act as GDF8 inhibitors (antagonists), and constitute an alternative means of blocking the functions of GDF8 and/or ActRIIB in vivo in DMD and BMD patients.

Similarly, the subject variant ActRIIB proteins provide an effective means to increase muscle mass in other disease conditions that are in need of muscle growth. For example, ALS, also called Lou Gehrig's disease (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

Variant ActRIIB protein-induced increased muscle mass might also benefit those suffering from muscle wasting diseases. Gonzalez-Cadavid et al. (supra) reported that that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 function is also associated with fat loss without diminution of nutrient intake (Zimmers et al., supra; McPherron and Lee, supra), the subject variant ActRIIB proteins may further be used as a therapeutic agent for slowing or preventing the development of obesity and type 2 diabetes.

Cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process. Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of GDF8 in adult mice was found to induce profound muscle and fat loss analogous to that seen in human cachexia syndromes (Zimmers et al., supra), the subject variant ActRIIB proteins as pharmaceutical compositions can be beneficially used to prevent, treat, or alleviate the symptoms of the cachexia syndrome, where muscle growth is desired.

In other embodiments, the present invention provides methods of inducing bone and/or cartilage formation, preventing bone loss, increasing bone mineralization or preventing the demineralization of bone. For example, the subject variant ActRIIB proteins have application in treating osteoporosis and the healing of bone fractures and cartilage defects in humans and other animals. Variant ActRIIB proteins may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject variant ActRIIB proteins may provide an environment to attract bone-forming cells, stimulate growth of bone-forming cells or induce differentiation of progenitors of bone-forming cells. Variant ActRIIB proteins of the invention may also be useful in the treatment of osteoporosis. Further, variant ActRIIB proteins may be used in cartilage defect repair and prevention/reversal of osteoarthritis.

In another specific embodiment, the invention provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See e.g., PCT Publication No. WO84/01106. Such compositions comprise a therapeutically effective amount of at least one of the variant ActRIIB proteins of the invention in admixture with a pharmaceutically acceptable vehicle, carrier or matrix.

In another specific embodiment, methods and variant ActRIIB proteins of the invention can be applied to conditions causing bone loss such as osteoporosis, hyperparathyroidism, Cushing's disease, thyrotoxicosis, chronic diarrheal state or malabsorption, renal tubular acidosis, or anorexia nervosa. Many people know that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Gum disease causes bone loss because these harmful bacteria in our mouths force our bodies to defend against them. The bacteria produce toxins and enzymes under the gum-line, causing a chronic infection.

In a further embodiment, the variant ActRIIB proteins of the present invention provide methods and therapeutic agents for treating diseases or disorders associated with abnormal or unwanted bone growth. For example, patients having the disease known as fibrodysplasia ossificans progressiva (FOP) grow an abnormal "second skeleton" that prevents any movement. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma.

In other embodiments, variant ActRIIB proteins of the present invention provide compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof a variant ActRIIB protein.

In one specific embodiment, the present invention relates to methods and compounds for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass.

In certain aspects, variant ActRIIB proteins can be used to increase red blood cell levels, treat or prevent an anemia, and/or treat or prevent ineffective erythropoiesis in a subject in need thereof. In certain aspects, a variant ActRIIB protein of the present disclosure may be used in combination with conventional therapeutic approaches for increasing red blood cell levels, particularly those used to treat anemias of multifactorial origin. Conventional therapeutic approaches for increasing red blood cell levels include, for example, red blood cell transfusion, administration of one or more EPO receptor activators, hematopoietic stem cell transplantation, immunosuppressive biologics and drugs (e.g., corticosteroids). In certain embodiments, a variant ActRIIB protein of the present disclosure can be used to treat or prevent an anemia in a subject in need thereof. In certain embodiments, a variant ActRIIB protein of the present disclosure can be used to treat or prevent ineffective erythropoiesis and/or the disorders associated with ineffective erythropoiesis in a subject in need thereof. In certain aspects, a variant ActRIIB protein of the present disclosure can be used in combination with conventional therapeutic approaches for treating or preventing an anemia or ineffective erythropoiesis disorder, particularly those used to treat anemias of multifactorial origin.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" as used herein includes amelioration or elimination of the condition once it has been established.

In either case, prevention or treatment may be discerned in the diagnosis provided by a physician or other health care provider and the intended result of administration of the therapeutic agent.

In general, treatment or prevention of a disease or condition as described in the present disclosure is achieved by administering one or more variant ActRIIB proteins of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

In certain embodiments, one or more variant ActRIIB proteins of the disclosure, optionally combined with an EPO receptor activator, may be used to increase red blood cell, hemoglobin, or reticulocyte levels in healthy individuals and selected patient populations. Examples of appropriate patient populations include those with undesirably low red blood cell or hemoglobin levels, such as patients having an anemia, and those that are at risk for developing undesirably low red blood cell or hemoglobin levels, such as those patients who are about to undergo major surgery or other procedures that may result in substantial blood loss. In one embodiment, a patient with adequate red blood cell levels is treated with one or more variant ActRIIB proteins to increase red blood cell levels, and then blood is drawn and stored for later use in transfusions.

One or more variant ActRIIB proteins of the disclosure, optionally combined with an EPO receptor activator, may be used to increase red blood cell levels, hemoglobin levels, and/or hematocrit levels in a patient having an anemia. When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in health adults, although, in terms of therapy, a lower target level may cause fewer cardiovascular side effects [see, e.g., Jacobs et al. (2000) Nephrol Dial Transplant 15, 15-19]. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

Anemia is frequently observed in patients having a tissue injury, an infection, and/or a chronic disease, particularly cancer. In some subjects, anemia is distinguished by low erythropoietin levels and/or an inadequate response to erythropoietin in the bone marrow [see, e.g., Adamson (2008) Harrison's Principles of Internal Medicine, 17th ed.; McGraw Hill, N.Y., pp 628-634]. Potential causes of anemia include, for example, blood loss, nutritional deficits (e.g. reduced dietary intake of protein), medication reaction, various problems associated with the bone marrow, and many diseases. More particularly, anemia has been associated with a variety of disorders and conditions that include, for example, bone marrow transplantation; solid tumors (e.g., breast cancer, lung cancer, and colon cancer); tumors of the lymphatic system (e.g., chronic lymphocyte leukemia, non-Hodgkins lymphoma, and Hodgkins lymphoma); tumors of the hematopoietic system (e.g., leukemia, a myelodysplastic syndrome and multiple myeloma); radiation therapy; chemotherapy (e.g., platinum containing regimens); inflammatory and autoimmune diseases, including, but not limited to, rheumatoid arthritis, other inflammatory arthritis, systemic lupus erythematosis (SLE), acute or chronic skin diseases (e.g., psoriasis), inflammatory bowel disease (e.g., Crohn's disease and ulcerative colitis); acute or chronic renal disease or failure, including idiopathic or congenital conditions; acute or chronic liver disease; acute or chronic bleeding; situations where transfusion of red blood cells is not possible due to patient allo- or autoantibodies and/or for religious reasons (e.g., some Jehovah's Witnesses); infections (e.g., malaria and osteomyelitis); hemoglobinopathies including, for example, sickle cell disease (anemia), thalassemias; drug use or abuse (e.g., alcohol misuse); pediatric patients with anemia from any cause to avoid transfusion; and elderly patients or patients with underlying cardiopulmonary disease with anemia who cannot receive transfusions due to concerns about circulatory overload [see, e.g., Adamson (2008) Harrison's Principles of Internal Medicine, 17th ed.; McGraw Hill, N.Y., pp 628-634]. In some embodiments, one or more variant ActRIIB proteins of the disclosure could be used to treat or prevent anemia associated with one or more of the disorders or conditions disclosed herein.

Many factors can contribute to cancer-related anemia. Some are associated with the disease process itself and the generation of inflammatory cytokines such as interleukin-1, interferon-gamma, and tumor necrosis factor [Bron et al. (2001) Semin Oncol 28(Suppl 8):1-6]. Among its effects, inflammation induces the key iron-regulatory peptide hepcidin, thereby inhibiting iron export from macrophages and generally limiting iron availability for erythropoiesis [see, e.g., Ganz (2007) J Am Soc Nephrol 18:394-400]. Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality. In some embodiments, one or more variant ActRIIB proteins of the disclosure, optionally combined with an EPO receptor activator, could be used to treat a cancer-related anemia.

A hypoproliferative anemia can result from primary dysfunction or failure of the bone marrow. Hypoproliferative anemias include: anemia of chronic disease, anemia of kidney disease, anemia associated with hypometabolic states, and anemia associated with cancer. In each of these types, endogenous erythropoietin levels are inappropriately low for the degree of anemia observed. Other hypoproliferative anemias include: early-stage iron-deficient anemia, and anemia caused by damage to the bone marrow. In these types, endogenous erythropoietin levels are appropriately elevated for the degree of anemia observed. Prominent examples would be myelosuppression caused by cancer and/or chemotherapeutic drugs or cancer radiation therapy. A broad review of clinical trials found that mild anemia can occur in 100% of patients after chemotherapy, while more severe anemia can occur in up to 80% of such patients [see, e.g., Groopman et al. (1999) J Natl Cancer Inst 91:1616-1634]. Myelosuppressive drugs include, for example: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). In addition, conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. In some embodiments, one or more variant ActRIIB proteins of the disclosure, optionally combined with an EPO receptor activator, could be used to treat a hyperproliferative anemia.

Chronic kidney disease is sometimes associated with hypoproliferative anemia, and the degree of the anemia varies in severity with the level of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function [see, e.g., Levin et al. (1999) Am J Kidney Dis 27:347-354; Nissenson (1992) Am J Kidney Dis 20(Suppl 1):21-24; Revicki et al. (1995) Am J Kidney Dis 25:548-554; Gafter et al., (1994) Kidney Int 45:224-231]. In some embodiments, one or more variant ActRIIB proteins, optionally combined with an EPO receptor activator, could be used to treat anemia associated with acute or chronic renal disease or failure.

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. In some embodiments, one or more variant ActRIIB proteins, optionally combined with an EPO receptor activator, could be used to treat anemia resulting from acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs [see, e.g., Adamson (2008) Harrison's Principles of Internal Medicine, 17th ed.; McGraw Hill, N.Y., pp 628-634]. Appropriate therapy for iron-deficiency anemia depends on its cause and severity, with oral iron preparations, parenteral iron formulations, and RBC transfusion as major conventional options. In some embodiments, one or more variant ActRIIB proteins of the disclosure, optionally combined with an EPO receptor activator, could be used to treat a chronic iron-deficiency.

Myelodysplastic syndrome (MDS) is a diverse collection of hematological conditions characterized by ineffective production of myeloid blood cells and risk of transformation to acute myelogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effects due to frequency of such therapies. For example, patients who receive frequent red blood cell transfusion can exhibit tissue and organ damage from the buildup of extra iron. Accordingly, one or more variant ActRIIB proteins of the disclosure, may be used to treat patients having MDS. In certain embodiments, patients suffering from MDS may be treated using one or more variant ActRIIB proteins of the disclosure, optionally in combination with an EPO receptor activator. In other embodiments, a patient suffering from MDS may be treated using a combination of one or more variant ActRIIB proteins of the disclosure and one or more additional therapeutic agents for treating MDS including, for example, thalidomide, lenalidomide, azacitadine, decitabine, erythropoietins, deferoxamine, antithymocyte globulin, and filgrastrim (G-CSF).

Originally distinguished from aplastic anemia, hemorrhage, or peripheral hemolysis on the basis of ferrokinetic studies [see, e.g., Ricketts et al. (1978) Clin Nucl Med 3:159-164], ineffective erythropoiesis describes a diverse group of anemias in which production of mature RBCs is less than would be expected given the number of erythroid precursors (erythroblasts) present in the bone marrow [Tanno et al. (2010) Adv Hematol 2010:358283]. In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis [see, e.g., Aizawa et al. (2003) Am J Hematol 74:68-72], erythroblast-induced bone pathology [see, e.g., Di Matteo et al. (2008) J Biol Regul Homeost Agents 22:211-216], and tissue iron overload, even in the absence of therapeutic RBC transfusions [see, e.g., Pippard et al. (1979) Lancet 2:819-821]. Thus, by boosting erythropoietic effectiveness, a variant ActRIIB protein of the present disclosure may break the aforementioned cycle and thus alleviate not only the underlying anemia but also the associated complications of elevated erythropoietin levels, splenomegaly, bone pathology, and tissue iron overload. In some embodiments, one or more variant ActRIIB proteins can be used to treat or prevent ineffective erythropoiesis, including anemia and elevated EPO levels as well as complications such as splenomegaly, erythroblast-induced bone pathology, iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors [see, e.g., Musallam et al. (2012) Cold Spring Harb Perspect Med 2:a013482]. With erythroblast-induced bone pathology, attendant pathologies include low bone mineral density, osteoporosis, and bone pain [see, e.g., Haidar et al. (2011) Bone 48:425-432]. With iron overload, attendant pathologies include hepcidin suppression and hyperabsorption of dietary iron [see, e.g., Musallam et al. (2012) Blood Rev 26(Suppl 1):S16-S19], multiple endocrinopathies and liver fibrosis/cirrhosis [see, e.g., Galanello et al. (2010) Orphanet J Rare Dis 5:11], and iron-overload cardiomyopathy [Lekawanvijit et al., 2009, Can J Cardiol 25:213-218].

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation [see, e.g., Schrier (2002) Curr Opin Hematol 9:123-126]. Thalassemias are collectively among the most frequent genetic disorders worldwide, with changing epidemiologic patterns predicted to contribute to a growing public health problem in both the U.S. and globally [Vichinsky (2005) Ann NY Acad Sci 1054:18-24]. Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia [see, e.g., Rund et al. (2005) N Engl J Med 353:1135-1146]. In certain embodiments, one or more variant ActRIIB proteins of the disclosure, optionally combined with an EPO receptor activator, can be used to treat or prevent a thalassemia syndrome.

In some embodiments, one or more variant ActRIIB proteins of the disclosure, optionally combined with an EPO receptor activator, can be used for treating disorders of ineffective erythropoiesis besides thalassemia syndromes. Such disorders include siderblastic anemia (inherited or acquired); dyserythropoietic anemia (types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anemia, refractory megaloblastic anemia, or erythroleukemia); myelophthisic anemias including, for example, myelofibrosis (myeloid metaplasia) and myelophthisis; congenital erythropoietic porphyria; and lead poisoning.

In certain embodiments, one or more variant ActRIIB proteins of the disclosure may be used in combination with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload [see, e.g., Hershko (2006) Haematologica 91:1307-1312; Cao et al. (2011), Pediatr Rep 3(2):e17]. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; Galanello et al. (2010) Ann NY Acad Sci 1202:79-86].

As used herein, "in combination with" or "conjoint administration" refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more variant ActRIIB proteins of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, one or more variant ActRIIB proteins of the disclosure may be used in combination with hepcidin or a hepcidin agonist for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis [see, e.g., Nemeth (2010) Adv Hematol 2010:750643]. This view is supported by beneficial effects of increased hepcidin expression in a mouse model of β-thalassemia [Gardenghi et al. (2010) J Clin Invest 120: 4466-4477].

One or more variant ActRIIB proteins of the disclosure, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

In certain embodiments, the present disclosure provides methods of treating or preventing anemia in an individual in need thereof by administering to the individual a therapeutically effective amount of one or more variant ActRIIB proteins of the disclosure and a EPO receptor activator. In certain embodiments, one or more variant ActRIIB proteins of the disclosure may be used in combination with EPO receptor activators to reduce the required dose of these activators in patients that are susceptible to adverse effects of EPO. These methods may be used for therapeutic and prophylactic treatments of a patient.

One or more variant ActRIIB proteins of the disclosure may be used in combination with EPO receptor activators to achieve an increase in red blood cells, particularly at lower dose ranges of EPO receptor activators. This may be beneficial in reducing the known off-target effects and risks associated with high doses of EPO receptor activators. The primary adverse effects of EPO include, for example, an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that variant ActRIIB proteins of the present disclosure act by a different mechanism than EPO, these antagonists may be useful for increasing red blood cell and hemoglobin levels in patients that do not respond well to EPO. For example, an antagonist of the present disclosure may be beneficial for a patient in which administration of a normal-to-increased dose of EPO (>300 IU/kg/week) does not result in the increase of hemoglobin level up to the target level. Patients with an inadequate EPO response are found in all types of anemia, but higher numbers of non-responders have been observed particularly frequently in patients with cancers and patients with end-stage renal disease. An inadequate response to EPO can be either constitutive (observed upon the first treatment with EPO) or acquired (observed upon repeated treatment with EPO).

In certain embodiments, the present disclosure provides methods for managing a patient that has been treated with, or is a candidate to be treated with, one or more variant ActRIIB proteins of the disclosure by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more variant ActRIIB proteins of the disclosure may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more variant ActRIIB proteins of the disclosure, then onset of administration of the one or more variant ActRIIB proteins of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more variant ActRIIB proteins of the disclosure may be delayed until the levels have returned to a normal or acceptable level.

In certain embodiments, if one or more hematologic parameters are outside the normal range or on the high side of normal in a patient who is a candidate to be treated with one or more variant ActRIIB proteins of the disclosure, then the onset of administration may not be delayed. However, the dosage amount or frequency of dosing of the one or more variant ActRIIB proteins of the disclosure may be set at an amount that would reduce the risk of an unacceptable increase in the hematologic parameters arising upon administration of the one or more variant ActRIIB proteins of the disclosure. Alternatively, a therapeutic regimen may be developed for the patient that combines one or more variant ActRIIB proteins of the disclosure with a therapeutic agent that addresses the undesirable level of the hematologic parameter. For example, if the patient has elevated blood pressure, then a therapeutic regimen involving administration of one or more variant ActRIIB proteins of the disclosure and a blood pressure-lowering agent may be designed. For a patient having lower than desired iron stores, a therapeutic regimen of one or more variant ActRIIB proteins and iron supplementation may be developed.

In one embodiment, baseline parameter(s) for one or more hematologic parameters may be established for a patient who is a candidate to be treated with one or more variant ActRIIB proteins of the disclosure and an appropriate dosing regimen established for that patient based on the baseline value(s). Alternatively, established baseline parameters based on a patient's medical history could be used to inform an appropriate antagonist-dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more variant ActRIIB proteins of the disclosure may also be used as the relevant comparative values for monitoring any changes to the hematologic parameters during treatment with the one or more antagonists of the disclosure.

In certain embodiments, one or more hematologic parameters are measured in patients who are being treated with a one or more variant ActRIIB proteins of the disclosure. The hematologic parameters may be used to monitor the patient during treatment and permit adjustment or termination of the dosing with the one or more antagonists of the disclosure or additional dosing with another therapeutic agent. For example, if administration of one or more variant ActRIIB proteins of the disclosure results in an increase in blood pressure, red blood cell level, or hemoglobin level, or a reduction in iron stores, then the dose of the one or more variant ActRIIB proteins of the disclosure may be reduced in amount or frequency in order to decrease the effects of the one or more variant ActRIIB proteins of the disclosure on the one or more hematologic parameters. If administration of one or more variant ActRIIB proteins of the disclosure results in a change in one or more hematologic parameters that is adverse to the patient, then the dosing of the one or more variant ActRIIB proteins of the disclosure may be terminated either temporarily, until the hematologic parameter(s) return to an acceptable level, or permanently. Similarly, if one or more hematologic parameters are not brought within an acceptable range after reducing the dose or frequency of administration of the one or more variant ActRIIB proteins of the disclosure, then the dosing may be terminated. As an alternative, or in addition to, reducing or terminating the dosing with the one or more variant ActRIIB proteins of the disclosure, the patient may be dosed with an additional therapeutic agent that addresses the undesirable level in the hematologic parameter(s), such as, for example, a blood pressure-lowering agent or an iron supplement. For example, if a patient being treated with one or more variant ActRIIB proteins of the disclosure has elevated blood pressure, then dosing with the one or more variant ActRIIB proteins of the disclosure may continue at the same level and a blood pressure-lowering agent is added to the treatment regimen, dosing with the one or more variant ActRIIB proteins of the disclosure may be reduced (e.g., in amount and/or frequency) and a blood pressure-lowering agent is added to the treatment regimen, or dosing with the one or more variant ActRIIB proteins of the disclosure may be terminated and the patient may be treated with a blood pressure-lowering agent.

7. Pharmaceutical Compositions

In certain embodiments, compounds of the present invention (e.g., variant ActRIIB proteins in either homomeric or heteromeric forms) are formulated with a pharmaceutically acceptable carrier. For example, a variant ActRIIB protein can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neurons), for example, a site having a tissue damage. Topical administration may be suitable for wound healing and tissue repair. Therapeutically useful agents other than the variant ActRIIB proteins which may also optionally be included in the composition as described above, may alternatively or additionally, be administered simultaneously or sequentially with the subject compounds (e.g., variant ActRIIB proteins) in the methods of the invention.

In certain embodiments, compositions of the present invention may include a matrix capable of delivering one or more therapeutic compounds (e.g., variant ActRIIB proteins) to a target tissue site, providing a structure for the developing tissue and optimally capable of being resorbed into the body. For example, the matrix may provide slow release of the variant ActRIIB proteins. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, variant ActRIIB proteins of the invention can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more variant ActRIIB proteins of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., a variant ActRIIB protein), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more variant ActRIIB proteins in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., variant ActRIIB proteins). The various factors will depend upon the disease to be treated. In the case of muscle disorders, factors may include, but are not limited to, amount of muscle mass desired to be formed, the muscles most affected by disease, the condition of the deteriorated muscle, the patient's age, sex, and diet, time of administration, and other clinical factors. The addition of other known growth factors to the final composition, may also affect the dosage. Progress can be monitored by periodic assessment of muscle growth and/or repair, for example, by strength testing, MRI assessment of muscle size and analysis of muscle biopsies.

In certain embodiments of the invention, one or more variant ActRIIB proteins can be administered, together (simultaneously) or at different times (sequentially or overlapping). In addition, variant ActRIIB proteins can be administered with another type of therapeutic agents, for example, a cartilage-inducing agent, a bone-inducing agent, a muscle-inducing agent, a fat-reducing, or a neuron-inducing agent. The two types of compounds may be administered simultaneously or at different times. It is expected that the variant ActRIIB proteins of the invention may act in concert with or perhaps synergistically with another therapeutic agent.

In a specific example, a variety of osteogenic, cartilage-inducing and bone-inducing factors have been described, particularly bisphosphonates. See e.g., European Patent Application Nos. 148,155 and 169,016. For example, other factors that can be combined with the subject variant ActRIIB proteins include various growth factors such as epidermal growth factor (EGF), platelet derived growth factor (PDGF), transforming growth factors (TGF-α and TGF-β), and insulin-like growth factor (IGF).

In certain embodiments, the present invention also provides gene therapy for the in vivo production of variant ActRIIB proteins. Such therapy would achieve its therapeutic effect by introduction of the variant ActRIIB polynucleotide sequences into cells or tissues having the disorders as listed above. Delivery of variant ActRIIB polynucleotide sequences can be achieved using a recombinant expression vector such as a chimeric virus or a colloidal dispersion system. Preferred for therapeutic delivery of variant ActRIIB polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the variant ActRIIB polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for variant ActRIIB polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidyletha-nolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of an ActRIIB-Fc Fusion Protein

Applicants constructed a soluble ActRIIB fusion protein that has the extracellular domain of human ActRIIB fused to a human G1Fc domain with a minimal linker (three glycine amino acids) in between. The construct is referred to as ActRIIB-G1Fc.

ActRIIB-G1Fc is shown below in SEQ ID NO: 5 (with the linker underlined) as purified from CHO cell lines:

(SEQ ID NO: 5)
GRGEAETRECIYYNANWELERTNQSGLERCEGEQDKRLHCYASWRNSSGT

IELVKKGCWLDDFNCYDRQECVATEENPQVYFCCCEGNFCNERFTHLPE

AGGPEVTYEPPPTAPTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

The ActRIIB-G1Fc protein was expressed in CHO cell lines. Three different leader sequences were considered:

(i) Honey bee mellitin (HBML):
(SEQ ID NO: 7)
MKFLVNVALVFMVVYISYIYA (ii) Tissue plasminogen activator (TPA):
(SEQ ID NO: 8)
MDAMKRGLCCVLLLCGAVFVSP (iii) Native:
(SEQ ID NO: 9)
MTAPWVALALLWGSLCAG.

The selected form employs the TPA leader and has the following unprocessed amino acid sequence:

(SEQ ID NO: 6)
MDAMKRGLCCVLLLCGAVFVSPGASGRGEAETRECIYYNANWELERTNQS

GLERCEGEQDKRLHCYASWRNSSGTIELVKKGCWLDDFNCYDRQECVATE

ENPQVYFCCCEGNFCNERFTHLPEAGGPEVTYEPPPTAPTGGGTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

This polypeptide is encoded by the following nucleic acid sequence (SEQ ID NO: 10):

(SEQ ID NO: 10)
A TGGATGCAAT GAAGAGAGGG CTCTGCTGTG TGCTGCTGCT GTGTGGAGCA GTCTTCGTTT

CGCCCGGCGC CTCTGGGCGT GGGGAGGCTG AGACACGGGA GTGCATCTAC TACAACGCCA

ACTGGGAGCT GGAGCGCACC AACCAGAGCG GCCTGGAGCG CTGCGAAGGC GAGCAGGACA

AGCGGCTGCA CTGCTACGCC TCCTGGCGCA ACAGCTCTGG CACCATCGAG CTCGTGAAGA

AGGGCTGCTG GCTAGATGAC TTCAACTGCT ACGATAGGCA GGAGTGTGTG GCCACTGAGG

AGAACCCCCA GGTGTACTTC TGCTGCTGTG AAGGCAACTT CTGCAACGAG CGCTTCACTC

ATTTGCCAGA GGCTGGGGGC CCGGAAGTCA CGTACGAGCC ACCCCCGACA GCCCCCACCG

GTGGTGGAAC TCACACATGC CCACCGTGCC CAGCACCTGA ACTCCTGGGG GGACCGTCAG

TCTTCCTCTT CCCCCCAAAA CCCAAGGACA CCCTCATGAT CTCCCGGACC CCTGAGGTCA

CATGCGTGGT GGTGGACGTG AGCCACGAAG ACCCTGAGGT CAAGTTCAAC TGGTACGTGG

ACGGCGTGGA GGTGCATAAT GCCAAGACAA AGCCGCGGGA GGAGCAGTAC AACAGCACGT

ACCGTGTGGT CAGCGTCCTC ACCGTCCTGC ACCAGGACTG GCTGAATGGC AAGGAGTACA

AGTGCAAGGT CTCCAACAAA GCCCTCCCAG CCCCCATCGA GAAAACCATC TCCAAAGCCA

AAGGGCAGCC CCGAGAACCA CAGGTGTACA CCCTGCCCCC ATCCCGGGAG GAGATGACCA

AGAACCAGGT CAGCCTGACC TGCCTGGTCA AAGGCTTCTA TCCCAGCGAC ATCGCCGTGG

AGTGGGAGAG CAATGGGCAG CCGGAGAACA ACTACAAGAC CACGCCTCCC GTGCTGGACT

```
                         -continued
CCGACGGCTC CTTCTTCCTC TATAGCAAGC TCACCGTGGA CAAGAGCAGG TGGCAGCAGG

GGAACGTCTT CTCATGCTCC GTGATGCATG AGGCTCTGCA CAACCACTAC ACGCAGAAGA

GCCTCTCCCT GTCTCCGGGT AAATGA
```

N-terminal sequencing of the CHO-cell produced material revealed a major sequence of -GRGEAE (SEQ ID NO: 11). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

The ActRIIB-Fc fusion protein was also expressed in HEK293 cells and COS cells. Although material from all cell lines and reasonable culture conditions provided protein with muscle-building activity in vivo, variability in potency was observed perhaps relating to cell line selection and/or culture conditions.

Example 2: Generation of Variant ActRIIB-Fc Proteins

Applicants generated a series of mutations (sequence variations) in the extracellular domain of ActRIIB and produced these variant polypeptides as soluble homodimeric fusion proteins comprising a variant ActRIIB extracellular domain and an Fc domain joined by an optional linker. The background ActRIIB-Fc fusion was ActRIIB-G1Fc as shown in SEQ ID NO: 5

Various substitution mutations were introduced into the background ActRIIB-Fc protein. Based on the data presented in Example 1, it is expected that these constructs, if expressed with a TPA leader, will lack the N-terminal serine. Mutations were generated in the ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into *E. coli* DH5 alpha, colonies were picked and DNAs were isolated. For murine constructs (mFc), a murine IgG2a was substituted for the human IgG1. All mutants were sequence verified.

The amino acid sequence of unprocessed ActRIIB (K55A)-G1Fc is shown below (SEQ ID NO: 31). The signal sequence and linker sequence are indicated by solid underline, and the K55A substitution is indicated by double underline. The amino acid sequence of SEQ ID NO:31 may optionally be provided with the lysine removed from the C-terminus.

```
                                                      (SEQ ID NO: 31)
  1 MDAMKRGLCC VLLLCGAVFV SPGASGRGEA ETRECIYYNA NWELERTNQS

51 GLERCEGEQD ARLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSREEMT KNQVSLTCLV KGFYPSDIAV

301 EWESNGQPEN NYKTTPPVLD SDGSFFLYSK LTVDKSRWQQ GNVFSCSVMH

351 EALHNHYTQK SLSLSPGK
```

This ActRIIB(K55A)-G1Fc fusion polypeptide is encoded by the following nucleic acid sequence (SEQ ID NO: 32):

```
                                                      (SEQ ID NO: 32)
  1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC GCCCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC
```

```
-continued
401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGGA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGGAC TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCCCCGGG

1101 TAAA
```

The mature ActRIIB(K55A)-G1Fc fusion polypeptide (SEQ ID NO: 33) is as follows and may optionally be provided with the lysine removed from the C-terminus.

```
                                                   (SEQ ID NO: 33)
  1 GRGEAETREC IYYNANWELE RTNQSGLERC EGEQDARLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYKTT PPVLDSDGSF

301 FLYSKLTVDK SRWQQGNVFS CSVMHEALHN HYTQKSLSLS PGK
```

The amino acid sequence of unprocessed ActRIIB (K55E)-G1Fc is shown below (SEQ ID NO: 34). The signal sequence and linker sequence are indicated by solid underline, and the K55E substitution is indicated by double underline. The amino acid sequence of SEQ ID NO:34 may optionally be provided with the lysine removed from the C-terminus.

```
                                                   (SEQ ID NO: 34)
  1 MDAMKRGLCC VLLLCGAVFV SPGASGRGEA ETRECIYYNA NWELERTNQS

51 GLERCEGEQD ERLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSREEMT KNQVSLTCLV KGFYPSDIAV

301 EWESNGQPEN NYKTTPPVLD SDGSFFLYSK LTVDKSRWQQ GNVFSCSVMH

351 EALHNHYTQK SLSLSPGK
```

This ActRIIB(K55E)-G1Fc fusion polypeptide is encoded by the following nucleic acid sequence (SEQ ID NO: 35):

```
                                              (SEQ ID NO: 35)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC GAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGGA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGGAC TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCCCCGGG

1101 TAAA
```

The mature ActRIIB(K55E)-G1Fc fusion polypeptide (SEQ ID NO: 36) is as follows and may optionally be provided with the lysine removed from the C-terminus.

```
                                              (SEQ ID NO: 36)
   1 GRGEAETREC IYYNANWELE RTNQSGLERC EGEQDERLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYKTT PPVLDSDGSF

301 FLYSKLTVDK SRWQQGNVFS CSVMHEALHN HYTQKSLSLS PGK
```

The amino acid sequence of unprocessed ActRIIB(F82I)-G1Fc is shown below (SEQ ID NO: 37). The signal sequence and linker sequence are indicated by solid underline, and the F82I substitution is indicated by double underline. The amino acid sequence of SEQ ID NO: 37 may optionally be provided with the lysine removed from the C-terminus.

```
                                                         (SEQ ID NO: 37)
   1 MDAMKRGLCC VLLLCGAVFV SPGASGRGEA ETRECIYYNA NWELERTNQS

51 GLERCEGEQD KRLHCYASWR NSSGTIELVK KGCWLDDINC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSREEMT KNQVSLTCLV KGFYPSDIAV

301 EWESNGQPEN NYKTTPPVLD SDGSFFLYSK LTVDKSRWQQ GNVFSCSVMH

351 EALHNHYTQK SLSLSPGK
```

15

This ActRIIB(F82I)-G1Fc fusion polypeptide is encoded by the following nucleic acid sequence (SEQ ID NO: 38):

```
                                                         (SEQ ID NO: 38)
    1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CATCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGGA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGGAC TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 TAAA
```

The mature ActRIIB(F82I)-G1Fc fusion polypeptide (SEQ ID NO: 39) is as follows and may optionally be provided with the lysine removed from the C-terminus.

```
                                                         (SEQ ID NO: 39)
   1 GRGEAETREC IYYNANWELE RTNQSGLERC EGEQDKRLHC YASWRNSSGT

51 IELVKKGCWL DDINCYDRQE CVATEENPQV YFCCCEGNFC NERFTHLPEA
```

```
101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYKTT PPVLDSDGSF

301 FLYSKLTVDK SRWQQGNVFS CSVMHEALHN HYTQKSLSLS PGK
```

The amino acid sequence of unprocessed ActRIIB (F82K)-G1Fc is shown below (SEQ ID NO: 40). The signal sequence and linker sequence are indicated by solid underline, and the F82K substitution is indicated by double underline. The amino acid sequence of SEQ ID NO: 40 may optionally be provided with the lysine removed from the C-terminus.

```
                                              (SEQ ID NO: 40)
  1 MDAMKRGLCC VLLLCGAVFV SPGASGRGEA ETRECIYYNA NWELERTNQS

51 GLERCEGEQD KRLHCYASWR NSSGTIELVK KGCWLDDKNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSREEMT KNQVSLTCLV KGFYPSDIAV

301 EWESNGQPEN NYKTTPPVLD SDGSFFLYSK LTVDKSRWQQ GNVFSCSVMH

351 EALHNHYTQK SLSLSPGK
```

This ActRIIB(F82K)-G1Fc fusion polypeptide is encoded by the following nucleic acid sequence (SEQ ID NO: 41):

```
                                              (SEQ ID NO: 41)
  1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CAAGAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCGAGAACC

801 ACAGGTGTAC ACCCTGCCCC CATCCCGGGA GGAGATGACC AAGAACCAGG

851 TCAGCCTGAC CTGCCTGGTC AAAGGCTTCT ATCCCAGCGA CATCGCCGTG
```

```
 901 GAGTGGGAGA GCAATGGGCA GCCGGAGAAC AACTACAAGA CCACGCCTCC

951 CGTGCTGGAC TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 TAAA
```

The mature ActRIIB(F82K)-G1Fc fusion polypeptide (SEQ ID NO: 42) is as follows and may optionally be provided with the lysine removed from the C-terminus.

```
                                                  (SEQ ID NO: 42)
  1 GRGEAETREC IYYNANWELE RTNQSGLERC EGEQDKRLHC YASWRNSSGT

51 IELVKKGCWL DDKNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYKTT PPVLDSDGSF

301 FLYSKLTVDK SRWQQGNVFS CSVMHEALHN HYTQKSLSLS PGK
```

Constructs were expressed in COS or CHO cells and purified by filtration and protein A chromatography. In some instances, assays were performed with conditioned medium rather than purified proteins. Purity of samples for reporter gene assays was evaluated by SDS-PAGE and Western blot analysis.

Mutants were tested in binding assays and/or bioassays described below.

Alternatively, similar mutations could be introduced into an ActRIIB extracelluar domain possessing an N-terminal truncation of five amino acids and a C-terminal truncation of three amino acids as shown below (SEQ ID NO: 53). This truncated ActRIIB extracellular domain is denoted ActRIIB (25-131) based on numbering in SEQ ID NO: 2.

```
                                                  (SEQ ID NO: 53)
 25 ETRECIYYNA NWELERTNQS GLERCEGEQD KRLHCYASWR NSSGTIELVK

75 KGCWLDDFNC YDRQECVATE ENPQVYFCCC EGNFCNERFT HLPEAGGPEV

125 TYEPPPT
```

The corresponding background fusion polypeptide, ActRIIB(25-131)-G1Fc, is shown below (SEQ ID NO: 12).

```
                                                  (SEQ ID NO: 12)
  1 ETRECIYYNA NWELERTNQS GLERCEGEQD KRLHCYASWR NSSGTIELVK

51 KGCWLDDFNC YDRQECVATE ENPQVYFCCC EGNFCNERFT HLPEAGGPEV

101 TYEPPPTGGG THTCPPCPAP ELLGGPSVFL FPPKPKDTLM ISRTPEVTCV

151 VVDVSHEDPE VKFNWYVDGV EVHNAKTKPR EEQYNSTYRV VSVLTVLHQD

201 WLNGKEYKCK VSNKALPAPI EKTISKAKGQ PREPQVYTLP PSREEMTKNQ

251 VSLTCLVKGF YPSDIAVEWE SNGQPENNYK TTPPVLDSDG SFFLYSKLTV

301 DKSRWQQGNV FSCSVMHEAL HNHYTQKSLS LSPGK
```

Example 3. Activity of Variant ActRIIB-Fc Proteins in a Cell-Based Assay

An A204 cell-based assay was used to compare effects among variant ActRIIB-Fc proteins on signaling by activin A, GDF11, and BMP9. In brief, this assay uses a human A204 rhabdomyosarcoma cell line (ATCC®: HTB-82™) derived from muscle and the reporter vector pGL3(CAGA) 12 (Dennler et al., 1998, EMBO 17: 3091-3100) as well as a *Renilla* reporter plasmid (pRLCMV) to control for transfection efficiency. The CAGA12 motif is present in TGF-β responsive genes (e.g., PAI-1 gene), so this vector is of general use for ligands that can signal through Smad2/3, including activin A, GDF11, and BMP9.

On day 1, A-204 cells were transferred into one or more 48-well plates. On day 2, these cells were transfected with 10 µg pGL3(CAGA)12 or pGL3(CAGA)12(10+pRLCMV (1 µg) and Fugene. On day 3, ligands diluted in medium containing 0.1% BSA were preincubated with ActRIIB-Fc proteins for 1 hr before addition to cells. Approximately six hour later, the cells were rinsed with PBS and lysed. Cell lysates were analyzed in a luciferase assay to determine the extent of Smad activation.

This assay was used to screen variant ActRIIB-Fc proteins for inhibitory effects on cell signaling by activin A, GDF11, and BMP9. Potencies of homodimeric Fc fusion proteins incorporating amino acid substitutions in the human ActRIIB extracellular domain were compared with that of an Fc fusion protein comprising unmodified human ActRIIB extracellular domain.

| Inhibitory Potency of Homodimeric ActRIIB-Fc Constructs | | | |
|---|---|---|---|
| ActRIIB protein | $IC_{50}$ (ng/mL) | | |
| | Activin A | GDF11 | BMP9 |
| Wild-type | 8 | 9 | 31 |
| A24N | 128 | 99 | 409 |
| R40A | — | 591 | 1210 |
| E50K | 132 | 180 | 721 |
| E50P | 756 | 638 | ~3000 |
| E52A | 198 | 71 | 359 |
| E52K | 762 | 296 | ~10000 |
| K55A | 15 | 11 | 122 |
| K55D | 396 | 365 | 5500 |
| K55E | 19 | 14 | 290 |
| K55R | 206 | 318 | 777 |
| Y60K | — | 414 | Neg |
| Y60P | — | 544 | Neg |
| K74R | — | 45 | 165 |
| K74Y | — | Neg | Neg |
| K74A/L79P | — | Neg | Neg |
| L79K | — | 477 | Neg |
| L79P | — | Neg | Neg |
| L79R | — | 234 | Neg |
| D80A | — | Neg | Neg |
| F82I | 11 | 9 | 277 |
| F82K | 10 | 15 | ~5000 |
| F82W | — | 276 | Neg |
| F82W/N83A | — | 389 | ~40000 |
| V99E | — | Neg | Neg |
| V99K | — | Neg | — |

Neg Absence of inhibition over concentration range tested
— Not tested

As shown in the table above, single amino acid substitutions in the ActRIIB extracellular domain can alter the balance between activin A or GDF11 inhibition and BMP9 inhibition in a cell-based reporter gene assay. Compared to a fusion protein containing unmodified ActRIIB extracellular domain, the variants ActRIIB(K55A)-Fc, ActRIIB(K55E)-Fc, ActRIIB(F82I)-Fc, and ActRIIB(F82K)-Fc showed less potent inhibition of BMP9 (increased $IC_{50}$ values) while maintaining essentially undiminished inhibition of activin A and GDF11.

These results indicate that variant ActRIIB-Fc proteins such as ActRIIB(K55A)-Fc, ActRIIB(K55E)-Fc, ActRIIB (F82I)-Fc, and ActRIIB(F82K)-Fc are more selective antagonists of activin A and GDF11 compared to an Fc fusion protein comprising unmodified ActRIIB extracellular domain. Accordingly, these variants may be more useful than ActRIIB-Fc in certain applications where such selective antagonism is advantageous. Examples include therapeutic applications where it is desirable to retain antagonism of one or more of activin A, GDF8, and GDF11 while reducing antagonism of BMP9 and potentially BMP10.

Example 4. Ligand Binding Profiles of Variant ActRIIB-Fc Homodimers

A Biacore™-based binding assay was used to compare ligand binding kinetics of certain variant ActRIIB-Fc proteins screened in Example 3 as well as other variant ActRIIB-Fc proteins not evaluated previously. ActRIIB-Fc proteins to be tested were independently captured onto the system using an anti-Fc antibody. Ligands were then injected and allowed to flow over the captured receptor protein. Results of variant ActRIIB-Fc proteins analyzed at 37° C. are shown in FIG. 8. Compared to Fc-fusion protein comprising unmodified ActRIIB extracellular domain, the variant proteins ActRIIB(K55A)-Fc, ActRIIB(K55E)-Fc, ActRIIB(F82I)-Fc, and ActRIIB(F82K)-Fc exhibited greater reduction in their affinity for BMP9 than for GDF11. Results of additional variant ActRIIB-Fc proteins analyzed at 25° C. are shown in FIG. 9.

These results confirm K55A, K55E, F82I, and F82K as substitutions that reduce ActRIIB binding affinity for BMP9 more than they reduce ActRIIB affinity for activin A or GDF11. Accordingly, these variant ActRIIB-Fc proteins may be more useful than unmodified ActRIIB-Fc protein in certain applications where such selective antagonism is advantageous. Examples include therapeutic applications where it is desirable to retain antagonism of one or more of activin A, activin B, GDF8, and GDF11 while reducing antagonism of BMP9.

Example 5. Activity of Variant ActRIIB-Fc Homodimers in Mice

Selected variant ActRIIB-G1Fc homodimers were tested in mice to investigate differences in their activity profiles in vivo. Adult wild-type C57BL/6 mice were dosed at 10 mg/kg (i.p.) with ActRIIB(K55A)-Fc, ActRIIB(K55E)-Fc, ActRIIB(F82I)-Fc, ActRIIB(F82K)-Fc, unmodified ActRIIB-Fc, or vehicle twice per week for 4 weeks (n=8 mice per group). Study endpoints included: body weight, CBC, and total lean mass and total adipose mass as determined by nuclear magnetic resonance (NMR) at baseline and study completion.

Treatment of mice with unmodified ActRIIB-Fc more than tripled the gain in body weight over the course of the study compared to vehicle-treated controls. The increase in body weight caused by ActRIIB(F82I)-Fc (25%) was nearly as large as that caused by unmodified ActRIIB-Fc (29%), while the other variant ActRIIB-Fc proteins produced body weight gains in the range of 12-17% (FIG. 10). NMR analysis revealed that ActRIIB(F82I)-Fc treatment significantly increased total lean mass and reduced total fat mass compared to vehicle as shown in the table below.

| Test Article | Change in lean mass from baseline | Change in fat mass from baseline |
|---|---|---|
| Vehicle | −2.3% ±0.6% | 17.6% ±5.8% |
| ActRIIB-G1Fc | 3.1% ±0.7% (P < 0.001 vs vehicle) | −40.1% ±5.6% (P = 0.0011 vs vehicle) |
| ActRIIB(F82I)-G1Fc | 1.5% ±0.7% (P < 0.001 vs vehicle) | −19.6% ±6.3% (P < 0.01 vs vehicle) |

ActRIIB(F82I)-Fc produced changes in lean mass and fat mass approximately half the magnitude of those produced by ActRIIB-Fc. It should be recognized that normalized (percentage-based) changes in lean and adipose tissues differ in their correspondence to absolute changes because lean mass (typically about 70% of body weight in a mouse) is much larger than adipose mass (typically about 10% of body weight). Individual skeletal muscles examined, including the gastrocnemius, femoris, and pectoralis all increased significantly in weight over the course of treatment with ActRIIB(F82I)-Fc compared to vehicle.

Figure 11:
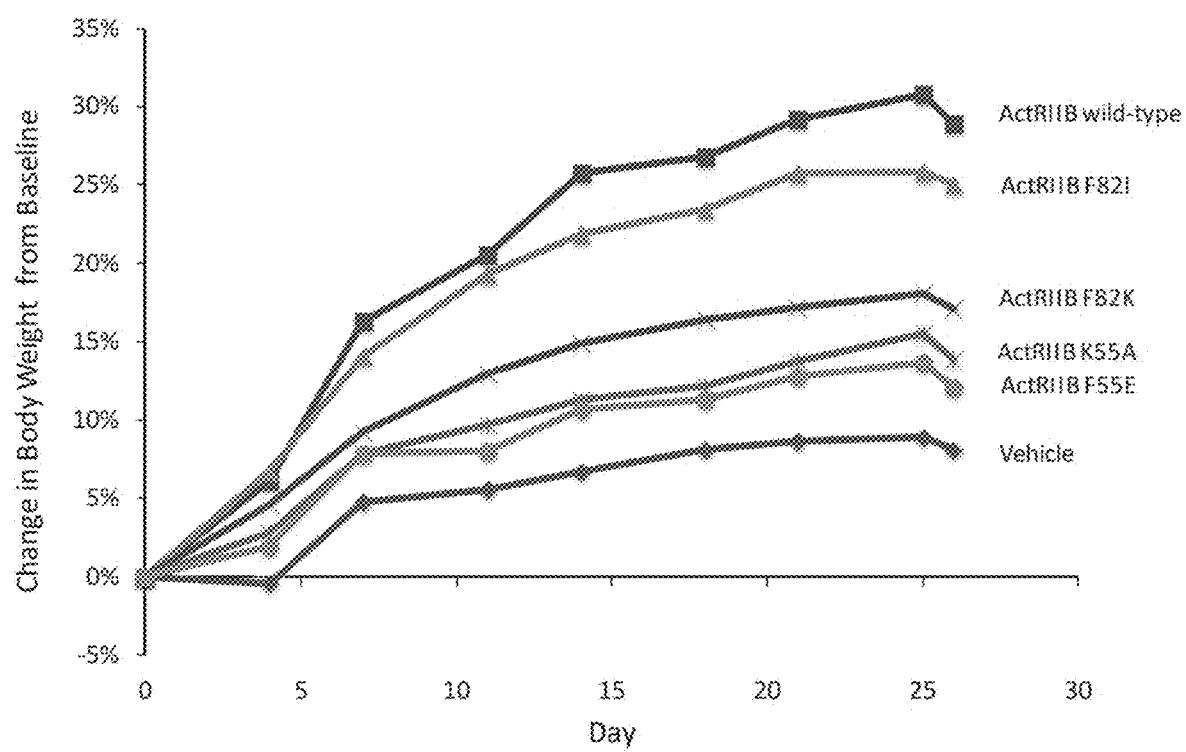
FIG. 11 shows changes in body weight from baseline for wild-type mice treated with vehicle or homodimeric Fc-fusion proteins comprising variant or unmodified ActRIIB domains.

All five of the ActRIIB-Fc fusion proteins evaluated produced significantly higher values for red blood cell parameters (RBC count, hematocrit, and hemoglobin concentration) than did vehicle, and the stimulatory effect of ActRIIB(F82I)-Fc on these parameters exceeded that of unmodified ActRIIB-Fc (FIG. 11).

Thus, homodimeric Fc-fusion proteins comprising a variant ActRIIB extracellular domain can exert beneficial anabolic effects on red blood cells and skeletal muscle as well as catabolic effects on adipose tissue similar to those of unmodified ActRIIB-Fc homodimer. However, variant ActRIIB-Fc homodimers bind with reduced affinity to BMP9 compared to unmodified ActRIIB-Fc and so will exert diminished inhibition of processes mediated by that ligand, such as angiogenesis. This novel selectivity will be useful, for example, in treating patients in need of stimulatory effects on red blood cells and muscle as well as inhibitory effects on fat, but not in need of altered angiogenesis.

Example 6. Activity of ActRIIB(F82I)-Fc Homodimer in Non-Human Primates

Figure 12:
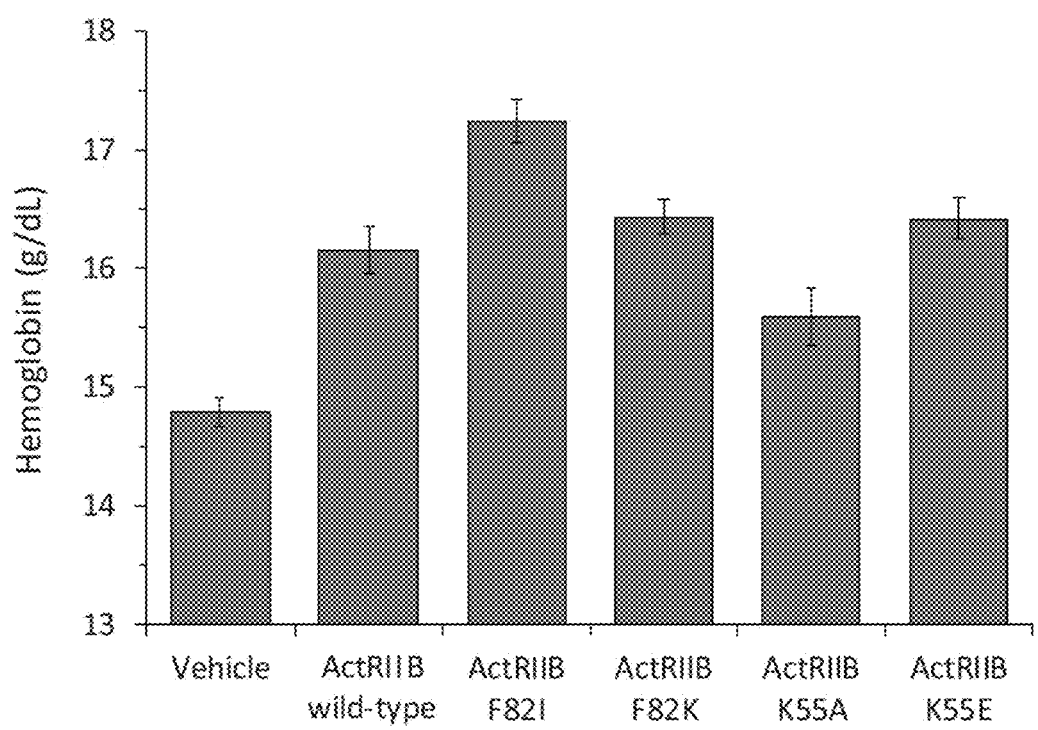
FIG. 12 shows hemoglobin concentrations in wild-type mice treated with vehicle or homodimeric Fc-fusion proteins comprising variant or unmodified ActRIIB domains.
Figure 13:
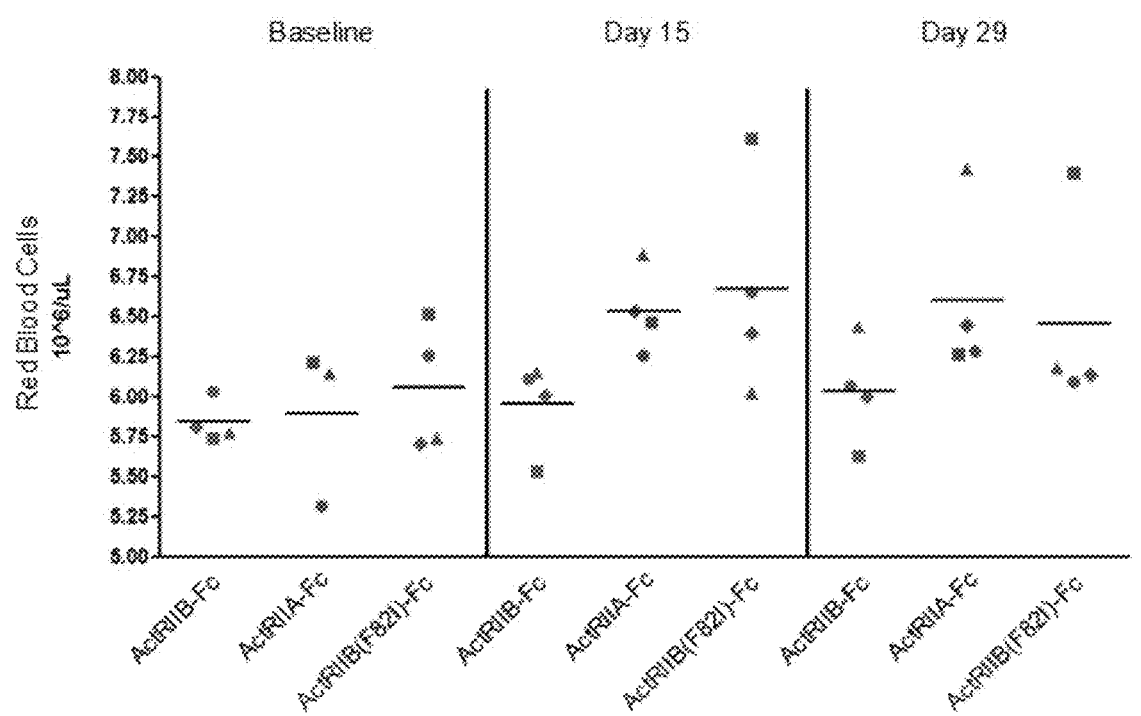
FIG. 13 shows red blood cell counts in cynomolgus monkeys treated with ActRIIB-Fc, ActRIIA-Fc, or ActRIIB (F82I)-Fc at 9 mg/kg (s.c.) on days 1 and 15. ActRIIB(F82I)-Fc treatment increased RBC counts compared to ActRIIB-Fc (negative control) by an amount similar to that of ActRIIA-Fc (positive control).

Applicants then investigated whether ActRIIB(F82I)-Fc homodimer alters RBC parameters in non-human primates. Cynomolgus monkeys (*M. fascicularis*) were treated with ActRIIB(F82I)-G1Fc, unmodified ActRIIB-G1Fc, or unmodified ActRIIA-G1Fc at 9 mg/kg (s.c.) on days 1 and 15 of a 29-day study (n=4 monkeys per group). As shown in FIG. 12, ActRIIB(F82I)-Fc treatment increased RBC counts compared to ActRIIB-Fc (negative control in primates) by an amount similar to that of ActRIIA-Fc (postitive control). Comparable results were obtained for hemoglobin concentration and hematocrit (data not shown). These data confirm that ActRIIB(F82I)-Fc homodimer possesses activity in vivo different from that of unmodified ActRIIB-Fc homodimer.

Example 7. Generation of an ActRIIB-Fc:ActRIIB(L79E)-Fc Heterodimer

Applicants envision generation of a soluble ActRIIB-Fc:ActRIIB(L79E)-Fc heteromeric complex comprising the extracellular domains of unmodified human ActRIIB and human ActRIIB with a leucine-to-glutamate substitution at position 79, which are each separately fused to an G1Fc domain with a linker positioned between the extracellular domain and the G1Fc domain. The individual constructs are referred to as ActRIIB-Fc fusion polypeptide and ActRIIB (L79E)-Fc fusion polypeptide, respectively, and the sequences for each are provided below.

A methodology for promoting formation of ActRIIB-Fc:ActRIIB(L79E)-Fc heteromeric complexes, as opposed to the ActRIIB-Fc or ActRIIB(L79E)-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB(L79E)-Fc and ActRIIB-Fc polypeptide sequences of SEQ ID NOs: 43-45 and 46-48, respectively, one Fc domain can be altered to introduce cationic amino acids at the interaction face, while the other Fc domain can be altered to introduce anionic amino acids at the interaction face. The ActRIIB(L79E)-Fc fusion polypeptide and ActRIIB-Fc fusion polypeptide can each employ the TPA leader (SEQ ID NO: 8).

The ActRIIB(L79E)-Fc polypeptide sequence (SEQ ID NO: 43) is shown below:

```
                                                      (SEQ ID NO: 43)
  1 MDAMKRGLCC VLLLCGAVFV SPGASGRGEA ETRECIYYNA NWELERTNQS

51 GLERCEGEQD KRLHCYASWR NSSGTIELVK KGCWEDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSREEMT KNQVSLTCLV KGFYPSDIAV

301 EWESNGQPEN NYDTTPPVLD SDGSFFLYSD LTVDKSRWQQ GNVFSCSVMH

351 EALHNHYTQK SLSLSPG
```

The leader (signal) sequence and linker are underlined, and the L79E substitution is indicated by double underline. To promote formation of the ActRIIB-Fc:ActRIIB(L79E)-Fc heterodimer rather than either of the possible homodimeric complexes, two amino acid substitutions (replacing lysines with acidic amino acids) can be introduced into the Fc domain of the ActRIIB fusion protein as indicated by double underline above. The amino acid sequence of SEQ ID NO: 43 may optionally be provided with lysine added to the C-terminus.

This ActRIIB(L79E)-Fc fusion protein can be encoded by the following nucleic acid sequence (SEQ ID NO: 44):

```
                                                  (SEQ ID NO: 44)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGGAAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGGA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACGACA CCACGCCTCC

951 CGTGCTGGAC TCCGACGGCT CCTTCTTCCT CTATAGCGAC CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 T
```

The mature ActRIIB(L79E)-Fc fusion polypeptide (SEQ ID NO: 45) is as follows, and may optionally be provided with lysine added to the C-terminus.

```
                                                  (SEQ ID NO: 45)
   1 GRGEAETREC IYYNANWELE RTNQSGLERC EGEQDKRLHC YASWRNSSGT

51 IELVKKGCWE DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYDTT PPVLDSDGSF

301 FLYSDLTVDK SRWQQGNVFS CSVMHEALHN HYTQKSLSLS PG
```

The complementary form of ActRIIB-Fc fusion polypeptide (SEQ ID NO: 46) is as follows:

```
                                                  (SEQ ID NO: 46)
   1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC
```

```
151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSRKEMT KNQVSLTCLV KGFYPSDIAV

301 EWESNGQPEN NYKTTPPVLK SDGSFFLYSK LTVDKSRWQQ GNVFSCSVMH

351 EALHNHYTQK SLSLSPGK
```

The leader sequence and linker sequence are underlined. To guide heterodimer formation with the ActRIIB(L79E)-Fc fusion polypeptide of SEQ ID NOs: 43 and 45 above, two amino acid substitutions (replacing a glutamate and an aspartate with lysines) can be introduced into the Fc domain of the ActRIIB-Fc fusion polypeptide as indicated by double underline above. The amino acid sequence of SEQ ID NO: 46 may optionally be provided with lysine removed from the C-terminus.

This ActRIIB-Fc fusion protein can be encoded by the following nucleic acid (SEQ ID NO: 47):

```
                                                (SEQ ID NO: 47)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGAA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGAAG TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 TAAA
```

The mature ActRIIB-Fc fusion protein sequence (SEQ ID NO: 48) is as follows and may optionally be provided with lysine removed from the C-terminus.

```
                                                              (SEQ ID NO: 48)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 RKEMTKNQVS LTCLVKGFYP SDIAVEWESN GQPENNYKTT PPVLKSDGSF

301 FLYSKLTVDK SRWQQGNVFS CSVMHEALHN HYTQKSLSLS PGK
```

The ActRIIB(L79E)-Fc and ActRIIB-Fc polypeptides of SEQ ID NO: 45 and SEQ ID NO: 48, respectively, may be co-expressed and purified from a CHO cell line, to give rise to a heteromeric protein complex comprising ActRIIB-Fc:ActRIIB(L79E)-Fc.

In another approach to promote the formation of heteromultimer complexes using asymmetric Fc fusion proteins, the Fc domains can be altered to introduce complementary hydrophobic interactions and an additional intermolecular disulfide bond as illustrated in the ActRIIB(L79E)-Fc and ActRIIB-Fc polypeptide sequences of SEQ ID NOs: 49-50 and 51-52, respectively. The ActRIIB(L79E)-Fc fusion polypeptide and ActRIIB-Fc fusion polypeptide can each employ the TPA leader (SEQ ID NO: 8).

The ActRIIB(L79E)-Fc polypeptide sequence (SEQ ID NO: 49) is shown below:

```
                                                              (SEQ ID NO: 49)
  1 MDAMKRGLCC VLLLCGAVFV SPGASGRGEA ETRECIYYNA NWELERTNQS

51 GLERCEGEQD KRLHCYASWR NSSGTIELVK KGCWEDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT KNQVSLWCLV KGFYPSDIAV

301 EWESNGQPEN NYKTTPPVLD SDGSFFLYSK LTVDKSRWQQ GNVFSCSVMH

351 EALHNHYTQK SLSLSPG
```

The signal sequence and linker sequence are underlined, and the L79E substitution is indicated by double underline. To promote formation of the ActRIIB-Fc:ActRIIB(L79E)-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 49 may optionally be provided with lysine added to the C-terminus.

The mature ActRIIB(L79E)-Fc fusion polypeptide (SEQ ID NO: 50) is as follows:

```
                                                              (SEQ ID NO: 50)
  1 GRGEAETREC IYYNANWELE RTNQSGLERC EGEQDKRLHC YASWRNSSGT

51 IELVKKGCWE DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTKNQVS LWCLVKGFYP SDIAVEWESN GQPENNYKTT PPVLDSDGSF

301 FLYSKLTVDK SRWQQGNVFS CSVMHEALHN HYTQKSLSLS PG
```

The complementary form of ActRIIB-Fc fusion polypeptide (SEQ ID NO: 51) is as follows and may optionally be provided with lysine removed from the C-terminus.

```
                                                           (SEQ ID NO: 51)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVC TLPPSREEMT KNQVSLSCAV KGFYPSDIAV

301 EWESNGQPEN NYKTTPPVLD SDGSFFLVSK LTVDKSRWQQ GNVFSCSVMH

351 EALHNHYTQK SLSLSPGK
```

The leader sequence and linker are underlined. To guide heterodimer formation with the ActRIIB(L79E)-Fc fusion polypeptide of SEQ ID NOs: 49-50 above, four amino acid substitutions (replacement of tyrosine with cysteine, threonine with serine, leucine with alanine, and tyrosine with valine) can be introduced into the Fc domain of the ActRIIB-Fc fusion polypeptide as indicated by double underline above. The amino acid sequence of SEQ ID NO: 51 may optionally be provided with lysine removed from the C-terminus.

The mature ActRIIB-Fc fusion protein sequence is as follows and may optionally be provided with lysine removed from the C-terminus.

```
                                                           (SEQ ID NO: 52)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVCTLPPS

251 REEMTKNQVS LSCAVKGFYP SDIAVEWESN GQPENNYKTT PPVLDSDGSF

301 FLVSKLTVDK SRWQQGNVFS CSVMHEALHN HYTQKSLSLS PGK
```

The ActRIIB(L79E)-Fc and ActRIIB-Fc polypeptides of SEQ ID NO: 50 and SEQ ID NO: 52, respectively, may be co-expressed and purified from a CHO cell line, to give rise to a heteromeric protein complex comprising ActRIIB-Fc: ActRIIB(L79E)-Fc.

Purification of various ActRIIB-Fc:ActRIIB(L79E)-Fc complexes can be achieved by a series of column chromatography steps, including, for example, three or more of the following, in any order: protein A chromatography, Q sepharose chromatography, phenylsepharose chromatography, size exclusion chromatography, cation exchange chromatography, multimodal chromatography (e.g., with resin containing both electrostatic and hydrophobic ligands), and epitope-based affinity chromatography (e.g., with an antibody or functionally equivalent ligand directed against an epitope of ActRIIB). The purification can be completed with viral filtration and buffer exchange.

Example 8. Ligand Binding Profile of ActRIIB-Fc:ActRIIB(L79E)-Fc Heteromer

A Biacore™-based binding assay was used to compare the ligand binding kinetics of an ActRIIB-Fc:ActRIIB (L79E)-Fc heterodimer with those of unmodified ActRIIB-Fc homodimer. Fusion proteins were captured onto the system using an anti-Fc antibody. Ligands were then injected and allowed to flow over the captured receptor protein at 37° C. Results are summarized in the table below, in which ligand off-rates ($k_d$) most indicative of effective ligand traps are denoted in bold.

Ligand binding of ActRIIB-Fc: ActRIIB(L79E)-Fc heterodimer compared to ActRII-Fc homodimer at 37° C.

| | ActRIIB-Fc homodimer | | | ActRIIB-Fc: ActRIIB(L79E)-Fc heterodimer | | |
|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) |
| Activin A | $7.4 \times 10^6$ | $\mathbf{1.9 \times 10^{-4}}$ | 25 | $8.8 \times 10^6$ | $1.5 \times 10^{-3}$ | 170 |
| Activin B | $8.1 \times 10^6$ | $6.6 \times 10^{-5}$ | 8 | $8.3 \times 10^6$ | $\mathbf{2.1 \times 10^{-4}}$ | 25 |
| GDF3 | $1.4 \times 10^6$ | $2.2 \times 10^{-3}$ | 1500 | $5.8 \times 10^5$ | $5.9 \times 10^{-3}$ | 10000 |
| GDF8 | $3.8 \times 10^6$ | $\mathbf{2.6 \times 10^{-4}}$ | 70 | $3.4 \times 10^6$ | $\mathbf{5.0 \times 10^{-4}}$ | 150 |
| GDF11 | $4.1 \times 10^7$ | $\mathbf{1.7 \times 10^{-4}}$ | 4 | $4.0 \times 10^7$ | $\mathbf{3.6 \times 10^{-4}}$ | 9 |
| BMP6 | $1.3 \times 10^8$ | $7.4 \times 10^{-3}$ | 56 | $3.3 \times 10^8$ | $1.8 \times 10^{-2}$ | 56 |
| BMP9 | $5.0 \times 10^6$ | $1.3 \times 10^{-3}$ | 250 | Transient* | | >2800 |
| BMP10 | $5.1 \times 10^7$ | $\mathbf{2.0 \times 10^{-4}}$ | 4 | $4.8 \times 10^7$ | $2.0 \times 10^{-3}$ | 42 |

*Indeterminate due to transient nature of interaction

In this example, a single amino acid substitution in one of two ActRIIB polypeptide chains altered ligand binding selectivity of the Fc-fusion protein relative to unmodifed ActRIIB-Fc homodimer. Compared to ActRIIB-Fc homodimer, the ActRIIB(L79E)-Fc heterodimer largely retained high-affinity binding to activin B, GDF8, GDF11, and BMP6 but exhibited approximately ten-fold faster off-rates for activin A and BMP10 and an even greater reduction in the strength of binding to BMP9. Accordingly, a variant ActRIIB-Fc heteromer may be more useful than unmodified ActRIIB-Fc homodimer in certain applications where such selective antagonism is advantageous. Examples include therapeutic applications where it is desirable to retain antagonism of one or more of activin B, GDF8, GDF11, and BMP6, while reducing antagonism of activin A, BMP9, or BMP10.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

(SEQ ID NO: 196)

ATGGGTCGGGGCTGCTCAGGGGCCTGTGGCCGCTGCACATCGTCCTGTGGACGCGTATCGC

CAGCACGATCCCACCGCACGTTCAGAAGTCGGTTAATAACGACATGATAGTCACTGACAACA

ACGGTGCAGTCAAGTTTCCACAACTGTGTAAATTTTGTGATGTGAGATTTTCCACCTGTGAC

AACCAGAAATCCTGCATGAGCAACTGCAGCATCACCTCCATCTGTGAGAAGCCACAGGAAGT

CTGTGTGGCTGTATGGAGAAAGAATGACGAGAACATAACACTAGAGACAGTTTGCCATGACC

CCAAGCTCCCCTACCATGACTTTATTCTGGAAGATGCTGCTTCTCCAAAGTGCATTATGAAG

GAAAAAAAAAGCCTGGTGAGACTTTCTTCATGTGTTCCTGTAGCTCTGATGAGTGCAATGA

CAACATCATCTTCTCAGAAGAATATAACACCAGCAATCCTGACTTGTTGCTAGTCATATTTC

AAGTGACAGGCATCAGCCTCCTGCCACCACTGGGAGTTGCCATATCTGTCATCATCATCTTC

TACTGCTACCGCGTTAACCGGCAGCAGAAGCTGAGTTCAACCTGGGAAACCGGCAAGACGCG

GAAGCTCATGGAGTTCAGCGAGCACTGTGCCATCATCCTGGAAGATGACCGCTCTGACATCA

GCTCCACGTGTGCCAACAACATCAACCACAACACAGAGCTGCTGCCCATTGAGCTGGACACC

CTGGTGGGAAAGGTCGCTTTGCTGAGGTCTATAAGGCCAAGCTGAAGCAGAACACTTCAGA

GCAGTTTGAGACAGTGGCAGTCAAGATCTTTCCCTATGAGGAGTATGCCTCTTGGAAGACAG

AGAAGGACATCTTCTCAGACATCAATCTGAAGCATGAGAACATACTCCAGTTCCTGACGGCT

GAGGAGCGGAAGACGGAGTTGGGGAAACAATACTGGCTGATCACCGCCTTCCACGCCAAGGG

CAACCTACAGGAGTACCTGACGCGGCATGTCATCAGCTGGGAGGACCTGCGCAAGCTGGGCA

GCTCCCTCGCCCGGGGGATTGCTCACCTCCACAGTGATCACACTCCATGTGGGAGGCCCAAG

ATGCCCATCGTGCACAGGGACCTCAAGAGCTCCAATATCCTCGTGAAGAACGACCTAACCTG

CTGCCTGTGTGACTTTGGGCTTTCCCTGCGTCTGGACCCTACTCTGTCTGTGGATGACCTGG

CTAACAGTGGGCAGGTGGGAACTGCAAGATACATGGCTCCAGAAGTCCTAGAATCCAGGATG

AATTTGGAGAATGTTGAGTCCTTCAAGCAGACCGATGTCTACTCCATGGCTCTGGTGCTCTG

GGAAATGACATCTCGCTGTAATGCAGTGGGAGAAGTAAAAGATTATGAGCCTCCATTTGGTT

CCAAGGTGCGGGAGCACCCCTGTGTCGAAAGCATGAAGGACAACGTGTTGAGAGATCGAGGG

CGACCAGAAATTCCCAGCTTCTGGCTCAACCACCAGGGCATCCAGATGGTGTGTGAGACGTT

GACTGAGTGCTGGGACCACGACCCAGAGGCCCGTCTCACAGCCCAGTGTGTGGCAGAACGCT

TCAGTGAGCTGGAGCATCTGGACAGGCTCTCGGGGAGGAGCTGCTCGGAGGAGAAGATTCCT

GAAGACGGCTCCCTAAACACTACCAAA (SEQ ID NO: 197)

ACGATCCCACCGCACGTTCAGAAGTCGGTTAATAACGACATGATAGTCACTGACAACAACGG

TGCAGTCAAGTTTCCACAACTGTGTAAATTTTGTGATGTGAGATTTTCCACCTGTGACAACC

-continued

AGAAATCCTGCATGAGCAACTGCAGCATCACCTCCATCTGTGAGAAGCCACAGGAAGTCTGT

GTGGCTGTATGGAGAAAGAATGACGAGAACATAACACTAGAGACAGTTTGCCATGACCCCAA

GCTCCCCTACCATGACTTTATTCTGGAAGATGCTGCTTCTCCAAAGTGCATTATGAAGGAAA

AAAAAAAGCCTGGTGAGACTTTCTTCATGTGTTCCTGTAGCTCTGATGAGTGCAATGACAAC

ATCATCTTCTCAGAAGAATATAACACCAGCAATCCTGACTTGTTGCTAGTCATATTTCAA (SEQ ID NO: 202)
<u>ATGGGTCGGGGCTGCTCAGGGGCCTGTGGCCGCTGCACATCGTCCTGTGGACGCGTATCGC</u>

<u>CAGC</u>ACGATCCCACCGCACGTTCAGAAGTCGGATGTGGAAATGGAGGCCCAGAAAGATGAAA

TCATCTGCCCCAGCTGTAATAGGACTGCCCATCCACTGAGACATATTAATAACGACATGATA

GTCACTGACAACAACGGTGCAGTCAAGTTTCCACAACTGTGTAAATTTTGTGATGTGAGATT

TTCCACCTGTGACAACCAGAAATCCTGCATGAGCAACTGCAGCATCACCTCCATCTGTGAGA

AGCCACAGGAAGTCTGTGTGGCTGTATGGAGAAAGAATGACGAGAACATAACACTAGAGACA

GTTTGCCATGACCCCAAGCTCCCCTACCATGACTTTATTCTGGAAGATGCTGCTTCTCCAAA

GTGCATTATGAAGGAAAAAAAAAGCCTGGTGAGACTTTCTTCATGTGTTCCTGTAGCTCTG

ATGAGTGCAATGACAACATCATCTTCTCAGAAGAATATAACACCAGCAATCCTGACTTGTTG

CTAGTCATATTTCAAGTGACAGGCATCAGCCTCCTGCCACCACTGGGAGTTGCCATATCTGT

CATCATCATCTTCTACTGCTACCGCGTTAACCGGCAGCAGAAGCTGAGTTCAACCTGGGAAA

CCGGCAAGACGCGGAAGCTCATGGAGTTCAGCGAGCACTGTGCCATCATCCTGGAAGATGAC

CGCTCTGACATCAGCTCCACGTGTGCCAACAACATCAACCACAACACAGAGCTGCTGCCCAT

TGAGCTGGACACCCTGGTGGGGAAAGGTCGCTTTGCTGAGGTCTATAAGGCCAAGCTGAAGC

AGAACACTTCAGAGCAGTTTGAGACAGTGGCAGTCAAGATCTTTCCCTATGAGGAGTATGCC

TCTTGGAAGACAGAGAAGGACATCTTCTCAGACATCAATCTGAAGCATGAGAACATACTCCA

GTTCCTGACGGCTGAGGAGCGGAAGACGGAGTTGGGGAAACAATACTGGCTGATCACCGCCT

TCCACGCCAAGGGCAACCTACAGGAGTACCTGACGCGGCATGTCATCAGCTGGGAGGACCTG

CGCAAGCTGGGCAGCTCCCTCGCCCGGGGGATTGCTCACCTCCACAGTGATCACACTCCATG

TGGGAGGCCCAAGATGCCCATCGTGCACAGGGACCTCAAGAGCTCCAATATCCTCGTGAAGA

ACGACCTAACCTGCTGCCTGTGTGACTTTGGGCTTTCCCTGCGTCTGGACCCTACTCTGTCT

GTGGATGACCTGGCTAACAGTGGGCAGGTGGGAACTGCAAGATACATGGCTCCAGAAGTCCT

AGAATCCAGGATGAATTTGGAGAATGTTGAGTCCTTCAAGCAGACCGATGTCTACTCCATGG

CTCTGGTGCTCTGGGAAATGACATCTCGCTGTAATGCAGTGGGAGAAGTAAAAGATTATGAG

CCTCCATTTGGTTCCAAGGTGCGGGAGCACCCCTGTGTCGAAAGCATGAAGGACAACGTGTT

GAGAGATCGAGGGCGACCAGAAATTCCCAGCTTCTGGCTCAACCACCAGGGCATCCAGATGG

TGTGTGAGACGTTGACTGAGTGCTGGGACCACGACCCAGAGGCCCGTCTCACAGCCCAGTGT

GTGGCAGAACGCTTCAGTGAGCTGGAGCATCTGGACAGGCTCTCGGGGAGGAGCTGCTCGGA

GGAGAAGATTCCTGAAGACGGCTCCCTAAACACTACCAAA (SEQ ID NO: 203)
ACGATCCCACCGCACGTTCAGAAGTCGGATGTGGAAATGGAGGCCCAGAAAGATGAAATCAT

CTGCCCCAGCTGTAATAGGACTGCCCATCCACTGAGACATATTAATAACGACATGATAGTCA

CTGACAACAACGGTGCAGTCAAGTTTCCACAACTGTGTAAATTTTGTGATGTGAGATTTTCC

ACCTGTGACAACCAGAAATCCTGCATGAGCAACTGCAGCATCACCTCCATCTGTGAGAAGCC

ACAGGAAGTCTGTGTGGCTGTATGGAGAAAGAATGACGAGAACATAACACTAGAGACAGTTT

GCCATGACCCCAAGCTCCCCTACCATGACTTTATTCTGGAAGATGCTGCTTCTCCAAAGTGC

```
ATTATGAAGGAAAAAAAAAAGCCTGGTGAGACTTTCTTCATGTGTTCCTGTAGCTCTGATGA

GTGCAATGACAACATCATCTTCTCAGAAGAATATAACACCAGCAATCCTGACTTGTTGCTAG

TCATATTTCAA.
```

(SEQ ID NO: 205)

```
ATGACTTCCTCGCTGCAGCGGCCCTGGCGGGTGCCCTGGCTACCATGGACCATCCTGCTGGTCAGCACTGCGGCT

GCTTCGCAGAATCAAGAACGGCTATGTGCGTTTAAAGATCCGTATCAGCAAGACCTTGGGATAGGTGAGAGTAGA

ATCTCTCATGAAAATGGGACAATATTATGCTCGAAAGGTAGCACCTGCTATGGCCTTTGGGAGAAATCAAAAGGG

GACATAAATCTTGTAAAACAAGGATGTTGGTCTCACATTGGAGATCCCCAAGAGTGTCACTATGAAGAATGTGTA

GTAACTACCACTCCTCCCTCAATTCAGAATGGAACATACCGTTTCTGCTGTTGTAGCACAGATTTATGTAATGTC

AACTTTACTGAGAATTTTCCACCTCCTGACACAACACCACTCAGTCCACCTCATTCATTTAACCGAGATGAGACA

ATAATCATTGCTTTGGCATCAGTCTCTGTATTAGCTGTTTTGATAGTTGCCTTATGCTTTGGATACAGAATGTTG

ACAGGAGACCGTAAACAAGGTCTTCACAGTATGAACATGATGGAGGCAGCAGCATCCGAACCCTCTCTTGATCTA

GATAATCTGAAACTGTTGGAGCTGATTGGCCGAGGTCGATATGGAGCAGTATATAAAGGCTCCTTGGATGAGCGT

CCAGTTGCTGTAAAAGTGTTTTCCTTTGCAAACCGTCAGAATTTTATCAACGAAAAGAACATTTACAGAGTGCCT

TTGATGGAACATGACAACATTGCCCGCTTTATAGTTGGAGATGAGAGAGTCACTGCAGATGGACGCATGGAATAT

TTGCTTGTGATGGAGTACTATCCCAATGGATCTTTATGCAAGTATTTAAGTCTCCACACAAGTGACTGGGTAAGC

TCTTGCCGTCTTGCTCATTCTGTTACTAGAGGACTGGCTTATCTTCACACAGAATTACCACGAGGAGATCATTAT

AAACCTGCAATTTCCCATCGAGATTTAAACAGCAGAAATGTCCTAGTGAAAAATGATGGAACCTGTGTTATTAGT

GACTTTGGACTGTCCATGAGGCTGACTGGAAATAGACTGGTGCGCCCAGGGGAGGAAGATAATGCAGCCATAAGC

GAGGTTGGCACTATCAGATATATGGCACCAGAAGTGCTAGAAGGAGCTGTGAACTTGAGGGACTGTGAATCAGCT

TTGAAACAAGTAGACATGTATGCTCTTGGACTAATCTATTGGGAGATATTTATGAGATGTACAGACCTCTTCCCA

GGGGAATCCGTACCAGAGTACCAGATGGCTTTTCAGACAGAGGTTGGAAACCATCCCACTTTTGAGGATATGCAG

GTTCTCGTGTCTAGGGAAAAACAGAGACCCAAGTTCCCAGAAGCCTGGAAAGAAAATAGCCTGGCAGTGAGGTCA

CTCAAGGAGACAATCGAAGACTGTTGGGACCAGGATGCAGAGGCTCGGCTTACTGCACAGTGTGCTGAGGAAAGG

ATGGCTGAACTTATGATGATTTGGGAAAGAAACAAATCTGTGAGCCCAACAGTCAATCCAATGTCTACTGCTATG

CAGAATGAACGCAACCTGTCACATAATAGGCGTGTGCCAAAAATTGGTCCTTATCCAGATTATTCTTCCTCCTCA

TACATTGAAGACTCTATCCATCATACTGACAGCATCGTGAAGAATATTTCCTCTGAGCATTCTATGTCCAGCACA

CCTTTGACTATAGGGGAAAAAAACCGAAATTCAATTAACTATGAACGACAGCAAGCACAAGCTCGAATCCCCAGC

CCTGAAACAAGTGTCACCAGCCTCTCCACCAACACAACAACCACAAACACCACAGGACTCACGCCAAGTACTGGC

ATGACTACTATATCTGAGATGCCATACCCAGATGAAACAAATCTGCATACCACAAATGTTGCACAGTCAATTGGG

CCAACCCCTGTCTGCTTACAGCTGACAGAAGAAGACTTGGAAACCAACAAGCTAGACCCAAAAGAAGTTGATAAG

AACCTCAAGGAAAGCTCTGATGAGAATCTCATGGAGCACTCTCTTAAACAGTTCAGTGGCCCAGACCCACTGAGC

AGTACTAGTTCTAGCTTGCTTTACCCACTCATAAAACTTGCAGTAGAAGCAACTGGACAGCAGGACTTCACACAG

ACTGCAAATGGCCAAGCATGTTTGATTCCTGATGTTCTGCCTACTCAGATCTATCCTCTCCCCAAGCAGCAGAAC

CTTCCCAAGAGACCTACTAGTTTGCCTTTGAACACCAAAAATTCAACAAAAGAGCCCCGGCTAAAATTTGGCAGC

AAGCACAAATCAAACTTGAAACAAGTCGAAACTGGAGTTGCCAAGATGAATACAATCAATGCAGCAGAACCTCAT

GTGGTGACAGTCACCATGAATGGTGTGGCAGGTAGAAACCACAGTGTTAACTCCCATGCTGCCACAACCCAATAT

GCCAATGGGACAGTACTATCTGGCCAAACAACCAACATAGTGACACATAGGGCCCAAGAAATGTTGCAGAATCAG

TTTATTGGTGAGGACACCCGGCTGAATATTAATTCCAGTCCTGATGAGCATGAGCCTTTACTGAGACGAGAGCAA

CAAGCTGGCCATGATGAAGGTGTTCTGGATCGTCTTGTGGACAGGAGGGAACGGCCACTAGAAGGTGGCCGAACT

AATTCCAATAACAACAACAGCAATCCATGTTCAGAACAAGATGTTCTTGCACAGGGTGTTCCAAGCACAGCAGCA
```

```
GATCCTGGGCCATCAAAGCCCAGAAGAGCACAGAGGCCTAATTCTCTGGATCTTTCAGCCACAAATGTCCTGGAT

GGCAGCAGTATACAGATAGGTGAGTCAACACAAGATGGCAAATCAGGATCAGGTGAAAAGATCAAGAAACGTGTG

AAAACTCCCTATTCTCTTAAGCGGTGGCGCCCCTCCACCTGGGTCATCTCCACTGAATCGCTGGACTGTGAAGTC

AACAATAATGGCAGTAACAGGGCAGTTCATTCCAAATCCAGCACTGCTGTTTACCTTGCAGAAGGAGGCACTGCT

ACAACCATGGTGTCTAAAGATATAGGAATGAACTGTCTG
```

(SEQ ID NO: 206)
```
TCGCAGAATCAAGAACGGCTATGTGCGTTTAAAGATCCGTATCAGCAAGACCTTGGGATAGGTGAGAGTAGAATC

TCTCATGAAAATGGGACAATATTATGCTCGAAAGGTAGCACCTGCTATGGCCTTTGGGAGAAATCAAAAGGGGAC

ATAAATCTTGTAAAACAAGGATGTTGGTCTCACATTGGAGATCCCCAAGAGTGTCACTATGAAGAATGTGTAGTA

ACTACCACTCCTCCCTCAATTCAGAATGGAACATACCGTTTCTGCTGTTGTAGCACAGATTTATGTAATGTCAAC

TTTACTGAGAATTTTCCACCTCCTGACACAACACCACTCAGTCCACCTCATTCATTTAACCGAGATGAGACA
```

(SEQ ID NO: 207)
```
ATGACTTCCTCGCTGCAGCGGCCCTGGCGGGTGCCCTGGCTACCATGGACCATCCTGCTGGT

CAGCACTGCGGCTGCTTCGCAGAATCAAGAACGGCTATGTGCGTTTAAAGATCCGTATCAGC

AAGACCTTGGGATAGGTGAGAGTAGAATCTCTCATGAAAATGGGACAATATTATGCTCGAAA

GGTAGCACCTGCTATGGCCTTTGGGAGAAATCAAAAGGGGACATAAATCTTGTAAAACAAGG

ATGTTGGTCTCACATTGGAGATCCCCAAGAGTGTCACTATGAAGAATGTGTAGTAACTACCA

CTCCTCCCTCAATTCAGAATGGAACATACCGTTTCTGCTGTTGTAGCACAGATTTATGTAAT

GTCAACTTTACTGAGAATTTTCCACCTCCTGACACAACACCACTCAGTCCACCTCATTCATT

TAACCGAGATGAGACAATAATCATTGCTTTGGCATCAGTCTCTGTATTAGCTGTTTTGATAG

TTGCCTTATGCTTTGGATACAGAATGTTGACAGGAGACCGTAAACAAGGTCTTCACAGTATG

AACATGATGGAGGCAGCAGCATCCGAACCCTCTCTTGATCTAGATAATCTGAAACTGTTGGA

GCTGATTGGCCGAGGTCGATATGGAGCAGTATATAAAGGCTCCTTGGATGAGCGTCCAGTTG

CTGTAAAAGTGTTTTCCTTTGCAAACCGTCAGAATTTTATCAACGAAAAGAACATTTACAGA

GTGCCTTTGATGGAACATGACAACATTGCCCGCTTTATAGTTGGAGATGAGAGAGTCACTGC

AGATGGACGCATGGAATATTTGCTTGTGATGGAGTACTATCCCAATGGATCTTTATGCAAGT

ATTTAAGTCTCCACACAAGTGACTGGGTAAGCTCTTGCCGTCTTGCTCATTCTGTTACTAGA

GGACTGGCTTATCTTCACACAGAATTACCACGAGGAGATCATTATAAACCTGCAATTTCCCA

TCGAGATTTAAACAGCAGAAATGTCCTAGTGAAAATGATGGAACCTGTGTTATTAGTGACT

TTGGACTGTCCATGAGGCTGACTGGAAATAGACTGGTGCGCCCAGGGGAGGAAGATAATGCA

GCCATAAGCGAGGTTGGCACTATCAGATATATGGCACCAGAAGTGCTAGAAGGAGCTGTGAA

CTTGAGGGACTGTGAATCAGCTTTGAAACAAGTAGACATGTATGCTCTTGGACTAATCTATT

GGGAGATATTTATGAGATGTACAGACCTCTTCCCAGGGGAATCCGTACCAGAGTACCAGATG

GCTTTTCAGACAGAGGTTGGAAACCATCCCACTTTTGAGGATATGCAGGTTCTCGTGTCTAG

GGAAAAACAGAGACCCAAGTTCCCAGAAGCCTGGAAAGAAAATAGCCTGGCAGTGAGGTCAC

TCAAGGAGACAATCGAAGACTGTTGGGACCAGGATGCAGAGGCTCGGCTTACTGCACAGTGT

GCTGAGGAAAGGATGGCTGAACTTATGATGATTTGGGAAAGAAACAAATCTGTGAGCCCAAC

AGTCAATCCAATGTCTACTGCTATGCAGAATGAACGTAGG
```

(SEQ ID NO: 208)
```
TCGCAGAATCAAGAACGGCTATGTGCGTTTAAAGATCCGTATCAGCAAGACCTTGGGATAGG

TGAGAGTAGAATCTCTCATGAAAATGGGACAATATTATGCTCGAAAGGTAGCACCTGCTATG

GCCTTTGGGAGAAATCAAAAGGGGACATAAATCTTGTAAAACAAGGATGTTGGTCTCACATT
```

-continued

GGAGATCCCCAAGAGTGTCACTATGAAGAATGTGTAGTAACTACCACTCCTCCCTCAATTCA

GAATGGAACATACCGTTTCTGCTGTTGTAGCACAGATTTATGTAATGTCAACTTTACTGAGA

ATTTTCCACCTCCTGACACAACACCACTCAGTCCACCTCATTCATTTAACCGAGATGAGACA (SEQ ID NO: 209)
ATGCTAGGGTCTTTGGGGCTTTGGGCATTACTTCCCACAGCTGTGGAAGCACCCCCAAACAGGCGAACCTGTGTG

TTCTTTGAGGCCCCTGGAGTGCGGGGAAGCACAAAGACACTGGGAGAGCTGCTAGATACAGGCACAGAGCTCCCC

AGAGCTATCCGCTGCCTCTACAGCCGCTGCTGCTTTGGGATCTGGAACCTGACCCAAGACCGGGCACAGGTGGAA

ATGCAAGGATGCCGAGACAGTGATGAGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAATGCCAATTACAGCCATCTGCCTCCT

CCAGGGAGCCCTGGGACTCCTGGCTCCCAGGGTCCCCAGGCTGCCCCAGGTGAGTCCATCTGGATGGCACTGGTG

CTGCTGGGGCTGTTCCTCCTCCTCCTGCTGCTGCTGGGCAGCATCATCTTGGCCCTGCTACAGCGAAAGAACTAC

AGAGTGCGAGGTGAGCCAGTGCCAGAGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGTTTGGGCCGGGCAGCTGCAAGGAAAA

CTGGTTGCCATCAAGGCCTTCCCACCGAGGTCTGTGGCTCAGTTCCAAGCTGAGAGAGCATTGTACGAACTTCCA

GGCCTACAGCACGACCACATTGTCCGATTTATCACTGCCAGCCGGGGGGTCCTGGCCGCCTGCTCTCTGGGCCC

CTGCTGGTACTGGAACTGCATCCCAAGGGCTCCCTGTGCCACTACTTGACCCAGTACACCAGTGACTGGGGAAGT

TCCCTGCGGATGGCACTGTCCCTGGCCCAGGGCCTGGCATTTCTCCATGAGGAGCGCTGGCAGAATGGCCAATAT

AAACCAGGTATTGCCCACCGAGATCTGAGCAGCCAGAATGTGCTCATTCGGGAAGATGGATCGTGTGCCATTGGA

GACCTGGGCCTTGCCTTGGTGCTCCCTGGCCTCACTCAGCCCCCTGCCTGGACCCCTACTCAACCACAAGGCCCA

GCTGCCATCATGGAAGCTGGCACCCAGAGGTACATGGCACCAGAGCTCTTGGACAAGACTCTGGACCTACAGGAT

TGGGGCATGGCCCTCCGACGAGCTGATATTTACTCTTTGGCTCTGCTCCTGTGGGAGATACTGAGCCGCTGCCCA

GATTTGAGGCCTGACAGCAGTCCACCACCCCTTCCAACTGGCCTATGAGGCAGAACTGGGCAATACCCCTACCTCT

GATGAGCTATGGGCCTTGGCAGTCAGGAGAGGAGGCGTCCCTACATCCCATCCACCTGGCGCTGCTTTGCCACA

GACCCTGATGGGCTGAGGGAGCTCCTAGAAGACTGTTGGGATGCAGACCCAGAAGCACGGCTGACAGCTGAGTGT

GTACAGCAGCGCCTGGCTGCCTTGGCCCATCCTCAAGAGAGCCACCCCTTTCCAGAGAGCTGTCCACGTGGCTGC

CCACCTCTCTGCCCAGAAGACTGTACTTCAATTCCTGCCCCTACCATCCTCCCCTGTAGGCCTCAGCGGAGTGCC

TGCCACTTCAGCGTTCAGCAAGGCCCTTGTTCCAGGAATCCTCAGCCTGCCTGTACCCTTTCTCCTGTG (SEQ ID NO: 210)
CCCCCAAACAGGCGAACCTGTGTGTTCTTTGAGGCCCCTGGAGTGCGGGGAAGCACAAAGAC

ACTGGGAGAGCTGCTAGATACAGGCACAGAGCTCCCCAGAGCTATCCGCTGCCTCTACAGCC

GCTGCTGCTTTGGGATCTGGAACCTGACCCAAGACCGGGCACAGGTGGAAATGCAAGGATGC

CGAGACAGTGATGAGCCAGGCTGTGAGTCCCTCCACTGTGACCCAAGTCCCCGAGCCCACCC

CAGCCCTGGCTCCACTCTCTTCACCTGCTCCTGTGGCACTGACTTCTGCAATGCCAATTACA

GCCATCTGCCTCCTCCAGGGAGCCCTGGGACTCCTGGCTCCCAGGGTCCCCAGGCTGCCCCA

GGTGAGTCCATCTGGATGGCACTG (SEQ ID NO: 211)
ATGCTAGGGTCTTTGGGGCTTTGGGCATTACTTCCCACAGCTGTGGAAGCACCCCCAAACAGGCGAACCTGTGTG

TTCTTTGAGGCCCCTGGAGTGCGGGGAAGCACAAAGACACTGGGAGAGCTGCTAGATACAGGCACAGAGCTCCCC

AGAGCTATCCGCTGCCTCTACAGCCGCTGCTGCTTTGGGATCTGGAACCTGACCCAAGACCGGGCACAGGTGGAA

ATGCAAGGATGCCGAGACAGTGATGAGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAATGCCAATTACAGCCATCTGCCTCCT

CCAGGGAGCCCTGGGACTCCTGGCTCCCAGGGTCCCCAGGCTGCCCCAGGTGAGTCCATCTGGATGGCACTGGTG

-continued

CTGCTGGGGCTGTTCCTCCTCCTCCTGCTGCTGCTGGGCAGCATCATCTTGGCCCTGCTACAGCGAAAGAACTAC

AGAGTGCGAGGTGAGCCAGTGCCAGAGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGTTTGGGCCGGGCAGCTGCAAGGAAAA

CTGGTTGCCATCAAGGCCTTCCCACCGAGGTCTGTGGCTCAGTTCCAAGCTGAGAGAGCATTGTACGAACTTCCA

GGCCTACAGCACGACCACATTGTCCGATTTATCACTGCCAGCCGGGGGGTCCTGGCCGCCTGCTCTCTGGGCCC

CTGCTGGTACTGGAACTGCATCCCAAGGGCTCCCTGTGCCACTACTTGACCCAGTACACCAGTGACTGGGGAAGT

TCCCTGCGGATGGCACTGTCCCTGGCCCAGGGCCTGGCATTTCTCCATGAGGAGCGCTGGCAGAATGGCCAATAT

AAACCAGGTATTGCCCACCGAGATCTGAGCAGCCAGAATGTGCTCATTCGGGAAGATGGATCGTGTGCCATTGGA

GACCTGGGCCTTGCCTTGGTGCTCCCTGGCCTCACTCAGCCCCTGCCTGGACCCCTACTCAACCACAAGGCCCA

GCTGCCATCATGGAAGCTGGCACCCAGAGGTACATGGCACCAGAGCTCTTGGACAAGACTCTGGACCTACAGGAT

TGGGGCATGGCCCTCCGACGAGCTGATATTTACTCTTTGGCTCTGCTCCTGTGGGAGATACTGAGCCGCTGCCCA

GATTTGAGGCCTGCAGTCCACCACCCTTCCAACTGGCCTATGAGGCAGAACTGGGCAATACCCCTACCTCTGATG

AGCTATGGGCCTTGGCAGTGCAGGAGAGGAGGCGTCCCTACATCCCATCCACCTGGCGCTGCTTTGCCACAGACC

CTGATGGGC (SEQ ID NO: 212)
CCCCCAAACAGGCGAACCTGTGTGTTCTTTGAGGCCCCTGGAGTGCGGGAAGCACAAAGAC

ACTGGGAGAGCTGCTAGATACAGGCACAGAGCTCCCCAGAGCTATCCGCTGCCTCTACAGCC

GCTGCTGCTTTGGGATCTGGAACCTGACCCAAGACCGGGCACAGGTGGAAATGCAAGGATGC

CGAGACAGTGATGAGCCAGGCTGTGAGTCCCTCCACTGTGACCCAAGTCCCCGAGCCCACCC

CAGCCCTGGCTCCACTCTCTTCACCTGCTCCTGTGGCACTGACTTCTGCAATGCCAATTACA

GCCATCTGCCTCCTCCAGGGAGCCCTGGGACTCCTGGCTCCCAGGGTCCCCAGGCTGCCCCA

GGTGAGTCCATCTGGATGGCACTG (SEQ ID NO: 213)
ATGCTAGGGTCTTTGGGGCTTTGGGCATTACTTCCCACAGCTGTGGAAGCACCCCCAAACAG

GCGAACCTGTGTGTTCTTTGAGGCCCCTGGAGTGCGGGAAGCACAAAGACACTGGGAGAGC

TGCTAGATACAGGCACAGAGCTCCCCAGAGCTATCCGCTGCCTCTACAGCCGCTGCTGCTTT

GGGATCTGGAACCTGACCCAAGACCGGGCACAGGTGGAAATGCAAGGATGCCGAGACAGTGA

TGAGCCAGGCTGTGAGTCCCTCCACTGTGACCCAAGTCCCCGAGCCCACCCCAGCCCTGGCT

CCACTCTCTTCACCTGCTCCTGTGGCACTGACTTCTGCAATGCCAATTACAGCCATCTGCCT

CCTCCAGGGAGCCCTGGGACTCCTGGCTCCCAGGGTCCCCAGGCTGCCCCAGGTGAGTCCAT

CTGGATGGCACTGGTGCTGCTGGGGCTGTTCCTCCTCCTCCTGCTGCTGCTGGGCAGCATCA

TCTTGGCCCTGCTACAGCGAAAGAACTACAGAGTGCGAGGTGAGCCAGTGCCAGAGCCAAGG

CCAGACTCAGGCAGGGACTGGAGTGTGGAGCTGCAGGAGCTGCCTGAGCTGTGTTTCTCCCA

GGTAATCCGGGAAGGAGGTCATGCAGTGGTTTGGGCCGGGCAGCTGCAAGGAAAACTGGTTG

CCATCAAGGCCTTCCCACCGAGGTCTGTGGCTCAGTTCCAAGCTGAGAGAGCATTGTACGAA

CTTCCAGGCCTACAGCACGACCACATTGTCCGATTTATCACTGCCAGCCGGGGGGTCCTGG

CCGCCTGCTCTCTGGGCCCCTGCTGGTACTGGAACTGCATCCCAAGGGCTCCCTGTGCCACT

ACTTGACCCAGTACACCAGTGACTGGGGAAGTTCCCTGCGGATGGCACTGTCCCTGGCCCAG

GGCCTGGCATTTCTCCATGAGGAGCGCTGGCAGAATGGCCAATATAAACCAGGTATTGCCCA

CCGAGATCTGAGCAGCCAGAATGTGCTCATTCGGGAAGATGGATCGTGTGCCATTGGAGACC

TGGGCCTTGCCTTGGTGCTCCCTGGCCTCACTCAGCCCCTGCCTGGACCCCTACTCAACCA

CAAGGCCCAGCTGCCATCATGGAAGACCCTGATGGGCTGAGGGAGCTCCTAGAAGACTGTTG

GGATGCAGACCCAGAAGCACGGCTGACAGCTGAGTGTGTACAGCAGCGCCTGGCTGCCTTGG

CCCATCCTCAAGAGAGCCACCCCTTTCCAGAGAGCTGTCCACGTGGCTGCCCACCTCTCTGC

CCAGAAGACTGTACTTCAATTCCTGCCCCTACCATCCTCCCCTGTAGGCCTCAGCGGAGTGC

CTGCCACTTCAGCGTTCAGCAAGGCCCTTGTTCCAGGAATCCTCAGCCTGCCTGTACCCTTT

CTCCTGTG (SEQ ID NO: 214)
CCCCCAAACAGGCGAACCTGTGTGTTCTTTGAGGCCCCTGGAGTGCGGGGAAGCACAAAGAC

ACTGGGAGAGCTGCTAGATACAGGCACAGAGCTCCCCAGAGCTATCCGCTGCCTCTACAGCC

GCTGCTGCTTTGGGATCTGGAACCTGACCCAAGACCGGGCACAGGTGGAAATGCAAGGATGC

CGAGACAGTGATGAGCCAGGCTGTGAGTCCCTCCACTGTGACCCAAGTCCCCGAGCCCACCC

CAGCCCTGGCTCCACTCTCTTCACCTGCTCCTGTGGCACTGACTTCTGCAATGCCAATTACA

GCCATCTGCCTCCTCCAGGGAGCCCTGGGACTCCTGGCTCCCAGGGTCCCCAGGCTGCCCCA

GGTGAGTCCATCTGGATGGCACTG (SEQ ID NO: 215)
<u>ATGACCTTGGGCTCCCCCAGGAAAGGCCTTCTGATGCTGCTGATGGCCTTGGTGACCCAGGGA</u>GACCCTGTGAAG

CCGTCTCGGGGCCCGCTGGTGACCTGCACGTGTGAGAGCCCACATTGCAAGGGGCCTACCTGCCGGGGGGCCTGG

TGCACAGTAGTGCTGGTGCGGGAGGAGGGGAGGCACCCCCAGGAACATCGGGGCTGCGGGAACTTGCACAGGGAG

CTCTGCAGGGGGCGCCCCACCGAGTTCGTCAACCACTACTGCTGCGACAGCCACCTCTGCAACCACAACGTGTCC

CTGGTGCTGGAGGCCACCCAACCTCCTTCGGAGCAGCCGGGAACAGATGGCCAGCTGGCCCTGATCCTGGGCCCC

GTGCTGGCCTTGCTGGCCCTGGTGGCCCTGGGTGTCCTGGGCCTGTGGCATGTCCGACGGAGGCAGGAGAAGCAG

CGTGGCCTGCACAGCGAGCTGGGAGAGTCCAGTCTCATCCTGAAAGCATCTGAGCAGGGCGACAGCATGTTGGGG

GACCTCCTGGACAGTGACTGCACCACAGGGAGTGGCTCAGGGCTCCCCTTCCTGGTGCAGAGGACAGTGGCACGG

CAGGTTGCCTTGGTGGAGTGTGTGGGAAAAGGCCGCTATGGCGAAGTGTGGCGGGGCTTGTGGCACGGTGAGAGT

GTGGCCGTCAAGATCTTCTCCTCGAGGGATGAACAGTCCTGGTTCCGGGAGACTGAGATCTATAACACAGTGTTG

CTCAGACACGACAACATCCTAGGCTTCATCGCCTCAGACATGACCTCCCGCAACTCGAGCACGCAGCTGTGGCTC

ATCACGCACTACCACGAGCACGGCTCCCTCTACGACTTTCTGCAGAGACAGACGCTGGAGCCCCATCTGGCTCTG

AGGCTAGCTGTGTCCGCGGCATGCGGCCTGGCGCACCTGCACGTGGAGATCTTCGGTACACAGGGCAAACCAGCC

ATTGCCCACCGCGACTTCAAGAGCCGCAATGTGCTGGTCAAGAGCAACCTGCAGTGTTGCATCGCCGACCTGGGC

CTGGCTGTGATGCACTCACAGGGCAGCGATTACCTGGACATCGGCAACAACCCGAGAGTGGGCACCAAGCGGTAC

ATGGCACCCGAGGTGCTGGACGAGCAGATCCGCACGGACTGCTTTGAGTCCTACAAGTGGACTGACATCTGGGCC

TTTGGCCTGGTGCTGTGGGAGATTGCCCGCCGGACCATCGTGAATGGCATCGTGGAGGACTATAGACCACCCTTC

TATGATGTGGTGCCCAATGACCCCAGCTTTGAGGACATGAAGAAGGTGGTGTGTGTGGATCAGCAGACCCCCACC

ATCCCTAACCGGCTGGCTGCAGACCCGGTCCTCTCAGGCCTAGCTCAGATGATGCGGGAGTGCTGGTACCCAAAC

CCCTCTGCCCGACTCACCGCGCTGCGGATCAAGAAGACACTACAAAAAATTAGCAACAGTCCAGAGAAGCCTAAA

GTGATTCAA (SEQ ID NO: 216)
GACCCTGTGAAGCCGTCTCGGGGCCCGCTGGTGACCTGCACGTGTGAGAGCCCACATTGCAA

GGGGCCTACCTGCCGGGGGGCCTGGTGCACAGTAGTGCTGGTGCGGGAGGAGGGGAGGCACC

CCCAGGAACATCGGGGCTGCGGGAACTTGCACAGGGAGCTCTGCAGGGGGCGCCCCACCGAG

TTCGTCAACCACTACTGCTGCGACAGCCACCTCTGCAACCACAACGTGTCCCTGGTGCTGGA

GGCCACCCAACCTCCTTCGGAGCAGCCGGGAACAGATGGCCAG

-continued (SEQ ID NO: 217)
<u>ATGGTAGATGGAGTGATGATTCTTCCTGTGCTTATCATGATTGCTCTCCCCTCCCCTAGT</u>ATGGAAGATGAGAAG

CCCAAGGTCAACCCCAAACTCTACATGTGTGTGTGTGAAGGTCTCTCCTGCGGTAATGAGGACCACTGTGAAGGC

CAGCAGTGCTTTTCCTCACTGAGCATCAACGATGGCTTCCACGTCTACCAGAAAGGCTGCTTCCAGGTTTATGAG

CAGGGAAAGATGACCTGTAAGACCCCGCCGTCCCCTGGCCAAGCCGTGGAGTGCTGCCAAGGGGACTGGTGTAAC

AGGAACATCACGGCCCAGCTGCCCACTAAAGGAAAATCCTTCCCTGGAACACAGAATTTCCACTTGGAGGTTGGC

CTCATTATTCTCTCTGTAGTGTTCGCAGTATGTCTTTTAGCCTGCCTGCTGGGAGTTGCTCTCCGAAAATTTAAA

AGGCGCAACCAAGAACGCCTCAATCCCCGAGACGTGGAGTATGGCACTATCGAAGGGCTCATCACCACCAATGTT

GGAGACAGCACTTTAGCAGATTTATTGGATCATTCGTGTACATCAGGAAGTGGCTCTGGTCTTCCTTTTCTGGTA

CAAAGAACAGTGGCTCGCCAGATTACACTGTTGGAGTGTGTCGGGAAAGGCAGGTATGGTGAGGTGTGGAGGGGC

AGCTGGCAAGGGGAGAATGTTGCCGTGAAGATCTTCTCCTCCCGTGATGAGAAGTCATGGTTCAGGGAAACGGAA

TTGTACAACACTGTGATGCTGAGGCATGAAAATATCTTAGGTTTCATTGCTTCAGACATGACATCAAGACACTCC

AGTACCCAGCTGTGGTTAATTACACATTATCATGAAATGGGATCGTTGTACGACTATCTTCAGCTTACTACTCTG

GATACAGTTAGCTGCCTTCGAATAGTGCTGTCCATAGCTAGTGGTCTTGCACATTTGCACATAGAGATATTTGGG

ACCCAAGGGAAACCAGCCATTGCCCATCGAGATTTAAAGAGCAAAAATATTCTGGTTAAGAAGAATGGACAGTGT

TGCATAGCAGATTTGGGCCTGGCAGTCATGCATTCCCAGAGCACCAATCAGCTTGATGTGGGGAACAATCCCCGT

GTGGGCACCAAGCGCTACATGGCCCCCGAAGTTCTAGATGAAACCATCCAGGTGGATTGTTTCGATTCTTATAAA

AGGGTCGATATTTGGGCCTTTGGACTTGTTTTGTGGGAAGTGGCCAGGCGGATGGTGAGCAATGGTATAGTGGAG

GATTACAAGCCACCGTTCTACGATGTGGTTCCCAATGACCCAAGTTTTGAAGATATGAGGAAGGTAGTCTGTGTG

GATCAACAAAGGCCAAACATACCCAACAGATGGTTCTCAGACCCGACATTAACCTCTCTGGCCAAGCTAATGAAA

GAATGCTGGTATCAAAATCCATCCGCAAGACTCACAGCACTGCGTATCAAAAAGACTTTGACCAAAATTGATAAT

TCCCTCGACAAATTGAAAACTGACTGT (SEQ ID NO: 218)
ATGGAAGATGAGAAGCCCAAGGTCAACCCCAAACTCTACATGTGTGTGTGTGAAGGTCTCTC

CTGCGGTAATGAGGACCACTGTGAAGGCCAGCAGTGCTTTTCCTCACTGAGCATCAACGATG

GCTTCCACGTCTACCAGAAAGGCTGCTTCCAGGTTTATGAGCAGGGAAAGATGACCTGTAAG

ACCCCGCCGTCCCCTGGCCAAGCCGTGGAGTGCTGCCAAGGGGACTGGTGTAACAGGAACAT

CACGGCCCAGCTGCCCACTAAAGGAAAATCCTTCCCTGGAACACAGAATTTCCACTTGGAG (SEQ ID NO: 219)
 1 <u>ATGCCTCAGC TATACATTTA CATCAGATTA TTGGGAGCCT ATTTGTTCAT CATTTCTCGT</u>

61 <u>GTTCAAGGAC</u> AGAATCTGGA TAGTATGCTT CATGGCACTG GGATGAAATC AGACTCCGAC

121 CAGAAAAAGT CAGAAAATGG AGTAACCTTA GCACCAGAGG ATACCTTGCC TTTTTTAAAG

181 TGCTATTGCT CAGGGCACTG TCCAGATGAT GCTATTAATA ACACATGCAT AACTAATGGA

241 CATTGCTTTG CCATCATAGA AGAAGATGAC CAGGGAGAAA CCACATTAGC TTCAGGGTGT

301 ATGAAATATG AAGGATCTGA TTTTCAGTGC AAAGATTCTC CAAAAGCCCA GCTACGCCGG

361 ACAATAGAAT GTTGTCGGAC CAATTTATGT AACCAGTATT TGCAACCCAC ACTGCCCCCT

421 GTTGTCATAG GTCCGTTTTT TGATGGCAGC ATTCGATGGC TGGTTTTGCT CATTTCTATG

481 GCTGTCTGCA TAATTGCTAT GATCATCTTC TCCAGCTGCT TTTGTTACAA ACATTATTGC

541 AAGAGCATCT CAAGCAGACG TCGTTACAAT CGTGATTTGG AACAGGATGA AGCATTTATT

601 CCAGTTGGAG AATCACTAAA AGACCTTATT GACCAGTCAC AAAGTTCTGG TAGTGGGTCT

661 GGACTACCTT TATTGGTTCA GCGAACTATT GCCAAACAGA TTCAGATGGT CCGGCAAGTT

721 GGTAAAGGCC GATATGGAGA AGTATGGATG GGCAAATGGC GTGGCGAAAA AGTGGCGGTG

-continued

```
 781 AAAGTATTCT TTACCACTGA AGAAGCCAGC TGGTTTCGAG AAACAGAAAT CTACCAAACT

841 GTGCTAATGC GCCATGAAAA CATACTTGGT TTCATAGCGG CAGACATTAA AGGTACAGGT

901 TCCTGGACTC AGCTCTATTT GATTACTGAT TACCATGAAA ATGGATCTCT CTATGACTTC

961 CTGAAATGTG CTACACTGGA CACCAGAGCC CTGCTTAAAT TGGCTTATTC AGCTGCCTGT

1021 GGTCTGTGCC ACCTGCACAC AGAAATTTAT GGCACCCAAG GAAAGCCCGC AATTGCTCAT

1081 CGAGACCTAA AGAGCAAAAA CATCCTCATC AAGAAAAATG GGAGTTGCTG CATTGCTGAC

1141 CTGGGCCTTG CTGTTAAATT CAACAGTGAC ACAAATGAAG TTGATGTGCC CTTGAATACC

1201 AGGGTGGGCA CCAAACGCTA CATGGCTCCC GAAGTGCTGG ACGAAAGCCT GAACAAAAC

1261 CACTTCCAGC CCTACATCAT GGCTGACATC TACAGCTTCG GCCTAATCAT TTGGGAGATG

1321 GCTCGTCGTT GTATCACAGG AGGGATCGTG GAAGAATACC AATTGCCATA TTACAACATG

1381 GTACCGAGTG ATCCGTCATA CGAAGATATG CGTGAGGTTG TGTGTGTCAA ACGTTTGCGG

1441 CCAATTGTGT CTAATCGGTG GAACAGTGAT GAATGTCTAC GAGCAGTTTT GAAGCTAATG

1501 TCAGAATGCT GGGCCCACAA TCCAGCCTCC AGACTCACAG CATTGAGAAT TAAGAAGACG

1561 CTTGCCAAGA TGGTTGAATC CCAAGATGTA AAAATC
                                                         (SEQ ID NO: 220)
   1 CAGAATCTGG ATAGTATGCT TCATGGCACT GGGATGAAAT CAGACTCCGA CCAGAAAAG

61 TCAGAAAATG GAGTAACCTT AGCACCAGAG GATACCTTGC CTTTTTTAAA GTGCTATTGC

121 TCAGGGCACT GTCCAGATGA TGCTATTAAT AACACATGCA TAACTAATGG ACATTGCTTT

181 GCCATCATAG AAGAAGATGA CCAGGGAGAA ACCACATTAG CTTCAGGGTG TATGAAATAT

241 GAAGGATCTG ATTTTCAGTG CAAAGATTCT CCAAAAGCCC AGCTACGCCG GACAATAGAA

301 TGTTGTCGGA CCAATTTATG TAACCAGTAT TTGCAACCCA CACTGCCCCC TGTTGTCATA

361 GGTCCGTTTT TTGATGGCAG CATTCGA
                                                         (SEQ ID NO: 221)
```

<u>ATGGCGGAGTCGGCCGGAGCCTCCTCCTTCTTCCCCCTTGTTGTCCTCCTGCTCGC</u>
<u>CGGCAGCGGCGGG</u>TCCGGGCCCCGGGGGGTCCAGGCTCTGCTGTGTGCGTG
CACCAGCTGCCTCCAGGCCAACTACACGTGTGAGACAGATGGGGCCTGCAT
GGTTTCCATTTTCAATCTGGATGGGATGGAGCACCATGTGCGCACCTGCATC
CCCAAAGTGGAGCTGGTCCCTGCCGGGAAGCCCTTCTACTGCCTGAGCTCG
GAGGACCTGCGCAACACCCACTGCTGCTACACTGACTACTGCAACAGGATC
GACTTGAGGGTGCCCAGTGGTCACCTCAAGGAGCCTGAGCACCCGTCCATG
TGGGGCCCGGTGGAGCTGGTAGGCATCATCGCCGGCCCGGTGTTCCTCCTGTTC
CTCATCATCATCATTGTTTTCCTTGTCATTAACTATCATCAGCGTGTCTATCACAA
CCGCCAGAGACTGGACATGGAAGATCCCTCATGTGAGATGTGTCTCTCCAAAGA
CAAGACGCTCCAGGATCTTGTCTACGATCTCTCCACCTCAGGGTCTGGCTCAGGG
TTACCCCTCTTTGTCCAGCGCACAGTGGCCCGAACCATCGTTTTACAAGAGATTA
TTGGCAAGGGTCGGTTTGGGGAAGTATGGCGGGGCCGCTGGAGGGGTGGTGATG
TGGCTGTGAAAATATTCTCTTCTCGTGAAGAACGGTCTTGGTTCAGGGAAGCAGA
GATATACCAGACGGTCATGCTGCGCCATGAAAACATCCTTGGATTTATTGCTGCT
GACAATAAAGATAATGGCACCTGGACACAGCTGTGGCTTGTTTCTGACTATCATG
AGCACGGGTCCCTGTTTGATTATCTGAACCGGTACACAGTGACAATTGAGGGGAT
GATTAAGCTGGCCTTGTCTGCTGCTAGTGGGCTGGCACACCTGCACATGGAGATC
GTGGGCACCCAAGGGAAGCCTGGAATTGCTCATCGAGACTTAAAGTCAAAGAAC

-continued

```
ATTCTGGTGAAGAAAAATGGCATGTGTGCCATAGCAGACCTGGGCCTGGCTGTCC

GTCATGATGCAGTCACTGACACCATTGACATTGCCCCGAATCAGAGGGTGGGGA

CCAAACGATACATGGCCCCTGAAGTACTTGATGAAACCATTAATATGAAACACTT

TGACTCCTTTAAATGTGCTGATATTTATGCCCTCGGGCTTGTATATTGGGAGATTG

CTCGAAGATGCAATTCTGGAGGAGTCCATGAAGAATATCAGCTGCCATATTACG

ACTTAGTGCCCTCTGACCCTTCCATTGAGGAAATGCGAAAGGTTGTATGTGATCA

GAAGCTGCGTCCCAACATCCCCAACTGGTGGCAGAGTTATGAGGCACTGCGGGT

GATGGGGAAGATGATGCGAGAGTGTTGGTATGCCAACGGCGCAGCCCGCCTGAC

GGCCCTGCGCATCAAGAAGACCCTCTCCCAGCTCAGCGTGCAGGAAGACGTGAA

GATC
```

(SEQ ID NO: 222)
```
TCCGGGCCCCGGGGGGTCCAGGCTCTGCTGTGTGCGTGCACCAGCTGCCTCCAGGCCAACTA

CACGTGTGAGACAGATGGGGCCTGCATGGTTTCCATTTTCAATCTGGATGGGATGGAGCACC

ATGTGCGCACCTGCATCCCCAAAGTGGAGCTGGTCCCTGCCGGGAAGCCCTTCTACTGCCTG

AGCTCGGAGGACCTGCGCAACACCCACTGCTGCTACACTGACTACTGCAACAGGATCGACTT

GAGGGTGCCCAGTGGTCACCTCAAGGAGCCTGAGCACCCGTCCATGTGGGGCCCGGTGGAG
```

(SEQ ID NO: 223)
<u>ATGGCGGAGTCGGCCGGAGCCTCCTCCTTCTTCCCCCTTGTTGTCCTCCTGCTCGCCGGCAGCGGCGGG</u>TCCGGG

CCCCGGGGGGTCCAGGCTCTGCTGTGTGCGTGCACCAGCTGCCTCCAGGCCAACTACACGTGTGAGACAGATGGG

GCCTGCATGGTTTCCATTTTCAATCTGGATGGGATGGAGCACCATGTGCGCACCTGCATCCCCAAAGTGGAGCTG

GTCCCTGCCGGGAAGCCCTTCTACTGCCTGAGCTCGGAGGACCTGCGCAACACCCACTGCTGCTACACTGACTAC

TGCAACAGGATCGACTTGAGGGTGCCCAGTGGTCACCTCAAGGAGCCTGAGCACCCGTCCATGTGGGGCCCGGTG

GAGCTGGTAGGCATCATCGCCGGCCCGGTGTTCCTCCTGTTCCTCATCATCATCATTGTTTTCCTTGTCATTAAC

TATCATCAGCGTGTCTATCACAACCGCCAGAGACTGGACATGGAAGATCCCTCATGTGAGATGTGTCTCTCCAAA

GACAAGACGCTCCAGGATCTTGTCTACGATCTCTCCACCTCAGGGTCTGGCTCAGGGTTACCCCTCTTTGTCCAG

CGCACAGTGGCCCGAACCATCGTTTTACAAGAGATTATTGGCAAGGGTCGGTTTGGGGAAGTATGGCGGGCCGC

TGGAGGGGTGGTGATGTGGCTGTGAAAATATTCTCTTCTCGTGAAGAACGGTCTTGGTTCAGGGAAGCAGAGATA

TACCAGACGGTCATGCTGCGCCATGAAAACATCCTTGGATTTATTGCTGCTGACAATAAAGCAGACTGCTCATTC

CTCACATTGCCATGGGAAGTTGTAATGGTCTCTGCTGCCCCCAAGCTGAGGAGCCTTAGACTCCAATACAAGGGA

GGAAGGGAAGAGCAAGATTTTTATTCCCACTGAATAATGGCACCTGGACACAGCTGTGGCTTGTTTCTGACTAT

CATGAGCACGGGTCCCTGTTTGATTATCTGAACCGGTACACAGTGACAATTGAGGGGATGATTAAGCTGGCCTTG

TCTGCTGCTAGTGGGCTGGCACACCTGCACATGGAGATCGTGGGCACCCAAGGGAAGCCTGGAATTGCTCATCGA

GACTTAAAGTCAAAGAACATTCTGGTGAAGAAAAATGGCATGTGTGCCATAGCAGACCTGGGCCTGGCTGTCCGT

CATGATGCAGTCACTGACACCATTGACATTGCCCCGAATCAGAGGGTGGGGACCAAACGATACATGGCCCCTGAA

GTACTTGATGAAACCATTAATATGAAACACTTTGACTCCTTTAAATGTGCTGATATTTATGCCCTCGGGCTTGTA

TATTGGGAGATTGCTCGAAGATGCAATTCTGGAGGAGTCCATGAAGAATATCAGCTGCCATATTACGACTTAGTG

CCCTCTGACCCTTCCATTGAGGAAATGCGAAAGGTTGTATGTGATCAGAAGCTGCGTCCCAACATCCCCAACTGG

TGGCAGAGTTATGAGGCACTGCGGGTGATGGGGAAGATGATGCGAGAGTGTTGGTATGCCAACGGCGCAGCCCGC

CTGACGGCCCTGCGCATCAAGAAGACCCTCTCCCAGCTCAGCGTGCAGGAAGACGTGAAGATC (SEQ ID NO: 224)
TCCGGGCCCCGGGGGGTCCAGGCTCTGCTGTGTGCGTGCACCAGCTGCCTCCAGGCCAACTA

CACGTGTGAGACAGATGGGGCCTGCATGGTTTCCATTTTCAATCTGGATGGGATGGAGCACC
```

-continued

ATGTGCGCACCTGCATCCCCAAAGTGGAGCTGGTCCCTGCCGGGAAGCCCTTCTACTGCCTG

AGCTCGGAGGACCTGCGCAACACCCACTGCTGCTACACTGACTACTGCAACAGGATCGACTT

GAGGGTGCCCAGTGGTCACCTCAAGGAGCCTGAGCACCCGTCCATGTGGGGCCCGGTGGAG (SEQ ID NO: 225)
<u>ATGGAGGCGGCGGTCGCTGCTCCGCGTCCCCGGCTGCTCCTCCTCGTGCTGGCGGCGGCGGCGGCGGCG</u>GCG

GCGCTGCTCCCGGGGGCGACGGCGTTACAGTGTTTCTGCCACCTCTGTACAAAAGACAATTTTACTTGTGTGACA

GATGGGCTCTGCTTTGTCTCTGTCACAGAGACCACAGACAAAGTTATACACAACAGCATGTGTATAGCTGAAATT

GACTTAATTCCTCGAGATAGGCCGTTTGTATGTGCACCCTCTTCAAAAACTGGGTCTGTGACTACAACATATTGC

TGCAATCAGGACCATTGCAATAAAATAGAACTTCCAACTACTGTAAAGTCATCACCTGGCCTTGGTCCTGTGGAA

CTGGCAGCTGTCATTGCTGGACCAGTGTGCTTCGTCTGCATCTCACTCATGTTGATGGTCTATATCTGCCACAAC

CGCACTGTCATTCACCATCGAGTGCCAAATGAAGAGGACCCTTCATTAGATCGCCCTTTTATTTCAGAGGGTACT

ACGTTGAAAGACTTAATTTATGATATGACAACGTCAGGTTCTGGCTCAGGTTTACCATTGCTTGTTCAGAGAACA

ATTGCGAGAACTATTGTGTTACAAGAAAGCATTGGCAAAGGTCGATTTGGAGAAGTTTGGAGAGGAAAGTGGCGG

GGAGAAGAAGTTGCTGTTAAGATATTCTCCTCTAGAGAAGAACGTTCGTGGTTCCGTGAGGCAGAGATTTATCAA

ACTGTAATGTTACGTCATGAAAACATCCTGGGATTTATAGCAGCAGACAATAAAGACAATGGTACTTGGACTCAG

CTCTGGTTGGTGTCAGATTATCATGAGCATGGATCCCTTTTTGATTACTTAAACAGATACACAGTTACTGTGGAA

GGAATGATAAAACTTGCTCTGTCCACGGCGAGCGGTCTTGCCCATCTTCACATGGAGATTGTTGGTACCCAAGGA

AAGCCAGCCATTGCTCATAGAGATTTGAAATCAAAGAATATCTTGGTAAAGAAGAATGGAACTTGCTGTATTGCA

GACTTAGGACTGGCAGTAAGACATGATTCAGCCACAGATACCATTGATATTGCTCCAAACCACAGAGTGGGAACA

AAAAGGTACATGGCCCCTGAAGTTCTCGATGATTCCATAAATATGAAACATTTTGAATCCTTCAAACGTGCTGAC

ATCTATGCAATGGGCTTAGTATTCTGGGAAATTGCTCGACGATGTTCCATTGGTGGAATTCATGAAGATTACCAA

CTGCCTTATTATGATCTTGTACCTTCTGACCCATCAGTTGAAGAAATGAGAAAAGTTGTTTGTGAACAGAAGTTA

AGGCCAAATATCCCAAACAGATGGCAGAGCTGTGAAGCCTTGAGAGTAATGGCTAAAATTATGAGAGAATGTTGG

TATGCCAATGGAGCAGCTAGGCTTACAGCATTGCGGATTAAGAAAACATTATCGCAACTCAGTCAACAGGAAGGC

ATCAAAATG (SEQ ID NO: 226)
GCGGCGCTGCTCCCGGGGGCGACGGCGTTACAGTGTTTCTGCCACCTCTGTACAAAAGACAA

TTTTACTTGTGTGACAGATGGGCTCTGCTTTGTCTCTGTCACAGAGACCACAGACAAAGTTA

TACACAACAGCATGTGTATAGCTGAAATTGACTTAATTCCTCGAGATAGGCCGTTTGTATGT

GCACCCTCTTCAAAAACTGGGTCTGTGACTACAACATATTGCTGCAATCAGGACCATTGCAA

TAAAATAGAACTTCCAACTACTGTAAAGTCATCACCTGGCCTTGGTCCTGTGGAACTG (SEQ ID NO: 227)
<u>ATGGAGGCGGCGGTCGCTGCTCCGCGTCCCCGGCTGCTCCTCCTCGTGCTGGCGGCGGCGG</u>

<u>GCGGCGGCGG</u>GCGGCGCTGCTCCCGGGGGCGACGGCGTTACAGTGTTTCTGCCACCTCTGTA

CAAAAGACAATTTTACTTGTGTGACAGATGGGCTCTGCTTTGTCTCTGTCACAGAGACCACA

GACAAAGTTATACACAACAGCATGTGTATAGCTGAAATTGACTTAATTCCTCGAGATAGGCC

GTTTGTATGTGCACCCTCTTCAAAAACTGGGTCTGTGACTACAACATATTGCTGCAATCAGG

ACCATTGCAATAAAATAGAACTTCCAACTACTGGCCCTTTTTCAGTAAAGTCATCACCTGGC

CTTGGTCCTGTGGAACTGGCAGCTGTCATTGCTGGACCAGTGTGCTTCGTCTGCATCTCACT

CATGTTGATGGTCTATATCTGCCACAACCGCACTGTCATTCACCATCGAGTGCCAAATGAAG

AGGACCCTTCATTAGATCGCCCTTTTATTTCAGAGGGTACTACGTTGAAAGACTTAATTTAT

GATATGACAACGTCAGGTTCTGGCTCAGGTTTACCATTGCTTGTTCAGAGAACAATTGCGAG

-continued

AACTATTGTGTTACAAGAAAGCATTGGCAAAGGTCGATTTGGAGAAGTTTGGAGAGGAAAGT

GGCGGGGAGAAGAAGTTGCTGTTAAGATATTCTCCTCTAGAGAAGAACGTTCGTGGTTCCGT

GAGGCAGAGATTTATCAAACTGTAATGTTACGTCATGAAAACATCCTGGGATTTATAGCAGC

AGACAATAAAGACAATGGTACTTGGACTCAGCTCTGGTTGGTGTCAGATTATCATGAGCATG

GATCCCTTTTTGATTACTTAAACAGATACACAGTTACTGTGGAAGGAATGATAAAACTTGCT

CTGTCCACGGCGAGCGGTCTTGCCCATCTTCACATGGAGATTGTTGGTACCCAAGGAAAGCC

AGCCATTGCTCATAGAGATTTGAAATCAAAGAATATCTTGGTAAAGAAGAATGGAACTTGCT

GTATTGCAGACTTAGGACTGGCAGTAAGACATGATTCAGCCACAGATACCATTGATATTGCT

CCAAACCACAGAGTGGGAACAAAAAGGTACATGGCCCCTGAAGTTCTCGATGATTCCATAAA

TATGAAACATTTTGAATCCTTCAAACGTGCTGACATCTATGCAATGGGCTTAGTATTCTGGG

AAATTGCTCGACGATGTTCCATTGGTGGAATTCATGAAGATTACCAACTGCCTTATTATGAT

CTTGTACCTTCTGACCCATCAGTTGAAGAAATGAGAAAAGTTGTTTGTGAACAGAAGTTAAG

GCCAAATATCCCAAACAGATGGCAGAGCTGTGAAGCCTTGAGAGTAATGGCTAAAATTATGA

GAGAATGTTGGTATGCCAATGGAGCAGCTAGGCTTACAGCATTGCGGATTAAGAAAACATTA

TCGCAACTCAGTCAACAGGAAGGCATCAAAATG (SEQ ID NO: 228)
GCGGCGCTGCTCCCGGGGGCGACGGCGTTACAGTGTTTCTGCCACCTCTGTACAAAAGACAA

TTTTACTTGTGTGACAGATGGGCTCTGCTTTGTCTCTGTCACAGAGACCACAGACAAAGTTA

TACACAACAGCATGTGTATAGCTGAAATTGACTTAATTCCTCGAGATAGGCCGTTTGTATGT

GCACCCTCTTCAAAAACTGGGTCTGTGACTACAACATATTGCTGCAATCAGGACCATTGCAA

TAAAATAGAACTTCCAACTACTGGCCCTTTTTCAGTAAAGTCATCACCTGGCCTTGGTCCTG

TGGAACTG (SEQ ID NO: 229)
<u>ATGCTTTTGCGAAGTGCAGGAAAATTAAATGTGGGCACC</u>AAGAAAGAGGATGGTGAGAGTACAGCCCCCACCCCC

CGTCCAAAGGTCTTGCGTTGTAAATGCCACCACCATTGTCCAGAAGACTCAGTCAACAATATTTGCAGCACAGAC

GGATATTGTTTCACGATGATAGAAGAGGATGACTCTGGGTTGCCTGTGGTCACTTCTGGTTGCCTAGGACTAGAA

GGCTCAGATTTTCAGTGTCGGGACACTCCCATTCCTCATCAAAGAAGATCAATTGAATGCTGCACAGAAAGGAAC

GAATGTAATAAAGACCTACACCCTACACTGCCTCCATTGAAAAACAGAGATTTTGTTGATGGACCTATACACCAC

AGGGCTTTACTTATATCTGTGACTGTCTGTAGTTTGCTCTTGGTCCTTATCATATTATTTTGTTACTTCCGGTAT

AAAAGACAAGAAACCAGACCTCGATACAGCATTGGGTTAGAACAGGATGAAACTTACATTCCTCCTGGAGAATCC

CTGAGAGACTTAATTGAGCAGTCTCAGAGCTCAGGAAGTGGATCAGGCCTCCCTCTGCTGGTCCAAAGGACTATA

GCTAAGCAGATTCAGATGGTGAAACAGATTGGAAAAGGTCGCTATGGGAAGTTTGGATGGGAAAGTGGCGTGGC

GAAAAGGTAGCTGTGAAAGTGTTCTTCACCACAGAGGAAGCCAGCTGGTTCAGAGAGACAGAAATATATCAGACA

GTGTTGATGAGGCATGAAAACATTTTGGGTTTCATTGCTGCAGATATCAAAGGGACAGGGTCCTGGACCCAGTTG

TACCTAATCACAGACTATCATGAAAATGGTTCCCTTTATGATTATCTGAAGTCCACCACCCTAGACGCTAAATCA

ATGCTGAAGTTAGCCTACTCTTCTGTCAGTGGCTTATGTCATTTACACACAGAAATCTTTAGTACTCAAGGCAAA

CCAGCAATTGCCCATCGAGATCTGAAAAGTAAAAACATTCTGGTGAAGAAAATGGAACTTGCTGTATTGCTGAC

CTGGGCCTGGCTGTTAAATTTATTAGTGATACAAATGAAGTTGACATACCACCTAACACTCGAGTTGGCACCAAA

CGCTATATGCCTCCAGAAGTGTTGGACGAGAGCTTGAACAGAAATCACTTCCAGTCTTACATCATGGCTGACATG

TATAGTTTTGGCCTCATCCTTTGGGAGGTTGCTAGGAGATGTGTATCAGGAGGTATAGTGGAAGAATACCAGCTT

CCTTATCATGACCTAGTGCCCAGTGACCCCTCTTATGAGGACATGAGGGAGATTGTGTGCATCAAGAAGTTACGC

```
CCCTCATTCCCAAACCGGTGGAGCAGTGATGAGTGTCTAAGGCAGATGGGAAAACTCATGACAGAATGCTGGGCT

CACAATCCTGCATCAAGGCTGACAGCCCTGCGGGTTAAGAAAACACTTGCCAAAATGTCAGAGTCCCAGGACATT

AAACTC
```

(SEQ ID NO: 230)
```
AAGAAAGAGGATGGTGAGAGTACAGCCCCCACCCCCCGTCCAAAGGTCTTGCGTTGTAAATG

CCACCACCATTGTCCAGAAGACTCAGTCAACAATATTTGCAGCACAGACGGATATTGTTTCA

CGATGATAGAAGAGGATGACTCTGGGTTGCCTGTGGTCACTTCTGGTTGCCTAGGACTAGAA

GGCTCAGATTTTCAGTGTCGGGACACTCCCATTCCTCATCAAAGAAGATCAATTGAATGCTG

CACAGAAAGGAACGAATGTAATAAAGACCTACACCCTACACTGCCTCCATTGAAAAACAGAG

ATTTTGTTGATGGACCTATACACCACAGG
```

(SEQ ID NO: 231)
<u>ATGGGTTGGCTGGAAGAACTAAACTGGCAGCTTCACATTTTCTTGCTCATTCTTCTCTATGCACACAAGGGCA</u>

AACTTCCTTGATAACATGCTTTTGCGAAGTGCAGGAAAATTAAATGTGGGCACCAAGAAAGAGGATGGTGAGAGT

ACAGCCCCCACCCCCCGTCCAAAGGTCTTGCGTTGTAAATGCCACCACCATTGTCCAGAAGACTCAGTCAACAAT

ATTTGCAGCACAGACGGATATTGTTTCACGATGATAGAAGAGGATGACTCTGGGTTGCCTGTGGTCACTTCTGGT

TGCCTAGGACTAGAAGGCTCAGATTTTCAGTGTCGGGACACTCCCATTCCTCATCAAAGAAGATCAATTGAATGC

TGCACAGAAAGGAACGAATGTAATAAAGACCTACACCCTACACTGCCTCCATTGAAAAACAGAGATTTTGTTGAT

GGACCTATACACCACAGGGCTTTACTTATATCTGTGACTGTCTGTAGTTTGCTCTTGGTCCTTATCATATTATTT

```
TGTTACTTCCGGTATAAAAGACAAGAAACCAGACCTCGATACAGCATTGGGTTAGAACAGGATGAAACTTACATT

CCTCCTGGAGAATCCCTGAGAGACTTAATTGAGCAGTCTCAGAGCTCAGGAAGTGGATCAGGCCTCCCTCTGCTG

GTCCAAAGGACTATAGCTAAGCAGATTCAGATGGTGAAACAGATTGGAAAAGGTCGCTATGGGGAAGTTTGGATG

GGAAAGTGGCGTGGCGAAAAGGTAGCTGTGAAAGTGTTCTTCACCACAGAGGAAGCCAGCTGGTTCAGAGAGACA

GAAATATATCAGACAGTGTTGATGAGGCATGAAAACATTTTGGGTTTCATTGCTGCAGATATCAAAGGGACAGGG

TCCTGGACCCAGTTGTACCTAATCACAGACTATCATGAAAATGGTTCCCTTTATGATTATCTGAAGTCCACCACC

CTAGACGCTAAATCAATGCTGAAGTTAGCCTACTCTTCTGTCAGTGGCTTATGTCATTTACACACAGAAATCTTT

AGTACTCAAGGCAAACCAGCAATTGCCCATCGAGATCTGAAAAGTAAAAACATTCTGGTGAAGAAAAATGGAACT

TGCTGTATTGCTGACCTGGGCCTGGCTGTTAAATTTATTAGTGATACAAATGAAGTTGACATACCACCTAACACT

CGAGTTGGCACCAAACGCTATATGCCTCCAGAAGTGTTGGACGAGAGCTTGAACAGAAATCACTTCCAGTCTTAC

ATCATGGCTGACATGTATAGTTTTGGCCTCATCCTTTGGGAGGTTGCTAGGAGATGTGTATCAGGAGGTATAGTG

GAAGAATACCAGCTTCCTTATCATGACCTAGTGCCCAGTGACCCCTCTTATGAGGACATGAGGGAGATTGTGTGC

ATCAAGAAGTTACGCCCCTCATTCCCAAACCGGTGGAGCAGTGATGAGTGTCTAAGGCAGATGGGAAAACTCATG

ACAGAATGCTGGGCTCACAATCCTGCATCAAGGCTGACAGCCCTGCGGGTTAAGAAAACACTTGCCAAAATGTCA

GAGTCCCAGGACATTAAACTC
```

(SEQ ID NO: 232)
```
AACTTCCTTGATAACATGCTTTTGCGAAGTGCAGGAAAATTAAATGTGGGCACCAAGAAAGA

GGATGGTGAGAGTACAGCCCCCACCCCCCGTCCAAAGGTCTTGCGTTGTAAATGCCACCACC

ATTGTCCAGAAGACTCAGTCAACAATATTTGCAGCACAGACGGATATTGTTTCACGATGATA

GAAGAGGATGACTCTGGGTTGCCTGTGGTCACTTCTGGTTGCCTAGGACTAGAAGGCTCAGA

TTTTCAGTGTCGGGACACTCCCATTCCTCATCAAAGAAGATCAATTGAATGCTGCACAGAAA

GGAACGAATGTAATAAAGACCTACACCCTACACTGCCTCCATTGAAAAACAGAGATTTTGTT

GATGGACCTATACACCACAGG
```

-continued (SEQ ID NO: 233)
<u>ATGACCCGGGCGCTCTGCTCAGCGCTCCGCCAGGCTCTCCTGCTGCTCGCAGCGGCCGCC</u>GAGCTCTCGCCAGGA

CTGAAGTGTGTATGTCTTTTGTGTGATTCTTCAAACTTTACCTGCCAAACAGAAGGAGCATGTTGGGCATCAGTC

ATGCTAACCAATGGAAAAGAGCAGGTGATCAAATCCTGTGTCTCCCTTCCAGAACTGAATGCTCAAGTCTTCTGT

CATAGTTCCAACAATGTTACCAAAACCGAATGCTGCTTCACAGATTTTTGCAACAACATAACACTGCACCTTCCA

ACAGCATCACCAAATGCCCCAAAACTTGGACCCATGGAGCTGGCCATCATTATTACTGTGCCTGTTTGCCTCCTG

TCCATAGCTGCGATGCTGACAGTATGGGCATGCCAGGGTCGACAGTGCTCCTACAGGAAGAAAAGAGACCAAAT

GTGGAGGAACCACTCTCTGAGTGCAATCTGGTAAATGCTGGAAAAACTCTGAAAGATCTGATTTATGATGTGACC

GCCTCTGGATCTGGCTCTGGTCTACCTCTGTTGGTTCAAAGGACAATTGCAAGGACGATTGTGCTTCAGGAAATA

GTAGGAAAAGGTAGATTTGGTGAGGTGTGGCATGGAAGATGGTGTGGGGAAGATGTGGCTGTGAAAATATTCTCC

TCCAGAGATGAAAGATCTTGGTTTCGTGAGGCAGAAATTTACCAGACGGTCATGCTGCGACATGAAAACATCCTT

GGTTTCATTGCTGCTGACAACAAAGATAATGGAACTTGGACTCAACTTTGGCTGGTATCTGAATATCATGAACAG

GGCTCCTTATATGACTATTTGAATAGAAATATAGTGACCGTGGCTGGAATGATCAAGCTGGCGCTCTCAATTGCT

AGTGGTCTGGCACACCTTCATATGGAGATTGTTGGTACACAAGGTAAACCTGCTATTGCTCATCGAGACATAAAA

TCAAAGAATATCTTAGTGAAAAAGTGTGAAACTTGTGCCATAGCGGACTTAGGGTTGGCTGTGAAGCATGATTCA

ATACTGAACACTATCGACATACCTCAGAATCCTAAAGTGGGAACCAAGAGGTATATGGCTCCTGAAATGCTTGAT

GATACAATGAATGTGAATATCTTTGAGTCCTTCAAACGAGCTGACATCTATTCTGTTGGTCTGGTTTACTGGGAA

ATAGCCCGGAGGTGTTCAGTCGGAGGAATTGTTGAGGAGTACCAATTGCCTTATTATGACATGGTGCCTTCAGAT

CCCTCGATAGAGGAAATGAGAAAGGTTGTTTGTGACCAGAAGTTTCGACCAAGTATCCCAAACCAGTGGCAAAGT

TGTGAAGCACTCCGAGTCATGGGGAGAATAATGCGTGAGTGTTGGTATGCCAACGGAGCGGCCCGCCTAACTGCT

CTTCGTATTAAGAAGACTATATCTCAACTTTGTGTCAAAGAAGACTGCAAAGCC (SEQ ID NO: 234)
GAGCTCTCGCCAGGACTGAAGTGTGTATGTCTTTTGTGTGATTCTTCAAACTTTACCTGCCA

AACAGAAGGAGCATGTTGGGCATCAGTCATGCTAACCAATGGAAAAGAGCAGGTGATCAAAT

CCTGTGTCTCCCTTCCAGAACTGAATGCTCAAGTCTTCTGTCATAGTTCCAACAATGTTACC

AAAACCGAATGCTGCTTCACAGATTTTTGCAACAACATAACACTGCACCTTCCAACAGCATC

ACCAAATGCCCCAAAACTTGGACCCATGGAG (SEQ ID NO: 235)
ATGCTAACCAATGGAAAAGAGCAGGTGATCAAATCCTGTGTCTCCCTTCCAGAACTGAATGC

TCAAGTCTTCTGTCATAGTTCCAACAATGTTACCAAAACCGAATGCTGCTTCACAGATTTTT

GCAACAACATAACACTGCACCTTCCAACAGCATCACCAAATGCCCCAAAACTTGGACCCATG

GAGCTGGCCATCATTATTACTGTGCCTGTTTGCCTCCTGTCCATAGCTGCGATGCTGACAGT

ATGGGCATGCCAGGGTCGACAGTGCTCCTACAGGAAGAAAAGAGACCAAATGTGGAGGAAC

CACTCTCTGAGTGCAATCTGGTAAATGCTGGAAAAACTCTGAAAGATCTGATTTATGATGTG

ACCGCCTCTGGATCTGGCTCTGGTCTACCTCTGTTGGTTCAAAGGACAATTGCAAGGACGAT

TGTGCTTCAGGAAATAGTAGGAAAAGGTAGATTTGGTGAGGTGTGGCATGGAAGATGGTGTG

GGGAAGATGTGGCTGTGAAAATATTCTCCTCCAGAGATGAAAGATCTTGGTTTCGTGAGGCA

GAAATTTACCAGACGGTCATGCTGCGACATGAAAACATCCTTGGTTTCATTGCTGCTGACAA

CAAAGATAATGGAACTTGGACTCAACTTTGGCTGGTATCTGAATATCATGAACAGGGCTCCT

TATATGACTATTTGAATAGAAATATAGTGACCGTGGCTGGAATGATCAAGCTGGCGCTCTCA

ATTGCTAGTGGTCTGGCACACCTTCATATGGAGATTGTTGGTACACAAGGTAAACCTGCTAT

TGCTCATCGAGACATAAAATCAAAGAATATCTTAGTGAAAAAGTGTGAAACTTGTGCCATAG

-continued

CGGACTTAGGGTTGGCTGTGAAGCATGATTCAATACTGAACACTATCGACATACCTCAGAAT

CCTAAAGTGGGAACCAAGAGGTATATGGCTCCTGAAATGCTTGATGATACAATGAATGTGAA

TATCTTTGAGTCCTTCAAACGAGCTGACATCTATTCTGTTGGTCTGGTTTACTGGGAAATAG

CCCGGAGGTGTTCAGTCGGAGGAATTGTTGAGGAGTACCAATTGCCTTATTATGACATGGTG

CCTTCAGATCCCTCGATAGAGGAAATGAGAAAGGTTGTTTGTGACCAGAAGTTTCGACCAAG

TATCCCAAACCAGTGGCAAAGTTGTGAAGCACTCCGAGTCATGGGGAGAATAATGCGTGAGT

GTTGGTATGCCAACGGAGCGGCCCGCCTAACTGCTCTTCGTATTAAGAAGACTATATCTCAA

CTTTGTGTCAAAGAAGACTGCAAAGCC (SEQ ID NO: 236)
ATGCTAACCAATGGAAAAGAGCAGGTGATCAAATCCTGTGTCTCCCTTCCAGAACTGAATGC

TCAAGTCTTCTGTCATAGTTCCAACAATGTTACCAAAACCGAATGCTGCTTCACAGATTTTT

GCAACAACATAACACTGCACCTTCCAACAGCATCACCAAATGCCCCAAAACTTGGACCCATG

GAG (SEQ ID NO: 237)
ATGACCCGGGCGCTCTGCTCAGCGCTCCGCCAGGCTCTCCTGCTGCTCGCAGCGGCCGCCGA

GCTCTCGCCAGGACTGAAGTGTGTATGTCTTTTGTGTGATTCTTCAAACTTTACCTGCCAAA

CAGAAGGAGCATGTTGGGCATCAGTCATGCTAACCAATGGAAAAGAGCAGGTGATCAAATCC

TGTGTCTCCCTTCCAGAACTGAATGCTCAAGTCTTCTGTCATAGTTCCAACAATGTTACCAA

AACCGAATGCTGCTTCACAGATTTTTGCAACAACATAACACTGCACCTTCCAACAGGTCTAC

CTCTGTTGGTTCAAAGGACAATTGCAAGGACGATTGTGCTTCAGGAAATAGTAGGAAAAGGT

AGATTTGGTGAGGTGTGGCATGGAAGATGGTGTGGGAAGATGTGGCTGTGAAAATATTCTC

CTCCAGAGATGAAAGATCTTGGTTTCGTGAGGCAGAAATTTACCAGACGGTCATGCTGCGAC

ATGAAAACATCCTTGGTTTCATTGCTGCTGACAACAAAGATAATGGAACTTGGACTCAACTT

TGGCTGGTATCTGAATATCATGAACAGGGCTCCTTATATGACTATTTGAATAGAAATATAGT

GACCGTGGCTGGAATGATCAAGCTGGCGCTCTCAATTGCTAGTGGTCTGGCACACCTTCATA

TGGAGATTGTTGGTACACAAGGTAAACCTGCTATTGCTCATCGAGACATAAAATCAAAGAAT

ATCTTAGTGAAAAAGTGTGAAACTTGTGCCATAGCGGACTTAGGGTTGGCTGTGAAGCATGA

TTCAATACTGAACACTATCGACATACCTCAGAATCCTAAAGTGGGAACCAAGAGGTATATGG

CTCCTGAAATGCTTGATGATACAATGAATGTGAATATCTTTGAGTCCTTCAAACGAGCTGAC

ATCTATTCTGTTGGTCTGGTTTACTGGGAAATAGCCCGGAGGTGTTCAGTCGGAGGAATTGT

TGAGGAGTACCAATTGCCTTATTATGACATGGTGCCTTCAGATCCCTCGATAGAGGAAATGA

GAAAGGTTGTTTGTGACCAGAAGTTTCGACCAAGTATCCCAAACCAGTGGCAAAGTTGTGAA

GCACTCCGAGTCATGGGGAGAATAATGCGTGAGTGTTGGTATGCCAACGGAGCGGCCCGCCT

AACTGCTCTTCGTATTAAGAAGACTATATCTCAACTTTGTGTCAAAGAAGACTGCAAAGCC (SEQ ID NO: 238)
GAGCTCTCGCCAGGACTGAAGTGTGTATGTCTTTTGTGTGATTCTTCAAACTTTACCTGCCA

AACAGAAGGAGCATGTTGGGCATCAGTCATGCTAACCAATGGAAAAGAGCAGGTGATCAAAT

CCTGTGTCTCCCTTCCAGAACTGAATGCTCAAGTCTTCTGTCATAGTTCCAACAATGTTACC

AAAACCGAATGCTGCTTCACAGATTTTTGCAACAACATAACACTGCACCTTCCAACAGGTCT

ACCTCTGTTGGTTCAAAGGACAATTGCAAGGACGATTGTGCTTCAGGAAATAGTAGGAAAAG

GTAGATTTGGTGAGGTGTGGCATGGAAGATGGTGTGGGAAGATGTGGCTGTGAAAATATTC

TCCTCCAGAGATGAAAGATCTTGGTTTCGTGAGGCAGAAATTTACCAGACGGTCATGCTGCG

-continued

ACATGAAAACATCCTTGGTTTCATTGCTGCTGACAACAAAGATAATGGAACTTGGACTCAAC
TTTGGCTGGTATCTGAATATCATGAACAGGGCTCCTTATATGACTATTTGAATAGAAATATA
GTGACCGTGGCTGGAATGATCAAGCTGGCGCTCTCAATTGCTAGTGGTCTGGCACACCTTCA
TATGGAGATTGTTGGTACACAAGGTAAACCTGCTATTGCTCATCGAGACATAAAATCAAAGA
ATATCTTAGTGAAAAAGTGTGAAACTTGTGCCATAGCGGACTTAGGGTTGGCTGTGAAGCAT
GATTCAATACTGAACACTATCGACATACCTCAGAATCCTAAAGTGGGAACCAAGAGGTATAT
GGCTCCTGAAATGCTTGATGATACAATGAATGTGAATATCTTTGAGTCCTTCAAACGAGCTG
ACATCTATTCTGTTGGTCTGGTTTACTGGGAAATAGCCCGGAGGTGTTCAGTCGGAGGAATT
GTTGAGGAGTACCAATTGCCTTATTATGACATGGTGCCTTCAGATCCCTCGATAGAGGAAAT
GAGAAAGGTTGTTTGTGACCAGAAGTTTCGACCAAGTATCCCAAACCAGTGGCAAAGTTGTG
AAGCACTCCGAGTCATGGGGAGAATAATGCGTGAGTGTTGGTATGCCAACGGAGCGGCCCGC
CTAACTGCTCTTCGTATTAAGAAGACTATATCTCAACTTTGTGTCAAAGAAGACTGCAAAGC
C (SEQ ID NO: 239)
<u>ATGACCCGGGCGCTCTGCTCAGCGCTCCGCCAGGCTCTCCTGCTGCTCGCAGCGGCCGCCGA</u>
GCTCTCGCCAGGACTGAAGTGTGTATGTCTTTTGTGTGATTCTTCAAACTTTACCTGCCAAA
CAGAAGGAGCATGTTGGGCATCAGTCATGCTAACCAATGGAAAAGAGCAGGTGATCAAATCC
TGTGTCTCCCTTCCAGAACTGAATGCTCAAGTCTTCTGTCATAGTTCCAACAATGTTACCAA
AACCGAATGCTGCTTCACAGATTTTTGCAACAACATAACACTGCACCTTCCAACAGATAATG
GAACTTGGACTCAACTTTGGCTGGTATCTGAATATCATGAACAGGGCTCCTTATATGACTAT
TTGAATAGAAATATAGTGACCGTGGCTGGAATGATCAAGCTGGCGCTCTCAATTGCTAGTGG
TCTGGCACACCTTCATATGGAGATTGTTGGTACACAAGGTAAACCTGCTATTGCTCATCGAG
ACATAAAATCAAAGAATATCTTAGTGAAAAAGTGTGAAACTTGTGCCATAGCGGACTTAGGG
TTGGCTGTGAAGCATGATTCAATACTGAACACTATCGACATACCTCAGAATCCTAAAGTGGG
AACCAAGAGGTATATGGCTCCTGAAATGCTTGATGATACAATGAATGTGAATATCTTTGAGT
CCTTCAAACGAGCTGACATCTATTCTGTTGGTCTGGTTTACTGGGAAATAGCCCGGAGGTGT
TCAGTCGGAGGAATTGTTGAGGAGTACCAATTGCCTTATTATGACATGGTGCCTTCAGATCC
CTCGATAGAGGAAATGAGAAAGGTTGTTTGTGACCAGAAGTTTCGACCAAGTATCCCAAACC
AGTGGCAAAGTTGTGAAGCACTCCGAGTCATGGGGAGAATAATGCGTGAGTGTTGGTATGCC
AACGGAGCGGCCCGCCTAACTGCTCTTCGTATTAAGAAGACTATATCTCAACTTTGTGTCAA
AGAAGACTGCAAAGCCTAA (SEQ ID NO: 240)
GAGCTCTCGCCAGGACTGAAGTGTGTATGTCTTTTGTGTGATTCTTCAAACTTTACCTGCCA
AACAGAAGGAGCATGTTGGGCATCAGTCATGCTAACCAATGGAAAAGAGCAGGTGATCAAAT
CCTGTGTCTCCCTTCCAGAACTGAATGCTCAAGTCTTCTGTCATAGTTCCAACAATGTTACC
AAAACCGAATGCTGCTTCACAGATTTTTGCAACAACATAACACTGCACCTTCCAACAGATAA
TGGAACTTGGACTCAACTTTGGCTGGTATCTGAATATCATGAACAGGGCTCCTTATATGACT
ATTTGAATAGAAATATAGTGACCGTGGCTGGAATGATCAAGCTGGCGCTCTCAATTGCTAGT
GGTCTGGCACACCTTCATATGGAGATTGTTGGTACACAAGGTAAACCTGCTATTGCTCATCG
AGACATAAAATCAAAGAATATCTTAGTGAAAAAGTGTGAAACTTGTGCCATAGCGGACTTAG
GGTTGGCTGTGAAGCATGATTCAATACTGAACACTATCGACATACCTCAGAATCCTAAAGTG
GGAACCAAGAGGTATATGGCTCCTGAAATGCTTGATGATACAATGAATGTGAATATCTTTGA

-continued
```
GTCCTTCAAACGAGCTGACATCTATTCTGTTGGTCTGGTTTACTGGGAAATAGCCCGGAGGT

GTTCAGTCGGAGGAATTGTTGAGGAGTACCAATTGCCTTATTATGACATGGTGCCTTCAGAT

CCCTCGATAGAGGAAATGAGAAAGGTTGTTTGTGACCAGAAGTTTCGACCAAGTATCCCAAA

CCAGTGGCAAAGTTGTGAAGCACTCCGAGTCATGGGGAGAATAATGCGTGAGTGTTGGTATG

CCAACGGAGCGGCCCGCCTAACTGCTCTTCGTATTAAGAAGACTATATCTCAACTTTGTGTC

AAAGAAGACTGCAAAGCCTAA
```

(SEQ ID NO: 241)

```
   1 ATGGGAGCTG CTGCAAAGTT GGCGTTTGCC GTCTTTCTTA TCTCCTGTTC

51 TTCAGGTGCT ATACTTGGTA GATCAGAAAC TCAGGAGTGT CTTTTCTTTA

101 ATGCTAATTG GGAAAAAGAC AGAACCAATC AAACTGGTGT TGAACCGTGT

151 TATGGTGACA AAGATAAACG GCGGCATTGT TTTGCTACCT GGAAGAATAT

201 TTCTGGTTCC ATTGAAATAG TGAAACAAGG TTGTTGGCTG GATGATATCA

251 ACTGCTATGA CAGGACTGAT TGTGTAGAAA AAAAGACAG CCCTGAAGTA

301 TATTTTTGTT GCTGTGAGGG CAATATGTGT AATGAAAAGT TTTCTTATTT

351 TCCGGAGATG GAAGTCACAC AGCCCACTTC AAATCCAGTT ACACCTAAGC

401 CACCCTATTA CAACATCCTG CTCTATTCCT TGGTGCCACT TATGTTAATT

451 GCGGGGATTG TCATTTGTGC ATTTTGGGTG TACAGGCATC ACAAGATGGC

501 CTACCCTCCT GTACTTGTTC CAACTCAAGA CCCAGGACCA CCCCCACCTT

551 CTCCATTACT AGGTTTGAAA CCACTGCAGT TATTAGAAGT GAAAGCAAGG

601 GGAAGATTTG GTTGTGTCTG GAAAGCCCAG TTGCTTAACG AATATGTGGC

651 TGTCAAAATA TTTCCAATAC AGGACAAACA GTCATGGCAA AATGAATACG

701 AAGTCTACAG TTTGCCTGGA ATGAAGCATG AGAACATATT ACAGTTCATT

751 GGTGCAGAAA AACGAGGCAC CAGTGTTGAT GTGGATCTTT GGCTGATCAC

801 AGCATTTCAT GAAAAGGGTT CACTATCAGA CTTTCTTAAG GCTAATGTGG

851 TCTCTTGGAA TGAACTGTGT CATATTGCAG AAACCATGGC TAGAGGATTG

901 GCATATTTAC ATGAGGATAT ACCTGGCCTA AAAGATGGCC ACAAACCTGC

951 CATATCTCAC AGGGACATCA AAGTAAAAA TGTGCTGTTG AAAAACAACC

1001 TGACAGCTTG CATTGCTGAC TTTGGGTTGG CCTTAAAATT TGAGGCTGGC

1051 AAGTCTGCAG GCGATACCCA TGGACAGGTT GGTACCCGGA GGTACATGGC

1101 TCCAGAGGTA TTAGAGGGTG CTATAAACTT CCAAGGGGAT GCATTTTTGA

1151 GGATAGATAT GTATGCCATG GGATTAGTCC TATGGGAACT GGCTTCTCGC

1201 TGTACTGCTG CAGATGGACC TGTAGATGAA TACATGTTGC CATTTGAGGA

1251 GGAAATTGGC CAGCATCCAT CTCTTGAAGA CATGCAGGAA GTTGTTGTGC

1301 ATAAAAAAA GAGGCCTGTT TTAAGAGATT ATTGGCAGAA ACATGCTGGA

1351 ATGGCAATGC TCTGTGAAAC CATTGAAGAA TGTTGGGATC ACGACGCAGA

1401 AGCCAGGTTA TCAGCTGGAT GTGTAGGTGA AAGAATTACC CAGATGCAGA

1451 GACTAACAAA TATTATTACC ACAGAGGACA TTGTAACAGT GGTCACAATG

1501 GTGACAAATG TTGACTTTCC TCCCAAGAA TCTAGTCTA
```

(SEQ ID NO: 242)

```
   1 ATACTTGGTA GATCAGAAAC TCAGGAGTGT CTTTTCTTTA ATGCTAATTG

51 GGAAAAAGAC AGAACCAATC AAACTGGTGT TGAACCGTGT TATGGTGACA

101 AAGATAAACG GCGGCATTGT TTTGCTACCT GGAAGAATAT TTCTGGTTCC
```

```
151 ATTGAAATAG TGAAACAAGG TTGTTGGCTG GATGATATCA ACTGCTATGA

201 CAGGACTGAT TGTGTAGAAA AAAAGACAG CCCTGAAGTA TATTTTTGTT

251 GCTGTGAGGG CAATATGTGT AATGAAAAGT TTTCTTATTT TCCGGAGATG

301 GAAGTCACAC AGCCCACTTC AAATCCAGTT ACACCTAAGC CACCC
```

---

SEQUENCE LISTING

```
<160> NUMBER OF SEQ ID NOS: 280

<210> SEQ ID NO 1
<211> LENGTH: 115
<212> TYPE: PRT
<213> ORGANISM: Homo sapiens

<400> SEQUENCE: 1

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 2
<211> LENGTH: 512
<212> TYPE: PRT
<213> ORGANISM: Homo sapiens

<400> SEQUENCE: 2

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
```

```
                130                 135                 140
Pro Ile Gly Gly Leu Ser Leu Ile Val Leu Leu Ala Phe Trp Met Tyr
145                 150                 155                 160

Arg His Arg Lys Pro Tyr Gly His Val Asp Ile His Glu Asp Pro
            165                 170                 175

Gly Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
                195                 200                 205

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
                260                 265                 270

Leu Thr Asp Tyr Leu Lys Gly Asn Ile Ile Thr Trp Asn Glu Leu Cys
            275                 280                 285

His Val Ala Glu Thr Met Ser Arg Gly Leu Ser Tyr Leu His Glu Asp
                290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
                340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510

<210> SEQ ID NO 3
<211> LENGTH: 345
<212> TYPE: DNA
<213> ORGANISM: Homo sapiens

<400> SEQUENCE: 3
```

```
gggcgtgggg aggctgagac acgggagtgc atctactaca acgccaactg ggagctggag      60
cgcaccaacc agagcggcct ggagcgctgc gaaggcgagc aggacaagcg gctgcactgc     120
tacgcctcct ggcgcaacag ctctggcacc atcgagctcg tgaagaaggg ctgctggcta     180
gatgacttca actgctacga taggcaggag tgtgtggcca ctgaggagaa cccccaggtg     240
tacttctgct gctgtgaagg caacttctgc aacgagcgct tcactcattt gccagaggct     300
gggggcccgg aagtcacgta cgagccaccc ccgacagccc ccacc                     345

<210> SEQ ID NO 4
<211> LENGTH: 1539
<212> TYPE: DNA
<213> ORGANISM: Homo sapiens

<400> SEQUENCE: 4
atgacggcgc cctgggtggc cctcgccctc ctctggggat cgctgtggcc cggctctggg      60
cgtggggagg ctgagacacg ggagtgcatc tactacaacg ccaactggga gctgagcgc      120 accaaccaga gcggcctgga gcgctgcgaa ggcgagcagg acaagcggct gcactgctac     180
gcctcctggc gcaacagctc tggcaccatc gagctcgtga agaagggctg ctggctagat     240
gacttcaact gctacgatag gcaggagtgt gtggccactg aggagaaccc caggtgtac      300 ttctgctgct gtgaaggcaa cttctgcaac gagcgcttca ctcatttgcc agaggctggg     360
ggcccggaag tcacgtacga gccaccccg acagccccca ccctgctcac ggtgctggcc     420
tactcactgc tgcccatcgg gggccttttcc ctcatcgtcc tgctggcctt ttggatgtac     480
cggcatcgca agccccccta cggtcatgtg acatccatg aggaccctgg gcctccacca     540
ccatcccctc tggtgggcct gaagccactg cagctgctgg agatcaaggc tcggggcgc      600 tttggctgtg tctggaaggc ccagctcatg aatgactttg tagctgtcaa gatcttccca     660
ctccaggaca gcagtcgtg gcagagtgaa cgggagatct tcagcacacc tggcatgaag     720
cacgagaacc tgctacagtt cattgctgcc gagaagcgag gctccaacct cgaagtagag     780
ctgtggctca tcacggcctt ccatgacaag ggctccctca cggattacct caaggggaac     840
atcatcacat ggaacgaact gtgtcatgta gcagagacga tgtcacgagg cctctcatac     900
ctgcatgagg atgtgccctg gtgccgtggc gagggccaca gccgtctat tgcccacagg     960 gactttaaaa gtaagaatgt attgctgaag agcgacctca gccgtgctg gctgactttt    1020 ggcttggctg ttcgatttga gccagggaaa cctccagggg acacccacgg acaggtaggc    1080
acgagacggt acatggctcc tgaggtgctc gagggagcca tcaacttcca gagagatgcc    1140
ttcctgcgca ttgacatgta tgccatgggg ttggtgctgt gggagcttgt gtctcgctgc    1200
aaggctgcag acggacccgt ggatgagtac atgctgccct ttgaggaaga gattggccag    1260 caccttcgt tggaggagct gcaggaggtg gtggtgcaca agaagatgag gcccaccatt    1320 aagatcact ggttgaaaca cccgggcctg gcccagcttt gtgtgaccat cgaggagtgc    1380
tgggaccatg atgcagaggc tcgcttgtcc gcgggctgtg tggaggagcg ggtgtccctg    1440
attcggaggt cggtcaacgg cactacctcg gactgtctcg tttccctggt gacctctgtc    1500
accaatgtgg acctgccccc taaagagtca agcatctaa                           1539

<210> SEQ ID NO 5
<211> LENGTH: 343
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 5

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340
```

<210> SEQ ID NO 6
<211> LENGTH: 368
<212> TYPE: PRT
<213> ORGANISM: Artificial Sequence
<220> FEATURE:
<223> OTHER INFORMATION: Description of Artificial Sequence: Synthetic
polypeptide

```
<400> SEQUENCE: 6

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 7
<211> LENGTH: 21
<212> TYPE: PRT
<213> ORGANISM: Apis mellifera

<400> SEQUENCE: 7
```

```
Met Lys Phe Leu Val Asn Val Ala Leu Val Phe Met Val Val Tyr Ile
1               5                   10                  15

Ser Tyr Ile Tyr Ala
            20

<210> SEQ ID NO 8
<211> LENGTH: 22
<212> TYPE: PRT
<213> ORGANISM: Unknown
<220> FEATURE:
<223> OTHER INFORMATION: Description of Unknown:
      Tissue plasminogen activator

<400> SEQUENCE: 8

Met Asp Ala Met Lys Arg Gly Leu Cys Cys Val Leu Leu Leu Cys Gly
1               5                   10                  15

Ala Val Phe Val Ser Pro
            20

<210> SEQ ID NO 9
<211> LENGTH: 18
<212> TYPE: PRT
<213> ORGANISM: Unknown
<220> FEATURE:
<223> OTHER INFORMATION: Description of Unknown:
      Native sequence

<400> SEQUENCE: 9

Met Thr Ala Pro Trp Val Ala Leu Ala Leu Leu Trp Gly Ser Leu Cys
1               5                   10                  15

Ala Gly

<210> SEQ ID NO 10
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
```

| | | |
|---|---|---|
| atggatgcaa tgaagagagg gctctgctgt gtgctgctgc tgtgtggagc agtcttcgtt | 60 |
| tcgcccggcg cctctgggcg tggggaggct gagacacggg agtgcatcta ctacaacgcc | 120 |
| aactgggagc tggagcgcac caaccagagc ggcctggagc gctgcgaagg cgagcaggac | 180 |
| aagcggctgc actgctacgc ctcctggcgc aacagctctg gcaccatcga gctcgtgaag | 240 |
| aagggctgct ggctagatga cttcaactgc tacgataggc aggagtgtgt ggccactgag | 300 |
| gagaaccccc aggtgtactt ctgctgctgt gaaggcaact tctgcaacga gcgcttcact | 360 |
| catttgccag aggctggggg cccggaagtc acgtacgagc accccccgac agcccccacc | 420 |
| ggtggtggaa ctcacacatg cccaccgtgc ccagcacctg aactcctggg gggaccgtca | 480 |
| gtcttcctct tccccccaaa acccaaggac accctcatga tctcccggac ccctgaggtc | 540 |
| acatgcgtgg tggtggacgt gagccacgaa gaccctgagg tcaagttcaa ctggtacgtg | 600 |
| gacggcgtgg aggtgcataa tgccaagaca aagccgcggg aggagcagta caacagcacg | 660 |
| taccgtgtgg tcagcgtcct caccgtcctg caccaggact ggctgaatgg caaggagtac | 720 |
| aagtgcaagg tctccaacaa agccctccca gcccccatcg agaaaaccat ctccaaagcc | 780 |
| aaagggcagc cccgagaacc acaggtgtac accctgcccc catcccggga ggagatgacc | 840 |
| aagaaccagg tcagcctgac ctgcctggtc aaaggcttct atcccagcga catcgccgtg | 900 |

```
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Arg Gly Glu Ala Glu
1               5

<210> SEQ ID NO 12
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

```
Pro Ser Arg Glu Glu Met Thr Lys Asn Gln Val Ser Leu Thr Cys Leu
            245                 250                 255

Val Lys Gly Phe Tyr Pro Ser Asp Ile Ala Val Glu Trp Glu Ser Asn
        260                 265                 270

Gly Gln Pro Glu Asn Asn Tyr Lys Thr Thr Pro Val Leu Asp Ser
        275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 13
<211> LENGTH: 225
<212> TYPE: PRT
<213> ORGANISM: Homo sapiens

<400> SEQUENCE: 13

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 14
<211> LENGTH: 223
<212> TYPE: PRT
<213> ORGANISM: Homo sapiens

<400> SEQUENCE: 14
```

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
                115                 120                 125

Pro Ser Arg Glu Glu Met Thr Lys Asn Gln Val Ser Leu Thr Cys Leu
            130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 15
<211> LENGTH: 232
<212> TYPE: PRT
<213> ORGANISM: Homo sapiens

<400> SEQUENCE: 15

Glu Pro Lys Ser Cys Asp Thr Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Lys Trp Tyr Val
    50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Thr Lys Gly Gln Pro
                115                 120                 125

Arg Glu Pro Gln Val Tyr Thr Leu Pro Pro Ser Arg Glu Glu Met Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
            165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
            195                 200                 205

Ser Cys Ser Val Met His Glu Ala Leu His Asn Arg Phe Thr Gln Lys
            210                 215                 220

Ser Leu Ser Leu Ser Pro Gly Lys
225                 230

<210> SEQ ID NO 16
<211> LENGTH: 279
<212> TYPE: PRT
<213> ORGANISM: Homo sapiens

<400> SEQUENCE: 16

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
            50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
            130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
            195                 200                 205

Ile Ala Val Glu Trp Glu Ser Ser Gly Gln Pro Glu Asn Asn Tyr Asn
            210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
            275

<210> SEQ ID NO 17
<211> LENGTH: 229
<212> TYPE: PRT
<213> ORGANISM: Homo sapiens

<400> SEQUENCE: 17

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Gly Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 18
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
```

```
                     85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125

Leu Pro Pro Ser Arg Lys Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Lys Ser Asp Gly Ser Phe Phe Leu Tyr Ser Lys Leu Thr Val Asp Lys
                180                 185                 190

Ser Arg Trp Gln Gln Gly Asn Val Phe Ser Cys Ser Val Met His Glu
                195                 200                 205

Ala Leu His Asn His Tyr Thr Gln Lys Ser Leu Ser Leu Ser Pro Gly
                210                 215                 220

Lys
225

<210> SEQ ID NO 19
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
                35                  40                  45

Pro Glu Val Lys Phe Asn Trp Tyr Val Asp Gly Val Glu Val His Asn
            50                  55                  60

Ala Lys Thr Lys Pro Arg Glu Glu Gln Tyr Asn Ser Thr Tyr Arg Val
65              70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Asp Thr Thr Pro Pro Val Leu
                165                 170                 175

Asp Ser Asp Gly Ser Phe Phe Leu Tyr Ser Asp Leu Thr Val Asp Lys
                180                 185                 190

Ser Arg Trp Gln Gln Gly Asn Val Phe Ser Cys Ser Val Met His Glu
                195                 200                 205
```

```
Ala Leu His Asn His Tyr Thr Gln Lys Ser Leu Ser Leu Ser Pro Gly
    210                 215                 220

Lys
225

<210> SEQ ID NO 20
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Tyr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 21
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30
```

```
Arg Thr Pro Glu Val Thr Cys Val Val Asp Val Ser His Glu Asp
         35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
             100                 105                 110

Thr Ile Ser Lys Ala Lys Gly Gln Pro Arg Glu Pro Gln Val Tyr Thr
         115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Thr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 22
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Thr His Thr Cys Pro Pro Cys Pro Ala Pro Glu Leu Leu Gly Gly Pro
 1               5                  10                  15

Ser Val Phe Leu Phe Pro Pro Lys Pro Lys Asp Thr Leu Met Ile Ser
                 20                  25                  30

Arg Thr Pro Glu Val Thr Cys Val Val Asp Val Ser His Glu Asp
         35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
             100                 105                 110

Thr Ile Ser Lys Ala Lys Gly Gln Pro Arg Glu Pro Gln Val Tyr Thr
         115                 120                 125

Leu Pro Pro Cys Arg Glu Glu Met Thr Lys Asn Gln Val Ser Leu Trp
130                 135                 140

Cys Leu Val Lys Gly Phe Tyr Pro Ser Asp Ile Ala Val Glu Trp Glu
145                 150                 155                 160
```

-continued

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
210                 215                 220

Lys
225

<210> SEQ ID NO 23
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Val Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
210                 215                 220

Lys
225

<210> SEQ ID NO 24
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Phe Arg Pro Glu Val His Leu
        115                 120                 125

Leu Pro Pro Ser Arg Glu Glu Met Thr Lys Asn Gln Val Ser Leu Thr
    130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
    210                 215                 220

Ser Pro Gly Lys
225

<210> SEQ ID NO 25
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys

```
            100                 105                 110
Thr Ile Ser Lys Ala Lys Gly Gln Pro Arg Glu Pro Gln Val Tyr Thr
        115                 120                 125

Leu Pro Pro Ser Glu Glu Leu Ala Leu Asn Glu Leu Val Thr Leu
    130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
                180                 185                 190

Val Ala Ala Glu Asp Trp Lys Lys Gly Asp Thr Phe Ser Cys Ser Val
            195                 200                 205

Met His Glu Ala Leu His Asn His Tyr Thr Gln Lys Ser Leu Asp Arg
        210                 215                 220

Ser Pro Gly Lys
225

<210> SEQ ID NO 26
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
                180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
        210                 215                 220
```

-continued

```
Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
            245                 250                 255

Ala Gln Gly Ala Thr
            260

<210> SEQ ID NO 27
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
        100                 105                 110

Thr Ile Ser Lys Ala Lys Gly Gln Pro Arg Glu Pro Gln Val Tyr Thr
    115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
210                 215                 220

Lys Gly Gly Ser Ala Gln Leu Lys Lys Leu Gln Ala Leu Lys Lys
225                 230                 235                 240

Lys Asn Ala Gln Leu Lys Trp Lys Leu Gln Ala Leu Lys Lys Lys Leu
            245                 250                 255

Ala Gln Gly Ala Thr
            260

<210> SEQ ID NO 28
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 28

```
Thr His Thr Cys Pro Pro Cys Pro Ala Pro Glu Leu Leu Gly Gly Pro
1               5                   10                  15
Ser Val Phe Leu Phe Pro Pro Lys Pro Lys Asp Thr Leu Met Ile Ser
            20                  25                  30
Arg Thr Pro Glu Val Thr Cys Val Val Val Asp Val Ser His Glu Asp
        35                  40                  45
Pro Glu Val Lys Phe Asn Trp Tyr Val Asp Gly Val Glu Val His Asn
    50                  55                  60
Ala Lys Thr Lys Pro Arg Glu Glu Gln Tyr Asn Ser Thr Tyr Arg Val
65                  70                  75                  80
Val Ser Val Leu Thr Val Leu His Gln Asp Trp Leu Asn Gly Lys Glu
            85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Cys Arg Glu Glu Met Thr Glu Asn Gln Val Ser Leu Trp
130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
            165                 170                 175
Asp Ser Asp Gly Ser Phe Phe Leu Tyr Ser Lys Leu Thr Val Asp Lys
        180                 185                 190
Ser Arg Trp Gln Gln Gly Asn Val Phe Ser Cys Ser Val Met His Glu
    195                 200                 205
Ala Leu His Asn His Tyr Thr Gln Asp Ser Leu Ser Leu Ser Pro Gly
    210                 215                 220
Lys
225
```

<210> SEQ ID NO 29
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Thr His Thr Cys Pro Pro Cys Pro Ala Pro Glu Leu Leu Gly Gly Pro
1               5                   10                  15
Ser Val Phe Leu Phe Pro Pro Lys Pro Lys Asp Thr Leu Met Ile Ser
            20                  25                  30
Arg Thr Pro Glu Val Thr Cys Val Val Val Asp Val Ser His Glu Asp
        35                  40                  45
Pro Glu Val Lys Phe Asn Trp Tyr Val Asp Gly Val Glu Val His Asn
    50                  55                  60
Ala Lys Thr Lys Pro Arg Glu Glu Gln Tyr Asn Ser Thr Tyr Arg Val
65                  70                  75                  80
Val Ser Val Leu Thr Val Leu His Gln Asp Trp Leu Asn Gly Lys Glu
            85                  90                  95
Tyr Lys Cys Lys Val Ser Asn Lys Ala Leu Pro Ala Pro Ile Glu Lys
            100                 105                 110
```

Thr Ile Ser Lys Ala Lys Gly Gln Pro Arg Glu Pro Gln Val Cys Thr
            115                 120                 125
Leu Pro Pro Ser Arg Glu Glu Met Thr Lys Asn Gln Val Ser Leu Ser
        130                 135                 140
Cys Ala Val Lys Gly Phe Tyr Pro Ser Asp Ile Ala Val Glu Trp Glu
145                 150                 155                 160
Ser Arg Gly Gln Pro Glu Asn Asn Tyr Lys Thr Thr Pro Pro Val Leu
                165                 170                 175
Asp Ser Arg Gly Ser Phe Phe Leu Val Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225

<210> SEQ ID NO 30
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr His Thr Cys Pro Pro Cys Pro Ala Pro Glu Leu Leu Gly Gly Pro
1               5                   10                  15
Ser Val Phe Leu Phe Pro Pro Lys Pro Lys Asp Thr Leu Met Ile Ser
            20                  25                  30
Arg Thr Pro Glu Val Thr Cys Val Val Val Asp Val Ser His Glu Asp
        35                  40                  45
Pro Glu Val Lys Phe Asn Trp Tyr Val Asp Gly Val Glu Val His Asn
    50                  55                  60
Ala Lys Thr Lys Pro Arg Glu Glu Gln Tyr Asn Ser Thr Tyr Arg Val
65                  70                  75                  80
Val Ser Val Leu Thr Val Leu His Gln Asp Trp Leu Asn Gly Lys Glu
                85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
            115                 120                 125
Leu Pro Pro Cys Arg Glu Glu Met Thr Lys Asn Gln Val Ser Leu Trp
        130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn Arg Tyr Thr Gln Lys Ser Leu Ser Leu Ser Pro Gly
    210                 215                 220
Lys

-continued

```
<210> SEQ ID NO 31
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Ala Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350
```

Leu His Asn His Tyr Thr Gln Lys Ser Leu Ser Leu Ser Pro Gly Lys
            355                 360                 365

<210> SEQ ID NO 32
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

| | | |
|---|---|---|
| atggatgcaa tgaagagagg gctctgctgt gtgctgctgc tgtgtggagc agtcttcgtt | 60 |
| tcgcccggcg cctctgggcg tggggaggct gagacacggg agtgcatcta ctacaacgcc | 120 |
| aactgggagc tggagcgcac caaccagagc ggcctggagc gctgcgaagg cgagcaggac | 180 |
| gcccggctgc actgctacgc ctcctggcgc aacagctctg gcaccatcga gctcgtgaag | 240 |
| aagggctgct ggctagatga cttcaactgc tacgataggc aggagtgtgt ggccactgag | 300 |
| gagaaccccc aggtgtactt ctgctgctgt gaaggcaact tctgcaacga gcgcttcact | 360 |
| catttgccag aggctggggg cccggaagtc acgtacgagc accccccgac agcccccacc | 420 |
| ggtggtggaa ctcacacatg cccaccgtgc ccagcacctg aactcctggg gggaccgtca | 480 |
| gtcttcctct tccccccaaa acccaaggac accctcatga tctcccggac ccctgaggtc | 540 |
| acatgcgtgg tggtggacgt gagccacgaa gaccctgagg tcaagttcaa ctggtacgtg | 600 |
| gacggcgtgg aggtgcataa tgccaagaca aagccgcggg aggagcagta caacagcacg | 660 |
| taccgtgtgg tcagcgtcct caccgtcctg caccaggact ggctgaatgg caaggagtac | 720 |
| aagtgcaagg tctccaacaa agccctccca gcccccatcg agaaaaccat ctccaaagcc | 780 |
| aaagggcagc cccgagaacc acaggtgtac accctgcccc catcccggga ggagatgacc | 840 |
| aagaaccagg tcagcctgac ctgcctggtc aaaggcttct atcccagcga catcgccgtg | 900 |
| gagtgggaga gcaatgggca gccggagaac aactacaaga ccacgcctcc cgtgctggac | 960 |
| tccgacggct ccttcttcct ctatagcaag ctcaccgtgg acaagagcag gtggcagcag | 1020 |
| gggaacgtct tctcatgctc cgtgatgcat gaggctctgc acaaccacta cacgcagaag | 1080 |
| agcctctccc tgtccccggg taaa | 1104 |

<210> SEQ ID NO 33
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Ala Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His

```
            85                  90                  95
Leu Pro Glu Ala Gly Gly Pro Glu Val Thr Tyr Glu Pro Pro Thr
            100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 34
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Glu Arg Leu His
            50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95
```

-continued

```
Val Ala Thr Glu Glu Asn Pro Gln Val Tyr Phe Cys Cys Cys Gly
                100                 105                 110
Asn Phe Cys Asn Glu Arg Phe Thr His Leu Pro Glu Ala Gly Gly Pro
            115                 120                 125
Glu Val Thr Tyr Glu Pro Pro Thr Ala Pro Thr Gly Gly Thr
        130                 135                 140
His Thr Cys Pro Pro Cys Pro Ala Pro Glu Leu Leu Gly Gly Pro Ser
145                 150                 155                 160
Val Phe Leu Phe Pro Pro Lys Pro Lys Asp Thr Leu Met Ile Ser Arg
                165                 170                 175
Thr Pro Glu Val Thr Cys Val Val Val Asp Val Ser His Glu Asp Pro
            180                 185                 190
Glu Val Lys Phe Asn Trp Tyr Val Asp Gly Val Glu Val His Asn Ala
        195                 200                 205
Lys Thr Lys Pro Arg Glu Glu Gln Tyr Asn Ser Thr Tyr Arg Val Val
    210                 215                 220
Ser Val Leu Thr Val Leu His Gln Asp Trp Leu Asn Gly Lys Glu Tyr
225                 230                 235                 240
Lys Cys Lys Val Ser Asn Lys Ala Leu Pro Ala Pro Ile Glu Lys Thr
                245                 250                 255
Ile Ser Lys Ala Lys Gly Gln Pro Arg Glu Pro Gln Val Tyr Thr Leu
            260                 265                 270
Pro Pro Ser Arg Glu Glu Met Thr Lys Asn Gln Val Ser Leu Thr Cys
        275                 280                 285
Leu Val Lys Gly Phe Tyr Pro Ser Asp Ile Ala Val Glu Trp Glu Ser
    290                 295                 300
Asn Gly Gln Pro Glu Asn Asn Tyr Lys Thr Thr Pro Pro Val Leu Asp
305                 310                 315                 320
Ser Asp Gly Ser Phe Phe Leu Tyr Ser Lys Leu Thr Val Asp Lys Ser
                325                 330                 335
Arg Trp Gln Gln Gly Asn Val Phe Ser Cys Ser Val Met His Glu Ala
            340                 345                 350
Leu His Asn His Tyr Thr Gln Lys Ser Leu Ser Leu Ser Pro Gly Lys
        355                 360                 365
```

<210> SEQ ID NO 35
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
atggatgcaa tgaagagagg gctctgctgt gtgctgctgc tgtgtggagc agtcttcgtt        60
tcgcccggcg cctctgggcg tggggaggct gagacacggg agtgcatcta ctacaacgcc       120
aactgggagc tggagcgcac caaccagagc ggcctggagc gctgcgaagg cgagcaggac       180
gagcggctgc actgctacgc ctcctggcgc aacagctctg gcaccatcga gctcgtgaag       240
aagggctgct ggctagatga cttcaactgc tacgataggc aggagtgtgt ggccactgag       300
gagaaccccc aggtgtactt ctgctgctgt gaaggcaact tctgcaacga cgcttcact        360 catttgccag aggctggggg cccggaagtc acgtacgagc caccccgac agccccacc         420 ggtggtggaa ctcacacatg cccaccgtgc ccagcacctg aactcctggg gggaccgtca       480
gtcttcctct tccccccaaa acccaaggac accctcatga tctcccggac ccctgaggtc       540
```

```
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtccccggg taaa                                          1104
```

<210> SEQ ID NO 36
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Glu Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255
```

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 37
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Ile Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu

```
              260                 265                 270
Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
            290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365
```

<210> SEQ ID NO 38
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc   120
aactgggagc tggagcgcac caaccagagc ggcctggagc gctgcgaagg cgagcaggac   180
aagcggctgc actgctacgc ctcctggcgc aacagctctg gcaccatcga gctcgtgaag   240
aagggctgct ggctagatga catcaactgc tacgataggc aggagtgtgt ggccactgag   300
gagaaccccc aggtgtactt ctgctgctgt gaaggcaact tctgcaacga gcgcttcact   360
catttgccag aggctggggg cccggaagtc acgtacgagc accccccgac agcccccacc   420
ggtggtggaa ctcacacatg cccaccgtgc ccagcacctg aactcctggg gggaccgtca   480
gtcttcctct tccccccaaa acccaaggac accctcatga tctcccggac ccctgaggtc   540
acatgcgtgg tggtggacgt gagccacgaa gaccctgagg tcaagttcaa ctggtacgtg   600
gacggcgtgg aggtgcataa tgccaagaca aagccgcggg aggagcagta caacagcacg   660
taccgtgtgg tcagcgtcct caccgtcctg caccaggact ggctgaatgg caaggagtac   720
aagtgcaagg tctccaacaa agccctccca gcccccatcg agaaaaccat ctccaaagcc   780
aaagggcagc cccgagaacc acaggtgtac accctgcccc catcccggga ggagatgacc   840
aagaaccagg tcagcctgac ctgcctggtc aaaggcttct atcccagcga catcgccgtg   900
gagtgggaga gcaatgggca gccggagaac aactacaaga ccacgcctcc cgtgctggac   960
tccgacggct ccttcttcct ctatagcaag ctcaccgtgg acaagagcag gtggcagcag  1020
gggaacgtct tctcatgctc cgtgatgcat gaggctctgc acaaccacta cacgcagaag  1080
agcctctccc tgtctccggg taaa                                         1104
```

<210> SEQ ID NO 39
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Ile Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 40
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Ala Met Lys Arg Gly Leu Cys Cys Val Leu Leu Leu Cys Gly

```
                1               5                      10                         15
            Ala Val Phe Val Ser Pro Gly Ala Ser Gly Arg Gly Glu Ala Glu Thr
                            20                      25                     30

Arg Glu Cys Ile Tyr Tyr Asn Ala Asn Trp Glu Leu Glu Arg Thr Asn
                            35                      40                     45

Gln Ser Gly Leu Glu Arg Cys Glu Gly Glu Gln Asp Lys Arg Leu His
                        50                      55                     60

Cys Tyr Ala Ser Trp Arg Asn Ser Ser Gly Thr Ile Glu Leu Val Lys
            65                      70                      75                     80

Lys Gly Cys Trp Leu Asp Asp Lys Asn Cys Tyr Asp Arg Gln Glu Cys
                                85                      90                     95

Val Ala Thr Glu Glu Asn Pro Gln Val Tyr Phe Cys Cys Cys Glu Gly
                            100                     105                    110

Asn Phe Cys Asn Glu Arg Phe Thr His Leu Pro Glu Ala Gly Gly Pro
                            115                     120                    125

Glu Val Thr Tyr Glu Pro Pro Pro Thr Ala Pro Thr Gly Gly Gly Thr
                        130                     135                    140

His Thr Cys Pro Pro Cys Pro Ala Pro Glu Leu Leu Gly Gly Pro Ser
            145                     150                     155                    160

Val Phe Leu Phe Pro Pro Lys Pro Lys Asp Thr Leu Met Ile Ser Arg
                            165                     170                    175

Thr Pro Glu Val Thr Cys Val Val Val Asp Val Ser His Glu Asp Pro
                            180                     185                    190

Glu Val Lys Phe Asn Trp Tyr Val Asp Gly Val Glu Val His Asn Ala
                        195                     200                    205

Lys Thr Lys Pro Arg Glu Glu Gln Tyr Asn Ser Thr Tyr Arg Val Val
                    210                     215                    220

Ser Val Leu Thr Val Leu His Gln Asp Trp Leu Asn Gly Lys Glu Tyr
            225                     230                     235                    240

Lys Cys Lys Val Ser Asn Lys Ala Leu Pro Ala Pro Ile Glu Lys Thr
                            245                     250                    255

Ile Ser Lys Ala Lys Gly Gln Pro Arg Glu Pro Gln Val Tyr Thr Leu
                        260                     265                    270

Pro Pro Ser Arg Glu Glu Met Thr Lys Asn Gln Val Ser Leu Thr Cys
                        275                     280                    285

Leu Val Lys Gly Phe Tyr Pro Ser Asp Ile Ala Val Glu Trp Glu Ser
                        290                     295                    300

Asn Gly Gln Pro Glu Asn Asn Tyr Lys Thr Thr Pro Pro Val Leu Asp
            305                     310                     315                    320

Ser Asp Gly Ser Phe Phe Leu Tyr Ser Lys Leu Thr Val Asp Lys Ser
                            325                     330                    335

Arg Trp Gln Gln Gly Asn Val Phe Ser Cys Ser Val Met His Glu Ala
                        340                     345                    350

Leu His Asn His Tyr Thr Gln Lys Ser Leu Ser Leu Ser Pro Gly Lys
                        355                     360                    365

<210> SEQ ID NO 41
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
```

```
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc   120
aactgggagc tggagcgcac caaccagagc ggcctggagc gctgcgaagg cgagcaggac   180
aagcggctgc actgctacgc ctcctggcgc aacagctctg gcaccatcga gctcgtgaag   240
aagggctgct ggctagatga caagaactgc tacgataggc aggagtgtgt ggccactgag   300
gagaaccccc aggtgtactt ctgctgctgt gaaggcaact tctgcaacga gcgcttcact   360
catttgccag aggctggggg cccggaagtc acgtacgagc cacccccgac agcccccacc   420
ggtggtggaa ctcacacatg cccaccgtgc ccagcacctg aactcctggg gggaccgtca   480
gtcttcctct tccccccaaa acccaaggac accctcatga tctcccggac ccctgaggtc   540
acatgcgtgg tggtggacgt gagccacgaa gaccctgagg tcaagttcaa ctggtacgtg   600
gacggcgtgg aggtgcataa tgccaagaca aagccgcggg aggagcagta caacagcacg   660
taccgtgtgg tcagcgtcct caccgtcctg caccaggact ggctgaatgg caaggagtac   720
aagtgcaagg tctccaacaa agccctccca gcccccatcg agaaaaccat ctccaaagcc   780
aaagggcagc cccgagaacc acaggtgtac accctgcccc catcccggga ggagatgacc   840
aagaaccagg tcagcctgac ctgcctggtc aaaggcttct atcccagcga catcgccgtg   900
gagtgggaga gcaatgggca gccggagaac aactacaaga ccacgcctcc cgtgctggac   960
tccgacggct ccttcttcct ctatagcaag ctcaccgtgg acaagagcag gtggcagcag  1020
gggaacgtct tctcatgctc cgtgatgcat gaggctctgc acaaccacta cacgcagaag  1080
agcctctccc tgtctccggg taaa                                         1104
```

<210> SEQ ID NO 42
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Lys Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

```
Asp Val Ser His Glu Asp Pro Glu Val Lys Phe Asn Trp Tyr Val Asp
            165                 170                 175

Gly Val Glu Val His Asn Ala Lys Thr Lys Pro Arg Glu Glu Gln Tyr
        180                 185                 190

Asn Ser Thr Tyr Arg Val Val Ser Val Leu Thr Val Leu His Gln Asp
    195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 43
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Glu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175
```

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Asp Thr Thr Pro Pro Val Leu Asp
305                 310                 315                 320

Ser Asp Gly Ser Phe Phe Leu Tyr Ser Asp Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly
        355                 360                 365

<210> SEQ ID NO 44
<211> LENGTH: 1101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggatgcaa tgaagagagg gctctgctgt gtgctgctgc tgtgtggagc agtcttcgtt      60
tcgcccggcg cctctgggcg tgggaggct gagacacggg agtgcatcta ctacaacgcc     120
aactgggagc tggagcgcac caaccagagc ggcctggagc gctgcgaagg cgagcaggac    180
aagcggctgc actgctacgc ctcctggcgc aacagctctg gcaccatcga gctcgtgaag    240
aagggctgct gggaagatga cttcaactgc tacgataggc aggagtgtgt ggccactgag    300
gagaaccccc aggtgtactt ctgctgctgt gaaggcaact tctgcaacga cgcttcact    360 catttgccag aggctggggg cccggaagtc acgtacgagc acccccgac agccccacc    420 ggtggtggaa ctcacacatg cccaccgtgc ccagcacctg aactcctggg gggaccgtca    480
gtcttcctct ccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gccccatcg agaaaccat ctccaaagcc     780 aaagggcagc ccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacgaca ccacgcctcc cgtgctggac    960

-continued

```
tccgacggct ccttcttcct ctatagcgac ctcaccgtgg acaagagcag gtggcagcag    1020
gggaacgtct tctcatgctc cgtgatgcat gaggctctgc acaaccacta cacgcagaag    1080
agcctctccc tgtctccggg t                                              1101
```

<210> SEQ ID NO 45
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Glu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Asp
        275                 280                 285

Thr Thr Pro Pro Val Leu Asp Ser Asp Gly Ser Phe Phe Leu Tyr Ser
    290                 295                 300

Asp Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
```

```
                       325                 330                 335
Leu Ser Leu Ser Pro Gly
            340

<210> SEQ ID NO 46
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Lys Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Lys
305                 310                 315                 320

Ser Asp Gly Ser Phe Phe Leu Tyr Ser Lys Leu Thr Val Asp Lys Ser
                325                 330                 335
```

```
Arg Trp Gln Gln Gly Asn Val Phe Ser Cys Ser Val Met His Glu Ala
                340                 345                 350

Leu His Asn His Tyr Thr Gln Lys Ser Leu Ser Leu Ser Pro Gly Lys
        355                 360                 365

<210> SEQ ID NO 47
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct ggctagatga cttcaactgc tacgataggc aggagtgtgt ggccactgag     300 gagaacccccc aggtgtactt ctgctgctgt gaaggcaact tctgcaacga gcgcttcact     360
catttgccag aggctggggg cccggaagtc acgtacgagc accccccgac agcccccacc     420
ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gcccccatcg agaaaaccat ctccaaagcc     780
aaagggcagc cccgagaacc acaggtgtac accctgcccc catcccggaa ggagatgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctgaag     960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaa                                           1104

<210> SEQ ID NO 48
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
```

```
            65                  70                  75                  80
Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Lys Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Lys Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
                340

<210> SEQ ID NO 49
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
        50                  55                  60

Cys Tyr Ala Ser Trp Arg Asn Ser Ser Gly Thr Ile Glu Leu Val Lys
65                  70                  75                  80
```

```
Lys Gly Cys Trp Glu Asp Asp Phe Asn Cys Tyr Asp Arg Gln Glu Cys
                85                  90                  95

Val Ala Thr Glu Glu Asn Pro Gln Val Tyr Phe Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
                260                 265                 270

Pro Pro Cys Arg Glu Glu Met Thr Lys Asn Gln Val Ser Leu Trp Cys
                275                 280                 285

Leu Val Lys Gly Phe Tyr Pro Ser Asp Ile Ala Val Glu Trp Glu Ser
            290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
                340                 345                 350

Leu His Asn His Tyr Thr Gln Lys Ser Leu Ser Leu Ser Pro Gly
            355                 360                 365

<210> SEQ ID NO 50
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Glu Asp Asp Phe Asn
        50                  55                  60

Cys Tyr Asp Arg Gln Glu Cys Val Ala Thr Glu Glu Asn Pro Gln Val
65                  70                  75                  80
```

Tyr Phe Cys Cys Cys Glu Gly Asn Phe Cys Asn Glu Arg Phe Thr His
            85                  90                  95

Leu Pro Glu Ala Gly Gly Pro Glu Val Thr Tyr Glu Pro Pro Pro Thr
        100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly
            340

<210> SEQ ID NO 51
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys 85                  90                  95
Val Ala Thr Glu Glu Asn Pro Gln Val Tyr Phe Cys Cys Glu Gly
                100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Cys Thr Leu
            260                 265                 270

Pro Pro Ser Arg Glu Glu Met Thr Lys Asn Gln Val Ser Leu Ser Cys
        275                 280                 285

Ala Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Val Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 52
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

```
Tyr Phe Cys Cys Cys Glu Gly Asn Phe Cys Asn Glu Arg Phe Thr His
                85                  90                  95
Leu Pro Glu Ala Gly Gly Pro Glu Val Thr Tyr Glu Pro Pro Pro Thr
            100                 105                 110
Ala Pro Thr Gly Gly Gly Thr His Thr Cys Pro Pro Cys Pro Ala Pro
        115                 120                 125
Glu Leu Leu Gly Gly Pro Ser Val Phe Leu Phe Pro Pro Lys Pro Lys
    130                 135                 140
Asp Thr Leu Met Ile Ser Arg Thr Pro Glu Val Thr Cys Val Val Val
145                 150                 155                 160
Asp Val Ser His Glu Asp Pro Glu Val Lys Phe Asn Trp Tyr Val Asp
                165                 170                 175
Gly Val Glu Val His Asn Ala Lys Thr Lys Pro Arg Glu Glu Gln Tyr
            180                 185                 190
Asn Ser Thr Tyr Arg Val Val Ser Val Leu Thr Val Leu His Gln Asp
        195                 200                 205
Trp Leu Asn Gly Lys Glu Tyr Lys Cys Lys Val Ser Asn Lys Ala Leu
    210                 215                 220
Pro Ala Pro Ile Glu Lys Thr Ile Ser Lys Ala Lys Gly Gln Pro Arg
225                 230                 235                 240
Glu Pro Gln Val Cys Thr Leu Pro Pro Ser Arg Glu Glu Met Thr Lys
                245                 250                 255
Asn Gln Val Ser Leu Ser Cys Ala Val Lys Gly Phe Tyr Pro Ser Asp
            260                 265                 270
Ile Ala Val Glu Trp Glu Ser Asn Gly Gln Pro Glu Asn Asn Tyr Lys
        275                 280                 285
Thr Thr Pro Pro Val Leu Asp Ser Asp Gly Ser Phe Phe Leu Val Ser
    290                 295                 300
Lys Leu Thr Val Asp Lys Ser Arg Trp Gln Gln Gly Asn Val Phe Ser
305                 310                 315                 320
Cys Ser Val Met His Glu Ala Leu His Asn His Tyr Thr Gln Lys Ser
                325                 330                 335
Leu Ser Leu Ser Pro Gly Lys
            340

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Glu Thr Arg Glu Cys Ile Tyr Tyr Asn Ala Asn Trp Glu Leu Glu Arg
1               5                   10                  15
Thr Asn Gln Ser Gly Leu Glu Arg Cys Glu Gly Glu Gln Asp Lys Arg
            20                  25                  30
Leu His Cys Tyr Ala Ser Trp Arg Asn Ser Ser Gly Thr Ile Glu Leu
        35                  40                  45
Val Lys Lys Gly Cys Trp Leu Asp Asp Phe Asn Cys Tyr Asp Arg Gln
    50                  55                  60
Glu Cys Val Ala Thr Glu Glu Asn Pro Gln Val Tyr Phe Cys Cys Cys
65                  70                  75                  80
Glu Gly Asn Phe Cys Asn Glu Arg Phe Thr His Leu Pro Glu Ala Gly
                85                  90                  95
```

Gly Pro Glu Val Thr Tyr Glu Pro Pro Pro Thr
            100                 105

<210> SEQ ID NO 54

<400> SEQUENCE: 54

000

<210> SEQ ID NO 55

<400> SEQUENCE: 55

000

<210> SEQ ID NO 56
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
    50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

```
Leu Val Lys Gly Phe Tyr Pro Ser Asp Ile Ala Val Glu Trp Glu Ser
            275                 280                 285

Asn Gly Gln Pro Glu Asn Asn Tyr Asp Thr Thr Pro Val Leu Asp
        290                 295                 300

Ser Asp Gly Ser Phe Phe Leu Tyr Ser Asp Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
                340                 345                 350

<210> SEQ ID NO 57
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Asp Thr Thr Pro Pro Val Leu Asp Ser Asp Gly Ser Phe Phe Leu Tyr
```

275                 280                 285
Ser Asp Leu Thr Val Asp Lys Ser Arg Trp Gln Gln Gly Asn Val Phe
            290                 295                 300

Ser Cys Ser Val Met His Glu Ala Leu His Asn His Tyr Thr Gln Lys
305                 310                 315                 320

Ser Leu Ser Leu Ser Pro Gly
                325

<210> SEQ ID NO 58

<400> SEQUENCE: 58

000

<210> SEQ ID NO 59

<400> SEQUENCE: 59

000

<210> SEQ ID NO 60
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
    50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr

|  |  |  |  |
|---|---|---|---|
| 225 | 230 | 235 | 240 |

Ile Ser Lys Ala Lys Gly Gln Pro Arg Glu Pro Gln Val Cys Thr Leu
                    245                        250                    255

Pro Pro Ser Arg Glu Glu Met Thr Lys Asn Gln Val Ser Leu Ser Cys
           260                        265                    270

Ala Val Lys Gly Phe Tyr Pro Ser Asp Ile Ala Val Glu Trp Glu Ser
        275                        280                    285

Asn Gly Gln Pro Glu Asn Asn Tyr Lys Thr Thr Pro Pro Val Leu Asp
    290                        295                    300

Ser Asp Gly Ser Phe Phe Leu Val Ser Lys Leu Thr Val Asp Lys Ser
305                    310                    315                    320

Arg Trp Gln Gln Gly Asn Val Phe Ser Cys Ser Val Met His Glu Ala
                    325                        330                    335

Leu His Asn His Tyr Thr Gln Lys Ser Leu Ser Leu Ser Pro Gly Lys
        340                        345                    350

<210> SEQ ID NO 61
<211> LENGTH: 328
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 61

Asp Pro Val Lys Pro Ser Arg Gly Pro Leu Val Thr Cys Thr Cys Glu
1                    5                        10                    15

Ser Pro His Cys Lys Gly Pro Thr Cys Arg Gly Ala Trp Cys Thr Val
           20                        25                    30

Val Leu Val Arg Glu Glu Gly Arg His Pro Gln Glu His Arg Gly Cys
        35                        40                    45

Gly Asn Leu His Arg Glu Leu Cys Arg Gly Arg Pro Thr Glu Phe Val
    50                        55                        60

Asn His Tyr Cys Cys Asp Ser His Leu Cys Asn His Asn Val Ser Leu
65                    70                    75                    80

Val Leu Glu Ala Thr Gln Pro Pro Ser Glu Gln Pro Gly Thr Asp Gly
           85                        90                    95

Gln Leu Ala Thr Gly Gly Gly Thr His Thr Cys Pro Pro Cys Pro Ala
              100                      105                  110

Pro Glu Leu Leu Gly Gly Pro Ser Val Phe Leu Phe Pro Pro Lys Pro
        115                        120                    125

Lys Asp Thr Leu Met Ile Ser Arg Thr Pro Glu Val Thr Cys Val Val
130                    135                    140

Val Asp Val Ser His Glu Asp Pro Glu Val Lys Phe Asn Trp Tyr Val
145                    150                    155                    160

Asp Gly Val Glu Val His Asn Ala Lys Thr Lys Pro Arg Glu Glu Gln
              165                      170                  175

Tyr Asn Ser Thr Tyr Arg Val Val Ser Val Leu Thr Val Leu His Gln
           180                      185                  190

Asp Trp Leu Asn Gly Lys Glu Tyr Lys Cys Lys Val Ser Asn Lys Ala
        195                        200                    205

Leu Pro Ala Pro Ile Glu Lys Thr Ile Ser Lys Ala Lys Gly Gln Pro
210                    215                    220

Arg Glu Pro Gln Val Cys Thr Leu Pro Pro Ser Arg Glu Glu Met Thr
225                    230                    235                    240

```
Lys Asn Gln Val Ser Leu Ser Cys Ala Val Lys Gly Phe Tyr Pro Ser
                    245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Val
            275                 280                 285

Ser Lys Leu Thr Val Asp Lys Ser Arg Trp Gln Gln Gly Asn Val Phe
        290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 62

<400> SEQUENCE: 62

000

<210> SEQ ID NO 63

<400> SEQUENCE: 63

000

<210> SEQ ID NO 64
<211> LENGTH: 509
<212> TYPE: PRT
<213> ORGANISM: Homo sapiens

<400> SEQUENCE: 64

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205
```

```
Thr Leu Leu Glu Cys Val Gly Lys Gly Arg Tyr Gly Glu Val Trp Arg
            210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
            275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
            325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
            355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
            405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
            485                 490                 495

Lys Ile Asp Asn Ser Leu Asp Lys Leu Lys Thr Asp Cys
            500                 505

<210> SEQ ID NO 65
<211> LENGTH: 103
<212> TYPE: PRT
<213> ORGANISM: Homo sapiens

<400> SEQUENCE: 65

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
            35                  40                  45

Gly Cys Phe Gln Val Tyr Glu Gln Gly Lys Met Thr Cys Lys Thr Pro
        50                  55                  60

Pro Ser Pro Gly Gln Ala Val Glu Cys Cys Gln Gly Asp Trp Cys Asn
65                  70                  75                  80
```

```
Arg Asn Ile Thr Ala Gln Leu Pro Thr Lys Gly Lys Ser Phe Pro Gly
                85                  90                  95

Thr Gln Asn Phe His Leu Glu
            100

<210> SEQ ID NO 66
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Asp Ala Met Lys Arg Gly Leu Cys Cys Val Leu Leu Leu Cys Gly
1               5                   10                  15

Ala Val Phe Val Ser Pro Gly Ala Met Glu Asp Glu Lys Pro Lys Val
                20                  25                  30

Asn Pro Lys Leu Tyr Met Cys Val Cys Glu Gly Leu Ser Cys Gly Asn
            35                  40                  45

Glu Asp His Cys Glu Gly Gln Gln Cys Phe Ser Ser Leu Ser Ile Asn
    50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
                85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
```

```
                    325                 330                 335
Met His Glu Ala Leu His Asn His Tyr Thr Gln Lys Ser Leu Ser Leu
                340                 345                 350

Ser Pro Gly
        355

<210> SEQ ID NO 67
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
                20                  25                  30

Cys Phe Ser Ser Leu Ser Ile Asn Asp Gly Phe His Val Tyr Gln Lys
            35                  40                  45

Gly Cys Phe Gln Val Tyr Glu Gln Gly Lys Met Thr Cys Lys Thr Pro
50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Asp Thr Thr Pro Pro Val Leu Asp Ser Asp Gly Ser
        275                 280                 285

Phe Phe Leu Tyr Ser Asp Leu Thr Val Asp Lys Ser Arg Trp Gln Gln
        290                 295                 300

Gly Asn Val Phe Ser Cys Ser Val Met His Glu Ala Leu His Asn His
305                 310                 315                 320
```

Tyr Thr Gln Lys Ser Leu Ser Leu Ser Pro Gly
            325                 330

<210> SEQ ID NO 68

<400> SEQUENCE: 68

000

<210> SEQ ID NO 69

<400> SEQUENCE: 69

000

<210> SEQ ID NO 70
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Asp Ala Met Lys Arg Gly Leu Cys Cys Val Leu Leu Cys Gly
1               5                   10                  15

Ala Val Phe Val Ser Pro Gly Ala Met Glu Asp Glu Lys Pro Lys Val
            20                  25                  30

Asn Pro Lys Leu Tyr Met Cys Val Cys Glu Gly Leu Ser Cys Gly Asn
            35                  40                  45

Glu Asp His Cys Glu Gly Gln Gln Cys Phe Ser Ser Leu Ser Ile Asn
50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
                85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
            115                 120                 125

Gly Gly Gly Thr His Thr Cys Pro Pro Cys Pro Ala Pro Glu Leu Leu
            130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
            210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

```
Ser Leu Ser Cys Ala Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
            355

<210> SEQ ID NO 71
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Asn Gly Gln Pro
            260                 265                 270
```

```
Glu Asn Asn Tyr Lys Thr Thr Pro Pro Val Leu Asp Ser Asp Gly Ser
            275                 280                 285

Phe Phe Leu Val Ser Lys Leu Thr Val Asp Lys Ser Arg Trp Gln Gln
290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330
```

<210> SEQ ID NO 72

<400> SEQUENCE: 72

000

<210> SEQ ID NO 73

<400> SEQUENCE: 73

000

<210> SEQ ID NO 74
<211> LENGTH: 532
<212> TYPE: PRT
<213> ORGANISM: Homo sapiens

<400> SEQUENCE: 74

```
Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
                20                  25                  30

Thr Gly Met Lys Ser Asp Ser Asp Gln Lys Lys Ser Glu Asn Gly Val
            35                  40                  45

Thr Leu Ala Pro Glu Asp Thr Leu Pro Phe Leu Lys Cys Tyr Cys Ser
50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175

Lys His Tyr Cys Lys Ser Ile Ser Ser Arg Arg Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
210                 215                 220

Leu Val Gln Arg Thr Ile Ala Lys Gln Ile Gln Met Val Arg Gln Val
225                 230                 235                 240
```

Gly Lys Gly Arg Tyr Gly Glu Val Trp Met Gly Lys Trp Arg Gly Glu
            245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
            275                 280                 285

Leu Gly Phe Ile Ala Ala Asp Ile Lys Gly Thr Gly Ser Trp Thr Gln
            290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
            325                 330                 335

Ser Ala Ala Cys Gly Leu Cys His Leu His Thr Glu Ile Tyr Gly Thr
            340                 345                 350

Gln Gly Lys Pro Ala Ile Ala His Arg Asp Leu Lys Ser Lys Asn Ile
            355                 360                 365

Leu Ile Lys Lys Asn Gly Ser Cys Cys Ile Ala Asp Leu Gly Leu Ala
            370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
            405                 410                 415

Leu Asn Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
            435                 440                 445

Ile Val Glu Glu Tyr Gln Leu Pro Tyr Tyr Asn Met Val Pro Ser Asp
            450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
            485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
            515                 520                 525

Asp Val Lys Ile
            530

<210> SEQ ID NO 75
<211> LENGTH: 129
<212> TYPE: PRT
<213> ORGANISM: Homo sapiens

<400> SEQUENCE: 75

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
            35                  40                  45

Ile Asn Asn Thr Cys Ile Thr Asn Gly His Cys Phe Ala Ile Ile Glu
            50                  55                  60

Glu Asp Asp Gln Gly Glu Thr Thr Leu Ala Ser Gly Cys Met Lys Tyr

```
                65                  70                  75                  80
Glu Gly Ser Asp Phe Gln Cys Lys Asp Ser Pro Lys Ala Gln Leu Arg
                    85                  90                  95

Arg Thr Ile Glu Cys Cys Arg Thr Asn Leu Cys Asn Gln Tyr Leu Gln
                100                 105                 110

Pro Thr Leu Pro Pro Val Val Ile Gly Pro Phe Phe Asp Gly Ser Ile
            115                 120                 125

Arg

<210> SEQ ID NO 76
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
                20                  25                  30

Gly Thr Gly Met Lys Ser Asp Ser Asp Gln Lys Lys Ser Glu Asn Gly
            35                  40                  45

Val Thr Leu Ala Pro Glu Asp Thr Leu Pro Phe Leu Lys Cys Tyr Cys
        50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Glu Glu Met Thr Lys Asn Gln Val Ser Leu Thr Cys Leu Val
```

```
                    290                 295                 300
Lys Gly Phe Tyr Pro Ser Asp Ile Ala Val Glu Trp Glu Ser Asn Gly
305                 310                 315                 320

Gln Pro Glu Asn Asn Tyr Asp Thr Thr Pro Val Leu Asp Ser Asp
                325                 330                 335

Gly Ser Phe Phe Leu Tyr Ser Asp Leu Thr Val Asp Lys Ser Arg Trp
                340                 345                 350

Gln Gln Gly Asn Val Phe Ser Cys Ser Val Met His Glu Ala Leu His
            355                 360                 365

Asn His Tyr Thr Gln Lys Ser Leu Ser Leu Ser Pro Gly
        370                 375                 380

<210> SEQ ID NO 77
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
                20                  25                  30

Asp Thr Leu Pro Phe Leu Lys Cys Tyr Cys Ser Gly His Cys Pro Asp
            35                  40                  45

Asp Ala Ile Asn Asn Thr Cys Ile Thr Asn Gly His Cys Phe Ala Ile
        50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Gly Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270
```

```
Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
        290                 295                 300

Asp Thr Thr Pro Pro Val Leu Asp Ser Asp Gly Ser Phe Phe Leu Tyr
305                 310                 315                 320

Ser Asp Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly
            355

<210> SEQ ID NO 78

<400> SEQUENCE: 78

000

<210> SEQ ID NO 79

<400> SEQUENCE: 79

000

<210> SEQ ID NO 80
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
            20                  25                  30

Gly Thr Gly Met Lys Ser Asp Ser Asp Gln Lys Lys Ser Glu Asn Gly
        35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
    130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190
```

Glu Val Thr Cys Val Val Asp Val Ser His Glu Asp Pro Glu Val
            195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
            245                 250                 255

Lys Val Ser Asn Lys Ala Leu Pro Ala Pro Ile Glu Lys Thr Ile Ser
                260                 265                 270

Lys Ala Lys Gly Gln Pro Arg Glu Pro Gln Val Cys Thr Leu Pro Pro
            275                 280                 285

Ser Arg Glu Glu Met Thr Lys Asn Gln Val Ser Leu Ser Cys Ala Val
290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Val Ser Lys Leu Thr Val Asp Lys Ser Arg Trp
            340                 345                 350

Gln Gln Gly Asn Val Phe Ser Cys Ser Val Met His Glu Ala Leu His
                355                 360                 365

Asn His Tyr Thr Gln Lys Ser Leu Ser Leu Ser Pro Gly Lys
            370                 375                 380

<210> SEQ ID NO 81
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
            20                  25                  30

Asp Thr Leu Pro Phe Leu Lys Cys Tyr Cys Ser Gly His Cys Pro Asp
        35                  40                  45

Asp Ala Ile Asn Asn Thr Cys Ile Thr Asn Gly His Cys Phe Ala Ile
    50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

```
Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Cys Thr Leu Pro Pro Ser Arg Glu Glu Met Thr
            260                 265                 270

Lys Asn Gln Val Ser Leu Ser Cys Ala Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Val
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 82

<400> SEQUENCE: 82

000

<210> SEQ ID NO 83

<400> SEQUENCE: 83

000

<210> SEQ ID NO 84
<211> LENGTH: 505
<212> TYPE: PRT
<213> ORGANISM: Homo sapiens

<400> SEQUENCE: 84

Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
                20                  25                  30

Leu Cys Ala Cys Thr Ser Cys Leu Gln Ala Asn Tyr Thr Cys Glu Thr
            35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
                100                 105                 110
```

Leu Lys Glu Pro Glu His Pro Ser Met Trp Gly Pro Val Glu Leu Val
            115                 120                 125

Gly Ile Ile Ala Gly Pro Val Phe Leu Leu Phe Leu Ile Ile Ile Ile
130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
        355                 360                 365

Ile Ala Pro Asn Gln Arg Val Gly Thr Lys Arg Tyr Met Ala Pro Glu
    370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415

Cys Asn Ser Gly Gly Val His Glu Glu Tyr Gln Leu Pro Tyr Tyr Asp
            420                 425                 430

Leu Val Pro Ser Asp Pro Ser Ile Glu Glu Met Arg Lys Val Val Cys
        435                 440                 445

Asp Gln Lys Leu Arg Pro Asn Ile Pro Asn Trp Trp Gln Ser Tyr Glu
    450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505

<210> SEQ ID NO 85
<211> LENGTH: 546

<212> TYPE: PRT
<213> ORGANISM: Homo sapiens

<400> SEQUENCE: 85

```
Met Ala Glu Ser Ala Gly Ala Ser Ser Phe Phe Pro Leu Val Val Leu
1               5                   10                  15

Leu Leu Ala Gly Ser Gly Ser Gly Pro Arg Gly Val Gln Ala Leu
            20                  25                  30

Leu Cys Ala Cys Thr Ser Cys Leu Gln Ala Asn Tyr Thr Cys Glu Thr
            35                  40                  45

Asp Gly Ala Cys Met Val Ser Ile Phe Asn Leu Asp Gly Met Glu His
            50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
                100                 105                 110

Leu Lys Glu Pro Glu His Pro Ser Met Trp Gly Pro Val Glu Leu Val
            115                 120                 125

Gly Ile Ile Ala Gly Pro Val Phe Leu Phe Leu Ile Ile Ile Ile
130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
            165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
            195                 200                 205

Leu Gln Glu Ile Ile Gly Lys Gly Arg Phe Gly Glu Val Trp Arg Gly
210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
            245                 250                 255

Arg His Glu Asn Ile Leu Gly Phe Ile Ala Ala Asp Asn Lys Ala Asp
            260                 265                 270

Cys Ser Phe Leu Thr Leu Pro Trp Glu Val Val Met Val Ser Ala Ala
            275                 280                 285

Pro Lys Leu Arg Ser Leu Arg Leu Gln Tyr Lys Gly Arg Gly Arg
            290                 295                 300

Ala Arg Phe Leu Phe Pro Leu Asn Asn Gly Thr Trp Thr Gln Leu Trp
305                 310                 315                 320

Leu Val Ser Asp Tyr His Glu His Gly Ser Leu Phe Asp Tyr Leu Asn
            325                 330                 335

Arg Tyr Thr Val Thr Ile Glu Gly Met Ile Lys Leu Ala Leu Ser Ala
            340                 345                 350

Ala Ser Gly Leu Ala His Leu His Met Glu Ile Val Gly Thr Gln Gly
            355                 360                 365

Lys Pro Gly Ile Ala His Arg Asp Leu Lys Ser Lys Asn Ile Leu Val
            370                 375                 380

Lys Lys Asn Gly Met Cys Ala Ile Ala Asp Leu Gly Leu Ala Val Arg
385                 390                 395                 400
```

```
His Asp Ala Val Thr Asp Thr Ile Asp Ile Ala Pro Asn Gln Arg Val
                405                 410                 415
Gly Thr Lys Arg Tyr Met Ala Pro Glu Val Leu Asp Glu Thr Ile Asn
            420                 425                 430
Met Lys His Phe Asp Ser Phe Lys Cys Ala Asp Ile Tyr Ala Leu Gly
        435                 440                 445
Leu Val Tyr Trp Glu Ile Ala Arg Arg Cys Asn Ser Gly Gly Val His
    450                 455                 460
Glu Glu Tyr Gln Leu Pro Tyr Tyr Asp Leu Val Pro Ser Asp Pro Ser
465                 470                 475                 480
Ile Glu Glu Met Arg Lys Val Val Cys Asp Gln Lys Leu Arg Pro Asn
                485                 490                 495
Ile Pro Asn Trp Trp Gln Ser Tyr Glu Ala Leu Arg Val Met Gly Lys
            500                 505                 510
Met Met Arg Glu Cys Trp Tyr Ala Asn Gly Ala Ala Arg Leu Thr Ala
        515                 520                 525
Leu Arg Ile Lys Lys Thr Leu Ser Gln Leu Ser Val Gln Glu Asp Val
    530                 535                 540
Lys Ile
545

<210> SEQ ID NO 86
<211> LENGTH: 103
<212> TYPE: PRT
<213> ORGANISM: Homo sapiens

<400> SEQUENCE: 86

Ser Gly Pro Arg Gly Val Gln Ala Leu Leu Cys Ala Cys Thr Ser Cys
1               5                   10                  15
Leu Gln Ala Asn Tyr Thr Cys Glu Thr Asp Gly Ala Cys Met Val Ser
            20                  25                  30
Ile Phe Asn Leu Asp Gly Met Glu His His Val Arg Thr Cys Ile Pro
        35                  40                  45
Lys Val Glu Leu Val Pro Ala Gly Lys Pro Phe Tyr Cys Leu Ser Ser
    50                  55                  60
Glu Asp Leu Arg Asn Thr His Cys Cys Tyr Thr Asp Tyr Cys Asn Arg
65                  70                  75                  80
Ile Asp Leu Arg Val Pro Ser Gly His Leu Lys Glu Pro Glu His Pro
                85                  90                  95
Ser Met Trp Gly Pro Val Glu
            100

<210> SEQ ID NO 87
<211> LENGTH: 103
<212> TYPE: PRT
<213> ORGANISM: Homo sapiens

<400> SEQUENCE: 87

Ser Gly Pro Arg Gly Val Gln Ala Leu Leu Cys Ala Cys Thr Ser Cys
1               5                   10                  15
Leu Gln Ala Asn Tyr Thr Cys Glu Thr Asp Gly Ala Cys Met Val Ser
            20                  25                  30
Ile Phe Asn Leu Asp Gly Met Glu His His Val Arg Thr Cys Ile Pro
        35                  40                  45
Lys Val Glu Leu Val Pro Ala Gly Lys Pro Phe Tyr Cys Leu Ser Ser
    50                  55                  60
```

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100

<210> SEQ ID NO 88
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
                20                  25                  30

Leu Leu Cys Ala Cys Thr Ser Cys Leu Gln Ala Asn Tyr Thr Cys Glu
            35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr

```
                        305                 310                 315                 320
Val Asp Lys Ser Arg Trp Gln Gln Gly Asn Val Phe Ser Cys Ser Val
                    325                 330                 335

Met His Glu Ala Leu His Asn His Tyr Thr Gln Lys Ser Leu Ser Leu
                340                 345                 350

Ser Pro Gly
        355

<210> SEQ ID NO 89
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
                20                  25                  30

Ile Phe Asn Leu Asp Gly Met Glu His His Val Arg Thr Cys Ile Pro
            35                  40                  45

Lys Val Glu Leu Val Pro Ala Gly Lys Pro Phe Tyr Cys Leu Ser Ser
        50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Asp Thr Thr Pro Pro Val Leu Asp Ser Asp Gly Ser
        275                 280                 285

Phe Phe Leu Tyr Ser Asp Leu Thr Val Asp Lys Ser Arg Trp Gln Gln
    290                 295                 300
```

```
Gly Asn Val Phe Ser Cys Ser Val Met His Glu Ala Leu His Asn His
305                 310                 315                 320

Tyr Thr Gln Lys Ser Leu Ser Leu Ser Pro Gly
            325                 330

<210> SEQ ID NO 90

<400> SEQUENCE: 90

000

<210> SEQ ID NO 91

<400> SEQUENCE: 91

000

<210> SEQ ID NO 92
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
                20                  25                  30

Leu Leu Cys Ala Cys Thr Ser Cys Leu Gln Ala Asn Tyr Thr Cys Glu
            35                  40                  45

Thr Asp Gly Ala Cys Met Val Ser Ile Phe Asn Leu Asp Gly Met Glu
        50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255
```

```
Val Cys Thr Leu Pro Pro Ser Arg Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 93
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255
```

```
Phe Tyr Pro Ser Asp Ile Ala Val Glu Trp Glu Ser Asn Gly Gln Pro
            260                 265                 270
Glu Asn Asn Tyr Lys Thr Thr Pro Val Leu Asp Ser Asp Gly Ser
            275                 280                 285
Phe Phe Leu Val Ser Lys Leu Thr Val Asp Lys Ser Arg Trp Gln Gln
    290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys
                325                 330
```

<210> SEQ ID NO 94

<400> SEQUENCE: 94

000

<210> SEQ ID NO 95

<400> SEQUENCE: 95

000

<210> SEQ ID NO 96
<211> LENGTH: 503
<212> TYPE: PRT
<213> ORGANISM: Homo sapiens

<400> SEQUENCE: 96

```
Met Glu Ala Val Ala Ala Pro Arg Pro Arg Leu Leu Leu Leu Val
1               5                   10                  15
Leu Ala Ala Ala Ala Ala Ala Ala Leu Leu Pro Gly Ala Thr
            20                  25                  30
Ala Leu Gln Cys Phe Cys His Leu Cys Thr Lys Asp Asn Phe Thr Cys
            35                  40                  45
Val Thr Asp Gly Leu Cys Phe Val Ser Val Thr Glu Thr Thr Asp Lys
    50                  55                  60
Val Ile His Asn Ser Met Cys Ile Ala Glu Ile Asp Leu Ile Pro Arg
65                  70                  75                  80
Asp Arg Pro Phe Val Cys Ala Pro Ser Ser Lys Thr Gly Ser Val Thr
                85                  90                  95
Thr Thr Tyr Cys Cys Asn Gln Asp His Cys Asn Lys Ile Glu Leu Pro
            100                 105                 110
Thr Thr Val Lys Ser Ser Pro Gly Leu Gly Pro Val Glu Leu Ala Ala
            115                 120                 125
Val Ile Ala Gly Pro Val Cys Phe Val Cys Ile Ser Leu Met Leu Met
    130                 135                 140
Val Tyr Ile Cys His Asn Arg Thr Val Ile His His Arg Val Pro Asn
145                 150                 155                 160
Glu Glu Asp Pro Ser Leu Asp Arg Pro Phe Ile Ser Glu Gly Thr Thr
                165                 170                 175
Leu Lys Asp Leu Ile Tyr Asp Met Thr Thr Ser Gly Ser Gly Ser Gly
            180                 185                 190
Leu Pro Leu Leu Val Gln Arg Thr Ile Ala Arg Thr Ile Val Leu Gln
            195                 200                 205
Glu Ser Ile Gly Lys Gly Arg Phe Gly Glu Val Trp Arg Gly Lys Trp
    210                 215                 220
```

```
Arg Gly Glu Glu Val Ala Val Lys Ile Phe Ser Ser Arg Glu Arg
225                 230                 235                 240

Ser Trp Phe Arg Glu Ala Glu Ile Tyr Gln Thr Val Met Leu Arg His
            245                 250                 255

Glu Asn Ile Leu Gly Phe Ile Ala Ala Asp Asn Lys Asp Asn Gly Thr
        260                 265                 270

Trp Thr Gln Leu Trp Leu Val Ser Asp Tyr His Glu His Gly Ser Leu
    275                 280                 285

Phe Asp Tyr Leu Asn Arg Tyr Thr Val Thr Val Glu Gly Met Ile Lys
290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
            325                 330                 335

Lys Asn Ile Leu Val Lys Lys Asn Gly Thr Cys Cys Ile Ala Asp Leu
        340                 345                 350

Gly Leu Ala Val Arg His Asp Ser Ala Thr Asp Thr Ile Asp Ile Ala
    355                 360                 365

Pro Asn His Arg Val Gly Thr Lys Arg Tyr Met Ala Pro Glu Val Leu
370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
            405                 410                 415

Ile Gly Gly Ile His Glu Asp Tyr Gln Leu Pro Tyr Tyr Asp Leu Val
        420                 425                 430

Pro Ser Asp Pro Ser Val Glu Glu Met Arg Lys Val Val Cys Glu Gln
    435                 440                 445

Lys Leu Arg Pro Asn Ile Pro Asn Arg Trp Gln Ser Cys Glu Ala Leu
450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
            485                 490                 495

Gln Gln Glu Gly Ile Lys Met
            500

<210> SEQ ID NO 97
<211> LENGTH: 507
<212> TYPE: PRT
<213> ORGANISM: Homo sapiens

<400> SEQUENCE: 97

Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
```

-continued

```
                    85                  90                  95
Thr Thr Tyr Cys Cys Asn Gln Asp His Cys Asn Lys Ile Glu Leu Pro
            100                 105                 110
Thr Thr Gly Pro Phe Ser Val Lys Ser Pro Gly Leu Gly Pro Val
        115                 120                 125
Glu Leu Ala Ala Val Ile Ala Gly Pro Val Cys Phe Val Cys Ile Ser
    130                 135                 140
Leu Met Leu Met Val Tyr Ile Cys His Asn Arg Thr Val Ile His His
145                 150                 155                 160
Arg Val Pro Asn Glu Glu Asp Pro Ser Leu Asp Arg Pro Phe Ile Ser
                165                 170                 175
Glu Gly Thr Thr Leu Lys Asp Leu Ile Tyr Asp Met Thr Thr Ser Gly
            180                 185                 190
Ser Gly Ser Gly Leu Pro Leu Leu Val Gln Arg Thr Ile Ala Arg Thr
        195                 200                 205
Ile Val Leu Gln Glu Ser Ile Gly Lys Gly Arg Phe Gly Glu Val Trp
    210                 215                 220
Arg Gly Lys Trp Arg Gly Glu Glu Val Ala Val Lys Ile Phe Ser Ser
225                 230                 235                 240
Arg Glu Glu Arg Ser Trp Phe Arg Glu Ala Glu Ile Tyr Gln Thr Val
                245                 250                 255
Met Leu Arg His Glu Asn Ile Leu Gly Phe Ile Ala Ala Asp Asn Lys
            260                 265                 270
Asp Asn Gly Thr Trp Thr Gln Leu Trp Leu Val Ser Asp Tyr His Glu
        275                 280                 285
His Gly Ser Leu Phe Asp Tyr Leu Asn Arg Tyr Thr Val Thr Val Glu
    290                 295                 300
Gly Met Ile Lys Leu Ala Leu Ser Thr Ala Ser Gly Leu Ala His Leu
305                 310                 315                 320
His Met Glu Ile Val Gly Thr Gln Gly Lys Pro Ala Ile Ala His Arg
                325                 330                 335
Asp Leu Lys Ser Lys Asn Ile Leu Val Lys Lys Asn Gly Thr Cys Cys
            340                 345                 350
Ile Ala Asp Leu Gly Leu Ala Val Arg His Asp Ser Ala Thr Asp Thr
        355                 360                 365
Ile Asp Ile Ala Pro Asn His Arg Val Gly Thr Lys Arg Tyr Met Ala
    370                 375                 380
Pro Glu Val Leu Asp Asp Ser Ile Asn Met Lys His Phe Glu Ser Phe
385                 390                 395                 400
Lys Arg Ala Asp Ile Tyr Ala Met Gly Leu Val Phe Trp Glu Ile Ala
                405                 410                 415
Arg Arg Cys Ser Ile Gly Gly Ile His Glu Asp Tyr Gln Leu Pro Tyr
            420                 425                 430
Tyr Asp Leu Val Pro Ser Asp Pro Ser Val Glu Glu Met Arg Lys Val
        435                 440                 445
Val Cys Glu Gln Lys Leu Arg Pro Asn Ile Pro Asn Arg Trp Gln Ser
    450                 455                 460
Cys Glu Ala Leu Arg Val Met Ala Lys Ile Met Arg Glu Cys Trp Tyr
465                 470                 475                 480
Ala Asn Gly Ala Ala Arg Leu Thr Ala Leu Arg Ile Lys Lys Thr Leu
                485                 490                 495
Ser Gln Leu Ser Gln Gln Glu Gly Ile Lys Met
            500                 505
```

<210> SEQ ID NO 98
<211> LENGTH: 102
<212> TYPE: PRT
<213> ORGANISM: Homo sapiens

<400> SEQUENCE: 98

```
Ala Ala Leu Leu Pro Gly Ala Thr Ala Leu Gln Cys Phe Cys His Leu
1               5                   10                  15
Cys Thr Lys Asp Asn Phe Thr Cys Val Thr Asp Gly Leu Cys Phe Val
            20                  25                  30
Ser Val Thr Glu Thr Thr Asp Lys Val Ile His Asn Ser Met Cys Ile
        35                  40                  45
Ala Glu Ile Asp Leu Ile Pro Arg Asp Arg Pro Phe Val Cys Ala Pro
    50                  55                  60
Ser Ser Lys Thr Gly Ser Val Thr Thr Thr Tyr Cys Cys Asn Gln Asp
65                  70                  75                  80
His Cys Asn Lys Ile Glu Leu Pro Thr Thr Val Lys Ser Ser Pro Gly
                85                  90                  95
Leu Gly Pro Val Glu Leu
            100
```

<210> SEQ ID NO 99
<211> LENGTH: 106
<212> TYPE: PRT
<213> ORGANISM: Homo sapiens

<400> SEQUENCE: 99

```
Ala Ala Leu Leu Pro Gly Ala Thr Ala Leu Gln Cys Phe Cys His Leu
1               5                   10                  15
Cys Thr Lys Asp Asn Phe Thr Cys Val Thr Asp Gly Leu Cys Phe Val
            20                  25                  30
Ser Val Thr Glu Thr Thr Asp Lys Val Ile His Asn Ser Met Cys Ile
        35                  40                  45
Ala Glu Ile Asp Leu Ile Pro Arg Asp Arg Pro Phe Val Cys Ala Pro
    50                  55                  60
Ser Ser Lys Thr Gly Ser Val Thr Thr Thr Tyr Cys Cys Asn Gln Asp
65                  70                  75                  80
His Cys Asn Lys Ile Glu Leu Pro Thr Thr Gly Pro Phe Ser Val Lys
                85                  90                  95
Ser Ser Pro Gly Leu Gly Pro Val Glu Leu
            100                 105
```

<210> SEQ ID NO 100
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Met Asp Ala Met Lys Arg Gly Leu Cys Cys Val Leu Leu Leu Cys Gly
1               5                   10                  15
Ala Val Phe Val Ser Pro Gly Ala Ala Leu Leu Pro Gly Ala Thr Ala
            20                  25                  30
Leu Gln Cys Phe Cys His Leu Cys Thr Lys Asp Asn Phe Thr Cys Val
        35                  40                  45
```

```
Thr Asp Gly Leu Cys Phe Val Ser Val Thr Glu Thr Thr Asp Lys Val
 50                  55                  60

Ile His Asn Ser Met Cys Ile Ala Glu Ile Asp Leu Ile Pro Arg Asp
 65                  70                  75                  80

Arg Pro Phe Val Cys Ala Pro Ser Ser Lys Thr Gly Ser Val Thr Thr
                 85                  90                  95

Thr Tyr Cys Cys Asn Gln Asp His Cys Asn Lys Ile Glu Leu Pro Thr
            100                 105                 110

Thr Val Lys Ser Ser Pro Gly Leu Gly Pro Val Glu Thr Gly Gly Gly
            115                 120                 125

Thr His Thr Cys Pro Pro Cys Pro Ala Pro Glu Leu Leu Gly Gly Pro
        130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Asp Thr Thr Pro Pro Val Leu
290                 295                 300

Asp Ser Asp Gly Ser Phe Phe Leu Tyr Ser Asp Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

<210> SEQ ID NO 101
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ala Leu Leu Pro Gly Ala Thr Ala Leu Gln Cys Phe Cys His Leu Cys
  1               5                  10                  15

Thr Lys Asp Asn Phe Thr Cys Val Thr Asp Gly Leu Cys Phe Val Ser
                 20                  25                  30

Val Thr Glu Thr Thr Asp Lys Val Ile His Asn Ser Met Cys Ile Ala
             35                  40                  45

Glu Ile Asp Leu Ile Pro Arg Asp Arg Pro Phe Val Cys Ala Pro Ser
 50                  55                  60
```

Ser Lys Thr Gly Ser Val Thr Thr Thr Tyr Cys Cys Asn Gln Asp His
65                  70                  75                  80

Cys Asn Lys Ile Glu Leu Pro Thr Thr Val Lys Ser Ser Pro Gly Leu
                85                  90                  95

Gly Pro Val Glu Thr Gly Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Asp Thr Thr Pro Pro Val Leu Asp Ser Asp Gly Ser Phe Phe Leu
        275                 280                 285

Tyr Ser Asp Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 102

<400> SEQUENCE: 102

000

<210> SEQ ID NO 103

<400> SEQUENCE: 103

000

<210> SEQ ID NO 104
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Asp Ala Met Lys Arg Gly Leu Cys Cys Val Leu Leu Leu Cys Gly
1               5                   10                  15

```
Ala Val Phe Val Ser Pro Gly Ala Ala Leu Pro Gly Ala Thr Ala
             20                  25                  30

Leu Gln Cys Phe Cys His Leu Cys Thr Lys Asp Asn Phe Thr Cys Val
         35                  40                  45

Thr Asp Gly Leu Cys Phe Val Ser Val Thr Glu Thr Thr Asp Lys Val
 50                  55                  60

Ile His Asn Ser Met Cys Ile Ala Glu Ile Asp Leu Ile Pro Arg Asp
 65                  70                  75                  80

Arg Pro Phe Val Cys Ala Pro Ser Ser Lys Thr Gly Ser Val Thr Thr
                 85                  90                  95

Thr Tyr Cys Cys Asn Gln Asp His Cys Asn Lys Ile Glu Leu Pro Thr
            100                 105                 110

Thr Val Lys Ser Ser Pro Gly Leu Gly Pro Val Glu Thr Gly Gly Gly
            115                 120                 125

Thr His Thr Cys Pro Pro Cys Pro Ala Pro Glu Leu Leu Gly Gly Pro
130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
                180                 185                 190

Ala Lys Thr Lys Pro Arg Glu Glu Gln Tyr Asn Ser Thr Tyr Arg Val
            195                 200                 205

Val Ser Val Leu Thr Val Leu His Gln Asp Trp Leu Asn Gly Lys Glu
        210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Cys Thr
                245                 250                 255

Leu Pro Pro Ser Arg Glu Glu Met Thr Lys Asn Gln Val Ser Leu Ser
            260                 265                 270

Cys Ala Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Val Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 105
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Leu Leu Pro Gly Ala Thr Ala Leu Gln Cys Phe Cys His Leu Cys
1               5                   10                  15
```

```
Thr Lys Asp Asn Phe Thr Cys Val Thr Asp Gly Leu Cys Phe Val Ser
            20                  25                  30

Val Thr Glu Thr Thr Asp Lys Val Ile His Asn Ser Met Cys Ile Ala
        35                  40                  45

Glu Ile Asp Leu Ile Pro Arg Asp Arg Pro Phe Val Cys Ala Pro Ser
 50                  55                  60

Ser Lys Thr Gly Ser Val Thr Thr Thr Tyr Cys Cys Asn Gln Asp His
 65                  70                  75                  80

Cys Asn Lys Ile Glu Leu Pro Thr Thr Val Lys Ser Ser Pro Gly Leu
                 85                  90                  95

Gly Pro Val Glu Thr Gly Gly Gly Thr His Thr Cys Pro Pro Cys Pro
                100                 105                 110

Ala Pro Glu Leu Leu Gly Gly Pro Ser Val Phe Leu Phe Pro Pro Lys
                115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
                195                 200                 205

Ala Leu Pro Ala Pro Ile Glu Lys Thr Ile Ser Lys Ala Lys Gly Gln
                210                 215                 220

Pro Arg Glu Pro Gln Val Cys Thr Leu Pro Pro Ser Arg Glu Glu Met
225                 230                 235                 240

Thr Lys Asn Gln Val Ser Leu Ser Cys Ala Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
                275                 280                 285

Val Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 106

<400> SEQUENCE: 106

000

<210> SEQ ID NO 107

<400> SEQUENCE: 107

000

<210> SEQ ID NO 108
<211> LENGTH: 502
<212> TYPE: PRT
```

-continued

```
<213> ORGANISM: Homo sapiens

<400> SEQUENCE: 108
```

| | | | | | | | | | | | | | | | |
|---|---|---|---|---|---|---|---|---|---|---|---|---|---|---|---|
| Met | Leu | Leu | Arg | Ser | Ala | Gly | Lys | Leu | Asn | Val | Gly | Thr | Lys | Lys | Glu |
| 1 | | | | 5 | | | | | 10 | | | | | 15 | |
| Asp | Gly | Glu | Ser | Thr | Ala | Pro | Thr | Pro | Arg | Pro | Lys | Val | Leu | Arg | Cys |
| | | | 20 | | | | | 25 | | | | | 30 | | |
| Lys | Cys | His | His | Cys | Pro | Glu | Asp | Ser | Val | Asn | Asn | Ile | Cys | Ser | |
| | | 35 | | | | | 40 | | | | | 45 | | | |
| Thr | Asp | Gly | Tyr | Cys | Phe | Thr | Met | Ile | Glu | Glu | Asp | Ser | Gly | Leu | |
| 50 | | | | | 55 | | | | | 60 | | | | | |
| Pro | Val | Val | Thr | Ser | Gly | Cys | Leu | Gly | Leu | Glu | Gly | Ser | Asp | Phe | Gln |
| 65 | | | | | 70 | | | | | 75 | | | | | 80 |
| Cys | Arg | Asp | Thr | Pro | Ile | Pro | His | Gln | Arg | Arg | Ser | Ile | Glu | Cys | Cys |
| | | | | 85 | | | | | 90 | | | | | 95 | |
| Thr | Glu | Arg | Asn | Glu | Cys | Asn | Lys | Asp | Leu | His | Pro | Thr | Leu | Pro | Pro |
| | | | 100 | | | | | 105 | | | | | 110 | | |
| Leu | Lys | Asn | Arg | Asp | Phe | Val | Asp | Gly | Pro | Ile | His | His | Arg | Ala | Leu |
| | | | 115 | | | | | 120 | | | | | 125 | | |
| Leu | Ile | Ser | Val | Thr | Val | Cys | Ser | Leu | Leu | Leu | Val | Leu | Ile | Ile | Leu |
| 130 | | | | | 135 | | | | | 140 | | | | | |
| Phe | Cys | Tyr | Phe | Arg | Tyr | Lys | Arg | Gln | Glu | Thr | Arg | Pro | Arg | Tyr | Ser |
| 145 | | | | | 150 | | | | | 155 | | | | | 160 |
| Ile | Gly | Leu | Glu | Gln | Asp | Glu | Thr | Tyr | Ile | Pro | Pro | Gly | Glu | Ser | Leu |
| | | | | 165 | | | | | 170 | | | | | 175 | |
| Arg | Asp | Leu | Ile | Glu | Gln | Ser | Gln | Ser | Ser | Gly | Ser | Gly | Ser | Gly | Leu |
| | | | 180 | | | | | 185 | | | | | 190 | | |
| Pro | Leu | Leu | Val | Gln | Arg | Thr | Ile | Ala | Lys | Gln | Ile | Gln | Met | Val | Lys |
| | | | 195 | | | | | 200 | | | | | 205 | | |
| Gln | Ile | Gly | Lys | Gly | Arg | Tyr | Gly | Glu | Val | Trp | Met | Gly | Lys | Trp | Arg |
| 210 | | | | | 215 | | | | | 220 | | | | | |
| Gly | Glu | Lys | Val | Ala | Val | Lys | Val | Phe | Phe | Thr | Thr | Glu | Glu | Ala | Ser |
| 225 | | | | | 230 | | | | | 235 | | | | | 240 |
| Trp | Phe | Arg | Glu | Thr | Glu | Ile | Tyr | Gln | Thr | Val | Leu | Met | Arg | His | Glu |
| | | | | 245 | | | | | 250 | | | | | 255 | |
| Asn | Ile | Leu | Gly | Phe | Ile | Ala | Ala | Asp | Ile | Lys | Gly | Thr | Gly | Ser | Trp |
| | | | 260 | | | | | 265 | | | | | 270 | | |
| Thr | Gln | Leu | Tyr | Leu | Ile | Thr | Asp | Tyr | His | Glu | Asn | Gly | Ser | Leu | Tyr |
| | | | 275 | | | | | 280 | | | | | 285 | | |
| Asp | Tyr | Leu | Lys | Ser | Thr | Thr | Leu | Asp | Ala | Lys | Ser | Met | Leu | Lys | Leu |
| | | 290 | | | | | 295 | | | | | 300 | | | |
| Ala | Tyr | Ser | Ser | Val | Ser | Gly | Leu | Cys | His | Leu | His | Thr | Glu | Ile | Phe |
| 305 | | | | | 310 | | | | | 315 | | | | | 320 |
| Ser | Thr | Gln | Gly | Lys | Pro | Ala | Ile | Ala | His | Arg | Asp | Leu | Lys | Ser | Lys |
| | | | | 325 | | | | | 330 | | | | | 335 | |
| Asn | Ile | Leu | Val | Lys | Lys | Asn | Gly | Thr | Cys | Cys | Ile | Ala | Asp | Leu | Gly |
| | | | 340 | | | | | 345 | | | | | 350 | | |
| Leu | Ala | Val | Lys | Phe | Ile | Ser | Asp | Thr | Asn | Glu | Val | Asp | Ile | Pro | Pro |
| | | | 355 | | | | | 360 | | | | | 365 | | |
| Asn | Thr | Arg | Val | Gly | Thr | Lys | Arg | Tyr | Met | Pro | Pro | Glu | Val | Leu | Asp |
| | | 370 | | | | | 375 | | | | | 380 | | | |
| Glu | Ser | Leu | Asn | Arg | Asn | His | Phe | Gln | Ser | Tyr | Ile | Met | Ala | Asp | Met |
| 385 | | | | | 390 | | | | | 395 | | | | | 400 |

```
Tyr Ser Phe Gly Leu Ile Leu Trp Glu Val Ala Arg Arg Cys Val Ser
                405                 410                 415
Gly Gly Ile Val Glu Glu Tyr Gln Leu Pro Tyr His Asp Leu Val Pro
            420                 425                 430
Ser Asp Pro Ser Tyr Glu Asp Met Arg Glu Ile Val Cys Ile Lys Lys
        435                 440                 445
Leu Arg Pro Ser Phe Pro Asn Arg Trp Ser Ser Asp Glu Cys Leu Arg
    450                 455                 460
Gln Met Gly Lys Leu Met Thr Glu Cys Trp Ala His Asn Pro Ala Ser
465                 470                 475                 480
Arg Leu Thr Ala Leu Arg Val Lys Lys Thr Leu Ala Lys Met Ser Glu
                485                 490                 495
Ser Gln Asp Ile Lys Leu
            500

<210> SEQ ID NO 109
<211> LENGTH: 113
<212> TYPE: PRT
<213> ORGANISM: Homo sapiens

<400> SEQUENCE: 109

Lys Lys Glu Asp Gly Glu Ser Thr Ala Pro Thr Pro Arg Pro Lys Val
1               5                   10                  15
Leu Arg Cys Lys Cys His His His Cys Pro Glu Asp Ser Val Asn Asn
            20                  25                  30
Ile Cys Ser Thr Asp Gly Tyr Cys Phe Thr Met Ile Glu Glu Asp Asp
        35                  40                  45
Ser Gly Leu Pro Val Val Thr Ser Gly Cys Leu Gly Leu Glu Gly Ser
    50                  55                  60
Asp Phe Gln Cys Arg Asp Thr Pro Ile Pro His Gln Arg Arg Ser Ile
65                  70                  75                  80
Glu Cys Cys Thr Glu Arg Asn Glu Cys Asn Lys Asp Leu His Pro Thr
                85                  90                  95
Leu Pro Pro Leu Lys Asn Arg Asp Phe Val Asp Gly Pro Ile His His
            100                 105                 110
Arg

<210> SEQ ID NO 110
<211> LENGTH: 532
<212> TYPE: PRT
<213> ORGANISM: Homo sapiens

<400> SEQUENCE: 110

Met Gly Trp Leu Glu Glu Leu Asn Trp Gln Leu His Ile Phe Leu Leu
1               5                   10                  15
Ile Leu Leu Ser Met His Thr Arg Ala Asn Phe Leu Asp Asn Met Leu
            20                  25                  30
Leu Arg Ser Ala Gly Lys Leu Asn Val Gly Thr Lys Lys Glu Asp Gly
        35                  40                  45
Glu Ser Thr Ala Pro Thr Pro Arg Pro Lys Val Leu Arg Cys Lys Cys
    50                  55                  60
His His His Cys Pro Glu Asp Ser Val Asn Asn Ile Cys Ser Thr Asp
65                  70                  75                  80
Gly Tyr Cys Phe Thr Met Ile Glu Glu Asp Asp Ser Gly Leu Pro Val
                85                  90                  95
Val Thr Ser Gly Cys Leu Gly Leu Glu Gly Ser Asp Phe Gln Cys Arg
```

```
                100                 105                 110
Asp Thr Pro Ile Pro His Gln Arg Arg Ser Ile Glu Cys Cys Thr Glu
            115                 120                 125
Arg Asn Glu Cys Asn Lys Asp Leu His Pro Thr Leu Pro Pro Leu Lys
        130                 135                 140
Asn Arg Asp Phe Val Asp Gly Pro Ile His Arg Ala Leu Leu Ile
145                 150                 155                 160
Ser Val Thr Val Cys Ser Leu Leu Val Leu Ile Ile Leu Phe Cys
                165                 170                 175
Tyr Phe Arg Tyr Lys Arg Gln Glu Thr Arg Pro Arg Tyr Ser Ile Gly
            180                 185                 190
Leu Glu Gln Asp Glu Thr Tyr Ile Pro Pro Gly Glu Ser Leu Arg Asp
        195                 200                 205
Leu Ile Glu Gln Ser Gln Ser Ser Gly Ser Gly Ser Gly Leu Pro Leu
    210                 215                 220
Leu Val Gln Arg Thr Ile Ala Lys Gln Ile Gln Met Val Lys Gln Ile
225                 230                 235                 240
Gly Lys Gly Arg Tyr Gly Glu Val Trp Met Gly Lys Trp Arg Gly Glu
                245                 250                 255
Lys Val Ala Val Lys Val Phe Phe Thr Thr Glu Glu Ala Ser Trp Phe
            260                 265                 270
Arg Glu Thr Glu Ile Tyr Gln Thr Val Leu Met Arg His Glu Asn Ile
        275                 280                 285
Leu Gly Phe Ile Ala Ala Asp Ile Lys Gly Thr Gly Ser Trp Thr Gln
    290                 295                 300
Leu Tyr Leu Ile Thr Asp Tyr His Glu Asn Gly Ser Leu Tyr Asp Tyr
305                 310                 315                 320
Leu Lys Ser Thr Thr Leu Asp Ala Lys Ser Met Leu Lys Leu Ala Tyr
                325                 330                 335
Ser Ser Val Ser Gly Leu Cys His Leu His Thr Glu Ile Phe Ser Thr
            340                 345                 350
Gln Gly Lys Pro Ala Ile Ala His Arg Asp Leu Lys Ser Lys Asn Ile
        355                 360                 365
Leu Val Lys Lys Asn Gly Thr Cys Cys Ile Ala Asp Leu Gly Leu Ala
    370                 375                 380
Val Lys Phe Ile Ser Asp Thr Asn Glu Val Asp Ile Pro Pro Asn Thr
385                 390                 395                 400
Arg Val Gly Thr Lys Arg Tyr Met Pro Pro Glu Val Leu Asp Glu Ser
            405                 410                 415
Leu Asn Arg Asn His Phe Gln Ser Tyr Ile Met Ala Asp Met Tyr Ser
        420                 425                 430
Phe Gly Leu Ile Leu Trp Glu Val Ala Arg Arg Cys Val Ser Gly Gly
    435                 440                 445
Ile Val Glu Glu Tyr Gln Leu Pro Tyr His Asp Leu Val Pro Ser Asp
450                 455                 460
Pro Ser Tyr Glu Asp Met Arg Glu Ile Val Cys Ile Lys Lys Leu Arg
465                 470                 475                 480
Pro Ser Phe Pro Asn Arg Trp Ser Ser Asp Glu Cys Leu Arg Gln Met
            485                 490                 495
Gly Lys Leu Met Thr Glu Cys Trp Ala His Asn Pro Ala Ser Arg Leu
        500                 505                 510
Thr Ala Leu Arg Val Lys Lys Thr Leu Ala Lys Met Ser Glu Ser Gln
    515                 520                 525
```

Asp Ile Lys Leu
    530

<210> SEQ ID NO 111
<211> LENGTH: 131
<212> TYPE: PRT
<213> ORGANISM: Homo sapiens

<400> SEQUENCE: 111

Asn Phe Leu Asp Asn Met Leu Leu Arg Ser Ala Gly Lys Leu Asn Val
1               5                   10                  15

Gly Thr Lys Lys Glu Asp Gly Glu Ser Thr Ala Pro Thr Pro Arg Pro
            20                  25                  30

Lys Val Leu Arg Cys Lys Cys His His His Cys Pro Glu Asp Ser Val
        35                  40                  45

Asn Asn Ile Cys Ser Thr Asp Gly Tyr Cys Phe Thr Met Ile Glu Glu
    50                  55                  60

Asp Asp Ser Gly Leu Pro Val Val Thr Ser Gly Cys Leu Gly Leu Glu
65                  70                  75                  80

Gly Ser Asp Phe Gln Cys Arg Asp Thr Pro Ile Pro His Gln Arg Arg
                85                  90                  95

Ser Ile Glu Cys Cys Thr Glu Arg Asn Glu Cys Asn Lys Asp Leu His
            100                 105                 110

Pro Thr Leu Pro Pro Leu Lys Asn Arg Asp Phe Val Asp Gly Pro Ile
        115                 120                 125

His His Arg
    130

<210> SEQ ID NO 112
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Asp Ala Met Lys Arg Gly Leu Cys Cys Val Leu Leu Leu Cys Gly
1               5                   10                  15

Ala Val Phe Val Ser Pro Gly Ala Lys Lys Glu Asp Gly Glu Ser Thr
            20                  25                  30

Ala Pro Thr Pro Arg Pro Lys Val Leu Arg Cys Lys Cys His His His
        35                  40                  45

Cys Pro Glu Asp Ser Val Asn Asn Ile Cys Ser Thr Asp Gly Tyr Cys
    50                  55                  60

Phe Thr Met Ile Glu Glu Asp Asp Ser Gly Leu Pro Val Val Thr Ser
65                  70                  75                  80

Gly Cys Leu Gly Leu Glu Gly Ser Asp Phe Gln Cys Arg Asp Thr Pro
                85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Thr His Thr
    130                 135                 140

Cys Pro Pro Cys Pro Ala Pro Glu Leu Leu Gly Gly Pro Ser Val Phe
145                 150                 155                 160

```
Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Asp Thr Thr Pro Pro Val Leu Asp Ser Asp
305                 310                 315                 320

Gly Ser Phe Phe Leu Tyr Ser Asp Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly
        355                 360                 365

<210> SEQ ID NO 113
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Lys Lys Glu Asp Gly Glu Ser Thr Ala Pro Thr Pro Arg Pro Lys Val
1               5                   10                  15

Leu Arg Cys Lys Cys His His Cys Pro Glu Asp Ser Val Asn Asn
                20                  25                  30

Ile Cys Ser Thr Asp Gly Tyr Cys Phe Thr Met Ile Glu Glu Asp Asp
            35                  40                  45

Ser Gly Leu Pro Val Val Thr Ser Gly Cys Leu Gly Leu Glu Gly Ser
        50                  55                  60

Asp Phe Gln Cys Arg Asp Thr Pro Ile Pro His Gln Arg Arg Ser Ile
65                  70                  75                  80

Glu Cys Cys Thr Glu Arg Asn Glu Cys Asn Lys Asp Leu His Pro Thr
                85                  90                  95

Leu Pro Pro Leu Lys Asn Arg Asp Phe Val Asp Gly Pro Ile His His
            100                 105                 110

Arg Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
```

```
                145                 150                 155                 160
Val Ser His Glu Asp Pro Glu Val Lys Phe Asn Trp Tyr Val Asp Gly
                165                 170                 175
Val Glu Val His Asn Ala Lys Thr Lys Pro Arg Glu Glu Gln Tyr Asn
                180                 185                 190
Ser Thr Tyr Arg Val Val Ser Val Leu Thr Val Leu His Gln Asp Trp
                195                 200                 205
Leu Asn Gly Lys Glu Tyr Lys Cys Lys Val Ser Asn Lys Ala Leu Pro
                210                 215                 220
Ala Pro Ile Glu Lys Thr Ile Ser Lys Ala Lys Gly Gln Pro Arg Glu
225                 230                 235                 240
Pro Gln Val Tyr Thr Leu Pro Pro Ser Arg Glu Glu Met Thr Lys Asn
                245                 250                 255
Gln Val Ser Leu Thr Cys Leu Val Lys Gly Phe Tyr Pro Ser Asp Ile
                260                 265                 270
Ala Val Glu Trp Glu Ser Asn Gly Gln Pro Glu Asn Asn Tyr Asp Thr
                275                 280                 285
Thr Pro Pro Val Leu Asp Ser Asp Gly Ser Phe Phe Leu Tyr Ser Asp
                290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly
                340

<210> SEQ ID NO 114

<400> SEQUENCE: 114

000

<210> SEQ ID NO 115

<400> SEQUENCE: 115

000

<210> SEQ ID NO 116
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Asp Ala Met Lys Arg Gly Leu Cys Cys Val Leu Leu Leu Cys Gly
1               5                   10                  15
Ala Val Phe Val Ser Pro Gly Ala Lys Lys Glu Asp Gly Glu Ser Thr
                20                  25                  30
Ala Pro Thr Pro Arg Pro Lys Val Leu Arg Cys Lys Cys His His His
                35                  40                  45
Cys Pro Glu Asp Ser Val Asn Asn Ile Cys Ser Thr Asp Gly Tyr Cys
                50                  55                  60
Phe Thr Met Ile Glu Glu Asp Asp Ser Gly Leu Pro Val Val Thr Ser
65                  70                  75                  80
Gly Cys Leu Gly Leu Glu Gly Ser Asp Phe Gln Cys Arg Asp Thr Pro
```

```
                    85                  90                  95
Ile Pro His Gln Arg Arg Ser Ile Glu Cys Cys Thr Glu Arg Asn Glu
                100                 105                 110

Cys Asn Lys Asp Leu His Pro Thr Leu Pro Leu Lys Asn Arg Asp
            115                 120                 125

Phe Val Asp Gly Pro Ile His Arg Thr Gly Gly Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
                180                 185                 190

Lys Phe Asn Trp Tyr Val Asp Gly Val Glu Val His Asn Ala Lys Thr
            195                 200                 205

Lys Pro Arg Glu Glu Gln Tyr Asn Ser Thr Tyr Arg Val Val Ser Val
            210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Cys Thr Leu Pro Pro
                260                 265                 270

Ser Arg Glu Glu Met Thr Lys Asn Gln Val Ser Leu Ser Cys Ala Val
            275                 280                 285

Lys Gly Phe Tyr Pro Ser Asp Ile Ala Val Glu Trp Glu Ser Asn Gly
            290                 295                 300

Gln Pro Glu Asn Asn Tyr Lys Thr Thr Pro Pro Val Leu Asp Ser Asp
305                 310                 315                 320

Gly Ser Phe Phe Leu Val Ser Lys Leu Thr Val Asp Lys Ser Arg Trp
                325                 330                 335

Gln Gln Gly Asn Val Phe Ser Cys Ser Val Met His Glu Ala Leu His
                340                 345                 350

Asn His Tyr Thr Gln Lys Ser Leu Ser Leu Ser Pro Gly Lys
            355                 360                 365

<210> SEQ ID NO 117
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Lys Lys Glu Asp Gly Glu Ser Thr Ala Pro Thr Pro Arg Pro Lys Val
1               5                   10                  15

Leu Arg Cys Lys Cys His His Cys Pro Glu Asp Ser Val Asn Asn
            20                  25                  30

Ile Cys Ser Thr Asp Gly Tyr Cys Phe Thr Met Ile Glu Glu Asp Asp
            35                  40                  45

Ser Gly Leu Pro Val Val Thr Ser Gly Cys Leu Gly Leu Glu Gly Ser
        50                  55                  60

Asp Phe Gln Cys Arg Asp Thr Pro Ile Pro His Gln Arg Arg Ser Ile
65                  70                  75                  80
```

```
Glu Cys Cys Thr Glu Arg Asn Glu Cys Asn Lys Asp Leu His Pro Thr
                85                  90                  95

Leu Pro Pro Leu Lys Asn Arg Asp Phe Val Asp Gly Pro Ile His His
            100                 105                 110

Arg Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Cys Thr Leu Pro Pro Ser Arg Glu Glu Met Thr Lys Asn
                245                 250                 255

Gln Val Ser Leu Ser Cys Ala Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Val Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 118

<400> SEQUENCE: 118

000

<210> SEQ ID NO 119

<400> SEQUENCE: 119

000

<210> SEQ ID NO 120
<211> LENGTH: 493
<212> TYPE: PRT
<213> ORGANISM: Homo sapiens

<400> SEQUENCE: 120

Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30
```

```
Cys Asp Ser Ser Asn Phe Thr Cys Gln Thr Glu Gly Ala Cys Trp Ala
            35                  40                  45

Ser Val Met Leu Thr Asn Gly Lys Glu Gln Val Ile Lys Ser Cys Val
 50                  55                  60

Ser Leu Pro Glu Leu Asn Ala Gln Val Phe Cys His Ser Ser Asn Asn
 65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Leu Ala Ile Ile Ile Thr Val Pro Val Cys Leu Leu Ser Ile Ala
            115                 120                 125

Ala Met Leu Thr Val Trp Ala Cys Gln Gly Arg Gln Cys Ser Tyr Arg
130                 135                 140

Lys Lys Lys Arg Pro Asn Val Glu Glu Pro Leu Ser Glu Cys Asn Leu
145                 150                 155                 160

Val Asn Ala Gly Lys Thr Leu Lys Asp Leu Ile Tyr Asp Val Thr Ala
                165                 170                 175

Ser Gly Ser Gly Ser Gly Leu Pro Leu Leu Val Gln Arg Thr Ile Ala
            180                 185                 190

Arg Thr Ile Val Leu Gln Glu Ile Val Gly Lys Gly Arg Phe Gly Glu
            195                 200                 205

Val Trp His Gly Arg Trp Cys Gly Glu Asp Val Ala Val Lys Ile Phe
            210                 215                 220

Ser Ser Arg Asp Glu Arg Ser Trp Phe Arg Glu Ala Glu Ile Tyr Gln
225                 230                 235                 240

Thr Val Met Leu Arg His Glu Asn Ile Leu Gly Phe Ile Ala Ala Asp
                245                 250                 255

Asn Lys Asp Asn Gly Thr Trp Thr Gln Leu Trp Leu Val Ser Glu Tyr
            260                 265                 270

His Glu Gln Gly Ser Leu Tyr Asp Tyr Leu Asn Arg Asn Ile Val Thr
            275                 280                 285

Val Ala Gly Met Ile Lys Leu Ala Leu Ser Ile Ala Ser Gly Leu Ala
            290                 295                 300

His Leu His Met Glu Ile Val Gly Thr Gln Gly Lys Pro Ala Ile Ala
305                 310                 315                 320

His Arg Asp Ile Lys Ser Lys Asn Ile Leu Val Lys Lys Cys Glu Thr
                325                 330                 335

Cys Ala Ile Ala Asp Leu Gly Leu Ala Val Lys His Asp Ser Ile Leu
            340                 345                 350

Asn Thr Ile Asp Ile Pro Gln Asn Pro Lys Val Gly Thr Lys Arg Tyr
            355                 360                 365

Met Ala Pro Glu Met Leu Asp Asp Thr Met Asn Val Asn Ile Phe Glu
            370                 375                 380

Ser Phe Lys Arg Ala Asp Ile Tyr Ser Val Gly Leu Val Tyr Trp Glu
385                 390                 395                 400

Ile Ala Arg Arg Cys Ser Val Gly Gly Ile Val Glu Glu Tyr Gln Leu
                405                 410                 415

Pro Tyr Tyr Asp Met Val Pro Ser Asp Pro Ser Ile Glu Glu Met Arg
            420                 425                 430

Lys Val Val Cys Asp Gln Lys Phe Arg Pro Ser Ile Pro Asn Gln Trp
            435                 440                 445

Gln Ser Cys Glu Ala Leu Arg Val Met Gly Arg Ile Met Arg Glu Cys
```

```
                  450              455             460
Trp Tyr Ala Asn Gly Ala Ala Arg Leu Thr Ala Leu Arg Ile Lys Lys
465                 470                 475                 480

Thr Ile Ser Gln Leu Cys Val Lys Glu Asp Cys Lys Ala
                485                 490

<210> SEQ ID NO 121
<211> LENGTH: 413
<212> TYPE: PRT
<213> ORGANISM: Homo sapiens

<400> SEQUENCE: 121

Met Thr Arg Ala Leu Cys Ser Ala Leu Arg Gln Ala Leu Leu Leu Leu
1               5                   10                  15

Ala Ala Ala Glu Leu Ser Pro Gly Leu Lys Cys Val Cys Leu Leu
                20                  25                  30

Cys Asp Ser Ser Asn Phe Thr Cys Gln Thr Glu Gly Ala Cys Trp Ala
                35                  40                  45

Ser Val Met Leu Thr Asn Gly Lys Glu Gln Val Ile Lys Ser Cys Val
50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Gly Leu Pro Leu Leu Val Gln Arg Thr Ile Ala
                100                 105                 110

Arg Thr Ile Val Leu Gln Glu Ile Val Gly Lys Gly Arg Phe Gly Glu
                115                 120                 125

Val Trp His Gly Arg Trp Cys Gly Glu Asp Val Ala Val Lys Ile Phe
130                 135                 140

Ser Ser Arg Asp Glu Arg Ser Trp Phe Arg Glu Ala Glu Ile Tyr Gln
145                 150                 155                 160

Thr Val Met Leu Arg His Glu Asn Ile Leu Gly Phe Ile Ala Ala Asp
                165                 170                 175

Asn Lys Asp Asn Gly Thr Trp Thr Gln Leu Trp Leu Val Ser Glu Tyr
                180                 185                 190

His Glu Gln Gly Ser Leu Tyr Asp Tyr Leu Asn Arg Asn Ile Val Thr
                195                 200                 205

Val Ala Gly Met Ile Lys Leu Ala Leu Ser Ile Ala Ser Gly Leu Ala
                210                 215                 220

His Leu His Met Glu Ile Val Gly Thr Gln Gly Lys Pro Ala Ile Ala
225                 230                 235                 240

His Arg Asp Ile Lys Ser Lys Asn Ile Leu Val Lys Lys Cys Glu Thr
                245                 250                 255

Cys Ala Ile Ala Asp Leu Gly Leu Ala Val Lys His Asp Ser Ile Leu
                260                 265                 270

Asn Thr Ile Asp Ile Pro Gln Asn Pro Lys Val Gly Thr Lys Arg Tyr
                275                 280                 285

Met Ala Pro Glu Met Leu Asp Asp Thr Met Asn Val Asn Ile Phe Glu
                290                 295                 300

Ser Phe Lys Arg Ala Asp Ile Tyr Ser Val Gly Leu Val Tyr Trp Glu
305                 310                 315                 320

Ile Ala Arg Arg Cys Ser Val Gly Gly Ile Val Glu Glu Tyr Gln Leu
                325                 330                 335
```

Pro Tyr Tyr Asp Met Val Pro Ser Asp Pro Ser Ile Glu Glu Met Arg
            340                 345                 350

Lys Val Val Cys Asp Gln Lys Phe Arg Pro Ser Ile Pro Asn Gln Trp
            355                 360                 365

Gln Ser Cys Glu Ala Leu Arg Val Met Gly Arg Ile Met Arg Glu Cys
            370                 375                 380

Trp Tyr Ala Asn Gly Ala Ala Arg Leu Thr Ala Leu Arg Ile Lys Lys
385                 390                 395                 400

Thr Ile Ser Gln Leu Cys Val Lys Glu Asp Cys Lys Ala
            405                 410

<210> SEQ ID NO 122
<211> LENGTH: 336
<212> TYPE: PRT
<213> ORGANISM: Homo sapiens

<400> SEQUENCE: 122

Met Thr Arg Ala Leu Cys Ser Ala Leu Arg Gln Ala Leu Leu Leu Leu
1               5                   10                  15

Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
            35                  40                  45

Ser Val Met Leu Thr Asn Gly Lys Glu Gln Val Ile Lys Ser Cys Val
            50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
            85                  90                  95

Leu His Leu Pro Thr Asp Asn Gly Thr Trp Thr Gln Leu Trp Leu Val
            100                 105                 110

Ser Glu Tyr His Glu Gln Gly Ser Leu Tyr Asp Tyr Leu Asn Arg Asn
            115                 120                 125

Ile Val Thr Val Ala Gly Met Ile Lys Leu Ala Leu Ser Ile Ala Ser
            130                 135                 140

Gly Leu Ala His Leu His Met Glu Ile Val Gly Thr Gln Gly Lys Pro
145                 150                 155                 160

Ala Ile Ala His Arg Asp Ile Lys Ser Lys Asn Ile Leu Val Lys Lys
            165                 170                 175

Cys Glu Thr Cys Ala Ile Ala Asp Leu Gly Leu Ala Val Lys His Asp
            180                 185                 190

Ser Ile Leu Asn Thr Ile Asp Ile Pro Gln Asn Pro Lys Val Gly Thr
            195                 200                 205

Lys Arg Tyr Met Ala Pro Glu Met Leu Asp Asp Thr Met Asn Val Asn
            210                 215                 220

Ile Phe Glu Ser Phe Lys Arg Ala Asp Ile Tyr Ser Val Gly Leu Val
225                 230                 235                 240

Tyr Trp Glu Ile Ala Arg Arg Cys Ser Val Gly Gly Ile Val Glu Glu
            245                 250                 255

Tyr Gln Leu Pro Tyr Tyr Asp Met Val Pro Ser Asp Pro Ser Ile Glu
            260                 265                 270

Glu Met Arg Lys Val Val Cys Asp Gln Lys Phe Arg Pro Ser Ile Pro
            275                 280                 285

Asn Gln Trp Gln Ser Cys Glu Ala Leu Arg Val Met Gly Arg Ile Met
            290                 295                 300

```
Arg Glu Cys Trp Tyr Ala Asn Gly Ala Ala Arg Leu Thr Ala Leu Arg
305                 310                 315                 320

Ile Lys Lys Thr Ile Ser Gln Leu Cys Val Lys Glu Asp Cys Lys Ala
                325                 330                 335

<210> SEQ ID NO 123
<211> LENGTH: 93
<212> TYPE: PRT
<213> ORGANISM: Homo sapiens

<400> SEQUENCE: 123

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
                20                  25                  30

Thr Asn Gly Lys Glu Gln Val Ile Lys Ser Cys Val Ser Leu Pro Glu
            35                  40                  45

Leu Asn Ala Gln Val Phe Cys His Ser Ser Asn Asn Val Thr Lys Thr
        50                  55                  60

Glu Cys Cys Phe Thr Asp Phe Cys Asn Asn Ile Thr Leu His Leu Pro
65                  70                  75                  80

Thr Ala Ser Pro Asn Ala Pro Lys Leu Gly Pro Met Glu
                85                  90

<210> SEQ ID NO 124
<211> LENGTH: 443
<212> TYPE: PRT
<213> ORGANISM: Homo sapiens

<400> SEQUENCE: 124

Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
                20                  25                  30

Lys Thr Glu Cys Cys Phe Thr Asp Phe Cys Asn Asn Ile Thr Leu His
            35                  40                  45

Leu Pro Thr Ala Ser Pro Asn Ala Pro Lys Leu Gly Pro Met Glu Leu
        50                  55                  60

Ala Ile Ile Ile Thr Val Pro Val Cys Leu Leu Ser Ile Ala Ala Met
65                  70                  75                  80

Leu Thr Val Trp Ala Cys Gln Gly Arg Gln Cys Ser Tyr Arg Lys Lys
                85                  90                  95

Lys Arg Pro Asn Val Glu Glu Pro Leu Ser Glu Cys Asn Leu Val Asn
                100                 105                 110

Ala Gly Lys Thr Leu Lys Asp Leu Ile Tyr Asp Val Thr Ala Ser Gly
            115                 120                 125

Ser Gly Ser Gly Leu Pro Leu Leu Val Gln Arg Thr Ile Ala Arg Thr
        130                 135                 140

Ile Val Leu Gln Glu Ile Val Gly Lys Gly Arg Phe Gly Glu Val Trp
145                 150                 155                 160

His Gly Arg Trp Cys Gly Glu Asp Val Ala Val Lys Ile Phe Ser Ser
                165                 170                 175

Arg Asp Glu Arg Ser Trp Phe Arg Glu Ala Glu Ile Tyr Gln Thr Val
                180                 185                 190

Met Leu Arg His Glu Asn Ile Leu Gly Phe Ile Ala Ala Asp Asn Lys
            195                 200                 205
```

```
Asp Asn Gly Thr Trp Thr Gln Leu Trp Leu Val Ser Glu Tyr His Glu
            210                 215                 220

Gln Gly Ser Leu Tyr Asp Tyr Leu Asn Arg Asn Ile Val Thr Val Ala
225                 230                 235                 240

Gly Met Ile Lys Leu Ala Leu Ser Ile Ala Ser Gly Leu Ala His Leu
                245                 250                 255

His Met Glu Ile Val Gly Thr Gln Gly Lys Pro Ala Ile Ala His Arg
            260                 265                 270

Asp Ile Lys Ser Lys Asn Ile Leu Val Lys Cys Glu Thr Cys Ala
            275                 280                 285

Ile Ala Asp Leu Gly Leu Ala Val Lys His Asp Ser Ile Leu Asn Thr
            290                 295                 300

Ile Asp Ile Pro Gln Asn Pro Lys Val Gly Thr Lys Arg Tyr Met Ala
305                 310                 315                 320

Pro Glu Met Leu Asp Asp Thr Met Asn Val Asn Ile Phe Glu Ser Phe
                325                 330                 335

Lys Arg Ala Asp Ile Tyr Ser Val Gly Leu Val Tyr Trp Glu Ile Ala
            340                 345                 350

Arg Arg Cys Ser Val Gly Gly Ile Val Glu Glu Tyr Gln Leu Pro Tyr
            355                 360                 365

Tyr Asp Met Val Pro Ser Asp Pro Ser Ile Glu Glu Met Arg Lys Val
370                 375                 380

Val Cys Asp Gln Lys Phe Arg Pro Ser Ile Pro Asn Gln Trp Gln Ser
385                 390                 395                 400

Cys Glu Ala Leu Arg Val Met Gly Arg Ile Met Arg Glu Cys Trp Tyr
                405                 410                 415

Ala Asn Gly Ala Ala Arg Leu Thr Ala Leu Arg Ile Lys Lys Thr Ile
            420                 425                 430

Ser Gln Leu Cys Val Lys Glu Asp Cys Lys Ala
            435                 440

<210> SEQ ID NO 125
<211> LENGTH: 63
<212> TYPE: PRT
<213> ORGANISM: Homo sapiens

<400> SEQUENCE: 125

Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
                20                  25                  30

Lys Thr Glu Cys Cys Phe Thr Asp Phe Cys Asn Asn Ile Thr Leu His
            35                  40                  45

Leu Pro Thr Ala Ser Pro Asn Ala Pro Lys Leu Gly Pro Met Glu
        50                  55                  60

<210> SEQ ID NO 126
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Leu Ser Pro Gly Leu Lys Cys Val Cys Leu Leu Cys Asp Ser Ser
1               5                   10                  15
```

```
Asn Phe Thr Cys Gln Thr Glu Gly Ala Cys Trp Ala Ser Val Met Leu
                20                  25                  30
Thr Asn Gly Lys Glu Gln Val Ile Lys Ser Cys Val Ser Leu Pro Glu
        35                  40                  45
Leu Asn Ala Gln Val Phe Cys His Ser Ser Asn Val Thr Lys Thr
 50                  55                  60
Glu Cys Cys Phe Thr Asp Phe Cys Asn Asn Ile Thr Leu His Leu Pro
 65                  70                  75                  80
Thr Gly Leu Pro Leu Leu Val Gln Arg Thr Ile Ala Arg Thr Ile Val
                 85                  90                  95
Leu Gln Glu Ile Val Gly Lys Gly Arg Phe Gly Glu Val Trp His Gly
                100                 105                 110
Arg Trp Cys Gly Glu Asp Val Ala Val Lys Ile Phe Ser Ser Arg Asp
        115                 120                 125
Glu Arg Ser Trp Phe Arg Glu Ala Glu Ile Tyr Gln Thr Val Met Leu
130                 135                 140
Arg His Glu Asn Ile Leu Gly Phe Ile Ala Ala Asp Asn Lys Asp Asn
145                 150                 155                 160
Gly Thr Trp Thr Gln Leu Trp Leu Val Ser Glu Tyr His Glu Gln Gly
                165                 170                 175
Ser Leu Tyr Asp Tyr Leu Asn Arg Asn Ile Val Thr Val Ala Gly Met
                180                 185                 190
Ile Lys Leu Ala Leu Ser Ile Ala Ser Gly Leu Ala His Leu His Met
            195                 200                 205
Glu Ile Val Gly Thr Gln Gly Lys Pro Ala Ile Ala His Arg Asp Ile
210                 215                 220
Lys Ser Lys Asn Ile Leu Val Lys Lys Cys Glu Thr Cys Ala Ile Ala
225                 230                 235                 240
Asp Leu Gly Leu Ala Val Lys His Asp Ser Ile Leu Asn Thr Ile Asp
                245                 250                 255
Ile Pro Gln Asn Pro Lys Val Gly Thr Lys Arg Tyr Met Ala Pro Glu
                260                 265                 270
Met Leu Asp Asp Thr Met Asn Val Asn Ile Phe Glu Ser Phe Lys Arg
            275                 280                 285
Ala Asp Ile Tyr Ser Val Gly Leu Val Tyr Trp Glu Ile Ala Arg Arg
290                 295                 300
Cys Ser Val Gly Gly Ile Val Glu Glu Tyr Gln Leu Pro Tyr Tyr Asp
305                 310                 315                 320
Met Val Pro Ser Asp Pro Ser Ile Glu Glu Met Arg Lys Val Val Cys
                325                 330                 335
Asp Gln Lys Phe Arg Pro Ser Ile Pro Asn Gln Trp Gln Ser Cys Glu
            340                 345                 350
Ala Leu Arg Val Met Gly Arg Ile Met Arg Glu Cys Trp Tyr Ala Asn
355                 360                 365
Gly Ala Ala Arg Leu Thr Ala Leu Arg Ile Lys Lys Thr Ile Ser Gln
            370                 375                 380
Leu Cys Val Lys Glu Asp Cys Lys Ala
385                 390

<210> SEQ ID NO 127
<211> LENGTH: 316
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 127

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Val Thr Lys Thr
    50                  55                  60

Glu Cys Cys Phe Thr Asp Phe Cys Asn Asn Ile Thr Leu His Leu Pro
65                  70                  75                  80

Thr Asp Asn Gly Thr Trp Thr Gln Leu Trp Leu Val Ser Glu Tyr His
                85                  90                  95

Glu Gln Gly Ser Leu Tyr Asp Tyr Leu Asn Arg Asn Ile Val Thr Val
            100                 105                 110

Ala Gly Met Ile Lys Leu Ala Leu Ser Ile Ala Ser Gly Leu Ala His
        115                 120                 125

Leu His Met Glu Ile Val Gly Thr Gln Gly Lys Pro Ala Ile Ala His
    130                 135                 140

Arg Asp Ile Lys Ser Lys Asn Ile Leu Val Lys Lys Cys Glu Thr Cys
145                 150                 155                 160

Ala Ile Ala Asp Leu Gly Leu Ala Val Lys His Asp Ser Ile Leu Asn
                165                 170                 175

Thr Ile Asp Ile Pro Gln Asn Pro Lys Val Gly Thr Lys Arg Tyr Met
            180                 185                 190

Ala Pro Glu Met Leu Asp Asp Thr Met Asn Val Asn Ile Phe Glu Ser
        195                 200                 205

Phe Lys Arg Ala Asp Ile Tyr Ser Val Gly Leu Val Tyr Trp Glu Ile
    210                 215                 220

Ala Arg Arg Cys Ser Val Gly Gly Ile Val Glu Glu Tyr Gln Leu Pro
225                 230                 235                 240

Tyr Tyr Asp Met Val Pro Ser Asp Pro Ser Ile Glu Glu Met Arg Lys
                245                 250                 255

Val Val Cys Asp Gln Lys Phe Arg Pro Ser Ile Pro Asn Gln Trp Gln
            260                 265                 270

Ser Cys Glu Ala Leu Arg Val Met Gly Arg Ile Met Arg Glu Cys Trp
        275                 280                 285

Tyr Ala Asn Gly Ala Ala Arg Leu Thr Ala Leu Arg Ile Lys Lys Thr
    290                 295                 300

Ile Ser Gln Leu Cys Val Lys Glu Asp Cys Lys Ala
305                 310                 315

<210> SEQ ID NO 128
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Lys Cys Val Cys Leu Leu Cys Asp Ser Ser Asn Phe Thr Cys Gln
1               5                   10                  15

```
Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro Thr Ala Ser Pro Asn
65                  70                  75                  80

Ala Pro Lys Leu Gly Pro Met Glu
                85

<210> SEQ ID NO 129
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Asp Thr
        275                 280                 285
```

```
Thr Pro Pro Val Leu Asp Ser Asp Gly Ser Phe Phe Leu Tyr Ser Asp
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
            340

<210> SEQ ID NO 130
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
    130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Tyr Thr Leu Pro Pro
    210                 215                 220

Ser Arg Glu Glu Met Thr Lys Asn Gln Val Ser Leu Thr Cys Leu Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Asp Thr Thr Pro Val Leu Asp Ser Asp
            260                 265                 270

Gly Ser Phe Phe Leu Tyr Ser Asp Leu Thr Val Asp Lys Ser Arg Trp
        275                 280                 285

Gln Gln Gly Asn Val Phe Ser Cys Ser Val Met His Glu Ala Leu His
```

```
                290                 295                 300
Asn His Tyr Thr Gln Lys Ser Leu Ser Leu Ser Pro Gly
305                 310                 315

<210> SEQ ID NO 131

<400> SEQUENCE: 131

000

<210> SEQ ID NO 132

<400> SEQUENCE: 132

000

<210> SEQ ID NO 133
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
                20                  25                  30

Cys Asp Ser Ser Asn Phe Thr Cys Gln Thr Glu Gly Ala Cys Trp Ala
            35                  40                  45

Ser Val Met Leu Thr Asn Gly Lys Glu Gln Val Ile Lys Ser Cys Val
        50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Cys Thr Leu Pro Pro Ser Arg Glu Glu Met Thr Lys Asn
                245                 250                 255

Gln Val Ser Leu Ser Cys Ala Val Lys Gly Phe Tyr Pro Ser Asp Ile
```

```
            260                 265                 270
Ala Val Glu Trp Glu Ser Asn Gly Gln Pro Glu Asn Tyr Lys Thr
        275                 280                 285

Thr Pro Pro Val Leu Asp Ser Asp Gly Ser Phe Phe Leu Val Ser Lys
        290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
                340

<210> SEQ ID NO 134
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
    130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Cys Thr Leu Pro Pro
    210                 215                 220

Ser Arg Glu Glu Met Thr Lys Asn Gln Val Ser Leu Ser Cys Ala Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Lys Thr Thr Pro Pro Val Leu Asp Ser Asp
            260                 265                 270
```

```
Gly Ser Phe Phe Leu Val Ser Lys Leu Thr Val Asp Lys Ser Arg Trp
            275                 280                 285

Gln Gln Gly Asn Val Phe Ser Cys Ser Val Met His Glu Ala Leu His
    290                 295                 300

Asn His Tyr Thr Gln Lys Ser Leu Ser Leu Ser Pro Gly Lys
305                 310                 315

<210> SEQ ID NO 135

<400> SEQUENCE: 135

000

<210> SEQ ID NO 136

<400> SEQUENCE: 136

000

<210> SEQ ID NO 137
<211> LENGTH: 513
<212> TYPE: PRT
<213> ORGANISM: Homo sapiens

<400> SEQUENCE: 137

Met Gly Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
        180                 185                 190

Gln Leu Leu Glu Val Lys Ala Arg Gly Arg Phe Gly Cys Val Trp Lys
    195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255
```

Thr Ser Val Asp Val Asp Leu Trp Leu Ile Thr Ala Phe His Glu Lys
                260                 265                 270

Gly Ser Leu Ser Asp Phe Leu Lys Ala Asn Val Val Ser Trp Asn Glu
            275                 280                 285

Leu Cys His Ile Ala Glu Thr Met Ala Arg Gly Leu Ala Tyr Leu His
        290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
        450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
            500                 505                 510

Leu

<210> SEQ ID NO 138
<211> LENGTH: 115
<212> TYPE: PRT
<213> ORGANISM: Homo sapiens

<400> SEQUENCE: 138

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 139
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
        100

<210> SEQ ID NO 140
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

-continued

```
Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
            245                 250                 255

Thr Ile Ser Lys Ala Lys Gly Gln Pro Arg Glu Pro Gln Val Tyr Thr
            260                 265                 270

Leu Pro Pro Ser Arg Lys Glu Met Thr Lys Asn Gln Val Ser Leu Thr
            275                 280                 285

Cys Leu Val Lys Gly Phe Tyr Pro Ser Asp Ile Ala Val Glu Trp Glu
            290                 295                 300

Ser Asn Gly Gln Pro Glu Asn Asn Tyr Lys Thr Thr Pro Pro Val Leu
305                 310                 315                 320

Lys Ser Asp Gly Ser Phe Phe Leu Tyr Ser Lys Leu Thr Val Asp Lys
            325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys
```

<210> SEQ ID NO 141
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
            85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
            115                 120                 125

Pro Glu Leu Leu Gly Gly Pro Ser Val Phe Leu Phe Pro Pro Lys Pro
            130                 135                 140

Lys Asp Thr Leu Met Ile Ser Arg Thr Pro Glu Val Thr Cys Val Val
145                 150                 155                 160
```

```
Val Asp Val Ser His Glu Asp Pro Glu Val Lys Phe Asn Trp Tyr Val
            165                 170                 175

Asp Gly Val Glu Val His Asn Ala Lys Thr Lys Pro Arg Glu Glu Gln
        180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Ala Lys Gly Gln Pro
225                 230                 235                 240

Arg Glu Pro Gln Val Tyr Thr Leu Pro Pro Ser Arg Lys Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Lys Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 142

<400> SEQUENCE: 142

000

<210> SEQ ID NO 143

<400> SEQUENCE: 143

000

<210> SEQ ID NO 144
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95
```

Val Glu Lys Lys Asp Ser Pro Glu Val Tyr Phe Cys Cys Gly
            100                 105                 110

Asn Met Cys Asn Glu Lys Phe Ser Tyr Phe Pro Glu Met Glu Val Thr
            115                 120                 125

Gln Pro Thr Ser Asn Pro Val Thr Pro Lys Pro Pro Thr Gly Gly Gly
        130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
        210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Cys Arg Glu Glu Met Thr Lys Asn Gln Val Ser Leu Trp
            275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 145
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

```
Tyr Phe Cys Cys Cys Glu Gly Asn Met Cys Asn Glu Lys Phe Ser Tyr
            85                  90                  95

Phe Pro Glu Met Glu Val Thr Gln Pro Thr Ser Asn Pro Val Thr Pro
        100                 105                 110

Lys Pro Pro Thr Gly Gly Thr His Thr Cys Pro Pro Cys Pro Ala
        115                 120                 125

Pro Glu Leu Leu Gly Gly Pro Ser Val Phe Leu Phe Pro Pro Lys Pro
        130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Cys Arg Glu Glu Met Thr
                245                 250                 255

Lys Asn Gln Val Ser Leu Trp Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 146

<400> SEQUENCE: 146

000

<210> SEQ ID NO 147

<400> SEQUENCE: 147

000

<210> SEQ ID NO 148
<211> LENGTH: 1038
<212> TYPE: PRT
<213> ORGANISM: Homo sapiens

<400> SEQUENCE: 148

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30
```

-continued

```
Leu Cys Ala Phe Lys Asp Pro Tyr Gln Gln Asp Leu Gly Ile Gly Glu
             35                  40                  45

Ser Arg Ile Ser His Glu Asn Gly Thr Ile Leu Cys Ser Lys Gly Ser
 50                  55                  60

Thr Cys Tyr Gly Leu Trp Glu Lys Ser Lys Gly Asp Ile Asn Leu Val
 65                  70                  75                  80

Lys Gln Gly Cys Trp Ser His Ile Gly Asp Pro Gln Glu Cys His Tyr
                 85                  90                  95

Glu Glu Cys Val Val Thr Thr Thr Pro Pro Ser Ile Gln Asn Gly Thr
                100                 105                 110

Tyr Arg Phe Cys Cys Cys Ser Thr Asp Leu Cys Asn Val Asn Phe Thr
             115                 120                 125

Glu Asn Phe Pro Pro Pro Asp Thr Thr Pro Leu Ser Pro Pro His Ser
130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
```

```
                450             455             460
Ala Trp Lys Glu Asn Ser Leu Ala Val Arg Ser Leu Lys Glu Thr Ile
465                     470                 475                 480

Glu Asp Cys Trp Asp Gln Asp Ala Glu Ala Arg Leu Thr Ala Gln Cys
                    485                 490                 495

Ala Glu Glu Arg Met Ala Glu Leu Met Met Ile Trp Glu Arg Asn Lys
                500                 505                 510

Ser Val Ser Pro Thr Val Asn Pro Met Ser Thr Ala Met Gln Asn Glu
            515                 520                 525

Arg Asn Leu Ser His Asn Arg Arg Val Pro Lys Ile Gly Pro Tyr Pro
            530                 535                 540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
                580                 585                 590

Gln Ala Gln Ala Arg Ile Pro Ser Pro Glu Thr Ser Val Thr Ser Leu
                595                 600                 605

Ser Thr Asn Thr Thr Thr Asn Thr Thr Gly Leu Thr Pro Ser Thr
            610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
                660                 665                 670

Val Asp Lys Asn Leu Lys Glu Ser Ser Asp Glu Asn Leu Met Glu His
                675                 680                 685

Ser Leu Lys Gln Phe Ser Gly Pro Asp Pro Leu Ser Ser Thr Ser Ser
                690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
                740                 745                 750

Lys Arg Pro Thr Ser Leu Pro Leu Asn Thr Lys Asn Ser Thr Lys Glu
                755                 760                 765

Pro Arg Leu Lys Phe Gly Ser Lys His Lys Ser Asn Leu Lys Gln Val
                770                 775                 780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                    805                 810                 815

Asn Ser His Ala Ala Thr Thr Gln Tyr Ala Asn Gly Thr Val Leu Ser
                820                 825                 830

Gly Gln Thr Thr Asn Ile Val Thr His Arg Ala Gln Glu Met Leu Gln
                835                 840                 845

Asn Gln Phe Ile Gly Glu Asp Thr Arg Leu Asn Ile Asn Ser Ser Pro
850                 855                 860

Asp Glu His Glu Pro Leu Leu Arg Arg Glu Gln Gln Ala Gly His Asp
865                 870                 875                 880
```

```
Glu Gly Val Leu Asp Arg Leu Val Asp Arg Arg Glu Arg Pro Leu Glu
            885                 890                 895

Gly Gly Arg Thr Asn Ser Asn Asn Asn Ser Asn Pro Cys Ser Glu
            900                 905                 910

Gln Asp Val Leu Ala Gln Gly Val Pro Ser Thr Ala Ala Asp Pro Gly
            915                 920                 925

Pro Ser Lys Pro Arg Arg Ala Gln Arg Pro Asn Ser Leu Asp Leu Ser
            930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
            965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
            995                 1000                1005

Val His Ser Lys Ser Ser Thr Ala Val Tyr Leu Ala Glu Gly Gly
            1010                1015                1020

Thr Ala Thr Thr Met Val Ser Lys Asp Ile Gly Met Asn Cys Leu
1025                1030                1035

<210> SEQ ID NO 149
<211> LENGTH: 530
<212> TYPE: PRT
<213> ORGANISM: Homo sapiens

<400> SEQUENCE: 149

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
            35                  40                  45

Ser Arg Ile Ser His Glu Asn Gly Thr Ile Leu Cys Ser Lys Gly Ser
        50                  55                  60

Thr Cys Tyr Gly Leu Trp Glu Lys Ser Lys Gly Asp Ile Asn Leu Val
65              70                  75                  80

Lys Gln Gly Cys Trp Ser His Ile Gly Asp Pro Gln Glu Cys His Tyr
                85                  90                  95

Glu Glu Cys Val Val Thr Thr Thr Pro Pro Ser Ile Gln Asn Gly Thr
            100                 105                 110

Tyr Arg Phe Cys Cys Cys Ser Thr Asp Leu Cys Asn Val Asn Phe Thr
            115                 120                 125

Glu Asn Phe Pro Pro Pro Asp Thr Thr Pro Leu Ser Pro Pro His Ser
            130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
            195                 200                 205

Ile Gly Arg Gly Arg Tyr Gly Ala Val Tyr Lys Gly Ser Leu Asp Glu
```

```
                210                 215                 220
Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255

Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
        275                 280                 285

Lys Tyr Leu Ser Leu His Thr Ser Asp Trp Val Ser Ser Cys Arg Leu
    290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
                325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
        355                 360                 365

Glu Asp Asn Ala Ala Ile Ser Glu Val Gly Thr Ile Arg Tyr Met Ala
    370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
                405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
        435                 440                 445

Met Gln Val Leu Val Ser Arg Glu Lys Gln Arg Pro Lys Phe Pro Glu
    450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
                485                 490                 495

Ala Glu Glu Arg Met Ala Glu Leu Met Met Ile Trp Gly Arg Asn Lys
            500                 505                 510

Ser Val Ser Pro Thr Val Asn Pro Met Ser Thr Ala Met Gln Asn Glu
        515                 520                 525

Arg Arg
    530

<210> SEQ ID NO 150
<211> LENGTH: 124
<212> TYPE: PRT
<213> ORGANISM: Homo sapiens

<400> SEQUENCE: 150

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45
```

```
Gly Asp Ile Asn Leu Val Lys Gln Gly Cys Trp Ser His Ile Gly Asp
         50                  55                  60

Pro Gln Glu Cys His Tyr Glu Glu Cys Val Val Thr Thr Thr Pro Pro
 65                  70                  75                  80

Ser Ile Gln Asn Gly Thr Tyr Arg Phe Cys Cys Cys Ser Thr Asp Leu
                 85                  90                  95

Cys Asn Val Asn Phe Thr Glu Asn Phe Pro Pro Pro Asp Thr Thr Pro
                100                 105                 110

Leu Ser Pro Pro His Ser Phe Asn Arg Asp Glu Thr
                115                 120
```

<210> SEQ ID NO 151
<211> LENGTH: 124
<212> TYPE: PRT
<213> ORGANISM: Homo sapiens

<400> SEQUENCE: 151

```
Ser Gln Asn Gln Glu Arg Leu Cys Ala Phe Lys Asp Pro Tyr Gln Gln
 1                   5                  10                  15

Asp Leu Gly Ile Gly Glu Ser Arg Ile Ser His Glu Asn Gly Thr Ile
                 20                  25                  30

Leu Cys Ser Lys Gly Ser Thr Cys Tyr Gly Leu Trp Glu Lys Ser Lys
                 35                  40                  45

Gly Asp Ile Asn Leu Val Lys Gln Gly Cys Trp Ser His Ile Gly Asp
         50                  55                  60

Pro Gln Glu Cys His Tyr Glu Glu Cys Val Val Thr Thr Thr Pro Pro
 65                  70                  75                  80

Ser Ile Gln Asn Gly Thr Tyr Arg Phe Cys Cys Cys Ser Thr Asp Leu
                 85                  90                  95

Cys Asn Val Asn Phe Thr Glu Asn Phe Pro Pro Pro Asp Thr Thr Pro
                100                 105                 110

Leu Ser Pro Pro His Ser Phe Asn Arg Asp Glu Thr
                115                 120
```

<210> SEQ ID NO 152
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Met Asp Ala Met Lys Arg Gly Leu Cys Cys Val Leu Leu Leu Cys Gly
 1                   5                  10                  15

Ala Val Phe Val Ser Pro Gly Ala Ser Gln Asn Gln Glu Arg Leu Cys
                 20                  25                  30

Ala Phe Lys Asp Pro Tyr Gln Gln Asp Leu Gly Ile Gly Glu Ser Arg
                 35                  40                  45

Ile Ser His Glu Asn Gly Thr Ile Leu Cys Ser Lys Gly Ser Thr Cys
         50                  55                  60

Tyr Gly Leu Trp Glu Lys Ser Lys Gly Asp Ile Asn Leu Val Lys Gln
 65                  70                  75                  80

Gly Cys Trp Ser His Ile Gly Asp Pro Gln Glu Cys His Tyr Glu Glu
                 85                  90                  95

Cys Val Val Thr Thr Thr Pro Pro Ser Ile Gln Asn Gly Thr Tyr Arg
                100                 105                 110
```

```
Phe Cys Cys Cys Ser Thr Asp Leu Cys Asn Val Asn Phe Thr Glu Asn
            115                 120                 125
Phe Pro Pro Pro Asp Thr Thr Pro Leu Ser Pro His Ser Phe Asn
130                 135                 140
Arg Asp Glu Thr Gly Gly Gly Thr His Thr Cys Pro Pro Cys Pro Ala
145                 150                 155                 160
Pro Glu Leu Leu Gly Gly Pro Ser Val Phe Leu Phe Pro Pro Lys Pro
            165                 170                 175
Lys Asp Thr Leu Met Ile Ser Arg Thr Pro Glu Val Thr Cys Val Val
            180                 185                 190
Val Asp Val Ser His Glu Asp Pro Glu Val Lys Phe Asn Trp Tyr Val
            195                 200                 205
Asp Gly Val Glu Val His Asn Ala Lys Thr Lys Pro Arg Glu Glu Gln
            210                 215                 220
Tyr Asn Ser Thr Tyr Arg Val Val Ser Val Leu Thr Val Leu His Gln
225                 230                 235                 240
Asp Trp Leu Asn Gly Lys Glu Tyr Lys Cys Lys Val Ser Asn Lys Ala
            245                 250                 255
Leu Pro Ala Pro Ile Glu Lys Thr Ile Ser Lys Ala Lys Gly Gln Pro
            260                 265                 270
Arg Glu Pro Gln Val Tyr Thr Leu Pro Pro Ser Arg Lys Glu Met Thr
            275                 280                 285
Lys Asn Gln Val Ser Leu Thr Cys Leu Val Lys Gly Phe Tyr Pro Ser
            290                 295                 300
Asp Ile Ala Val Glu Trp Glu Ser Asn Gly Gln Pro Glu Asn Asn Tyr
305                 310                 315                 320
Lys Thr Thr Pro Pro Val Leu Lys Ser Asp Gly Ser Phe Phe Leu Tyr
            325                 330                 335
Ser Lys Leu Thr Val Asp Lys Ser Arg Trp Gln Gln Gly Asn Val Phe
            340                 345                 350
Ser Cys Ser Val Met His Glu Ala Leu His Asn His Tyr Thr Gln Lys
            355                 360                 365
Ser Leu Ser Leu Ser Pro Gly Lys
            370                 375

<210> SEQ ID NO 153
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ser Gln Asn Gln Glu Arg Leu Cys Ala Phe Lys Asp Pro Tyr Gln Gln
1               5                   10                  15
Asp Leu Gly Ile Gly Glu Ser Arg Ile Ser His Glu Asn Gly Thr Ile
            20                  25                  30
Leu Cys Ser Lys Gly Ser Thr Cys Tyr Gly Leu Trp Glu Lys Ser Lys
            35                  40                  45
Gly Asp Ile Asn Leu Val Lys Gln Gly Cys Trp Ser His Ile Gly Asp
50                  55                  60
Pro Gln Glu Cys His Tyr Glu Glu Cys Val Val Thr Thr Pro Pro Pro
65                  70                  75                  80
Ser Ile Gln Asn Gly Thr Tyr Arg Phe Cys Cys Cys Ser Thr Asp Leu
            85                  90                  95
```

```
Cys Asn Val Asn Phe Thr Glu Asn Phe Pro Pro Asp Thr Thr Pro
                100                 105                 110

Leu Ser Pro Pro His Ser Phe Asn Arg Asp Glu Thr Gly Gly Thr
            115                 120                 125

His Thr Cys Pro Pro Cys Pro Ala Pro Glu Leu Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Lys Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Lys
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 154

<400> SEQUENCE: 154

000

<210> SEQ ID NO 155

<400> SEQUENCE: 155

000

<210> SEQ ID NO 156
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
            20                  25                  30
```

```
Ala Phe Lys Asp Pro Tyr Gln Gln Asp Leu Gly Ile Gly Glu Ser Arg
         35                  40                  45

Ile Ser His Glu Asn Gly Thr Ile Leu Cys Ser Lys Gly Ser Thr Cys
 50                  55                  60

Tyr Gly Leu Trp Glu Lys Ser Lys Gly Asp Ile Asn Leu Val Lys Gln
 65                  70                  75                  80

Gly Cys Trp Ser His Ile Gly Asp Pro Gln Glu Cys His Tyr Glu Glu
                 85                  90                  95

Cys Val Val Thr Thr Thr Pro Pro Ser Ile Gln Asn Gly Thr Tyr Arg
            100                 105                 110

Phe Cys Cys Cys Ser Thr Asp Leu Cys Asn Val Asn Phe Thr Glu Asn
            115                 120                 125

Phe Pro Pro Pro Asp Thr Thr Pro Leu Ser Pro His Ser Phe Asn
        130                 135                 140

Arg Asp Glu Thr Gly Gly Gly Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
        210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Cys Arg Glu Glu Met Thr
        275                 280                 285

Lys Asn Gln Val Ser Leu Trp Cys Leu Val Lys Gly Phe Tyr Pro Ser
        290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
    370                 375

<210> SEQ ID NO 157
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ser Gln Asn Gln Glu Arg Leu Cys Ala Phe Lys Asp Pro Tyr Gln Gln
```

```
               1               5                  10                 15
            Asp Leu Gly Ile Gly Glu Ser Arg Ile Ser His Glu Asn Gly Thr Ile
                           20                 25                 30

Leu Cys Ser Lys Gly Ser Thr Cys Tyr Gly Leu Trp Glu Lys Ser Lys
                           35                 40                 45

Gly Asp Ile Asn Leu Val Lys Gln Gly Cys Trp Ser His Ile Gly Asp
                50                 55                 60

Pro Gln Glu Cys His Tyr Glu Glu Cys Val Val Thr Thr Thr Pro Pro
            65                 70                 75                 80

Ser Ile Gln Asn Gly Thr Tyr Arg Phe Cys Cys Ser Thr Asp Leu
                           85                 90                 95

Cys Asn Val Asn Phe Thr Glu Asn Phe Pro Pro Asp Thr Thr Pro
                          100                105                110

Leu Ser Pro Pro His Ser Phe Asn Arg Asp Thr Gly Gly Gly Thr
                          115                120                125

His Thr Cys Pro Pro Cys Pro Ala Pro Glu Leu Leu Gly Gly Pro Ser
                          130                135                140

Val Phe Leu Phe Pro Pro Lys Pro Lys Asp Thr Leu Met Ile Ser Arg
            145                150                155                160

Thr Pro Glu Val Thr Cys Val Val Val Asp Val Ser His Glu Asp Pro
                          165                170                175

Glu Val Lys Phe Asn Trp Tyr Val Asp Gly Val Glu Val His Asn Ala
                          180                185                190

Lys Thr Lys Pro Arg Glu Glu Gln Tyr Asn Ser Thr Tyr Arg Val Val
                          195                200                205

Ser Val Leu Thr Val Leu His Gln Asp Trp Leu Asn Gly Lys Glu Tyr
                210                215                220

Lys Cys Lys Val Ser Asn Lys Ala Leu Pro Ala Pro Ile Glu Lys Thr
            225                230                235                240

Ile Ser Lys Ala Lys Gly Gln Pro Arg Glu Pro Gln Val Tyr Thr Leu
                          245                250                255

Pro Pro Cys Arg Glu Glu Met Thr Lys Asn Gln Val Ser Leu Trp Cys
                          260                265                270

Leu Val Lys Gly Phe Tyr Pro Ser Asp Ile Ala Val Glu Trp Glu Ser
                          275                280                285

Asn Gly Gln Pro Glu Asn Asn Tyr Lys Thr Thr Pro Pro Val Leu Asp
                290                295                300

Ser Asp Gly Ser Phe Phe Leu Tyr Ser Lys Leu Thr Val Asp Lys Ser
            305                310                315                320

Arg Trp Gln Gln Gly Asn Val Phe Ser Cys Ser Val Met His Glu Ala
                          325                330                335

Leu His Asn His Tyr Thr Gln Lys Ser Leu Ser Leu Ser Pro Gly Lys
                          340                345                350

<210> SEQ ID NO 158

<400> SEQUENCE: 158

000

<210> SEQ ID NO 159

<400> SEQUENCE: 159

000
```

<210> SEQ ID NO 160
<211> LENGTH: 592
<212> TYPE: PRT
<213> ORGANISM: Homo sapiens

<400> SEQUENCE: 160

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380
```

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
            405                 410                 415

Thr Cys Cys Leu Cys Asp Phe Gly Leu Ser Leu Arg Leu Asp Pro Thr
        420                 425                 430

Leu Ser Val Asp Asp Leu Ala Asn Ser Gly Gln Val Gly Thr Ala Arg
    435                 440                 445

Tyr Met Ala Pro Glu Val Leu Glu Ser Arg Met Asn Leu Glu Asn Val
450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 161
<211> LENGTH: 567
<212> TYPE: PRT
<213> ORGANISM: Homo sapiens

<400> SEQUENCE: 161

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu 165                 170                 175
Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
            210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
                275                 280                 285

Thr Glu Lys Asp Ile Phe Ser Asp Ile Asn Leu Lys His Glu Asn Ile
            290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
            370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
            450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
                515                 520                 525

Leu Thr Ala Gln Cys Val Ala Glu Arg Phe Ser Glu Leu Glu His Leu
            530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 162

```
<211> LENGTH: 144
<212> TYPE: PRT
<213> ORGANISM: Homo sapiens

<400> SEQUENCE: 162

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140

<210> SEQ ID NO 163
<211> LENGTH: 169
<212> TYPE: PRT
<213> ORGANISM: Homo sapiens

<400> SEQUENCE: 163

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Leu Leu Leu Val Ile Phe Gln
                165

<210> SEQ ID NO 164
<211> LENGTH: 390
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 164

Met Asp Ala Met Lys Arg Gly Leu Cys Cys Val Leu Leu Leu Cys Gly
1               5                   10                  15

Ala Val Phe Val Ser Pro Gly Ala Thr Ile Pro His Val Gln Lys
            20                  25                  30

Ser Val Asn Asn Asp Met Ile Val Thr Asp Asn Asn Gly Ala Val Lys
            35                  40                  45

Phe Pro Gln Leu Cys Lys Phe Cys Asp Val Arg Phe Ser Thr Cys Asp
50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
                100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
        210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Lys Glu Met Thr Lys Asn
        290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Lys Ser Asp Gly Ser Phe Phe Leu Tyr Ser Lys
            340                 345                 350

Leu Thr Val Asp Lys Ser Arg Trp Gln Gln Gly Asn Val Phe Ser Cys
            355                 360                 365

Ser Val Met His Glu Ala Leu His Asn His Tyr Thr Gln Lys Ser Leu
370                 375                 380

Ser Leu Ser Pro Gly Lys
```

385            390

<210> SEQ ID NO 165
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Lys Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Tyr Lys Thr Thr Pro Pro Val Leu Lys Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

```
Asn His Tyr Thr Gln Lys Ser Leu Ser Leu Ser Pro Gly Lys
        355                 360                 365

<210> SEQ ID NO 166
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Asp Ala Met Lys Arg Gly Leu Cys Cys Val Leu Leu Cys Gly
1               5                   10                  15

Ala Val Phe Val Ser Pro Gly Ala Thr Ile Pro His Val Gln Lys
                20                  25                  30

Ser Asp Val Glu Met Glu Ala Gln Lys Asp Glu Ile Ile Cys Pro Ser
                35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
                100                 105                 110

Ala Val Trp Arg Lys Asn Asp Glu Asn Ile Thr Leu Glu Thr Val Cys
                115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Thr His
                180                 185                 190

Thr Cys Pro Pro Cys Pro Ala Pro Glu Leu Leu Gly Gly Pro Ser Val
    195                 200                 205

Phe Leu Phe Pro Pro Lys Pro Lys Asp Thr Leu Met Ile Ser Arg Thr
210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
            275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Lys Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
                340                 345                 350
```

```
Gly Gln Pro Glu Asn Asn Tyr Lys Thr Thr Pro Pro Val Leu Lys Ser
            355                 360                 365

Asp Gly Ser Phe Phe Leu Tyr Ser Lys Leu Thr Val Asp Lys Ser Arg
    370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 167
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Thr Gly Gly Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
    210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Ser Arg Lys Glu Met Thr Lys
```

```
                290                 295                 300
Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Lys Ser Asp Gly Ser Phe Phe Leu Tyr Ser
                340                 345                 350

Lys Leu Thr Val Asp Lys Ser Arg Trp Gln Gln Gly Asn Val Phe Ser
            355                 360                 365

Cys Ser Val Met His Glu Ala Leu His Asn His Tyr Thr Gln Lys Ser
        370                 375                 380

Leu Ser Leu Ser Pro Gly Lys
385                 390

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Met Asp Ala Met Lys Arg Gly Leu Cys Cys Val Leu Leu Leu Cys Gly
1               5                   10                  15

Ala Val Phe Val Ser Pro Gly Ala Thr Ile Pro His Val Gln Lys
                20                  25                  30

Ser Val Asn Asn Asp Met Ile Val Thr Asp Asn Asn Gly Ala Val Lys
            35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
                100                 105                 110
```

```
Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
        130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
                180                 185                 190

Thr Leu Met Ile Ser Arg Thr Pro Glu Val Thr Cys Val Val Val Asp
            195                 200                 205

Val Ser His Glu Asp Pro Glu Val Lys Phe Asn Trp Tyr Val Asp Gly
        210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
                260                 265                 270

Ala Pro Ile Glu Lys Thr Ile Ser Lys Ala Lys Gly Gln Pro Arg Glu
            275                 280                 285

Pro Gln Val Tyr Thr Leu Pro Pro Cys Arg Glu Glu Met Thr Lys Asn
        290                 295                 300

Gln Val Ser Leu Trp Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
                340                 345                 350

Leu Thr Val Asp Lys Ser Arg Trp Gln Gln Gly Asn Val Phe Ser Cys
            355                 360                 365

Ser Val Met His Glu Ala Leu His Asn His Tyr Thr Gln Lys Ser Leu
        370                 375                 380

Ser Leu Ser Pro Gly Lys
385                 390

<210> SEQ ID NO 173
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
```

```
                65                  70                  75                  80
Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
               100                 105                 110

Met Cys Ser Cys Ser Ser Asp Glu Cys Asn Asp Asn Ile Ile Phe Ser
               115                 120                 125

Glu Glu Tyr Asn Thr Ser Asn Pro Asp Thr Gly Gly Thr His Thr
   130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
               180                 185                 190

Lys Phe Asn Trp Tyr Val Asp Gly Val Glu Val His Asn Ala Lys Thr
           195                 200                 205

Lys Pro Arg Glu Glu Gln Tyr Asn Ser Thr Tyr Arg Val Val Ser Val
   210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
           260                 265                 270

Cys Arg Glu Glu Met Thr Lys Asn Gln Val Ser Leu Trp Cys Leu Val
       275                 280                 285

Lys Gly Phe Tyr Pro Ser Asp Ile Ala Val Glu Trp Glu Ser Asn Gly
   290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
           340                 345                 350

Asn His Tyr Thr Gln Lys Ser Leu Ser Leu Ser Pro Gly Lys
   355                 360                 365

<210> SEQ ID NO 174
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
                20                  25                  30

Ser Asp Val Glu Met Glu Ala Gln Lys Asp Glu Ile Ile Cys Pro Ser
            35                  40                  45

Cys Asn Arg Thr Ala His Pro Leu Arg His Ile Asn Asn Asp Met Ile
        50                  55                  60
```

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
            85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
            115                 120                 125

His Asp Pro Lys Leu Pro Tyr His Asp Phe Ile Leu Glu Asp Ala Ala
            130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
            165                 170                 175

Ser Glu Glu Tyr Asn Thr Ser Asn Pro Asp Thr Gly Gly Thr His
            180                 185                 190

Thr Cys Pro Pro Cys Pro Ala Pro Glu Leu Leu Gly Gly Pro Ser Val
        195                 200                 205

Phe Leu Phe Pro Pro Lys Pro Lys Asp Thr Leu Met Ile Ser Arg Thr
210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
            245                 250                 255

Thr Lys Pro Arg Glu Glu Gln Tyr Asn Ser Thr Tyr Arg Val Val Ser
        260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
290                 295                 300

Ser Lys Ala Lys Gly Gln Pro Arg Glu Pro Gln Val Tyr Thr Leu Pro
305                 310                 315                 320

Pro Cys Arg Glu Glu Met Thr Lys Asn Gln Val Ser Leu Trp Cys Leu
            325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
            355                 360                 365

Asp Gly Ser Phe Phe Leu Tyr Ser Lys Leu Thr Val Asp Lys Ser Arg
370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
            405                 410                 415

<210> SEQ ID NO 175
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Thr Ile Pro Pro His Val Gln Lys Ser Asp Val Glu Met Glu Ala Gln
1               5                   10                  15

```
Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Thr Gly Gly Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
    210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Cys Arg Glu Glu Met Thr Lys
    290                 295                 300

Asn Gln Val Ser Leu Trp Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
    370                 375                 380

Leu Ser Leu Ser Pro Gly Lys
385                 390

<210> SEQ ID NO 176

<400> SEQUENCE: 176

000
```

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180
<211> LENGTH: 573
<212> TYPE: PRT
<213> ORGANISM: Homo sapiens

<400> SEQUENCE: 180

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
```

```
              260                 265                 270
    Ser Gly Pro Leu Leu Val Leu Glu Leu His Pro Lys Gly Ser Leu Cys
                275                 280                 285

His Tyr Leu Thr Gln Tyr Thr Ser Asp Trp Gly Ser Ser Leu Arg Met
                290                 295                 300

Ala Leu Ser Leu Ala Gln Gly Leu Ala Phe Leu His Glu Glu Arg Trp
    305                 310                 315                 320

Gln Asn Gly Gln Tyr Lys Pro Gly Ile Ala His Arg Asp Leu Ser Ser
                    325                 330                 335

Gln Asn Val Leu Ile Arg Glu Asp Gly Ser Cys Ala Ile Gly Asp Leu
                340                 345                 350

Gly Leu Ala Leu Val Leu Pro Gly Leu Thr Gln Pro Pro Ala Trp Thr
                355                 360                 365

Pro Thr Gln Pro Gln Gly Pro Ala Ala Ile Met Glu Ala Gly Thr Gln
                370                 375                 380

Arg Tyr Met Ala Pro Glu Leu Leu Asp Lys Thr Leu Asp Leu Gln Asp
    385                 390                 395                 400

Trp Gly Met Ala Leu Arg Arg Ala Asp Ile Tyr Ser Leu Ala Leu Leu
                    405                 410                 415

Leu Trp Glu Ile Leu Ser Arg Cys Pro Asp Leu Arg Pro Asp Ser Ser
                420                 425                 430

Pro Pro Pro Phe Gln Leu Ala Tyr Glu Ala Glu Leu Gly Asn Thr Pro
                435                 440                 445

Thr Ser Asp Glu Leu Trp Ala Leu Ala Val Gln Glu Arg Arg Arg Pro
    450                 455                 460

Tyr Ile Pro Ser Thr Trp Arg Cys Phe Ala Thr Asp Pro Asp Gly Leu
    465                 470                 475                 480

Arg Glu Leu Leu Glu Asp Cys Trp Asp Ala Asp Pro Glu Ala Arg Leu
                    485                 490                 495

Thr Ala Glu Cys Val Gln Gln Arg Leu Ala Ala Leu Ala His Pro Gln
                500                 505                 510

Glu Ser His Pro Phe Pro Glu Ser Cys Pro Arg Gly Cys Pro Pro Leu
                515                 520                 525

Cys Pro Glu Asp Cys Thr Ser Ile Pro Ala Pro Thr Ile Leu Pro Cys
                530                 535                 540

Arg Pro Gln Arg Ser Ala Cys His Phe Ser Val Gln Gln Gly Pro Cys
    545                 550                 555                 560

Ser Arg Asn Pro Gln Pro Ala Cys Thr Leu Ser Pro Val
                    565                 570

<210> SEQ ID NO 181
<211> LENGTH: 478
<212> TYPE: PRT
<213> ORGANISM: Homo sapiens

<400> SEQUENCE: 181

Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
                20                  25                  30

Arg Gly Ser Thr Lys Thr Leu Gly Glu Leu Leu Asp Thr Gly Thr Glu
            35                  40                  45

Leu Pro Arg Ala Ile Arg Cys Leu Tyr Ser Arg Cys Cys Phe Gly Ile
        50                  55                  60
```

```
Trp Asn Leu Thr Gln Asp Arg Ala Gln Val Glu Met Gln Gly Cys Arg
 65                  70                  75                  80

Asp Ser Asp Glu Pro Gly Cys Glu Ser Leu His Cys Asp Pro Ser Pro
                 85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Ala Gly Thr Gln
    370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
                405                 410                 415

Leu Trp Glu Ile Leu Ser Arg Cys Pro Asp Leu Arg Pro Ala Val His
            420                 425                 430

His Pro Ser Asn Trp Pro Met Arg Gln Asn Trp Ala Ile Pro Leu Pro
        435                 440                 445

Leu Met Ser Tyr Gly Pro Trp Gln Cys Arg Arg Gly Gly Val Pro Thr
    450                 455                 460

Ser His Pro Pro Gly Ala Ala Leu Pro Gln Thr Leu Met Gly
465                 470                 475
```

```
<210> SEQ ID NO 182
<211> LENGTH: 478
<212> TYPE: PRT
<213> ORGANISM: Homo sapiens

<400> SEQUENCE: 182

Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Asp Pro Asp Gly
    370                 375                 380
```

```
Leu Arg Glu Leu Leu Glu Asp Cys Trp Asp Ala Asp Pro Glu Ala Arg
385                 390                 395                 400

Leu Thr Ala Glu Cys Val Gln Gln Arg Leu Ala Leu Ala His Pro
            405                 410                 415

Gln Glu Ser His Pro Phe Pro Glu Ser Cys Pro Arg Gly Cys Pro Pro
            420                 425                 430

Leu Cys Pro Glu Asp Cys Thr Ser Ile Pro Ala Pro Thr Ile Leu Pro
            435                 440                 445

Cys Arg Pro Gln Arg Ser Ala Cys His Phe Ser Val Gln Gln Gly Pro
            450                 455                 460

Cys Ser Arg Asn Pro Gln Pro Ala Cys Thr Leu Ser Pro Val
465                 470                 475

<210> SEQ ID NO 183
<211> LENGTH: 132
<212> TYPE: PRT
<213> ORGANISM: Homo sapiens

<400> SEQUENCE: 183

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu
    130

<210> SEQ ID NO 184
<211> LENGTH: 132
<212> TYPE: PRT
<213> ORGANISM: Homo sapiens

<400> SEQUENCE: 184

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95
```

```
Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu
        130

<210> SEQ ID NO 185
<211> LENGTH: 132
<212> TYPE: PRT
<213> ORGANISM: Homo sapiens

<400> SEQUENCE: 185

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
            85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu
        130

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000
```

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194
<211> LENGTH: 567
<212> TYPE: PRT
<213> ORGANISM: Homo sapiens

<400> SEQUENCE: 194

```
Met Gly Arg Gly Leu Arg Gly Leu Trp Pro Leu His Ile Val Leu
 1               5                  10                  15

Trp Thr Arg Ile Ala Ser Thr Ile Pro Pro His Val Gln Lys Ser Val
                 20                  25                  30

Asn Asn Asp Met Ile Val Thr Asp Asn Asn Gly Ala Val Lys Phe Pro
                 35                  40                  45

Gln Leu Cys Lys Phe Cys Asp Val Arg Phe Ser Thr Cys Asp Asn Gln
     50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
                115                 120                 125

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
                180                 185                 190

Arg Gln Gln Lys Leu Ser Ser Thr Trp Glu Thr Gly Lys Thr Arg Lys
                195                 200                 205

Leu Met Glu Phe Ser Glu His Cys Ala Ile Ile Leu Glu Asp Asp Arg
            210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270
```

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
        290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 195
<211> LENGTH: 144
<212> TYPE: PRT
<213> ORGANISM: Homo sapiens

<400> SEQUENCE: 195

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His

```
                65                  70                  75                  80
Asp Pro Lys Leu Pro Tyr His Asp Phe Ile Leu Glu Asp Ala Ala Ser
                    85                  90                  95
Pro Lys Cys Ile Met Lys Glu Lys Lys Lys Pro Gly Glu Thr Phe Phe
                100                 105                 110
Met Cys Ser Cys Ser Ser Asp Glu Cys Asn Asp Asn Ile Ile Phe Ser
                115                 120                 125
Glu Glu Tyr Asn Thr Ser Asn Pro Asp Leu Leu Leu Val Ile Phe Gln
                130                 135                 140
```

<210> SEQ ID NO 196
<211> LENGTH: 1701
<212> TYPE: DNA
<213> ORGANISM: Homo sapiens

<400> SEQUENCE: 196

| | | |
|---|---|---|
| atgggtcggg ggctgctcag gggcctgtgg ccgctgcaca tcgtcctgtg acgcgtatc | | 60 |
| gccagcacga tcccaccgca cgttcagaag tcggttaata cgacatgat agtcactgac | | 120 |
| aacaacggtg cagtcaagtt tccacaactg tgtaaatttt gtgatgtgag attttccacc | | 180 |
| tgtgacaacc agaaatcctg catgagcaac tgcagcatca cctccatctg tgagaagcca | | 240 |
| caggaagtct gtgtggctgt atggagaaag aatgacgaga acataacact agagacagtt | | 300 |
| tgccatgacc ccaagctccc ctaccatgac tttattctgg aagatgctgc ttctccaaag | | 360 |
| tgcattatga aggaaaaaaa aaagcctggt gagactttct tcatgtgttc ctgtagctct | | 420 |
| gatgagtgca atgacaacat catcttctca gaagaatata acaccagcaa tcctgacttg | | 480 |
| ttgctagtca tatttcaagt gacaggcatc agcctcctgc caccactggg agttgccata | | 540 |
| tctgtcatca tcatcttcta ctgctaccgc gttaaccggc agcagaagct gagttcaacc | | 600 |
| tgggaaaccg gcaagacgcg gaagctcatg gagttcagcg agcactgtgc catcatcctg | | 660 |
| gaagatgacc gctctgacat cagctccacg tgtgccaaca catcaacca aacacagag | | 720 |
| ctgctgccca ttgagctgga caccctggtg ggaaaggtc gctttgctga ggtctataag | | 780 |
| gccaagctga agcagaacac ttcagagcag tttgagacag tggcagtcaa gatctttccc | | 840 |
| tatgaggagt atgcctcttg gaagacagag aaggacatct tctcagacat caatctgaag | | 900 |
| catgagaaca tactccagtt cctgacggct gaggagcgga agacggagtt ggggaaacaa | | 960 |
| tactggctga tcaccgcctt ccacgccaag ggcaacctac aggagtacct gacgcggcat | | 1020 |
| gtcatcagct gggaggacct gcgcaagctg gcagctccc tcgcccgggg gattgctcac | | 1080 |
| ctccacagtg atcacactcc atgtgggagg cccaagatgc catcgtgca cagggacctc | | 1140 |
| aagagctcca atatcctcgt gaagaacgac ctaacctgct gcctgtgtga ctttgggctt | | 1200 |
| tccctgcgtc tggaccctac tctgtctgtg gatgacctgg ctaacagtgg gcaggtggga | | 1260 |
| actgcaagat acatggctcc agaagtccta gaatccagga tgaatttgga gaatgttgag | | 1320 |
| tccttcaagc agaccgatgt ctactccatg gctctggtgc tctgggaaat gacatctcgc | | 1380 |
| tgtaatgcag tgggagaagt aaaagattat gagcctccat ttggttccaa ggtgcgggag | | 1440 |
| caccctgtg tcgaaagcat gaaggacaac gtgttgagag atcgagggcg accagaaatt | | 1500 |
| cccagcttct ggctcaacca ccagggcatc cagatggtgt gtgagacgtt gactgagtgc | | 1560 |
| tgggaccacg acccagaggc ccgtctcaca gcccagtgtg tggcagaacg cttcagtgag | | 1620 |
| ctggagcatc tggacaggct ctcggggagg agctgctcgg aggagaagat tcctgaagac | | 1680 |
| ggctccctaa acactaccaa a | | 1701 |

<210> SEQ ID NO 197
<211> LENGTH: 432
<212> TYPE: DNA
<213> ORGANISM: Homo sapiens

<400> SEQUENCE: 197

```
acgatcccac cgcacgttca gaagtcggtt aataacgaca tgatagtcac tgacaacaac    60
ggtgcagtca agtttccaca actgtgtaaa ttttgtgatg tgagattttc cacctgtgac   120
aaccagaaat cctgcatgag caactgcagc atcacctcca tctgtgagaa gccacaggaa   180
gtctgtgtgg ctgtatggag aaagaatgac gagaacataa cactagagac agtttgccat   240
gaccccaagc tcccctacca tgactttatt ctggaagatg ctgcttctcc aaagtgcatt   300
atgaaggaaa aaaaaaagcc tggtgagact ttcttcatgt gttcctgtag ctctgatgag   360
tgcaatgaca acatcatctt ctcagaagaa tataacacca gcaatcctga cttgttgcta   420
gtcatatttc aa                                                       432
```

<210> SEQ ID NO 198
<211> LENGTH: 592
<212> TYPE: PRT
<213> ORGANISM: Homo sapiens

<400> SEQUENCE: 198

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
```

```
                    245                 250                 255
Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
            325                 330                 335

Glu Arg Lys Thr Glu Leu Gly Lys Gln Tyr Trp Leu Ile Thr Ala Phe
        340                 345                 350

His Ala Lys Gly Asn Leu Gln Glu Tyr Leu Thr Arg His Val Ile Ser
    355                 360                 365

Trp Glu Asp Leu Arg Lys Leu Gly Ser Ser Leu Ala Arg Gly Ile Ala
370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
            405                 410                 415

Thr Cys Cys Leu Cys Asp Phe Gly Leu Ser Leu Arg Leu Asp Pro Thr
        420                 425                 430

Leu Ser Val Asp Asp Leu Ala Asn Ser Gly Gln Val Gly Thr Ala Arg
    435                 440                 445

Tyr Met Ala Pro Glu Val Leu Glu Ser Arg Met Asn Leu Glu Asn Val
450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
            485                 490                 495

Pro Pro Phe Gly Ser Lys Val Arg Glu His Pro Cys Val Glu Ser Met
        500                 505                 510

Lys Asp Asn Val Leu Arg Asp Arg Gly Arg Pro Glu Ile Pro Ser Phe
    515                 520                 525

Trp Leu Asn His Gln Gly Ile Gln Met Val Cys Glu Thr Leu Thr Glu
530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
            565                 570                 575

Cys Ser Glu Glu Lys Ile Pro Glu Asp Gly Ser Leu Asn Thr Thr Lys
        580                 585                 590

<210> SEQ ID NO 199
<211> LENGTH: 169
<212> TYPE: PRT
<213> ORGANISM: Homo sapiens

<400> SEQUENCE: 199

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30
```

```
Arg His Ile Asn Asn Asp Met Ile Val Thr Asp Asn Asn Gly Ala Val
             35                  40                  45

Lys Phe Pro Gln Leu Cys Lys Phe Cys Asp Val Arg Phe Ser Thr Cys
 50                  55                  60

Asp Asn Gln Lys Ser Cys Met Ser Asn Cys Ser Ile Thr Ser Ile Cys
 65                  70                  75                  80

Glu Lys Pro Gln Glu Val Cys Val Ala Val Trp Arg Lys Asn Asp Glu
                 85                  90                  95

Asn Ile Thr Leu Glu Thr Val Cys His Asp Pro Lys Leu Pro Tyr His
                100                 105                 110

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr Asn Thr Ser Asn
145                 150                 155                 160

Pro Asp Leu Leu Leu Val Ile Phe Gln
                165
```

<210> SEQ ID NO 200

<400> SEQUENCE: 200

000

<210> SEQ ID NO 201

<400> SEQUENCE: 201

000

<210> SEQ ID NO 202
<211> LENGTH: 1776
<212> TYPE: DNA
<213> ORGANISM: Homo sapiens

<400> SEQUENCE: 202

```
atgggtcggg ggctgctcag gggcctgtgg ccgctgcaca tcgtcctgtg gacgcgtatc      60
gccagcacga tcccaccgca cgttcagaag tcggatgtgg aaatggaggc cagaaagat     120 gaaatcatct gccccagctg taataggact gcccatccac tgagacatat taataacgac     180
atgatagtca ctgacaacaa cggtgcagtc aagtttccac aactgtgtaa attttgtgat     240
gtgagatttt ccacctgtga caaccagaaa tcctgcatga gcaactgcag catcacctcc     300
atctgtgaga agccacagga agtctgtgtg ctgtatgga gaaagaatga cgagaacata     360
acactagaga cagtttgcca tgaccccaag ctcccctacc atgactttat tctggaagat     420
gctgcttctc caaagtgcat tatgaaggaa aaaaaaaagc ctggtgagac tttcttcatg     480
tgttcctgta gctctgatga gtgcaatgac aacatcatct ctcagaaga atataacacc     540 agcaatcctg acttgttgct agtcatattt caagtgacag gcatcagcct cctgccacca     600
ctgggagttg ccatatctgt catcatcatc ttctactgct accgcgttaa ccggcagcag     660
aagctgagtt caacctggga accggcaag acgcggaagc tcatggagtt cagcgagcac     720
tgtgccatca tcctggaaga tgaccgctct gacatcagct ccacgtgtgc caacaacatc     780
aaccacaaca cagagctgct gcccattgag ctggacaccc tggtggggaa aggtcgcttt     840
gctgaggtct ataaggccaa gctgaagcag aacacttcag agcagtttga gacagtggca     900
```

```
gtcaagatct ttccctatga ggagtatgcc tcttggaaga cagagaagga catcttctca    960
gacatcaatc tgaagcatga aacatactc cagttcctga cggctgagga gcggaagacg   1020
gagttgggga aacaatactg gctgatcacc gccttccacg ccaagggcaa cctacaggag   1080
tacctgacgc ggcatgtcat cagctgggag gacctgcgca agctgggcag ctccctcgcc   1140
cgggggattg ctcacctcca cagtgatcac actccatgtg ggaggcccaa gatgcccatc   1200
gtgcacaggg acctcaagag ctccaatatc ctcgtgaaga acgacctaac ctgctgcctg   1260
tgtgactttg gcttccct gcgtctggac cctactctgt ctgtggatga cctggctaac   1320
agtgggcagg tgggaactgc aagatacatg gctccagaag tcctagaatc caggatgaat   1380
ttggagaatg ttgagtcctt caagcagacc gatgtctact ccatggctct ggtgctctgg   1440
gaaatgacat ctcgctgtaa tgcagtggga gaagtaaaag attatgagcc tccatttggt   1500
tccaaggtgc gggagcaccc ctgtgtcgaa agcatgaagg acaacgtgtt gagagatcga   1560
gggcgaccag aaattcccag cttctggctc aaccaccagg gcatccagat ggtgtgtgag   1620
acgttgactg agtgctggga ccacgaccca gaggcccgtc tcacagccca gtgtgtggca   1680
gaacgcttca gtgagctgga gcatctggac aggctctcgg ggaggagctg ctcggaggag   1740
aagattcctg aagacggctc cctaaacact accaaa                            1776

<210> SEQ ID NO 203
<211> LENGTH: 507
<212> TYPE: DNA
<213> ORGANISM: Homo sapiens

<400> SEQUENCE: 203
acgatcccac cgcacgttca gaagtcggat gtggaaatgg aggcccagaa agatgaaatc     60
atctgcccca gctgtaatag gactgcccat ccactgagac atattaataa cgacatgata    120
gtcactgaca acaacggtgc agtcaagttt ccacaactgt gtaaattttg tgatgtgaga    180
ttttccacct gtgacaacca gaaatcctgc atgagcaact gcagcatcac ctccatctgt    240
gagaagccac aggaagtctg tgtggctgta tggagaaaga atgacgagaa cataacacta    300
gagacagttt gccatgaccc caagctcccc taccatgact ttattctgga agatgctgct    360
tctccaaagt gcattatgaa ggaaaaaaaa aagcctggtg agactttctt catgtgttcc    420
tgtagctctg atgagtgcaa tgacaacatc atcttctcag aagaatataa caccagcaat    480
cctgacttgt tgctagtcat atttcaa                                       507

<210> SEQ ID NO 204
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Arg Cys Lys Ile Arg His Ile Gly Ser Asn Asn Arg Leu Gln Arg
1               5                   10                  15

Ser Thr Cys Gln Asn Thr Gly Trp Glu Ser Ala His Val Met Lys Thr
            20                  25                  30

Pro Gly Phe Arg
        35

<210> SEQ ID NO 205
<211> LENGTH: 3114
```

```
<212> TYPE: DNA
<213> ORGANISM: Homo sapiens

<400> SEQUENCE: 205
atgacttcct cgctgcagcg gccctggcgg gtgccctggc taccatggac catcctgctg      60
gtcagcactg cggctgcttc gcagaatcaa gaacggctat gtgcgtttaa agatccgtat     120
cagcaagacc ttgggatagg tgagagtaga atctctcatg aaaatgggac aatattatgc     180
tcgaaaggta gcacctgcta tggcctttgg gagaaatcaa aagggacat aaatcttgta      240
aaacaaggat gttggtctca cattggagat ccccaagagt gtcactatga agaatgtgta     300
gtaactacca ctcctccctc aattcagaat ggaacatacc gtttctgctg ttgtagcaca     360
gatttatgta atgtcaactt tactgagaat tttccacctc ctgacacaac accactcagt     420
ccacctcatt catttaaccg agatgagaca ataatcattg ctttggcatc agtctctgta     480
ttagctgttt tgatagttgc cttatgcttt ggatacagaa tgttgacagg agaccgtaaa     540
caaggtcttc acagtatgaa catgatggag gcagcagcat ccgaaccctc tcttgatcta     600
gataatctga aactgttgga gctgattggc cgaggtcgat atggagcagt atataaaggc     660
tccttggatg agcgtccagt tgctgtaaaa gtgttttcct ttgcaaaccg tcagaatttt     720
atcaacgaaa agaacattta cagagtgcct ttgatggaac atgacaacat tgcccgcttt     780
atagttggag atgagagagt cactgcagat ggacgcatgg aatatttgct tgtgatggag     840
tactatccca atggatcttt atgcaagtat ttaagtctcc acacaagtga ctgggtaagc     900
tcttgccgtc ttgctcattc tgttactaga ggactggctt atcttcacac agaattacca     960
cgaggagatc attataaacc tgcaatttcc catcgagatt taaacagcag aaatgtccta    1020
gtgaaaaatg atggaacctg tgttattagt gactttggac tgtccatgag ctgactggaa    1080
aatagactgg tgcgcccagg ggaggaagat aatgcagcca taagcgaggt tggcactatc    1140
agatatatgg caccagaagt gctagaagga gctgtgaact tgagggactg tgaatcagct    1200
ttgaaacaag tagacatgta tgctcttgga ctaatctatt gggagatatt tatgagatgt    1260
acagacctct tcccagggga atccgtacca gagtaccaga tggcttttca gacagaggtt    1320
ggaaaccatc ccacttttga ggatatgcag gttctcgtgt ctagggaaaa acagagaccc    1380
aagttcccag aagcctggaa agaaaatagc ctggcagtga ggtcactcaa ggagacaatc    1440
gaagactgtt gggaccagga tgcagaggct cggcttactg cacagtgtgc tgaggaaagg    1500
atggctgaac ttatgatgat ttgggaaaga acaaatctg tgagcccaac agtcaatcca    1560
atgtctactg ctatgcagaa tgaacgcaac ctgtcacata taggcgtgt gccaaaaatt    1620
ggtccttatc cagattattc ttcctcctca tacattgaag actctatcca tcatactgac    1680
agcatcgtga agaatatttc ctctgagcat tctatgtcca gcacaccttt gactataggg    1740
gaaaaaaacc gaaattcaat taactatgaa cgacagcaag cacaagctcg aatccccagc    1800
cctgaaacaa gtgtcaccag cctctccacc aacacaacaa ccacaaacac cacaggactc    1860
acgccaagta ctggcatgac tactatatct gagatgccat acccagatga aacaaatctg    1920
cataccacaa atgttgcaca gtcaattggg ccaaccctg tctgcttaca gctgacagaa    1980
gaagacttgg aaaccaacaa gctagaccca aagaagttg ataagaacct caaggaaagc    2040
tctgatgaga atctcatgga gcactctctt aaacagttca gtggcccaga cccactgagc    2100
agtactagtt ctagccttgct ttacccactc ataaaacttg cagtagaagc aactggacag    2160
caggacttca cacagactgc aaatggccaa gcatgtttga ttcctgatgt tctgcctact    2220
```

```
cagatctatc ctctccccaa gcagcagaac cttcccaaga gacctactag tttgcctttg    2280
aacaccaaaa attcaacaaa agagccccgg ctaaaatttg gcagcaagca caaatcaaac    2340
ttgaaacaag tcgaaactgg agttgccaag atgaatacaa tcaatgcagc agaacctcat    2400
gtggtgacag tcaccatgaa tggtgtggca ggtagaaacc acagtgttaa ctcccatgct    2460
gccacaaccc aatatgccaa tgggacagta ctatctggcc aaacaaccaa catagtgaca    2520
catagggccc aagaaatgtt gcagaatcag tttattggtg aggacacccg gctgaatatt    2580
aattccagtc ctgatgagca tgagcctttta ctgagacgag agcaacaagc tggccatgat    2640
gaaggtgttc tggatcgtct tgtgacagg agggaacggc cactagaagg tggccgaact     2700
aattccaata caacaacag caatccatgt tcagaacaag atgttcttgc acagggtgtt     2760
ccaagcacag cagcagatcc tgggccatca aagcccagaa gagcacagag gcctaattct    2820
ctggatcttt cagccacaaa tgtcctggat ggcagcagta tacagatagg tgagtcaaca    2880
caagatggca atcaggatc aggtgaaaag atcaagaaac gtgtgaaaac tccctattct     2940
cttaagcggt ggcgcccctc cacctgggtc atctccactg aatcgctgga ctgtgaagtc    3000
aacaataatg gcagtaacag ggcagttcat tccaaatcca gcactgctgt ttaccttgca    3060
gaaggaggca ctgctacaac catggtgtct aaagatatag aatgaactg tctg           3114

<210> SEQ ID NO 206
<211> LENGTH: 372
<212> TYPE: DNA
<213> ORGANISM: Homo sapiens

<400> SEQUENCE: 206
tcgcagaatc aagaacggct atgtgcgttt aaagatccgt atcagcaaga ccttgggata      60
ggtgagagta gaatctctca tgaaaatggg acaatattat gctcgaaagg tagcacctgc    120
tatggccttt gggagaaatc aaaggggac ataaatcttg taaaacaagg atgttggtct     180
cacattggag atccccaaga gtgtcactat gaagaatgtg tagtaactac cactcctccc    240
tcaattcaga atggaacata ccgtttctgc tgttgtagca cagatttatg taatgtcaac    300
tttactgaga atttccacc tcctgacaca acaccactca gtccacctca ttcatttaac    360
cgagatgaga ca                                                        372

<210> SEQ ID NO 207
<211> LENGTH: 1590
<212> TYPE: DNA
<213> ORGANISM: Homo sapiens

<400> SEQUENCE: 207
atgacttcct cgctgcagcg gccctggcgg gtgccctggc taccatggac catcctgctg      60
gtcagcactg cggctgcttc gcagaatcaa gaacggctat gtgcgtttaa agatccgtat    120
cagcaagacc ttgggatagg tgagagtaga atctctcatg aaaatgggac aatattatgc    180
tcgaaaggta gcacctgcta tggcctttgg gagaaatcaa aggggacat aaatcttgta    240 aaacaaggat gttggtctca cattggagat ccccaagagt gtcactatga agaatgtta    300 gtaactacca ctcctccctc aattcagaat ggaacatacc gtttctgctg ttgtagcaca    360
gatttatgta atgtcaactt tactgagaat tttccacctc ctgacacaac accactcagt    420
ccacctcatt catttaaccg agatgagaca ataatcattg ctttggcatc agtctctgta    480
ttagctgttt tgatagttgc cttatgcttt ggatacagaa tgttgacagg agaccgtaaa    540
caaggtcttc acagtatgaa catgatggag gcagcagcat ccgaaccctc tcttgatcta    600
```

```
gataatctga aactgttgga gctgattggc cgaggtcgat atggagcagt atataaaggc      660
tccttggatg agcgtccagt tgctgtaaaa gtgttttcct ttgcaaaccg tcagaatttt      720
atcaacgaaa agaacattta cagagtgcct ttgatggaac atgacaacat tgcccgcttt      780
atagttggag atgagagagt cactgcagat ggacgcatgg aatatttgct tgtgatggag      840
tactatccca atggatcttt atgcaagtat ttaagtctcc acacaagtga ctgggtaagc      900
tcttgccgtc ttgctcattc tgttactaga ggactggctt atcttcacac agaattacca      960
cgaggagatc attataaacc tgcaatttcc catcgagatt taaacagcag aaatgtccta     1020
gtgaaaaatg atggaacctg tgttattagt gactttggac tgtccatgag ctgactgga     1080 aatagactgg tgcgcccagg ggaggaagat aatgcagcca aagcgaggt tggcactatc     1140 agatatatgg caccagaagt gctagaagga gctgtgaact tgagggactg tgaatcagct     1200
ttgaaacaag tagacatgta tgctcttgga ctaatctatt gggagatatt tatgagatgt     1260
acagacctct tcccagggga atccgtacca gagtaccaga tggctttttca gacagaggtt     1320 ggaaaccatc ccacttttga ggatatgcag gttctcgtgt ctagggaaaa acagagaccc     1380
aagttcccag aagcctggaa agaaaatagc ctggcagtga ggtcactcaa ggagacaatc     1440
gaagactgtt gggaccagga tgcagaggct cggcttactg cacagtgtgc tgaggaaagg     1500
atggctgaac ttatgatgat ttgggaaaga aacaaatctg tgagcccaac agtcaatcca     1560
atgtctactg ctatgcagaa tgaacgtagg                                      1590

<210> SEQ ID NO 208
<211> LENGTH: 372
<212> TYPE: DNA
<213> ORGANISM: Homo sapiens

<400> SEQUENCE: 208
tcgcagaatc aagaacggct atgtgcgttt aaagatccgt atcagcaaga ccttgggata       60
ggtgagagta gaatctctca tgaaaatggg acaatattat gctcgaaagg tagcacctgc      120
tatggccttt gggagaaatc aaaaggggac ataaatcttg taaaacaagg atgttggtct      180
cacattggag atccccaaga gtgtcactat gaagaatgtg tagtaactac cactcctccc      240
tcaattcaga tggaacata ccgtttctgc tgttgtagca cagatttatg taatgtcaac      300
tttactgaga attttccacc tcctgacaca acaccactca gtccacctca ttcatttaac      360
cgagatgaga ca                                                         372

<210> SEQ ID NO 209
<211> LENGTH: 1719
<212> TYPE: DNA
<213> ORGANISM: Homo sapiens

<400> SEQUENCE: 209
atgctagggt cttgggggct ttgggcatta cttcccacag ctgtggaagc accccaaac       60 aggcgaacct gtgtgttctt tgaggcccct ggagtgcggg aagcacaaa gacactggga      120 gagctgctag atacaggcac agagctcccc agagctatcc gctgcctcta cagccgctgc      180
tgctttggga tctggaacct gacccaagac cgggcacagg tggaaatgca aggatgccga      240
gacagtgatg agccaggctg tgagtccctc cactgtgacc caagtccccg agcccacccc      300
agccctggct ccactctctt cacctgctcc tgtggcactg acttctgcaa tgccaattac      360
agccatctgc ctcctccagg gagccctggg actcctggct cccagggtcc ccaggctgcc      420
```

```
ccaggtgagt ccatctggat ggcactggtg ctgctggggc tgttcctcct cctcctgctg      480
ctgctgggca gcatcatctt ggccctgcta cagcgaaaga actacagagt gcgaggtgag      540
ccagtgccag agccaaggcc agactcaggc agggactgga gtgtggagct gcaggagctg      600
cctgagctgt gtttctccca ggtaatccgg aaggaggtc atgcagtggt ttgggccggg       660
cagctgcaag gaaaactggt tgccatcaag gccttccac cgaggtctgt ggctcagttc       720
caagctgaga gagcattgta cgaacttcca ggcctacagc acgaccacat tgtccgattt      780
atcactgcca gccgggggg tcctggccgc ctgctctctg ggcccctgct ggtactggaa       840
ctgcatccca agggctccct gtgccactac ttgacccagt acaccagtga ctggggaagt      900
tccctgcgga tggcactgtc cctggcccag ggcctggcat ttctccatga ggagcgctgg      960
cagaatggcc aatataaacc aggtattgcc caccgagatc tgagcagcca aatgtgctc     1020 attcgggaag atggatcgtg tgccattgga gacctgggcc ttgccttggt gctccctggc    1080
ctcactcagc cccctgcctg gaccctact caaccacaag gcccagctgc catcatggaa     1140
gctggcaccc agaggtacat ggcaccgag ctcttggaca agactctgga cctacaggat     1200 tgggcatgg ccctccgacg agctgatatt tactctttgg ctctgctcct gtgggagata    1260
ctgagccgct gcccagattt gaggcctgac agcagtccac cacccttcca actggcctat   1320
gaggcagaac tgggcaatac ccctacctct gatgagctat gggccttggc agtgcaggag   1380
aggaggcgtc cctacatccc atccacctgg cgctgctttg ccacagaccc tgatgggctg   1440
agggagctcc tagaagactg ttgggatgca gacccagaag cacggctgac agctgagtgt   1500
gtacagcagc gcctggctgc cttggcccat cctcaagaga gccacccctt tccagagagc   1560
tgtccacgtg gctgcccacc tctctgccca gaagactgta cttcaattcc tgccccctacc 1620 atcctccct gtaggcctca gcggagtgcc tgccacttca gcgttcagca aggcccttgt    1680
tccaggaatc ctcagcctgc ctgtacccctt tctcctgtg                          1719

<210> SEQ ID NO 210
<211> LENGTH: 396
<212> TYPE: DNA
<213> ORGANISM: Homo sapiens

<400> SEQUENCE: 210
cccccaaaca ggcgaacctg tgtgttcttt gaggcccctg gagtgcgggg aagcacaaag    60
acactgggag agctgctaga tacaggcaca gagctcccca gagctatccg ctgcctctac   120
agccgctgct gctttgggat ctggaacctg acccaagacc gggcacaggt ggaaatgcaa   180
ggatgccgag acagtgatga ccaggctgt gagtccctcc actgtgaccc aagtccccga   240
gcccacccca gccctggctc cactctcttc acctgctcct gtggcactga cttctgcaat   300
gccaattaca gccatctgcc tcctccaggg agccctggga ctcctggctc ccagggtccc   360
caggctgccc caggtgagtc catctggatg gcactg                             396

<210> SEQ ID NO 211
<211> LENGTH: 1434
<212> TYPE: DNA
<213> ORGANISM: Homo sapiens

<400> SEQUENCE: 211
atgctagggt cttgggggct ttgggcatta cttcccacag ctgtggaagc accccccaaac   60 aggcgaacct gtgtgttctt tgaggcccct ggagtgcggg gaagcacaaa gacactggga   120
gagctgctag atacaggcac agagctcccc agagctatcc gctgcctcta cagccgctgc   180
```

```
tgctttggga tctggaacct gacccaagac cgggcacagg tggaaatgca aggatgccga    240
gacagtgatg agccaggctg tgagtccctc cactgtgacc caagtccccg agcccacccc    300
agccctggct ccactctctt cacctgctcc tgtggcactg acttctgcaa tgccaattac    360
agccatctgc ctcctccagg gagccctggg actcctggct cccagggtcc ccaggctgcc    420
ccaggtgagt ccatctggat ggcactggtg ctgctggggc tgttcctcct cctcctgctg    480
ctgctgggca gcatcatctt ggccctgcta gcgcgaaaga actacagagt gcgaggtgag    540
ccagtgccag agccaaggcc agactcaggc agggactgga gtgtggagct gcaggagctg    600
cctgagctgt gtttctccca ggtaatccgg aaggaggtc atgcagtggt ttgggccggg    660
cagctgcaag gaaaactggt tgccatcaag gccttccac cgaggtctgt ggctcagttc    720
caagctgaga gagcattgta cgaacttcca ggcctacagc acgaccacat tgtccgattt    780
atcactgcca gccggggggg tcctggccgc ctgctctctg gcccctgct ggtactggaa    840 ctgcatccca agggctccct gtgccactac ttgacccagt acaccagtga ctggggaagt    900
tccctgcgga tggcactgtc cctggcccag ggcctggcat ttctccatga ggagcgctgg    960
cagaatggcc aatataaacc aggtattgcc caccgagatc tgagcagcca gaatgtgctc   1020
attcgggaag atggatcgtg tgccattgga gacctgggcc ttgccttggt gctccctggc   1080
ctcactcagc cccctgcctg gacccctact caaccacaag gcccagctgc catcatggaa   1140
gctggcaccc agaggtacat ggcaccagag ctcttggaca agactctgga cctacaggat   1200
tggggcatgg ccctccgacg agctgatatt tactcttttgg ctctgctcct gtgggagata   1260
ctgagccgct gcccagattt gaggcctgca gtccaccacc cttccaactg gcctatgagg   1320
cagaactggg caatacccct acctctgatg agctatgggc cttggcagtg caggagagga   1380
ggcgtcccta catcccatcc acctggcgct gctttgccac agaccctgat gggc         1434

<210> SEQ ID NO 212
<211> LENGTH: 396
<212> TYPE: DNA
<213> ORGANISM: Homo sapiens

<400> SEQUENCE: 212
cccccaaaca ggcgaacctg tgtgttcttt gaggcccctg gagtgcgggg aagcacaaag     60
acactgggag agctgctaga tacaggcaca gagctcccca gagctatccg ctgcctctac    120
agccgctgct gctttgggat ctggaacctg acccaagacc gggcacaggt ggaaatgcaa    180
ggatgccgag acagtgatga gccaggctgt gagtccctcc actgtgaccc aagtccccga    240
gcccacccca gccctggctc cactctcttc acctgctcct gtggcactga cttctgcaat    300
gccaattaca gccatctgcc tcctccaggg agccctggga ctcctggctc ccagggtccc    360
caggctgccc caggtgagtc catctggatg gcactg                              396

<210> SEQ ID NO 213
<211> LENGTH: 1434
<212> TYPE: DNA
<213> ORGANISM: Homo sapiens

<400> SEQUENCE: 213
atgctagggt ctttggggct ttgggcatta cttcccacag ctgtggaagc accccaaac     60 aggcgaacct gtgtgttctt tgaggcccct ggagtgcggg gaagcacaaa gacactggga    120
gagctgctag atacaggcac agagctcccc agagctatcc gctgcctcta cagccgctgc    180
```

| | |
|---|---|
| tgctttggga tctggaacct gacccaagac cgggcacagg tggaaatgca aggatgccga | 240 |
| gacagtgatg agccaggctg tgagtccctc cactgtgacc caagtccccg agcccacccc | 300 |
| agccctggct ccactctctt cacctgctcc tgtggcactg acttctgcaa tgccaattac | 360 |
| agccatctgc ctcctccagg gagccctggg actcctggct cccagggtcc caggctgcc | 420 |
| ccaggtgagt ccatctggat ggcactggtg ctgctgggc tgttcctcct cctcctgctg | 480 |
| ctgctgggca gcatcatctt ggccctgcta cagcgaaaga actacagagt gcgaggtgag | 540 |
| ccagtgccag agccaaggcc agactcaggc agggactgga gtgtggagct gcaggagctg | 600 |
| cctgagctgt gtttctccca ggtaatccgg aaggaggtc atgcagtggt ttgggccggg | 660 |
| cagctgcaag gaaaactggt tgccatcaag gccttcccac cgaggtctgt ggctcagttc | 720 |
| caagctgaga gagcattgta cgaacttcca ggcctacagc acgaccacat tgtccgattt | 780 |
| atcactgcca gccggggggg tcctggccgc ctgctctctg ggcccctgct ggtactggaa | 840 |
| ctgcatccca agggctccct gtgccactac ttgacccagt acaccagtga ctggggaagt | 900 |
| tccctgcgga tggcactgtc cctggcccag ggcctggcat ttctccatga ggagcgctgg | 960 |
| cagaatggcc aatataaacc aggtattgcc caccgagatc tgagcagcca gaatgtgctc | 1020 |
| attcgggaag atggatcgtg tgccattgga gacctgggcc ttgccttggt gctccctggc | 1080 |
| ctcactcagc ccctgcctg gaccctact caaccacaag gcccagctgc catcatggaa | 1140 |
| gacccctgatg ggctgaggga gctcctagaa gactgttggg atgcagaccc agaagcacgg | 1200 |
| ctgacagctg agtgtgtaca gcagcgcctg gctgccttgg cccatcctca agagagccac | 1260 |
| ccctttccag agagctgtcc acgtggctgc ccacctctct gcccagaaga ctgtacttca | 1320 |
| attcctgccc ctaccatcct cccctgtagg cctcagcgga gtgcctgcca cttcagcgtt | 1380 |
| cagcaaggcc cttgttccag gaatcctcag cctgcctgta cccttttctcc tgtg | 1434 |

<210> SEQ ID NO 214
<211> LENGTH: 396
<212> TYPE: DNA
<213> ORGANISM: Homo sapiens

<400> SEQUENCE: 214

| | |
|---|---|
| cccccaaaca ggcgaacctg tgtgttcttt gaggcccctg gagtgcgggg aagcacaaag | 60 |
| acactgggag agctgctaga tacaggcaca gagctcccca gagctatccg ctgcctctac | 120 |
| agccgctgct gctttgggat ctggaacctg acccaagacc gggcacaggt ggaaatgcaa | 180 |
| ggatgccgag acagtgatga gccaggctgt gagtccctcc actgtgaccc aagtccccga | 240 |
| gcccacccca gccctggctc cactctcttc acctgctcct gtggcactga cttctgcaat | 300 |
| gccaattaca gccatctgcc tcctccaggg agccctggga ctcctggctc ccagggtccc | 360 |
| caggctgccc caggtgagtc catctggatg gcactg | 396 |

<210> SEQ ID NO 215
<211> LENGTH: 1509
<212> TYPE: DNA
<213> ORGANISM: Homo sapiens

<400> SEQUENCE: 215

| | |
|---|---|
| atgaccttgg gctcccccag gaaaggcctt ctgatgctgc tgatggcctt ggtgacccag | 60 |
| ggagaccctg tgaagccgtc tcggggcccg ctggtgacct gcacgtgtga gagcccacat | 120 |
| tgcaaggggc ctacctgccg gggggcctgg tgcacagtag tgctggtgcg ggaggagggg | 180 |
| aggcaccccc aggaacatcg gggctgcggg aacttgcaca gggagctctg caggggcgc | 240 |

```
cccaccgagt tcgtcaacca ctactgctgc gacagccacc tctgcaacca caacgtgtcc    300
ctggtgctgg aggccaccca acctccttcg gagcagccgg aacagatgg  ccagctggcc    360 ctgatcctgg gccccgtgct ggccttgctg gccctggtgg ccctgggtgt cctgggcctg    420
tggcatgtcc gacggaggca ggagaagcag cgtggcctgc acagcgagct gggagagtcc    480
agtctcatcc tgaaagcatc tgagcagggc gacagcatgt tgggggaccct cctggacagt    540 gactgcacca cagggagtgg ctcagggctc cccttcctgg tgcagaggac agtggcacgg    600
caggttgcct tggtggagtg tgtgggaaaa ggccgctatg gcgaagtgtg gcggggcttg    660
tggcacggtg agagtgtggc cgtcaagatc ttctcctcga gggatgaaca gtcctggttc    720
cgggagactg agatctataa cacagtgttg ctcagacacg acaacatcct aggcttcatc    780
gcctcagaca tgacctcccg caactcgagc acgcagctgt ggctcatcac gcactaccac    840
gagcacggct ccctctacga ctttctgcag agacagacgc tggagcccca tctggctctg    900
aggctagctg tgtccgcggc atgcggcctg gcgcacctgc acgtggagat cttcggtaca    960
cagggcaaac cagccattgc ccaccgcgac ttcaagagcc gcaatgtgct ggtcaagagc    1020
aacctgcagt gttgcatcgc cgacctgggc ctggctgtga tgcactcaca gggcagcgat    1080
tacctggaca tcggcaacaa cccgagagtg ggcaccaagc ggtacatggc acccgaggtg    1140
ctggacgagc agatccgcac ggactgcttt gagtcctaca gtggactga  catctgggcc    1200 tttggcctgg tgctgtggga gattgcccgc cggaccatcg tgaatggcat cgtggaggac    1260
tatagaccac ccttctatga tgtggtgccc aatgaccccca gctttgagga catgaagaag    1320
gtggtgtgtg tggatcagca gacccccacc atccctaacc ggctggctgc agacccggtc    1380
ctctcaggcc tagctcagat gatgcgggag tgctggtacc caaacccctc tgcccgactc    1440
accgcgctgc ggatcaagaa gacactacaa aaaattagca acagtccaga gaagcctaaa    1500
gtgattcaa                                                            1509
```

<210> SEQ ID NO 216
<211> LENGTH: 291
<212> TYPE: DNA
<213> ORGANISM: Homo sapiens

<400> SEQUENCE: 216

```
gaccctgtga agccgtctcg gggcccgctg gtgacctgca cgtgtgagag cccacattgc     60
aaggggccta cctgccgggg ggcctggtgc acagtagtgc tggtgcggga ggaggggagg    120
cacccccagg aacatcgggg ctgcgggaac ttgcacaggg agctctgcag ggggcgcccc    180
accgagttcg tcaaccacta ctgctgcgac agccacctct gcaaccacaa cgtgtccctg    240
gtgctggagg ccacccaacc tccttcggag cagccgggaa cagatggcca g            291
```

<210> SEQ ID NO 217
<211> LENGTH: 1527
<212> TYPE: DNA
<213> ORGANISM: Homo sapiens

<400> SEQUENCE: 217

```
atggtagatg gagtgatgat tcttcctgtg cttatcatga ttgctctccc ctcccctagt     60
atggaagatg agaagcccaa ggtcaacccc aaactctaca tgtgtgtgtg tgaaggtctc    120
tcctgcggta atgaggacca ctgtgaaggc cagcagtgct tttcctcact gagcatcaac    180
gatggcttcc acgtctacca gaaaggctgc ttccaggttt atgagcaggg aaagatgacc    240
```

| | |
|---|---|
| tgtaagaccc cgccgtcccc tggccaagcc gtggagtgct gccaagggga ctggtgtaac | 300 |
| aggaacatca cggcccagct gcccactaaa ggaaaatcct tccctggaac acagaatttc | 360 |
| cacttggagg ttggcctcat tattctctct gtagtgttcg cagtatgtct tttagcctgc | 420 |
| ctgctgggag ttgctctccg aaaatttaaa aggcgcaacc aagaacgcct caatccccga | 480 |
| gacgtggagt atggcactat cgaagggctc atcaccacca atgttggaga cagcacttta | 540 |
| gcagatttat tggatcattc gtgtacatca ggaagtggct ctggtcttcc ttttctggta | 600 |
| caaagaacag tggctcgcca gattacactg ttggagtgtg tcgggaaagg caggtatggt | 660 |
| gaggtgtgga ggggcagctg gcaagggggag aatgttgccg tgaagatctt ctcctcccgt | 720 |
| gatgagaagt catggttcag ggaaacggaa ttgtacaaca ctgtgatgct gaggcatgaa | 780 |
| aatatcttag gtttcattgc ttcagacatg acatcaagac actccagtac ccagctgtgg | 840 |
| ttaattacac attatcatga atgggatcg ttgtacgact atcttcagct tactactctg | 900 |
| gatacagtta gctgccttcg aatagtgctg tccatagcta gtggtcttgc acatttgcac | 960 |
| atagagatat ttgggaccca agggaaacca gccattgccc atcgagattt aaagagcaaa | 1020 |
| aatattctgg ttaagaagaa tggacagtgt tgcatagcag atttgggcct ggcagtcatg | 1080 |
| cattcccaga gcaccaatca gcttgatgtg gggaacaatc cccgtgtggg caccaagcgc | 1140 |
| tacatggccc ccgaagttct agatgaaacc atccaggtgg attgtttcga ttcttataaa | 1200 |
| agggtcgata tttgggcctt tggacttgtt ttgtgggaag tggccaggcg gatggtgagc | 1260 |
| aatggtatag tggaggatta caagccaccg ttctacgatg tggttcccaa tgacccaagt | 1320 |
| tttgaagata tgaggaaggt agtctgtgtg gatcaacaaa ggccaaacat acccaacaga | 1380 |
| tggttctcag acccgacatt aacctctctg gccaagctaa tgaaagaatg ctggtatcaa | 1440 |
| aatccatccg caagactcac agcactgcgt atcaaaaaga ctttgaccaa aattgataat | 1500 |
| tccctcgaca aattgaaaac tgactgt | 1527 |

<210> SEQ ID NO 218
<211> LENGTH: 309
<212> TYPE: DNA
<213> ORGANISM: Homo sapiens

<400> SEQUENCE: 218

| | |
|---|---|
| atggaagatg agaagcccaa ggtcaacccc aaactctaca tgtgtgtgtg tgaaggtctc | 60 |
| tcctgcggta atgaggacca ctgtgaaggc cagcagtgct tttcctcact gagcatcaac | 120 |
| gatggcttcc acgtctacca gaaaggctgc ttccaggttt atgagcaggg aaagatgacc | 180 |
| tgtaagaccc cgccgtcccc tggccaagcc gtggagtgct gccaagggga ctggtgtaac | 240 |
| aggaacatca cggcccagct gcccactaaa ggaaaatcct tccctggaac acagaatttc | 300 |
| cacttggag | 309 |

<210> SEQ ID NO 219
<211> LENGTH: 1596
<212> TYPE: DNA
<213> ORGANISM: Homo sapiens

<400> SEQUENCE: 219

| | |
|---|---|
| atgcctcagc tatacattta catcagatta ttgggagcct atttgttcat catttctcgt | 60 |
| gttcaaggac agaatctgga tagtatgctt catggcactg ggatgaaatc agactccgac | 120 |
| cagaaaaagt cagaaaatgg agtaacctta gcaccagagg ataccttgcc tttttttaaag | 180 |
| tgctattgct cagggcactg tccagatgat gctattaata acacatgcat aactaatgga | 240 |

```
cattgctttg ccatcataga agaagatgac cagggagaaa ccacattagc ttcagggtgt      300
atgaaatatg aaggatctga ttttcagtgc aaagattctc caaaagccca gctacgccgg      360
acaatagaat gttgtcggac caatttatgt aaccagtatt tgcaacccac actgcccct       420 gttgtcatag gtccgttttt tgatggcagc attcgatggc tggttttgct catttctatg      480
gctgtctgca taattgctat gatcatcttc tccagctgct tttgttacaa acattattgc      540
aagagcatct caagcagacg tcgttacaat cgtgatttgg aacaggatga agcatttatt      600
ccagttggag aatcactaaa agaccttatt gaccagtcac aaagttctgg tagtgggtct      660
ggactacctt tattggttca gcgaactatt gccaaacaga ttcagatggt ccggcaagtt      720
ggtaaaggcc gatatggaga agtatggatg gcaaatggc gtggcgaaaa agtggcggtg       780
aaagtattct ttaccactga agaagccagc tggtttcgag aaacagaaat ctaccaaact      840
gtgctaatgc gccatgaaaa catacttggt ttcatagcgg cagacattaa aggtacaggt      900
tcctggactc agctctattt gattactgat taccatgaaa atggatctct ctatgacttc      960
ctgaaatgtg ctacactgga caccagagcc ctgcttaaat tggcttattc agctgcctgt     1020
ggtctgtgcc acctgcacac agaaatttat ggcacccaag aaagcccgc aattgctcat      1080 cgagacctaa agagcaaaaa catcctcatc aagaaaaatg ggagttgctg cattgctgac     1140
ctgggccttg ctgttaaatt caacagtgac acaaatgaag ttgatgtgcc cttgaatacc     1200
agggtgggca ccaaacgcta catggctccc gaagtgctgg acgaaagcct gaacaaaaac     1260
cacttccagc cctacatcat ggctgacatc tacagcttcg gcctaatcat ttgggagatg     1320
gctcgtcgtt gtatcacagg agggatcgtg aagaataccc aattgccata ttacaacatg     1380
gtaccgagtg atccgtcata cgaagatatg cgtgaggttg tgtgtgtcaa acgtttgcgg     1440
ccaattgtgt ctaatcggtg gaacagtgat gaatgtctac gagcagtttt gaagctaatg     1500
tcagaatgct gggcccacaa tccagcctcc agactcacag cattgagaat taagaagacg     1560
cttgccaaga tggttgaatc ccaagatgta aaaatc                                1596

<210> SEQ ID NO 220
<211> LENGTH: 387
<212> TYPE: DNA
<213> ORGANISM: Homo sapiens

<400> SEQUENCE: 220
cagaatctgg atagtatgct tcatggcact gggatgaaat cagactccga ccagaaaaag       60
tcagaaaatg gagtaacctt agcaccagag gataccttgc cttttttaaa gtgctattgc      120
tcagggcact gtccagatga tgctattaat aacacatgca taactaatgg acattgcttt      180
gccatcatag aagaagatga ccaggagaa accacattag cttcagggtg tatgaaatat      240
gaaggatctg attttcagtg caaagattct ccaaaagccc agctacgccg gacaatagaa      300
tgttgtcgga ccaatttatg taaccagtat ttgcaaccca cactgccccc tgttgtcata     360
ggtccgtttt ttgatggcag cattcga                                          387

<210> SEQ ID NO 221
<211> LENGTH: 1515
<212> TYPE: DNA
<213> ORGANISM: Homo sapiens

<400> SEQUENCE: 221
atggcggagt cggccggagc ctcctccttc ttccccttg ttgtcctcct gctcgccggc        60
```

| | |
|---|---|
| agcggcgggt ccgggccccg gggggtccag gctctgctgt gtgcgtgcac cagctgcctc | 120 |
| caggccaact acacgtgtga gacagatggg gcctgcatgg tttccatttt caatctggat | 180 |
| gggatggagc accatgtgcg cacctgcatc cccaaagtgg agctggtccc tgccgggaag | 240 |
| cccttctact gcctgagctc ggaggacctg cgcaacaccc actgctgcta cactgactac | 300 |
| tgcaacagga tcgacttgag ggtgcccagt ggtcacctca aggagcctga gcacccgtcc | 360 |
| atgtggggcc cggtggagct ggtaggcatc atcgccggcc cggtgttcct cctgttcctc | 420 |
| atcatcatca ttgttttcct tgtcattaac tatcatcagc gtgtctatca caaccgccag | 480 |
| agactggaca tggaagatcc ctcatgtgag atgtgtctct ccaaagacaa gacgctccag | 540 |
| gatcttgtct acgatctctc cacctcaggg tctggctcag ggttacccct ctttgtccag | 600 |
| cgcacagtgg cccgaaccat cgttttacaa gagattattg gcaagggtcg gtttggggaa | 660 |
| gtatggcggg gccgctggag gggtggtgat gtggctgtga aaatattctc ttctcgtgaa | 720 |
| gaacggtctt ggttcaggga agcagagata taccagacgg tcatgctgcg ccatgaaaac | 780 |
| atccttggat ttattgctgc tgacaataaa gataatggca cctggacaca gctgtggctt | 840 |
| gtttctgact atcatgagca cgggtccctg tttgattatc tgaaccggta cacagtgaca | 900 |
| attgagggga tgattaagct ggccttgtct gctgctagtg gctggcaca cctgcacatg | 960 |
| gagatcgtgg gcacccaagg gaagcctgga attgctcatc gagacttaaa gtcaaagaac | 1020 |
| attctggtga agaaaaatgg catgtgtgcc atagcagacc tgggcctggc tgtccgtcat | 1080 |
| gatgcagtca ctgacaccat tgacattgcc ccgaatcaga gggtggggac caaacgatac | 1140 |
| atggcccctg aagtacttga tgaaaccatt aatatgaaac actttgactc ctttaaatgt | 1200 |
| gctgatattt atgccctcgg gcttgtatat tgggagattg ctcgaagatg caattctgga | 1260 |
| ggagtccatg aagaatatca gctgccatat tacgacttag tgccctctga cccttccatt | 1320 |
| gaggaaatgc gaaaggttgt atgtgatcag aagctgcgtc caacatccc caactggtgg | 1380 |
| cagagttatg aggcactgcg ggtgatgggg aagatgatgc gagagtgttg gtatgccaac | 1440 |
| ggcgcagccc gcctgacggc cctgcgcatc aagaagaccc tctcccagct cagcgtgcag | 1500 |
| gaagacgtga agatc | 1515 |

<210> SEQ ID NO 222
<211> LENGTH: 309
<212> TYPE: DNA
<213> ORGANISM: Homo sapiens

<400> SEQUENCE: 222

| | |
|---|---|
| tccgggcccc gggggtcca ggctctgctg tgtgcgtgca ccagctgcct ccaggccaac | 60 |
| tacacgtgtg agacagatgg ggcctgcatg gtttccattt tcaatctgga tgggatggag | 120 |
| caccatgtgc gcacctgcat ccccaaagtg gagctggtcc ctgccgggaa gcccttctac | 180 |
| tgcctgagct cggaggacct gcgcaacacc cactgctgct acactgacta ctgcaacagg | 240 |
| atcgacttga gggtgcccag tggtcacctc aaggagcctg agcacccgtc catgtggggc | 300 |
| ccggtggag | 309 |

<210> SEQ ID NO 223
<211> LENGTH: 1638
<212> TYPE: DNA
<213> ORGANISM: Homo sapiens

<400> SEQUENCE: 223

| | |
|---|---|
| atggcggagt cggccggagc ctcctccttc ttccccttg ttgtcctcct gctcgccggc | 60 |

```
agcggcgggt ccgggccccg gggggtccag gctctgctgt gtgcgtgcac cagctgcctc       120
caggccaact acacgtgtga gacagatggg gcctgcatgg tttccatttt caatctggat       180
gggatggagc accatgtgcg cacctgcatc cccaaagtgg agctggtccc tgccgggaag       240
cccttctact gcctgagctc ggaggacctg cgcaacaccc actgctgcta cactgactac       300
tgcaacagga tcgacttgag ggtgcccagt ggtcacctca aggagcctga gcacccgtcc       360
atgtggggcc cggtggagct ggtaggcatc atcgccggcc cggtgttcct cctgttcctc       420
atcatcatca ttgttttcct tgtcattaac tatcatcagc gtgtctatca aaccgccag        480 agactggaca tggaagatcc ctcatgtgag atgtgtctct ccaaagacaa gacgctccag       540
gatcttgtct acgatctctc cacctcaggg tctggctcag ggttacccct ctttgtccag       600
cgcacagtgg cccgaaccat cgttttacaa gagattattg gcaagggtcg gtttggggaa       660
gtatggcggg gccgctggag gggtggtgat gtggctgtga aaatattctc ttctcgtgaa       720
gaacggtctt ggttcaggga agcagagata taccagacgg tcatgctgcg ccatgaaaac       780
atccttggat ttattgctgc tgacaataaa gcagactgct cattcctcac attgccatgg       840
gaagttgtaa tggtctctgc tgcccccaag ctgaggagcc ttagactcca atacaaggga       900
ggaaggggaa gagcaagatt tttattccca ctgaataatg gcacctggac acagctgtgg       960
cttgtttctg actatcatga gcacgggtcc ctgtttgatt atctgaaccg gtacacagtg      1020
acaattgagg ggatgattaa gctggccttg tctgctgcta gtgggctggc acacctgcac      1080
atggagatcg tgggcaccca agggaagcct ggaattgctc atcgagactt aaagtcaaag      1140
aacattctgg tgaagaaaaa tggcatgtgt gccatagcag acctgggcct ggctgtccgt      1200
catgatgcag tcactgacac cattgacatt gccccgaatc agagggtggg gaccaaacga      1260
tacatggccc ctgaagtact tgatgaaacc attaatatga aacactttga ctccttttaaa     1320 tgtgctgata tttatgccct cgggcttgta tattgggaga ttgctcgaag atgcaattct      1380
ggaggagtcc atgaagaata tcagctgcca tattacgact tagtgccctc tgacccttcc      1440
attgaggaaa tgcgaaaggt tgtatgtgat cagaagctgc gtcccaacat ccccaactgg      1500
tggcagagtt atgaggcact gcgggtgatg gggaagatga tgcgagagtg ttggtatgcc      1560
aacggcgcag cccgcctgac ggccctgcgc atcaagaaga ccctctccca gctcagcgtg      1620
caggaagacg tgaagatc                                                   1638
```

<210> SEQ ID NO 224
<211> LENGTH: 309
<212> TYPE: DNA
<213> ORGANISM: Homo sapiens

<400> SEQUENCE: 224

```
tccgggcccc gggggtcca ggctctgctg tgtgcgtgca ccagctgcct ccaggccaac         60
tacacgtgtg agacagatgg ggcctgcatg gtttccattt tcaatctgga tgggatggag       120
caccatgtgc gcacctgcat ccccaaagtg gagctggtcc ctgccgggaa gcccttctac       180
tgcctgagct cggaggacct gcgcaacacc cactgctgct acactgacta ctgcaacagg       240
atcgacttga gggtgcccag tggtcacctc aaggagcctg agcacccgtc catgtggggc       300
ccggtggag                                                              309
```

<210> SEQ ID NO 225
<211> LENGTH: 1509
<212> TYPE: DNA

<213> ORGANISM: Homo sapiens

<400> SEQUENCE: 225

| | |
|---|---|
| atggaggcgg cggtcgctgc tccgcgtccc cggctgctcc tcctcgtgct ggcggcggcg | 60 |
| gcggcggcgg cggcggcgct gctcccgggg gcgacggcgt tacagtgttt ctgccacctc | 120 |
| tgtacaaaag acaattttac ttgtgtgaca gatgggctct gctttgtctc tgtcacagag | 180 |
| accacagaca agttataca caacagcatg tgtatagctg aaattgactt aattcctcga | 240 |
| gataggccgt ttgtatgtgc accctcttca aaaactgggt ctgtgactac aacatattgc | 300 |
| tgcaatcagg accattgcaa taaaatagaa cttccaacta ctgtaaagtc atcacctggc | 360 |
| cttggtcctg tggaactggc agctgtcatt gctggaccag tgtgcttcgt ctgcatctca | 420 |
| ctcatgttga tggtctatat ctgccacaac cgcactgtca ttcaccatcg agtgccaaat | 480 |
| gaagaggacc cttcattaga tcgcccttttt atttcagagg gtactacgtt gaaagactta | 540 |
| atttatgata tgcaacgtc aggttctggc tcaggtttac cattgcttgt tcagagaaca | 600 |
| attgcgagaa ctattgtgtt acaagaaagc attggcaaag gtcgatttgg agaagtttgg | 660 |
| agaggaaagt ggcggggaga agaagttgct gttaagatat tctcctctag agaagaacgt | 720 |
| tcgtggttcc gtgaggcaga gatttatcaa actgtaatgt tacgtcatga aaacatcctg | 780 |
| ggatttatag cagcagacaa taaagacaat ggtacttgga ctcagctctg gttggtgtca | 840 |
| gattatcatg agcatggatc ccttttttgat tacttaaaca gatacacagt tactgtggaa | 900 |
| ggaatgataa aacttgctct gtccacggcg agcggtcttg cccatcttca catggagatt | 960 |
| gttggtaccc aaggaaagcc agccattgct catagagatt tgaaatcaaa gaatatcttg | 1020 |
| gtaaagaaga atggaacttg ctgtattgca gacttaggac tggcagtaag acatgattca | 1080 |
| gccacagata ccattgatat tgctccaaac cacagagtgg gaacaaaaag gtacatggcc | 1140 |
| cctgaagttc tcgatgattc cataaatatg aaacattttg aatccttcaa acgtgctgac | 1200 |
| atctatgcaa tgggcttagt attctgggaa attgctcgac gatgttccat ggtggaattt | 1260 |
| catgaagatt accaactgcc ttattatgat cttgtacctt ctgacccatc agttgaagaa | 1320 |
| atgagaaaag ttgtttgtga acagaagtta aggccaaata tcccaaacag atggcagagc | 1380 |
| tgtgaagcct tgagagtaat ggctaaaatt atgagagaat gttggtatgc caatggagca | 1440 |
| gctaggctta cagcattgcg gattaagaaa acattatcgc aactcagtca acaggaaggc | 1500 |
| atcaaaatg | 1509 |

<210> SEQ ID NO 226
<211> LENGTH: 306
<212> TYPE: DNA
<213> ORGANISM: Homo sapiens

<400> SEQUENCE: 226

| | |
|---|---|
| gcggcgctgc tcccgggggc gacggcgtta cagtgtttct gccacctctg tacaaaagac | 60 |
| aattttactt gtgtgacaga tgggctctgc tttgtctctg tcacagagac cacagacaaa | 120 |
| gttatacaca acagcatgtg tatagctgaa attgacttaa ttcctcgaga taggccgttt | 180 |
| gtatgtgcac cctcttcaaa aactgggtct gtgactacaa catattgctg caatcaggac | 240 |
| cattgcaata aaatagaact tccaactact gtaaagtcat cacctggcct tggtcctgtg | 300 |
| gaactg | 306 |

<210> SEQ ID NO 227
<211> LENGTH: 1521

```
<212> TYPE: DNA
<213> ORGANISM: Homo sapiens

<400> SEQUENCE: 227
atggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc     120
tgtacaaaag acaatttttac ttgtgtgaca gatgggctct gctttgtctc tgtcacagag    180
accacagaca aagttataca caacagcatg tgtatagctg aaattgactt aattcctcga    240
gataggccgt ttgtatgtgc accctcttca aaaactgggt ctgtgactac aacatattgc    300
tgcaatcagg accattgcaa taaaatagaa cttccaacta ctggcccttt ttcagtaaag    360
tcatcacctg gccttggtcc tgtggaactg gcagctgtca ttgctggacc agtgtgcttc    420
gtctgcatct cactcatgtt gatggtctat atctgccaca accgcactgt cattcaccat    480
cgagtgccaa atgaagagga cccttcatta gatcgccctt ttatttcaga gggtactacg    540
ttgaaagact taatttatga tatgacaacg tcaggttctg gctcaggttt accattgctt    600
gttcagagaa caattgcgag aactattgtg ttacaagaaa gcattggcaa aggtcgattt    660
ggagaagttt ggagaggaaa gtggcgggga aagaagttg ctgttaagat attctcctct    720
agagaagaac gttcgtggtt ccgtgaggca gagatttatc aaactgtaat gttacgtcat    780
gaaaacatcc tgggatttat agcagcagac aataaagaca atggtacttg gactcagctc    840
tggttggtgt cagattatca tgagcatgga tcccttttg attacttaaa cagatacaca    900
gttactgtgg aaggaatgat aaaacttgct ctgtccacgg cgagcggtct tgcccatctt    960
cacatggaga ttgttggtac ccaaggaaag ccagccattg ctcatagaga tttgaaatca   1020
aagaatatct tggtaaagaa gaatggaact tgctgtattg cagacttagg actggcagta   1080
agacatgatt cagccacaga taccattgat attgctccaa accacagagt gggaacaaaa   1140
aggtacatgg cccctgaagt tctcgatgat tccataaata tgaaacattt tgaatccttc   1200
aaacgtgctg acatctatgc aatgggctta gtattctggg aaattgctcg acgatgttcc   1260
attggtggaa ttcatgaaga ttaccaactg ccttattatg atcttgtacc ttctgaccca   1320
tcagttgaag aaatgagaaa agttgtttgt gaacagaagt taaggccaaa tatcccaaac   1380
agatggcaga gctgtgaagc cttgagagta atggctaaaa ttatgagaga atgttggtat   1440
gccaatggag cagctaggct tacagcattg cggattaaga aacattatc gcaactcagt   1500 caacaggaag gcatcaaaat g                                             1521

<210> SEQ ID NO 228
<211> LENGTH: 318
<212> TYPE: DNA
<213> ORGANISM: Homo sapiens

<400> SEQUENCE: 228
gcggcgctgc tcccgggggc gacggcgtta cagtgtttct gccacctctg tacaaaagac      60
aattttactt gtgtgacaga tgggctctgc tttgtctctg tcacagagac cacagacaaa    120
gttatacaca acagcatgtg tatagctgaa attgacttaa ttcctcgaga taggccgttt    180
gtatgtgcac cctcttcaaa aactgggtct gtgactacaa catattgctg caatcaggac    240
cattgcaata aaatagaact tccaactact ggccctttt cagtaaagtc atcacctggc    300
cttggtcctg tggaactg                                                 318

<210> SEQ ID NO 229
```

```
<211> LENGTH: 1506
<212> TYPE: DNA
<213> ORGANISM: Homo sapiens

<400> SEQUENCE: 229
atgcttttgc gaagtgcagg aaaattaaat gtgggcacca agaaagagga tggtgagagt      60
acagccccca ccccccgtcc aaaggtcttg cgttgtaaat gccaccacca ttgtccagaa     120
gactcagtca acaatatttg cagcacagac ggatattgtt tcacgatgat agaagaggat     180
gactctgggt tgcctgtggt cacttctggt tgcctaggac tagaaggctc agattttcag     240
tgtcgggaca ctcccattcc tcatcaaaga agatcaattg aatgctgcac agaaaggaac     300
gaatgtaata aagacctaca ccctacactg cctccattga aaaacagaga ttttgttgat     360
ggacctatac accacagggc tttacttata tctgtgactg tctgtagttt gctcttggtc     420
cttatcatat tattttgtta cttccggtat aaaagacaag aaaccagacc tcgatacagc     480
attgggttag aacaggatga aacttacatt cctcctggag aatccctgag agacttaatt     540
gagcagtctc agagctcagg aagtggatca ggcctccctc tgctggtcca aaggactata     600
gctaagcaga ttcagatggt gaaacagatt ggaaaaggtc gctatgggga agtttggatg     660
ggaaagtggc gtggcgaaaa ggtagctgtg aaagtgttct tcaccacaga ggaagccagc     720
tggttcagag agacagaaat atatcagaca gtgttgatga ggcatgaaaa cattttgggt     780
ttcattgctg cagatatcaa agggacaggg tcctggaccc agttgtacct aatcacagac     840
tatcatgaaa atggttccct ttatgattat ctgaagtcca ccaccctaga cgctaaatca     900
atgctgaagt tagcctactc ttctgtcagt ggcttatgtc atttacacac agaaatcttt     960
agtactcaag gcaaaccagc aattgcccat cgagatctga aaagtaaaaa cattctggtg    1020
aagaaaaatg gaacttgctg tattgctgac ctgggcctgg ctgttaaatt tattagtgat    1080
acaaatgaag ttgacatacc acctaacact cgagttggca ccaaacgcta tatgcctcca    1140
gaagtgttgg acgagagctt gaacagaaat cacttccagt cttacatcat ggctgacatg    1200
tatagttttg gcctcatcct ttgggaggtt gctaggagat gtgtatcagg aggtatagtg    1260
gaagaatacc agcttcctta tcatgaccta gtgcccagtg acccctctta tgaggacatg    1320
agggagattg tgtgcatcaa gaagttacgc ccctcattcc caaaccggtg gagcagtgat    1380
gagtgtctaa ggcagatggg aaaactcatg acagaatgct gggctcacaa tcctgcatca    1440
aggctgacag ccctgcgggt taagaaaaca cttgccaaaa tgtcagagtc ccaggacatt    1500
aaactc                                                                1506

<210> SEQ ID NO 230
<211> LENGTH: 339
<212> TYPE: DNA
<213> ORGANISM: Homo sapiens

<400> SEQUENCE: 230
aagaaagagg atggtgagag tacagccccc acccccgtc caaaggtctt gcgttgtaaa      60
tgccaccacc attgtccaga agactcagtc aacaatattt gcagcacaga cggatattgt     120
ttcacgatga tagaagagga tgactctggg ttgcctgtgg tcacttctgg ttgcctagga     180
ctagaaggct cagattttca gtgtcgggac actcccattc ctcatcaaag aagatcaatt     240
gaatgctgca cagaaaggaa cgaatgtaat aaagacctac ccctacact gcctccattg      300 aaaacagag attttgttga tggacctata caccacagg                              339
```

<210> SEQ ID NO 231
<211> LENGTH: 1596
<212> TYPE: DNA
<213> ORGANISM: Homo sapiens

<400> SEQUENCE: 231

| | | | | | | |
|---|---|---|---|---|---|---|
| atgggttggc | tggaagaact | aaactggcag | cttcacattt | tcttgctcat | tcttctctct | 60 |
| atgcacacaa | gggcaaactt | ccttgataac | atgcttttgc | gaagtgcagg | aaaattaaat | 120 |
| gtgggcacca | agaaagagga | tggtgagagt | acagccccca | cccccgtcc | aaaggtcttg | 180 |
| cgttgtaaat | gccaccacca | ttgtccagaa | gactcagtca | acaatatttg | cagcacagac | 240 |
| ggatattgtt | tcacgatgat | agaagaggat | gactctgggt | tgcctgtggt | cacttctggt | 300 |
| tgcctaggac | tagaaggctc | agattttcag | tgtcgggaca | ctcccattcc | tcatcaaaga | 360 |
| agatcaattg | aatgctgcac | agaaaggaac | gaatgtaata | aagacctaca | ccctacactg | 420 |
| cctccattga | aaacagaga | ttttgttgat | ggacctatac | accacagggc | tttacttata | 480 |
| tctgtgactg | tctgtagttt | gctcttggtc | cttatcatat | tattttgtta | cttccggtat | 540 |
| aaaagacaag | aaaccagacc | tcgatacagc | attgggttag | acaggatga | aacttacatt | 600 |
| cctcctggag | aatccctgag | agacttaatt | gagcagtctc | agagctcagg | aagtggatca | 660 |
| ggcctccctc | tgctggtcca | aaggactata | gctaagcaga | ttcagatggt | gaaacagatt | 720 |
| ggaaaaggtc | gctatgggga | gtttggatg | gaaagtggc | gtggcgaaaa | ggtagctgtg | 780 |
| aaagtgttct | tcaccacaga | ggaagccagc | tggttcagag | agacagaaat | atatcagaca | 840 |
| gtgttgatga | ggcatgaaaa | cattttgggt | ttcattgctg | cagatatcaa | agggacaggg | 900 |
| tcctggaccc | agttgtacct | aatcacagac | tatcatgaaa | atggttccct | ttatgattat | 960 |
| ctgaagtcca | ccaccctaga | cgctaaatca | atgctgaagt | tagcctactc | ttctgtcagt | 1020 |
| ggcttatgtc | atttacacac | agaaatcttt | agtactcaag | gcaaaccagc | aattgcccat | 1080 |
| cgagatctga | aaagtaaaaa | cattctggtg | aagaaaaatg | gaacttgctg | tattgctgac | 1140 |
| ctgggcctgg | ctgttaaatt | tattagtgat | acaaatgaag | ttgacatacc | acctaacact | 1200 |
| cgagttggca | ccaaacgcta | tatgcctcca | gaagtgttgg | acgagagctt | gaacagaaat | 1260 |
| cacttccagt | cttacatcat | ggctgacatg | tatagttttg | gcctcatcct | ttgggaggtt | 1320 |
| gctaggagat | gtgtatcagg | aggtatagtg | gaagaatacc | agcttcctta | tcatgaccta | 1380 |
| gtgcccagtg | acccctctta | tgaggacatg | agggagattg | tgtgcatcaa | gaagttacgc | 1440 |
| ccctcattcc | caaaccggtg | gagcagtgat | gagtgtctaa | ggcagatggg | aaaactcatg | 1500 |
| acagaatgct | gggctcacaa | tcctgcatca | aggctgacag | ccctgcgggt | taagaaaaca | 1560 |
| cttgccaaaa | tgtcagagtc | ccaggacatt | aaactc | | | 1596 |

<210> SEQ ID NO 232
<211> LENGTH: 393
<212> TYPE: DNA
<213> ORGANISM: Homo sapiens

<400> SEQUENCE: 232

| | | | | | | |
|---|---|---|---|---|---|---|
| aacttccttg | ataacatgct | tttgcgaagt | gcaggaaaat | taaatgtggg | caccaagaaa | 60 |
| gaggatggtg | agagtacagc | ccccaccccc | cgtccaaagg | tcttgcgttg | taaatgccac | 120 |
| caccattgtc | cagaagactc | agtcaacaat | atttgcagca | cagacggata | ttgtttcacg | 180 |
| atgatagaag | aggatgactc | tgggttgcct | gtggtcactt | ctggttgcct | aggactagaa | 240 |
| ggctcagatt | ttcagtgtcg | ggacactccc | attcctcatc | aaagaagatc | aattgaatgc | 300 |

```
tgcacagaaa ggaacgaatg taataaagac ctacacccta cactgcctcc attgaaaaac      360
agagattttg ttgatggacc tatacaccac agg                                   393
```

<210> SEQ ID NO 233
<211> LENGTH: 1479
<212> TYPE: DNA
<213> ORGANISM: Homo sapiens

<400> SEQUENCE: 233

```
atgacccggg cgctctgctc agcgctccgc caggctctcc tgctgctcgc agcggccgcc       60
gagctctcgc caggactgaa gtgtgtatgt cttttgtgtg attcttcaaa ctttacctgc      120
caaacagaag gagcatgttg ggcatcagtc atgctaacca atggaaaaga gcaggtgatc      180
aaatcctgtg tctcccttcc agaactgaat gctcaagtct tctgtcatag ttccaacaat      240
gttaccaaaa ccgaatgctg cttcacagat ttttgcaaca acataacact gcaccttcca      300
acagcatcac caaatgcccc aaaacttgga cccatggagc tggccatcat tattactgtg      360
cctgtttgcc tcctgtccat agctgcgatg ctgacagtat gggcatgcca gggtcgacag      420
tgctcctaca ggaagaaaaa gagaccaaat gtggaggaac cactctctga gtgcaatctg      480
gtaaatgctg gaaaaactct gaaagatctg atttatgatg tgaccgcctc tggatctggc      540
tctggtctac ctctgttggt tcaaaggaca attgcaagga cgattgtgct tcaggaaata      600
gtaggaaaag gtagatttgg tgaggtgtgg catggaagat ggtgtgggga agatgtggct      660
gtgaaaatat tctcctccag agatgaaaga tcttggtttc gtgaggcaga aatttaccag      720
acggtcatgc tgcgacatga aaacatcctt ggtttcattg ctgctgacaa caagataat       780 ggaacttgga ctcaactttg gctggtatct gaatatcatg aacagggctc cttatatgac      840
tatttgaata gaaatatagt gaccgtggct ggaatgatca agctggcgct ctcaattgct      900
agtggtctgg cacaccttca tatggagatt gttggtacac aaggtaaacc tgctattgct      960
catcgagaca taaaatcaaa gaatatctta gtgaaaaagt gtgaaacttg gccatagcg     1020 gacttagggt tggctgtgaa gcatgattca atactgaaca ctatcgacat acctcagaat     1080
cctaaagtgg gaaccaagag gtatatggct cctgaaatgc ttgatgatac aatgaatgtg     1140
aatatctttg agtccttcaa acgagctgac atctattctg ttggtctggt ttactgggaa     1200
atagcccgga ggtgttcagt cggaggaatt gttgaggagt accaattgcc ttattatgac     1260
atggtgcctt cagatccctc gatagaggaa atgagaaagg ttgtttgtga ccagaagttt     1320
cgaccaagta tcccaaacca gtggcaaagt tgtgaagcac tccgagtcat ggggagaata     1380
atgcgtgagt gttggtatgc caacggagcg gcccgcctaa ctgctcttcg tattaagaag     1440
actatatctc aactttgtgt caagaagac tgcaaagcc                            1479
```

<210> SEQ ID NO 234
<211> LENGTH: 279
<212> TYPE: DNA
<213> ORGANISM: Homo sapiens

<400> SEQUENCE: 234

```
gagctctcgc caggactgaa gtgtgtatgt cttttgtgtg attcttcaaa ctttacctgc       60
caaacagaag gagcatgttg ggcatcagtc atgctaacca atggaaaaga gcaggtgatc      120
aaatcctgtg tctcccttcc agaactgaat gctcaagtct tctgtcatag ttccaacaat      180
gttaccaaaa ccgaatgctg cttcacagat ttttgcaaca acataacact gcaccttcca      240
acagcatcac caaatgcccc aaaacttgga cccatggag                              279
```

<210> SEQ ID NO 235
<211> LENGTH: 1329
<212> TYPE: DNA
<213> ORGANISM: Homo sapiens

<400> SEQUENCE: 235

```
atgctaacca atggaaaaga gcaggtgatc aaatcctgtg tctcccttcc agaactgaat      60
gctcaagtct tctgtcatag ttccaacaat gttaccaaaa ccgaatgctg cttcacagat     120
ttttgcaaca acataacact gcaccttcca acagcatcac caaatgcccc aaaacttgga     180
cccatggagc tggccatcat tattactgtg cctgtttgcc tcctgtccat agctgcgatg     240
ctgacagtat gggcatgcca gggtcgacag tgctcctaca ggaagaaaaa gagaccaaat     300
gtggaggaac cactctctga gtgcaatctg gtaaatgctg aaaaactct gaaagatctg     360
atttatgatg tgaccgcctc tggatctggc tctggtctac ctctgttggt tcaaaggaca     420
attgcaagga cgattgtgct tcaggaaata gtaggaaaag gtagatttgg tgaggtgtgg     480
catggaagat ggtgtgggga agatgtggct gtgaaaatat ctcctccag agatgaaaga     540
tcttggtttc gtgaggcaga aatttaccag acggtcatgc tgcgacatga aaacatcctt     600
ggtttcattg ctgctgacaa caaagataat ggaacttgga ctcaactttg gctggtatct     660
gaatatcatg aacagggctc cttatatgac tatttgaata aaatatagt gaccgtggct     720
ggaatgatca agctggcgct ctcaattgct agtggtctgg cacaccttca tatggagatt     780
gttggtacac aagtaaaacc tgctattgct catcgagaca taaaatcaaa gaatatctta     840
gtgaaaaagt gtgaaacttg tgccatagcg gacttagggt tggctgtgaa gcatgattca     900
atactgaaca ctatcgacat acctcagaat cctaaagtgg gaaccaagag gtatatggct     960
cctgaaatgc ttgatgatac aatgaatgtg aatatctttg agtccttcaa acgagctgac    1020
atctattctg ttggtctggt ttactgggaa atagcccgga ggtgttcagt cggaggaatt    1080
gttgaggagt accaattgcc ttattatgac atggtgcctt cagatccctc gatagaggaa    1140
atgagaaagg ttgtttgtga ccagaagttt cgaccaagta tcccaaacca gtggcaaagt    1200
tgtgaagcac tccgagtcat ggggagaata atgcgtgagt gttggtatgc aacggagcg    1260
gcccgcctaa ctgctcttcg tattaagaag actatatctc aactttgtgt caagaagac    1320
tgcaaagcc                                                            1329
```

<210> SEQ ID NO 236
<211> LENGTH: 189
<212> TYPE: DNA
<213> ORGANISM: Homo sapiens

<400> SEQUENCE: 236

```
atgctaacca atggaaaaga gcaggtgatc aaatcctgtg tctcccttcc agaactgaat      60
gctcaagtct tctgtcatag ttccaacaat gttaccaaaa ccgaatgctg cttcacagat     120
ttttgcaaca acataacact gcaccttcca acagcatcac caaatgcccc aaaacttgga     180
cccatggag                                                             189
```

<210> SEQ ID NO 237
<211> LENGTH: 1239
<212> TYPE: DNA
<213> ORGANISM: Homo sapiens

<400> SEQUENCE: 237

```
atgacccggg cgctctgctc agcgctccgc caggctctcc tgctgctcgc agcggccgcc    60
gagctctcgc caggactgaa gtgtgtatgt cttttgtgtg attcttcaaa ctttacctgc   120
caaacagaag gagcatgttg ggcatcagtc atgctaacca atggaaaaga gcaggtgatc   180
aaatcctgtg tctcccttcc agaactgaat gctcaagtct tctgtcatag ttccaacaat   240
gttaccaaaa ccgaatgctg cttcacagat ttttgcaaca acataacact gcaccttcca   300
acaggtctac ctctgttggt tcaaaggaca attgcaagga cgattgtgct tcaggaaata   360
gtaggaaaag gtagatttgg tgaggtgtgg catggaagat ggtgtgggga agatgtggct   420
gtgaaaatat tctcctccag agatgaaaga tcttggtttc gtgaggcaga aatttaccag   480
acggtcatgc tgcgacatga aaacatcctt ggtttcattg ctgctgacaa caaagataat   540
ggaacttgga ctcaactttg gctggtatct gaatatcatg aacagggctc cttatatgac   600
tatttgaata gaaatatagt gaccgtggct ggaatgatca agctggcgct ctcaattgct   660
agtggtctgg cacaccttca tatggagatt gttggtacac aaggtaaacc tgctattgct   720
catcgagaca taaaatcaaa gaatatctta gtgaaaaagt gtgaaacttg tgccatagcg   780
gacttagggt tggctgtgaa gcatgattca atactgaaca ctatcgacat acctcagaat   840
cctaaagtgg gaaccaagag gtatatggct cctgaaatgc ttgatgatac aatgaatgtg   900
aatatctttg agtccttcaa acgagctgac atctattctg ttggtctggt ttactgggaa   960
atagcccgga ggtgttcagt cggaggaatt gttgaggagt accaattgcc ttattatgac  1020
atggtgcctt cagatccctc gatagaggaa atgagaaagg ttgtttgtga ccagaagttt  1080
cgaccaagta tcccaaacca gtggcaaagt tgtgaagcac tccgagtcat ggggagaata  1140
atgcgtgagt gttggtatgc caacggagcg gcccgcctaa ctgctcttcg tattaagaag  1200
actatatctc aactttgtgt caaagaagac tgcaaagcc                         1239
```

<210> SEQ ID NO 238
<211> LENGTH: 1179
<212> TYPE: DNA
<213> ORGANISM: Homo sapiens

<400> SEQUENCE: 238

```
gagctctcgc caggactgaa gtgtgtatgt cttttgtgtg attcttcaaa ctttacctgc    60
caaacagaag gagcatgttg ggcatcagtc atgctaacca atggaaaaga gcaggtgatc   120
aaatcctgtg tctcccttcc agaactgaat gctcaagtct tctgtcatag ttccaacaat   180
gttaccaaaa ccgaatgctg cttcacagat ttttgcaaca acataacact gcaccttcca   240
acaggtctac ctctgttggt tcaaaggaca attgcaagga cgattgtgct tcaggaaata   300
gtaggaaaag gtagatttgg tgaggtgtgg catggaagat ggtgtgggga agatgtggct   360
gtgaaaatat tctcctccag agatgaaaga tcttggtttc gtgaggcaga aatttaccag   420
acggtcatgc tgcgacatga aaacatcctt ggtttcattg ctgctgacaa caaagataat   480
ggaacttgga ctcaactttg gctggtatct gaatatcatg aacagggctc cttatatgac   540
tatttgaata gaaatatagt gaccgtggct ggaatgatca agctggcgct ctcaattgct   600
agtggtctgg cacaccttca tatggagatt gttggtacac aaggtaaacc tgctattgct   660
catcgagaca taaaatcaaa gaatatctta gtgaaaaagt gtgaaacttg tgccatagcg   720
gacttagggt tggctgtgaa gcatgattca atactgaaca ctatcgacat acctcagaat   780
cctaaagtgg gaaccaagag gtatatggct cctgaaatgc ttgatgatac aatgaatgtg   840
aatatctttg agtccttcaa acgagctgac atctattctg ttggtctggt ttactgggaa   900
```

```
atagcccgga ggtgttcagt cggaggaatt gttgaggagt accaattgcc ttattatgac    960
atggtgcctt cagatccctc gatagaggaa atgagaaagg ttgtttgtga ccagaagttt   1020
cgaccaagta tcccaaacca gtggcaaagt tgtgaagcac tccgagtcat ggggagaata   1080
atgcgtgagt gttggtatgc caacggagcg gcccgcctaa ctgctcttcg tattaagaag   1140
actatatctc aactttgtgt caaagaagac tgcaaagcc                          1179
```

<210> SEQ ID NO 239
<211> LENGTH: 1011
<212> TYPE: DNA
<213> ORGANISM: Homo sapiens

<400> SEQUENCE: 239

```
atgacccggg cgctctgctc agcgctccgc caggctctcc tgctgctcgc agcggccgcc     60
gagctctcgc caggactgaa gtgtgtatgt cttttgtgtg attcttcaaa ctttacctgc    120
caaacagaag gagcatgttg ggcatcagtc atgctaacca atggaaaaga gcaggtgatc    180
aaatcctgtg tctcccttcc agaactgaat gctcaagtct tctgtcatag ttccaacaat    240
gttaccaaaa ccgaatgctg cttcacagat ttttgcaaca acataacact gcaccttcca    300
acagataatg gaacttggac tcaactttgg ctggtatctg aatatcatga cagggctcc     360 ttatatgact atttgaatag aaatatagtg accgtggctg aatgatcaa gctggcgctc     420 tcaattgcta gtggtctggc acccttcat atggagattg ttggtacaca aggtaaacct     480
gctattgctc atcgagacat aaaatcaaag aatatcttag tgaaaaagtg tgaaacttgt    540
gccatagcgg acttagggtt ggctgtgaag catgattcaa tactgaacac tatcgacata    600
cctcagaatc ctaaagtggg aaccaagagg tatatggctc ctgaaatgct tgatgataca    660
atgaatgtga atatctttga gtccttcaaa cgagctgaca tctattctgt tggtctggtt    720
tactgggaaa tagcccggag gtgttcagtc ggaggaattg ttgaggagta ccaattgcct    780
tattatgaca tggtgccttc agatccctcg atagaggaaa tgagaaaggt tgtttgtgac    840
cagaagtttc gaccaagtat cccaaaccag tggcaaagtt gtgaagcact ccgagtcatg    900
gggagaataa tgcgtgagtg ttggtatgcc aacggagcgg cccgcctaac tgctcttcgt    960
attaagaaga ctatatctca actttgtgtc aaagaagact gcaaagccta a            1011
```

<210> SEQ ID NO 240
<211> LENGTH: 951
<212> TYPE: DNA
<213> ORGANISM: Homo sapiens

<400> SEQUENCE: 240

```
gagctctcgc caggactgaa gtgtgtatgt cttttgtgtg attcttcaaa ctttacctgc     60
caaacagaag gagcatgttg ggcatcagtc atgctaacca atggaaaaga gcaggtgatc    120
aaatcctgtg tctcccttcc agaactgaat gctcaagtct tctgtcatag ttccaacaat    180
gttaccaaaa ccgaatgctg cttcacagat ttttgcaaca acataacact gcaccttcca    240
acagataatg gaacttggac tcaactttgg ctggtatctg aatatcatga cagggctcc     300 ttatatgact atttgaatag aaatatagtg accgtggctg aatgatcaa gctggcgctc     360 tcaattgcta gtggtctggc acccttcat atggagattg ttggtacaca aggtaaacct     420
gctattgctc atcgagacat aaaatcaaag aatatcttag tgaaaaagtg tgaaacttgt    480
gccatagcgg acttagggtt ggctgtgaag catgattcaa tactgaacac tatcgacata    540
```

| | |
|---|---|
| cctcagaatc ctaaagtggg aaccaagagg tatatggctc ctgaaatgct tgatgataca | 600 |
| atgaatgtga atatctttga gtccttcaaa cgagctgaca tctattctgt tggtctggtt | 660 |
| tactgggaaa tagcccggag gtgttcagtc ggaggaattg ttgaggagta ccaattgcct | 720 |
| tattatgaca tggtgccttc agatccctcg atagaggaaa tgagaaaggt tgtttgtgac | 780 |
| cagaagtttc gaccaagtat cccaaaccag tggcaaagtt gtgaagcact ccgagtcatg | 840 |
| gggagaataa tgcgtgagtg ttggtatgcc aacggagcgg cccgcctaac tgctcttcgt | 900 |
| attaagaaga ctatatctca actttgtgtc aaagaagact gcaaagccta a | 951 |

<210> SEQ ID NO 241
<211> LENGTH: 1539
<212> TYPE: DNA
<213> ORGANISM: Homo sapiens

<400> SEQUENCE: 241

| | |
|---|---|
| atgggagctg ctgcaaagtt ggcgtttgcc gtctttctta tctcctgttc ttcaggtgct | 60 |
| atacttggta gatcagaaac tcaggagtgt cttttcttta atgctaattg ggaaaaagac | 120 |
| agaaccaatc aaactggtgt tgaaccgtgt tatggtgaca agataaacg gcggcattgt | 180 |
| tttgctacct ggaagaatat ttctggttcc attgaaatag tgaaacaagg ttgttggctg | 240 |
| gatgatatca actgctatga caggactgat tgtgtagaaa aaaagacag ccctgaagta | 300 |
| tattttgtt gctgtgaggg caatatgtgt aatgaaaagt ttctttatttt tccggagatg | 360 |
| gaagtcacac agcccacttc aaatccagtt acacctaagc caccctatta caacatcctg | 420 |
| ctctattcct tggtgccact tatgttaatt gcggggattg tcatttgtgc attttgggtg | 480 |
| tacaggcatc acaagatggc ctacctcct gtacttgttc caactcaaga cccaggacca | 540 |
| ccccccacctt ctccattact aggtttgaaa ccactgcagt tattagaagt gaaagcaagg | 600 |
| ggaagatttg gttgtgtctg gaaagcccag ttgcttaacg aatatgtggc tgtcaaaata | 660 |
| tttccaatac aggacaaaca gtcatggcaa aatgaatacg aagtctacag tttgcctgga | 720 |
| atgaagcatg agaacatatt acagttcatt ggtgcagaaa acgaggcac cagtgttgat | 780 |
| gtggatctt ggctgatcac agcatttcat gaaaagggtt cactatcaga ctttcttaag | 840 |
| gctaatgtgg tctcttggaa tgaactgtgt catattgcag aaaccatggc tagaggattg | 900 |
| gcatatttac atgaggatat acctggccta aagatggcc acaaacctgc catatctcac | 960 |
| agggacatca aaagtaaaaa tgtgctgttg aaaaacaacc tgacagcttg cattgctgac | 1020 |
| tttgggttgg ccttaaaatt tgaggctggc aagtctgcag gcgataccca tggacaggtt | 1080 |
| ggtacccgga ggtacatggc tccagaggta ttagagggtg ctataaactt ccaaagggat | 1140 |
| gcatttttga ggatagatat gtatgccatg ggattagtcc tatgggaact ggcttctcgc | 1200 |
| tgtactgctg cagatggacc tgtagatgaa tacatgttgc catttgagga ggaaattggc | 1260 |
| cagcatccat ctcttgaaga catgcaggaa gttgttgtgc ataaaaaaaa gaggcctgtt | 1320 |
| ttaagagatt attggcagaa acatgctgga atggcaatgc tctgtgaaac cattgaagaa | 1380 |
| tgttgggatc acgacgcaga agccaggtta tcagctggat gtgtaggtga agaattacc | 1440 |
| cagatgcaga gactaacaaa tattattacc acagaggaca ttgtaacagt ggtcacaatg | 1500 |
| gtgacaaatg ttgactttcc tcccaaagaa tctagtcta | 1539 |

<210> SEQ ID NO 242
<211> LENGTH: 345
<212> TYPE: DNA
<213> ORGANISM: Homo sapiens

<400> SEQUENCE: 242

```
atacttggta gatcagaaac tcaggagtgt cttttcttta atgctaattg ggaaaaagac      60
agaaccaatc aaactggtgt tgaaccgtgt tatggtgaca agataaacg gcggcattgt      120
tttgctacct ggaagaatat ttctggttcc attgaaatag tgaaacaagg ttgttggctg     180
gatgatatca actgctatga caggactgat tgtgtagaaa aaaagacag ccctgaagta      240
tattttgtt gctgtgaggg caatatgtgt aatgaaagt tttcttattt tccggagatg       300
gaagtcacac agcccacttc aaatccagtt acacctaagc caccc                     345
```

<210> SEQ ID NO 243
<211> LENGTH: 1065
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 243

```
atggatgcaa tgaagagagg gctctgctgt gtgctgctgc tgtgtggagc agtcttcgtt      60
tcgcccggcg cctccgggcc ccgggggggtc caggctctgc tgtgtgcgtg caccagctgc    120
ctccaggcca actacacgtg tgagacagat ggggcctgca tggtttccat tttcaatctg     180
gatgggatgg agcaccatgt gcgcacctgc atccccaaag tggagctggt ccctgccggg     240
aagcccttct actgcctgag ctcggaggac ctgcgcaaca cccactgctg ctacactgac     300
tactgcaaca ggatcgactt gagggtgccc agtggtcacc tcaaggagcc tgagcacccg     360
tccatgtggg gcccggtgga gaccggtggt ggaactcaca catgcccacc gtgcccagca     420
cctgaactcc tggggggacc gtcagtcttc ctcttcccc caaaacccaa ggacaccctc      480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
gacaccacgc ctcccgtgct ggactccgac ggctccttct cctctatag cgacctcacc      960
gtggacaaga gcaggtggca gcagggggaac gtcttctcat gctccgtgat gcatgaggct    1020
ctgcacaacc actacacgca gaagagcctc tccctgtctc cgggt                    1065
```

<210> SEQ ID NO 244
<211> LENGTH: 1065
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 244

```
atggatgcaa tgaagagagg gctctgctgt gtgctgctgc tgtgtggagc agtcttcgtt      60
tcgcccggcg ccatggaaga tgagaagccc aaggtcaacc ccaaactcta catgtgtgtg    120
tgtgaaggtc tctcctgcgg taatgaggac cactgtgaag gccagcagtg cttttcctca     180
```

```
ctgagcatca acgatggctt ccacgtctac cagaaaggct gcttccaggt ttatgagcag      240
ggaaagatga cctgtaagac cccgccgtcc cctggccaag ctgtggagtg ctgccaaggg      300
gactggtgta acaggaacat cacggcccag ctgcccacta aaggaaaatc cttccctgga      360
acacagaatt ccacttggac gaccggtggt ggaactcaca catgcccacc gtgcccagca      420
cctgaactcc tggggggacc gtcagtcttc ctcttccccc caaaacccaa ggacaccctc      480
atgatctccc ggacccctga ggtcacatgc gtggtggtgg acgtgagcca cgaagaccct      540
gaggtcaagt tcaactggta cgtggacggc gtggaggtgc ataatgccaa gacaaagccg      600
cgggaggagc agtacaacag cacgtaccgt gtggtcagcg tcctcaccgt cctgcaccag      660
gactggctga atggcaagga gtacaagtgc aaggtctcca acaaagccct cccagccccc      720
atcgagaaaa ccatctccaa agccaaaggg cagccccgag aaccacaggt gtacaccctg      780
cccccatccc gggaggagat gaccaagaac caggtcagcc tgacctgcct ggtcaaaggc      840
ttctatccca gcgacatcgc cgtggagtgg gagagcaatg ggcagccgga gaacaactac      900
gacaccacgc ctcccgtgct ggactccgac ggctccttct cctctatagc gacctcacc       960 gtggacaaga gcaggtggca gcaggggaac gtcttctcat gctccgtgat gcatgaggct     1020
ctgcacaacc actacacgca gaagagcctc tccctgtctc cgggt                     1065
```

<210> SEQ ID NO 245
<211> LENGTH: 1143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245

```
atggatgcaa tgaagagagg gctctgctgt gtgctgctgc tgtgtggagc agtcttcgtt       60
tcgcccggcg cccagaatct ggatagtatg cttcatggca ctgggatgaa atcagactcc      120
gaccagaaaa agtcagaaaa tggagtaacc ttagcaccag aggataccttt gccttttta      180 aagtgctatt gctcagggca ctgtccagat gatgctatta ataacacatg cataactaat      240
ggacattgct ttgccatcat agaagaagat gaccaggag aaaccacatt agcttcaggg      300
tgtatgaaat atgaaggatc tgattttcag tgcaaagatt ctccaaaagc ccagctacgc      360
cggacaatag aatgttgtcg gaccaattta tgtaaccagt atttgcaacc cacactgccc      420
cctgttgtca taggtccgtt ttttgatggc agcattcgaa ccggtggtgg aactcacaca      480
tgcccaccgt gcccagcacc tgaactcctg ggggaccgt cagtcttcct cttccccca       540 aaacccaagg acaccctcat gatctcccgg acccctgagg tcacatgcgt ggtggtggac      600
gtgagccaca agaccctga ggtcaagttc aactggtacg tggacggcgt ggaggtgcat      660
aatgccaaga caaagccgcg ggaggagcag tacaacagca cgtaccgtgt ggtcagcgtc      720
ctcaccgtcc tgcaccagga ctggctgaat ggcaaggagt acaagtgcaa ggtctccaac      780
aaagccctcc cagcccccat cgagaaaacc atctccaaag ccaaaggca gccccgagaa      840 ccacaggtgt acaccctgcc cccatcccgg gaggagatga ccaagaacca ggtcagcctg      900
acctgcctgg tcaaaggctt ctatcccagc gacatcgccg tggagtggga gagcaatggg      960
cagccggaga caactacga caccacgcct cccgtgctgg actccgacgg ctccttcttc     1020
ctctatagcg acctcaccgt ggacaagagc aggtggcagc aggggaacgt cttctcatgc     1080
tccgtgatgc atgaggctct gcacaaccac tacacgcaga agagcctctc cctgtctccg     1140
```

```
ggt                                                               1143
```

<210> SEQ ID NO 246
<211> LENGTH: 22
<212> TYPE: PRT
<213> ORGANISM: Unknown
<220> FEATURE:
<223> OTHER INFORMATION: Description of Unknown:
      Tissue plasminogen activator

<400> SEQUENCE: 246

Met Asp Ala Met Lys Arg Gly Leu Cys Cys Val Leu Leu Leu Cys Gly
1               5                   10                  15

Ala Val Phe Val Ser Pro
            20

<210> SEQ ID NO 247
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val

```
                260                 265                 270
Ser Leu Ser Cys Ala Val Lys Gly Phe Tyr Pro Ser Asp Ile Ala Val
            275                 280                 285

Glu Trp Glu Ser Arg Gly Gln Pro Glu Asn Asn Tyr Lys Thr Thr Pro
        290                 295                 300

Pro Val Leu Asp Ser Arg Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 248
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248
atggatgcaa tgaagagagg gctctgctgt gtgctgctgc tgtgtggagc agtcttcgtt      60
tcgcccggcg cctccgggcc ccgggggggtc caggctctgc tgtgtgcgtg caccagctgc    120
ctccaggcca actacacgtg tgagacagat ggggcctgca tggtttccat tttcaatctg    180
gatgggatgg agcaccatgt gcgcacctgc atccccaaag tggagctggt ccctgccggg    240
aagcccttct actgcctgag ctcggaggac ctgcgcaaca cccactgctg ctacactgac    300
tactgcaaca ggatcgactt gagggtgccc agtggtcacc tcaaggagcc tgagcacccg    360
tccatgtggg gcccggtgga gaccggtggt ggaactcaca catgcccacc gtgcccagca    420
cctgaactcc tggggggacc gtcagtcttc ctcttccccc caaaacccaa ggacaccctc    480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtgcaccctg    780
cccccatccc gggaggagat gaccaagaac caggtcagcc tgtcctgcgc cgtcaaaggc    840
ttctatccca gcgacatcgc cgtggagtgg gagagccgcg gcagccggga gaacaactac    900
aagaccacgc ctcccgtgct ggactccgcg ggctccttct cctcgtgag caagctcacc    960 gtggacaaga gcaggtggca gcagggaaac gtcttctcat gctccgtgat gcatgaggct   1020
ctgcacaacc actacacgca gaagagcctc tccctgtctc cgggtaaa              1068

<210> SEQ ID NO 249
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Ser Gly Pro Arg Gly Val Gln Ala Leu Leu Cys Ala Cys Thr Ser Cys
```

```
  1               5                   10                  15
Leu Gln Ala Asn Tyr Thr Cys Glu Thr Asp Gly Ala Cys Met Val Ser
                20                  25                  30
Ile Phe Asn Leu Asp Gly Met Glu His His Val Arg Thr Cys Ile Pro
                35                  40                  45
Lys Val Glu Leu Val Pro Ala Gly Lys Pro Phe Tyr Cys Leu Ser Ser
                50                  55                  60
Glu Asp Leu Arg Asn Thr His Cys Cys Tyr Thr Asp Tyr Cys Asn Arg
 65                 70                  75                  80
Ile Asp Leu Arg Val Pro Ser Gly His Leu Lys Glu Pro His Pro
                    85                  90                  95
Ser Met Trp Gly Pro Val Glu Thr Gly Gly Thr His Thr Cys Pro
                    100                 105                 110
Pro Cys Pro Ala Pro Glu Leu Leu Gly Gly Pro Ser Val Phe Leu Phe
                    115                 120                 125
Pro Pro Lys Pro Lys Asp Thr Leu Met Ile Ser Arg Thr Pro Glu Val
                    130                 135                 140
Thr Cys Val Val Val Asp Val Ser His Glu Asp Pro Glu Val Lys Phe
145                 150                 155                 160
Asn Trp Tyr Val Asp Gly Val Glu Val His Asn Ala Lys Thr Lys Pro
                    165                 170                 175
Arg Glu Glu Gln Tyr Asn Ser Thr Tyr Arg Val Val Ser Val Leu Thr
                    180                 185                 190
Val Leu His Gln Asp Trp Leu Asn Gly Lys Glu Tyr Lys Cys Lys Val
                    195                 200                 205
Ser Asn Lys Ala Leu Pro Ala Pro Ile Glu Lys Thr Ile Ser Lys Ala
                    210                 215                 220
Lys Gly Gln Pro Arg Glu Pro Gln Val Cys Thr Leu Pro Pro Ser Arg
225                 230                 235                 240
Glu Glu Met Thr Lys Asn Gln Val Ser Leu Ser Cys Ala Val Lys Gly
                    245                 250                 255
Phe Tyr Pro Ser Asp Ile Ala Val Glu Trp Glu Ser Arg Gly Gln Pro
                    260                 265                 270
Glu Asn Asn Tyr Lys Thr Thr Pro Pro Val Leu Asp Ser Arg Gly Ser
                    275                 280                 285
Phe Phe Leu Val Ser Lys Leu Thr Val Asp Lys Ser Arg Trp Gln Gln
                    290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys
                    325                 330
```

<210> SEQ ID NO 250
<211> LENGTH: 996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250
tccgggcccc gggggtcca ggctctgctg tgtgcgtgca ccagctgcct ccaggccaac      60
tacacgtgtg agacagatgg ggcctgcatg gtttccattt tcaatctgga tgggatggag    120
caccatgtgc gcacctgcat ccccaaagtg gagctggtcc ctgccgggaa gcccttctac    180

-continued

```
tgcctgagct cggaggacct gcgcaacacc cactgctgct acactgacta ctgcaacagg    240
atcgacttga gggtgcccag tggtcacctc aaggagcctg agcacccgtc catgtggggc    300
ccggtggaga ccggtggtgg aactcacaca tgcccaccgt gcccagcacc tgaactcctg    360
gggggaccgt cagtcttcct cttccccca aaacccaagg acaccctcat gatctcccgg     420
acccctgagg tcacatgcgt ggtggtggac gtgagccacg aagaccctga ggtcaagttc    480
aactggtacg tggacggcgt ggaggtgcat aatgccaaga caaagccgcg ggaggagcag    540
tacaacagca cgtaccgtgt ggtcagcgtc ctcaccgtcc tgcaccagga ctggctgaat    600
ggcaaggagt acaagtgcaa ggtctccaac aaagccctcc cagcccccat cgagaaaacc    660
atctccaaag ccaaagggca gccccgagaa ccacaggtgt gcaccctgcc cccatcccgg    720
gaggagatga ccaagaacca ggtcagcctg tcctgcgccg tcaaaggctt ctatcccagc    780
gacatcgccg tggagtggga gagccgcggg cagccggaga caactacaa gaccacgcct     840 cccgtgctgg actcccgcgg ctccttcttc ctcgtgagca agctcaccgt ggacaagagc    900
aggtggcagc aggggaacgt cttctcatgc tccgtgatgc atgaggctct gcacaaccac    960
tacacgcaga gagcctctc cctgtctccg ggtaaa                               996
```

<210> SEQ ID NO 251
<211> LENGTH: 1068
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 251

```
atggatgcaa tgaagagagg gctctgctgt gtgctgctgc tgtgtggagc agtcttcgtt    60
tcgcccggcg cctccgggcc ccgggggggtc caggctctgc tgtgtgcgtg caccagctgc    120
ctccaggcca actacacgtg tgagacagat ggggcctgca tggtttccat tttcaatctg    180
gatgggatgg agcaccatgt gcgcacctgc atccccaaag tggagctggt ccctgccggg    240
aagcccttct actgcctgag ctcggaggac ctgcgcaaca cccactgctg ctacactgac    300
tactgcaaca ggatcgactt gagggtgccc agtggtcacc tcaaggagcc tgagcacccg    360
tccatgtggg gcccggtgga gaccggtggt ggaactcaca catgcccacc gtgcccagca    420
cctgaactcc tggggggacc gtcagtcttc ctcttccccc caaaacccaa ggacaccctc    480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtgcaccctg    780
cccccatccc gggaggagat gaccaagaac caggtcagcc tgtcctgcgc cgtcaaaggc    840
ttctatccca gcgacatcgc cgtggagtgg gagagcaatg ggcagccgga gaacaactac    900
aagaccacgc ctcccgtgct ggactccgac ggctccttct cctcgtgag caagctcacc     960 gtggacaaga gcaggtggca gcaggggaac gtcttctcat gctccgtgat gcatgaggct    1020
ctgcacaacc actacacgca gaagagcctc tccctgtctc cgggtaaa                 1068
```

<210> SEQ ID NO 252
<211> LENGTH: 996
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 252

```
tccgggcccc ggggggtcca ggctctgctg tgtgcgtgca ccagctgcct ccaggccaac    60
tacacgtgtg agacagatgg ggcctgcatg gtttccattt tcaatctgga tgggatggag   120
caccatgtgc gcacctgcat ccccaaagtg gagctggtcc ctgccgggaa gcccttctac   180
tgcctgagct cggaggacct gcgcaacacc cactgctgct acactgacta ctgcaacagg   240
atcgacttga gggtgcccag tggtcacctc aaggagcctg agcacccgtc catgtggggc   300
ccggtggaga ccggtggtgg aactcacaca tgcccaccgt gcccagcacc tgaactcctg   360
gggggaccgt cagtcttcct cttccccca aaacccaagg acaccctcat gatctcccgg   420
accctgagg tcacatgcgt ggtggtggac gtgagccacg aagaccctga ggtcaagttc    480
aactggtacg tggacggcgt ggaggtgcat aatgccaaga caaagccgcg ggaggagcag   540
tacaacagca cgtaccgtgt ggtcagcgtc ctcaccgtcc tgcaccagga ctggctgaat   600
ggcaaggagt acaagtgcaa ggtctccaac aaagcccctcc cagcccccat cgagaaaacc   660
atctccaaag ccaaagggca gccccgagaa ccacaggtgt gcaccctgcc cccatcccgg   720
gaggagatga ccaagaacca ggtcagcctg tcctgcgccg tcaaaggctt ctatcccagc   780
gacatcgccg tggagtggga gagcaatggg cagccggaga caactacaa gaccacgcct    840
cccgtgctgg actccgacgg ctccttcttc ctcgtgagca agctcaccgt ggacaagagc   900
aggtggcagc aggggaacgt cttctcatgc tccgtgatgc atgaggctct gcacaaccac   960
tacacgcaga agagcctctc cctgtctccg ggtaaa                             996
```

<210> SEQ ID NO 253
<211> LENGTH: 1056
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 253

```
atggatgcaa tgaagagagg gctctgctgt gtgctgctgc tgtgtggagc agtcttcgtt    60
tcgcccggcg ccgcgctgct cccgggggcg acggcgttac agtgtttctg ccacctctgt   120
acaaaagaca attttacttg tgtgacagat gggctctgct ttgtctctgt cacagagacc   180
acagacaaag ttatacacaa cagcatgtgt atagctgaaa ttgacttaat tcctcgagat   240
aggccgtttg tatgtgcacc ctcttcaaaa actgggtctg tgactacaac atattgctgc   300
aatcaggacc attgcaataa aatagaactt ccaactactg taaagtcatc acctggcctt   360
ggtcctgtgg aaaccggtgg tggaactcac acatgcccac cgtgcccagc acctgaactc   420
ctggggggac cgtcagtctt cctcttcccc ccaaaaccca aggacaccct catgatctcc   480
cggacccctg aggtcacatg cgtggtggtg gacgtgagcc acgaagaccc tgaggtcaag   540
ttcaactggt acgtggacgg cgtggaggtg cataatgcca agacaaagcc gcgggaggag   600
cagtacaaca gcacgtaccg tgtggtcagc gtcctcaccg tcctgcacca ggactggctg   660
aatggcaagg agtacaagtg caaggtctcc aacaaagccc tcccagcccc catcgagaaa   720
accatctcca agccaaagg gcagccccga gaaccacagg tgtacaccct gcccccatcc   780
cgggaggaga tgaccaagaa ccaggtcagc ctgacctgcc tggtcaaagg cttctatccc   840
```

```
agcgacatcg ccgtggagtg ggagagcaat gggcagccgg agaacaacta cgacaccacg    900
cctcccgtgc tggactccga cggctccttc ttcctctata cgacctcac cgtggacaag    960 agcaggtggc agcaggggaa cgtcttctca tgctccgtga tgcatgaggc tctgcacaac   1020
cactacacgc agaagagcct ctccctgtct ccgggt                             1056
```

<210> SEQ ID NO 254
<211> LENGTH: 1095
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 254

```
atggatgcaa tgaagagagg gctctgctgt gtgctgctgc tgtgtggagc agtcttcgtt     60
tcgcccggcg ccaagaaaga ggatggtgag agtacagccc ccaccccccg tccaaaggtc    120
ttgcgttgta aatgccacca ccattgtcca gaagactcag tcaacaatat ttgcagcaca    180
gacggatatt gtttcacgat gatagaagag gatgactctg ggttgcctgt ggtcacttct    240
ggttgcctag gactagaagg ctcagatttt cagtgtcggg acactccat tcctcatcaa     300 agaagatcaa ttgaatgctg cacagaaagg aacgaatgta ataaagacct acaccctaca    360
ctgcctccat tgaaaaacag agattttgtt gatggaccta tacaccacag gaccggtggt    420
ggaactcaca catgcccacc gtgcccagca cctgaactcc tggggggacc gtcagtcttc    480
ctcttccccc caaaacccaa ggacaccctc atgatctccc ggacccctga ggtcacatgc    540
gtggtggtgg acgtgagcca cgaagaccct gaggtcaagt tcaactggta cgtggacggc    600
gtggaggtgc ataatgccaa gacaaagccg cgggaggagc agtacaacag cacgtaccgt    660
gtggtcagcg tcctcaccgt cctgcaccag gactggctga atggcaagga gtacaagtgc    720
aaggtctcca acaaagccct cccagccccc atcgagaaaa ccatctccaa agccaaaggg    780
cagccccgag aaccacaggt gtacaccctg cccccatccc gggaggagat gaccaagaac    840
caggtcagcc tgacctgcct ggtcaaaggc ttctatccca gcgacatcgc cgtggagtgg    900
gagagcaatg ggcagccgga gaacaactac gacaccacgc ctcccgtgct ggactccgac    960
ggctccttct tcctctatag cgacctcacc gtggacaaga gcaggtggca gcaggggaac   1020
gtcttctcat gctccgtgat gcatgaggct ctgcacaacc actacacgca gaagagcctc   1080
tccctgtctc cgggt                                                    1095
```

<210> SEQ ID NO 255
<211> LENGTH: 1023
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 255

```
atggatgcaa tgaagagagg gctctgctgt gtgctgctgc tgtgtggagc agtcttcgtt     60
tcgcccggcg ccggactgaa gtgtgtatgt cttttgtgtg attcttcaaa ctttacctgc    120
caaacagaag gagcatgttg ggcatcagtc atgctaacca atggaaaaga gcaggtgatc    180
aaatcctgtg tctcccttcc agaactgaat gctcaagtct tctgtcatag ttccaacaat    240
gttaccaaaa ccgaatgctg cttcacagat ttttgcaaca acataacact gcaccttcca    300
```

| | |
|---|---|
| acagcatcac caaatgcccc aaaacttgga cccatggaga ccggtggtgg aactcacaca | 360 |
| tgcccaccgt gcccagcacc tgaactcctg gggggaccgt cagtcttcct cttcccccca | 420 |
| aaacccaagg acaccctcat gatctcccgg acccctgagg tcacatgcgt ggtggtggac | 480 |
| gtgagccacg aagaccctga ggtcaagttc aactggtacg tggacggcgt ggaggtgcat | 540 |
| aatgccaaga caaagccgcg ggaggagcag tacaacagca cgtaccgtgt ggtcagcgtc | 600 |
| ctcaccgtcc tgcaccagga ctggctgaat ggcaaggagt acaagtgcaa ggtctccaac | 660 |
| aaagccctcc cagcccccat cgagaaaacc atctccaaag ccaagggca gccccgagaa | 720 |
| ccacaggtgt acaccctgcc cccatcccgg gaggagatga ccaagaacca ggtcagcctg | 780 |
| acctgcctgg tcaaaggctt ctatcccagc gacatcgccg tggagtggga gagcaatggg | 840 |
| cagccggaga caactacga caccacgcct ccgtgctgg actccgacgg ctccttcttc | 900 |
| ctctatagcg acctcaccgt ggacaagagc aggtggcagc aggggaacgt cttctcatgc | 960 |
| tccgtgatgc atgaggctct gcacaaccac tacacgcaga gagcctctc cctgtctccg | 1020 |
| ggt | 1023 |

<210> SEQ ID NO 256
<211> LENGTH: 1107
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 256

| | |
|---|---|
| atggatgcaa tgaagagagg gctctgctgt gtgctgctgc tgtgtggagc agtcttcgtt | 60 |
| tcgcccggcg ccgctatact tggtagatca gaaactcagg agtgtctttt ctttaatgct | 120 |
| aattgggaaa aagacagaac caatcaaact ggtgttgaac cgtgttatgg tgacaaagat | 180 |
| aaacggcggc attgttttgc tacctggaag aatatttctg gttccattga atagtgaaa | 240 |
| caaggttgtt ggctggatga tatcaactgc tatgacagga ctgattgtgt agaaaaaaaa | 300 |
| gacagccctg aagtatattt ctgttgctgt gagggcaata tgtgtaatga aaagttttct | 360 |
| tattttccgg agatggaagt cacacagccc acttcaaatc cagttacacc taagccaccc | 420 |
| accggtggtg aactcacac atgcccaccg tgcccagcac ctgaactcct gggggaccg | 480 |
| tcagtcttcc tcttcccccc aaaacccaag gacaccctca tgatctcccg gacccctgag | 540 |
| gtcacatgcg tggtggtgga cgtgagccac gaagaccctg aggtcaagtt caactggtac | 600 |
| gtggacggcg tggaggtgca taatgccaag acaaagccgc gggaggagca gtacaacagc | 660 |
| acgtaccgtg tggtcagcgt cctcaccgtc ctgcaccagg actggctgaa tggcaaggag | 720 |
| tacaagtgca aggtctccaa caaagccctc cagcccccca tcgagaaaac catctccaaa | 780 |
| gccaaagggc agccccgaga accacaggtg tacaccctgc ccccatcccg gaaggagatg | 840 |
| accaagaacc aggtcagcct gacctgcctg gtcaaaggct tctatcccag cgacatcgcc | 900 |
| gtggagtggg agagcaatgg gcagccggag aacaactaca agaccacgcc tcccgtgctg | 960 |
| aagtccgacg gctccttctt cctctatagc aagctcaccg tggacaagag caggtggcag | 1020 |
| caggggaacg tcttctcatg ctccgtgatg catgaggctc tgcacaacca ctacacgcag | 1080 |
| aagagcctct ccctgtctcc gggtaaa | 1107 |

<210> SEQ ID NO 257
<211> LENGTH: 1128
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 257

```
atggatgcaa tgaagagagg gctctgctgt gtgctgctgc tgtgtggagc agtcttcgtt      60
tcgcccggcg cctcgcagaa tcaagaacgc ctatgtgcgt ttaaagatcc gtatcagcaa     120
gaccttggga taggtgagag tagaatctct catgaaaatg gacaatatt atgctcgaaa      180
ggtagcacct gctatggcct ttgggagaaa tcaaaagggg acataaatct tgtaaaacaa    240
ggatgttggt ctcacattgg agatccccaa gagtgtcact atgaagaatg tgtagtaact    300
accactcctc cctcaattca gaatggaaca taccgtttct gctgttgtag cacagattta    360
tgtaatgtca actttactga gaattttcca cctcctgaca caacaccact cagtccacct    420
cattcattta accgagatga gaccggtggt ggaactcaca catgcccacc gtgcccagca    480
cctgaactcc tggggggacc gtcagtcttc ctcttccccc caaaacccaa ggacaccctc    540
atgatctccc ggacccctga ggtcacatgc gtggtggtgg acgtgagcca cgaagaccct    600
gaggtcaagt tcaactggta cgtggacggc gtggaggtgc ataatgccaa gacaaagccg    660
cgggaggagc agtacaacag cacgtaccgt gtggtcagcg tcctcaccgt cctgcaccag    720
gactggctga atggcaagga gtacaagtgc aaggtctcca acaaagccct cccagccccc    780
atcgagaaaa ccatctccaa agccaaaggg cagccccgag aaccacaggt gtacaccctg    840
cccccatccc ggaaggagat gaccaagaac caggtcagcc tgacctgcct ggtcaaaggc    900
ttctatccca gcgacatcgc cgtggagtgg gagagcaatg ggcagccgga gaacaactac    960
aagaccacgc ctcccgtgct ggagtccgac ggctccttct cctctatag caagctcacc   1020
gtggacaaga gcaggtggca gcaggggaac gtcttctcat gctccgtgat gcatgaggct   1080
ctgcacaacc actacacgca gaagagcctc tccctgtctc cgggtaaa              1128
```

<210> SEQ ID NO 258
<211> LENGTH: 1053
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 258

```
atggatgcaa tgaagagagg gctctgctgt gtgctgctgc tgtgtggagc agtcttcgtt      60
tcgcccggcg ccgaccctgt gaagccgtct cggggcccgc tggtgacctg cacgtgtgag    120
agcccacatt gcaaggggcc tacctgccgg ggggcctggt gcacagtagt gctggtgcgg    180
gaggagggga ggcacccca ggaacatcgg ggctgcggga acttgcacag ggagctctgc     240
aggggccgcc ccaccgagtt cgtcaaccac tactgctgcg acagccacct ctgcaaccac    300
aacgtgtccc tggtgctgga ggccacccaa cctccttcgg agcagccggg aacagatggc    360
cagctggcca ccggtggtgg aactcacaca tgcccaccgt gcccagcacc tgaactcctg    420
gggggaccgt cagtcttcct cttccccca aaacccaagg acaccctcat gatctcccgg     480
accccgagg tcacatgcgt ggtggtggac gtgagccacg aagaccctga ggtcaagttc     540
aactggtacg tggacggcgt ggaggtgcat aatgccaaga caaagccgcg ggaggagcag    600
tacaacagca cgtaccgtgt ggtcagcgtc ctcaccgtcc tgcaccagga ctggctgaat    660
ggcaaggagt acaagtgcaa ggtctccaac aaagccctcc cagcccccat cgagaaaacc    720
```

```
atctccaaag ccaaagggca gccccgagaa ccacaggtgt acaccctgcc cccatcccgg    780
gaggagatga ccaagaacca ggtcagcctg acctgcctgg tcaaaggctt ctatcccagc    840
gacatcgccg tggagtggga gagcaatggg cagccggaga caactacga caccacgcct    900 cccgtgctgg actccgacgg ctccttcttc ctctatagcg acctcaccgt ggacaagagc    960
aggtggcagc aggggaacgt cttctcatgc tccgtgatgc atgaggctct gcacaaccac    1020
tacacgcaga gagcctctc cctgtctccg ggt    1053

<210> SEQ ID NO 259
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
atggatgcaa tgaagagagg gctctgctgt gtgctgctgc tgtgtggagc agtcttcgtt    60
tcgcccggcg ccacgatccc accgcacgtt cagaagtcgg ttaataacga catgatagtc    120
actgacaaca acggtgcagt caagtttcca caactgtgta aattttgtga tgtgagattt    180
tccacctgtg acaaccagaa atcctgcatg agcaactgca gcatcacctc catctgtgag    240
aagccacagg aagtctgtgt ggctgtatgg agaaagaatg acgagaacat aacactagag    300
acagtttgcc atgaccccaa gctcccctac catgacttta ttctggaaga tgctgcttct    360
ccaaagtgca ttatgaagga aaaaaaaaag cctggtgaga cttcttcat gtgttcctgt    420 agctctgatg agtgcaatga acacatcatc ttctcagaag aatataacac cagcaatcct    480
gacaccggtg tggaactca cacatgccca ccgtgcccag cacctgaact cctgggggga    540
ccgtcagtct tcctcttccc cccaaaaccc aaggacaccc tcatgatctc ccggacccct    600
gaggtcacat gcgtggtggt ggacgtgagc cacgaagacc ctgaggtcaa gttcaactgg    660
tacgtggacg gcgtggaggt gcataatgcc aagacaaagc cgcgggagga gcagtacaac    720
agcacgtacc gtgtggtcag cgtcctcacc gtcctgcacc aggactggct gaatggcaag    780
gagtacaagt gcaaggtctc caacaaagcc ctcccagccc ccatcgagaa aaccatctcc    840
aaagccaaag gcagccccg agaaccacag gtgtacaccc tgcccccatc ccggaaggag    900
atgaccaaga accaggtcag cctgacctgc ctggtcaaag gcttctatcc cagcgacatc    960
gccgtggagt gggagagcaa tgggcagccg gagaacaact acaagaccac gcctcccgtg    1020
ctgaagtccg acggctcctt cttcctctat agcaagctca ccgtggacaa gagcaggtgg    1080
cagcagggga acgtcttctc atgctccgtg atgcatgagg ctctgcacaa ccactacacg    1140
cagaagagcc tctccctgtc tccgggtaaa    1170

<210> SEQ ID NO 260
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260
atggatgcaa tgaagagagg gctctgctgt gtgctgctgc tgtgtggagc agtcttcgtt    60
tcgcccggcg ccacgatccc accgcacgtt cagaagtcgg atgtggaaat ggaggcccag    120
```

```
aaagatgaaa tcatctgccc cagctgtaat aggactgccc atccactgag acatattaat    180
aacgacatga tagtcactga caacaacggt gcagtcaagt ttccacaact gtgtaaattt    240
tgtgatgtga gattttccac ctgtgacaac cagaaatcct gcatgagcaa ctgcagcatc    300
acctccatct gtgagaagcc acaggaagtc tgtgtggctg tatggagaaa gaatgacgag    360
aacataacac tagagacagt ttgccatgac cccaagctcc cctaccatga ctttattctg    420
gaagatgctg cttctccaaa gtgcattatg aaggaaaaaa aaaagcctgg tgagactttc    480
ttcatgtgtt cctgtagctc tgatgagtgc aatgacaaca tcatcttctc agaagaatat    540
aacaccagca atcctgacac cggtggtgga actcacacat gcccaccgtg cccagcacct    600
gaactcctgg ggggaccgtc agtcttcctc ttccccccaa acccaaggac caccctcatg    660
atctcccgga cccctgaggt cacatgcgtg gtggtggacg tgagccacga agaccctgag    720
gtcaagttca actggtacgt ggacggcgtg gaggtgcata atgccaagac aaagccgcgg    780
gaggagcagt acaacagcac gtaccgtgtg gtcagcgtcc tcaccgtcct gcaccaggac    840
tggctgaatg gcaaggagta caagtgcaag gtctccaaca aagcccctcc cagcccccatc    900 gagaaaacca tctccaaagc caaagggcag ccccgagaac cacaggtgta caccctgccc    960
ccatcccgga aggagatgac caagaaccag gtcagcctga cctgcctggt caaaggcttc    1020
tatcccagcg acatcgccgt ggagtgggag agcaatgggc agccggagaa caactacaag    1080
accacgcctc ccgtgctgaa gtccgacggc tccttcttcc tctatagcaa gctcaccgtg    1140
gacaagagca ggtggcagca ggggaacgtc ttctcatgct ccgtgatgca tgaggctctg    1200
cacaaccact acacgcagaa gagcctctcc ctgtctccgg gtaaa              1245
```

<210> SEQ ID NO 261
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Gly Gly
1

<210> SEQ ID NO 262
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Gly Gly Gly Gly
1

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Thr Gly Gly Gly Gly
1               5

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Gly Gly Gly Gly
1               5

<210> SEQ ID NO 265
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Thr Gly Gly Gly
1

<210> SEQ ID NO 266
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Gly Gly Gly
1

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Gly Gly Gly Ser
1               5

<210> SEQ ID NO 268
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 268

His His His His His His
1               5

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MISC_FEATURE
<222> LOCATION: (1)..(10)
<223> OTHER INFORMATION: This sequence may encompass 2-10 residues

<400> SEQUENCE: 269

Gly Gly Gly Gly Gly Gly Gly Gly Gly
1               5                   10

<210> SEQ ID NO 270
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This sequence may encompass 2-5 residues

<400> SEQUENCE: 270

Gly Gly Gly Gly Gly
1               5

<210> SEQ ID NO 271
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This sequence may encompass 2-4 residues

<400> SEQUENCE: 271

Gly Gly Gly Gly
1

<210> SEQ ID NO 272
<211> LENGTH: 116
<212> TYPE: PRT
<213> ORGANISM: Homo sapiens

<400> SEQUENCE: 272

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115
```

```
<210> SEQ ID NO 273
<211> LENGTH: 115
<212> TYPE: PRT
<213> ORGANISM: Homo sapiens

<400> SEQUENCE: 273

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 274
<211> LENGTH: 150
<212> TYPE: PRT
<213> ORGANISM: Rattus sp.

<400> SEQUENCE: 274

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 275
<211> LENGTH: 150
<212> TYPE: PRT
<213> ORGANISM: Sus sp.

<400> SEQUENCE: 275

Met Thr Ala Pro Trp Ala Ala Leu Ala Leu Leu Trp Gly Ser Leu Cys
1               5                   10                  15
```

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 276
<211> LENGTH: 150
<212> TYPE: PRT
<213> ORGANISM: Mus sp.

<400> SEQUENCE: 276

Met Thr Ala Pro Trp Ala Ala Leu Ala Leu Leu Trp Gly Ser Leu Cys
 1                5                  10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
 50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 277
<211> LENGTH: 150
<212> TYPE: PRT
<213> ORGANISM: Homo sapiens

<400> SEQUENCE: 277

Met Thr Ala Pro Trp Val Ala Leu Ala Leu Leu Trp Gly Ser Leu Cys
 1                5                  10                  15

Ala Gly Ser Gly Arg Gly Glu Ala Glu Thr Arg Glu Cys Ile Tyr Tyr
            20                  25                  30

```
Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
     50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
    130                 135                 140

Pro Ile Gly Gly Leu Ser
145             150

<210> SEQ ID NO 278
<211> LENGTH: 150
<212> TYPE: PRT
<213> ORGANISM: Bos sp.

<400> SEQUENCE: 278

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
            35                  40                  45

Cys Glu Gly Glu Arg Asp Lys Arg Leu His Cys Tyr Ala Ser Trp Arg
     50                  55                  60

Asn Ser Ser Gly Thr Ile Glu Leu Val Lys Lys Gly Cys Trp Leu Asp
 65                  70                  75                  80

Asp Phe Asn Cys Tyr Asp Arg Gln Glu Cys Val Ala Thr Glu Glu Asn
                 85                  90                  95

Pro Gln Val Tyr Phe Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
    130                 135                 140

Pro Val Gly Gly Leu Ser
145             150

<210> SEQ ID NO 279
<211> LENGTH: 150
<212> TYPE: PRT
<213> ORGANISM: Xenopus sp.

<400> SEQUENCE: 279

Met Gly Ala Ser Val Ala Leu Thr Phe Leu Leu Leu Ala Thr Phe
1               5                   10                  15

Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
            35                  40                  45
```

```
Arg Leu Val Glu Gly Lys Lys Asp Lys Arg Leu His Cys Tyr Ala Ser
    50              55                  60

Trp Arg Asn Asn Ser Gly Phe Ile Glu Leu Val Lys Lys Gly Cys Trp
65              70                  75              80

Leu Asp Asp Phe Asn Cys Tyr Asp Arg Gln Glu Cys Ile Ala Lys Glu
            85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
            115                 120                 125

Gln Pro Ser Ala Ser Val Leu Asn Ile Leu Ile Tyr Ser Leu Leu Pro
            130                 135                 140

Ile Val Gly Leu Ser Met
145                 150

<210> SEQ ID NO 280
<211> LENGTH: 150
<212> TYPE: PRT
<213> ORGANISM: Homo sapiens

<400> SEQUENCE: 280

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
            50                  55                  60

Lys Asn Ile Ser Gly Ser Ile Glu Ile Val Lys Gln Gly Cys Trp Leu
65              70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
            130                 135                 140

Val Pro Leu Met Leu Ile
145                 150
```

We claim:

1. An isolated ActRIIB polypeptide comprising:
   (a) an amino acid sequence that is at least 90% identical to an amino acid sequence that begins at any one of amino acids 20 to 29 of SEQ ID NO: 2 and
   (b) ends at any one of amino acids 109 to 134 of SEQ ID NO: 2; and wherein the polypeptide comprises a lysine at the position corresponding to position 82 of SEQ ID NO: 2, wherein the ActRIIB polypeptide maintains inhibition of activin A and GDF11, and demonstrates less potent inhibition of BMP9, compared to a wild-type ActRIIB polypeptide.

2. The polypeptide of claim 1, wherein the ActRIIB polypeptide comprises an amino acid sequence that is at least 90% identical to amino acids 29-109 of SEQ ID NO: 2.

3. The polypeptide of claim 1, wherein the ActRIIB polypeptide comprises an amino acid sequence that is at least 90% identical to amino acids 20-134 of SEQ ID NO: 2.

4. The polypeptide of claim 1, wherein the ActRIIB polypeptide comprises an amino acid sequence that is at least 90% identical to amino acids 25-131 of SEQ ID NO: 2.

5. The polypeptide of claim 4, wherein the ActRIIB polypeptide comprises an amino acid sequence that is at least 90% identical to SEQ ID NO: 53.

6. The polypeptide of claim 1, wherein the ActRIIB polypeptide is a fusion protein further comprising an Fc polypeptide domain.

7. The polypeptide of claim 6, wherein the fusion protein further comprises a linker domain positioned between the ActRIIB polypeptide and the Fc polypeptide domain.

8. The polypeptide of claim 7, wherein the linker domain is selected from the group consisting of TGGG (SEQ ID NO: 265), TGGGG (SEQ ID NO: 263), SGGGG (SEQ ID NO: 264), GGGGS (SEQ ID NO: 267), GGG (SEQ ID NO: 261), GGGG (SEQ ID NO: 262), and SGGG (SEQ ID NO: 266).

9. The polypeptide of claim 7, wherein the linker domain comprises GGG.

10. The polypeptide of claim 6, wherein the fusion protein comprises an amino acid sequence that is at least 90% identical to the amino acid sequence of SEQ ID NO: 5.

11. The polypeptide of claim 6, wherein the fusion protein comprises an amino acid sequence that is at least 90% identical to the amino acid sequence of SEQ ID NO: 6.

12. The polypeptide of claim 6, wherein the fusion protein comprises an amino acid sequence that is at least 90% identical to the amino acid sequence of SEQ ID NO: 12.

13. The polypeptide of claim 6, wherein the fusion protein comprises an amino acid sequence that is at least 90% identical to the amino acid sequence of SEQ ID NO: 40.

14. The polypeptide of claim 6, wherein the fusion protein comprises an amino acid sequence that is at least 90% identical to the amino acid sequence of SEQ ID NO: 42.

15. The polypeptide of claim 6, wherein the fusion protein is encoded by a nucleic acid sequence that is at least 90% identical to the nucleic acid sequence of SEQ ID NO: 41.

16. The polypeptide of claim 1, wherein the ActRIIB polypeptide is a homodimer protein.

17. The polypeptide of claim 1, wherein the ActRIIB polypeptide is a heterodimer protein.

18. The polypeptide of claim 17, wherein the heterodimer comprises a second ActRIIB polypeptide, wherein the first ActRIIB polypeptide comprises a different amino acid sequence compared to the second ActRIIB polypeptide.

19. The polypeptide of claim 18, wherein the second ActRIIB polypeptide is a wild-type ActRIIB extracellular domain polypeptide.

20. The polypeptide of claim 1, wherein the ActRIIB polypeptide is glycosylated and has a glycosylation pattern obtainable from expression of the polypeptide in a CHO cell.

21. A pharmaceutical composition comprising the ActRIIB polypeptide of claim 1, and a pharmaceutically acceptable carrier.

* * * * *